(12) United States Patent
Ding et al.

(10) Patent No.: US 10,494,373 B2
(45) Date of Patent: Dec. 3, 2019

(54) FUSED-RING OR TRICYCLIC ARYL PYRIMIDINE COMPOUND USED AS KINASE INHIBITOR

(71) Applicant: GUANGDONG ZHONGSHENG PHARMACEUTICAL CO., LTD., Dongguan, Guangdong (CN)

(72) Inventors: Charles Z. Ding, Shanghai (CN); Shuhui Chen, Shanghai (CN); Baoping Zhao, Shanghai (CN); Xile Liu, Shanghai (CN); Linxia Xiao, Shanghai (CN); Chao Ding, Shanghai (CN); Fei Wang, Shanghai (CN); Jian Li, Shanghai (CN)

(73) Assignee: Guangdong Zhongsheng Pharmaceutical Co., Ltd, Dongguan (CN)

( * ) Notice: Subject to any disclaimer, the term of this patent is extended or adjusted under 35 U.S.C. 154(b) by 0 days.

(21) Appl. No.: 15/570,627

(22) PCT Filed: Apr. 20, 2016

(86) PCT No.: PCT/CN2016/079715
§ 371 (c)(1),
(2) Date: Oct. 30, 2017

(87) PCT Pub. No.: WO2016/173438
PCT Pub. Date: Nov. 3, 2016

(65) Prior Publication Data
US 2018/0354953 A1 Dec. 13, 2018

(30) Foreign Application Priority Data
Apr. 29, 2015 (CN) .......................... 2015 1 0213398

(51) Int. Cl.
| *C07D 487/04* | (2006.01) |
| *C07D 471/04* | (2006.01) |
| *C07D 498/04* | (2006.01) |
| *C07D 498/14* | (2006.01) |
| *C07D 403/04* | (2006.01) |
| *C07D 401/04* | (2006.01) |
| *A61K 31/506* | (2006.01) |
| *A61K 31/5383* | (2006.01) |
| *A61K 31/5377* | (2006.01) |
| *A61P 35/00* | (2006.01) |

(52) U.S. Cl.
CPC .......... *C07D 487/04* (2013.01); *A61K 31/506* (2013.01); *A61K 31/5377* (2013.01); *A61K 31/5383* (2013.01); *A61P 35/00* (2018.01); *C07D 401/04* (2013.01); *C07D 403/04* (2013.01); *C07D 471/04* (2013.01); *C07D 498/04* (2013.01); *C07D 498/14* (2013.01)

(58) Field of Classification Search
CPC .. C07D 487/04; C07D 471/04; C07D 498/04; C07D 498/06; C07D 405/04; C07D 403/04; C07D 401/04; A61K 31/506; A61K 31/5383; A61K 31/5377; A61P 35/00
USPC ........ 544/14, 89, 99, 315; 514/224.5, 229.5, 514/275
See application file for complete search history.

(56) References Cited

U.S. PATENT DOCUMENTS

| 4,624,952 A | 11/1986 | Biziere et al. |
| 5,863,924 A | 1/1999 | Berger et al. |
| 10,093,656 B2 * | 10/2018 | Ding ................. C07D 401/04 |
| 2013/0116213 A1 | 5/2013 | Cha et al. |

FOREIGN PATENT DOCUMENTS

| WO | WO-2013014448 A1 | 1/2013 |
| WO | WO-2013138495 A1 | 9/2013 |
| WO | WO-2014025486 A1 | 2/2014 |
| WO | WO-2015003658 A1 | 1/2015 |
| WO | WO-2015175632 A1 | 11/2015 |
| WO | WO-2017088746 A1 | 6/2017 |

OTHER PUBLICATIONS

U.S. Appl. No. 158/812,142, filed Nov. 14, 2017, C.Z. Ding.
(Continued)

*Primary Examiner* — Venkataraman Balasubramanian
(74) *Attorney, Agent, or Firm* — Harness, Dickey & Pierce, P.L.C.

(57) ABSTRACT

Disclosed is a fused-ring or tricyclic aryl pyrimidine compound used as a mutation selectivity EGFR inhibitor. Specifically, disclosed is a compound represented by formula (I) and used as an EGFR inhibitor or a pharmaceutically acceptable salt thereof.

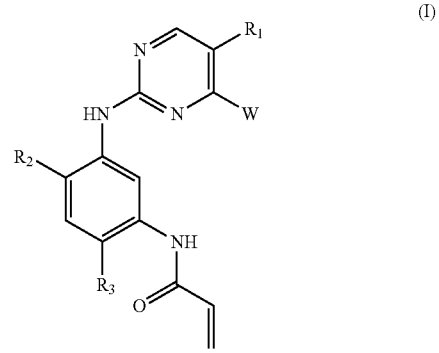

13 Claims, No Drawings

(56) References Cited

OTHER PUBLICATIONS

Mar. 18, 2018 European Search Report issued in European Patent Application No. EP16785869.5.
Mar. 23, 2018 European Search Report issued in European Patent Application No. EP17203374.8.
Chinese Patent Application No. 201510213398.1 (not published).
Lynch TJ et. al.—"Activating mutations in the epidermal growth factor receptor underlying responsiveness of non-small-cell lung cancer to gefitinib."—J. Med., 2004, 350:2129-39.
Zhou C et. al.—"Erlotinib versus chemotherapy as first-line treatment for patients with advanced EGFR mutation-positive non-small-cell lung cancer (OPTIMAL, CTONG-0802): a multicentre, open-label, randomised, phase 3 study."—Lancet Oncol, 2011,12:735-42.
Sharma SV et. al.—"Epidermal growth factor receptor mutations in lung cancer."—Nat Rev Cancer, 2007,7:169-81.
Shih JY et. al.—"EGFR mutation conferring primary resistance to gefitinib in non-small-cell lung cancer."—N Engl J Med, 2005,353:207-8.
Wu YL et. al.—"Afatinib versus cisplatin plus gemcitabine for first-line treatment of Asian patients with advanced non-small-cell lung cancer harbouring EGFR mutations (LUX-Lung 6): an open-label, randomised phase 3 trial."—Lancet Oncol, 2014,15:213-22.
Reckamp KL et. al.—"A phase 2 trial of dacomitinib (PF-00299804), an oral, irreversible pan-HER (human epidermal growth factor receptor) inhibitor, in patients with advanced non-small cell lung cancer after failure of prior chemotherapy and erlotinib."—Cancer, 2014, 120:1145-54.
Johnston JB et. al.—"Targeting the EGFR pathway for cancer therapy."—Curr. Med. Chem., 2006,13,3483-3492.
Cross DA et. al.,—"AZD9291, an irreversible EGFR TKI, overcomes T790M-mediated resistance to EGFR inhibitors in lung cancer."—Cancer Discov, 2014,4:1046-61.
Yu et. al.,—"Analysis of Tumor Specimens at the Time of Acquired Resistance to EGFR-TKI Therapy in 155 Patients with EGFR-Mutant Lung Cancers"—Cancer Res.,2013,19:2240-2247.
Pasi A. Janne et. al.,—"Clinical activity of the mutantselective EGFR inhibitor AZD9291 in patients (pts) with EGFR inhibitor-resistant nonsmall cell lung cancer (NSCLC)."—J Clin Oncol 2014;32:abstr 8009.
Lecia V. Sequist et. al.First-in-human evaluation of CO-1686, an irreversible, highly selective tyrosine kinase inhibitor of mutations of EGFR (activating and T790M) J Clin Oncol 2014;32:abstr 8010.
Berge et al.—"Pharmaceutical salts",—Journal of pharmaceutical Science, 1977 66:1-19.
H Maehr,—"A proposed new convention for graphic presentation of molecular geometry and topography."—J. Chem. Ed., 1985, 62:114-120.
Remington: The Science and Practice of Pharmacy, 21st Ed., Lippincott, Williams & Wilkins (2005).
Nov. 3, 2016 Written Opinion of the International Searching Authority issued in International Patent Application No. PCT/CN2016/079715.

\* cited by examiner

FUSED-RING OR TRICYCLIC ARYL PYRIMIDINE COMPOUND USED AS KINASE INHIBITOR

CROSS REFERENCE TO RELATED APPLICATIONS

This application is a U.S. National Phase Application under 35 U.S.C. 371 of International Application No. PCT/CN2016/079715 filed on Apr. 20, 2016 and published in Chinese as WO 2016/173438 A1 on Nov. 3, 2016. This application is based on and claims the benefit of priority from Chinese Patent Application No 201510213398.1 filed Apr. 29, 2015. The entire disclosures of all of the above applications are incorporated herein by reference.

FIELD OF INVENTION

The present invention relates to a fused-ring or tricyclic aryl pyrimidine compound used as a mutation selective EGFR inhibitor. Specifically, the present invention relates to a compound represented by formula (I) used as an EGFR inhibitor or a pharmaceutically acceptable salt thereof.

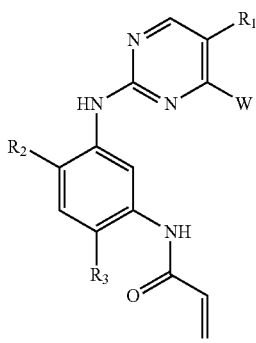

(I)

BACKGROUND OF THE INVENTION

Protein tyrosine kinase is an enzyme that catalyzes the transfer of the phosphate group on a protein substrate from ATP or GTP to a tyrosine residue. Receptor tyrosine kinase activates the secondary signaling pathway by phosphorylation caused by the transmission of signals from extracellular to intracellular. A variety of cellular processes are regulated by these signals, including proliferation, carbohydrate utilization, protein synthesis, angiogenesis, cell growth and cell survival. In addition, many diseases or conditions are associated with the abnormal, disorder or imbalance of one or more than one kinase(s).

Epidermal growth factor receptor belongs to the transmembrane tyrosine kinase receptor ErbB family, the family includes EGFR (also known as ErbB or HER1), (HER2 or neu gene) of ErbB2, (HER3) of ErbB3 and ErbB4 (HER4), which all have tyrosine kinase activity except for HER3. The EGFR/ErbB family tyrosine kinase receptor has an indispensable role in cell proliferation, differentiation and apoptosis, and thus becomes an effective target for preventing tumor growth and metastasis. The first generation of epidermal growth factor receptor tyrosine kinase inhibitor (EGFR-TKI), including Gefitinib (J Med 2004; 350: 2129-39) and Erlotinib (Lancet Oncol 2011; 12: 735-42), have been shown to be effective in patients with advanced NSCLC with somatic cell activation mutations. These mutations are in the kinase domain that encodes epidermal growth factor receptor, such as in-frame deletion of polynucleotide 19 exon and point mutation that the 858-position leucine on exon 21 is replaced by arginine (L858R) (Nat Rev Cancer 2007; 7: 169-81). However, after receiving the first generation of EGFR-TKIs, the patient will eventually be subject to a secondary growth of the tumor due to drug resistance. The secondary mutation that the 790-position threonine is replaced by methionine (T790M) is the most commonly recognized drug resistance mechanism for drug resistance. This mutation is detected in tumor cells of 50% to 60% patients with developed condition (N Engl J Med 2005; 353:207-8). The development of the second generation of EGFR-TKIs, such as Alfatinib (lancet oncol 2014; 15: 213-22) and Dacomitinib (Cancer 2014; 120: 1145-54), is used to overcome the resistance of the first generation of TKIs. They could irreversibly covalently bind to 797-position cysteine on EGFR. The covalent mechanism is believed to overcome the increased ATP affinity of the double mutant. However, cysteine-797 is present in all forms of EGFR. Thus, these second generation compounds are active not only for EGFR with active mutation and secondary mutation, but also for wild-type EGFR. Inhibition of wild-type EGFR is not considered to contribute to its clinical efficacy, but can lead to side effects of rash and diarrhea (Curr. Med. Chem. 2006, 13, 3483-3492).

Thus, the third generation of EGFR-TKIs includes AZD9291 (Cancer Discov 2014; 4: 1046-61), CO-1686 (Cancer Res. 2013; 19: 2240-2247) and HM61713 (US 2013011213), they are oral irreversible EGFR-TIKs with mutation selectivity, which can inhibit the mutation of T790M and the traditional EGFR, but do not have activity against wild-type EGFR. They are highly effective against T790M-positive tumors, but they still have some toxicity, such as diarrhea, rash, nausea and even high blood sugar and other clinical side effects (J Clin Oncol 2014; 32:abstr 8009; J Clin Oncol 2014; 32:abstr 8010). It is obvious that a compound with higher activity and lower toxicity will bring greater benefits.

The present invention relates to a series of novel fused or tricyclic aryl pyrimidine compounds, the series of compounds show excellent activity against EGFR with sensitive mutation and double mutation (sensitive and T790M resistant) and have a high selectivity for wild-type EGFR. They may provide more effective treatment for the diseases caused by abnormal enzymes of the epidermal growth factor receptor.

CONTENT OF THE PRESENT INVENTION

An object of the present invention is to provide a compound of formula (I) or a pharmaceutically acceptable salt thereof,

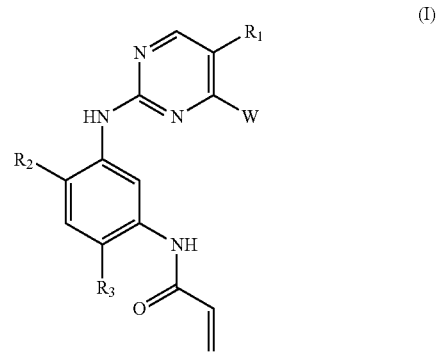

(I)

wherein,
W is

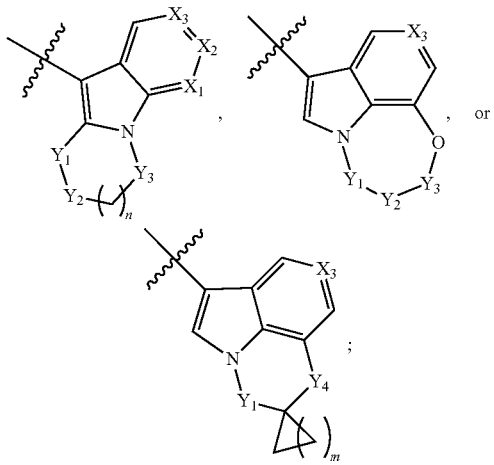

n=0, 1, or 2;
m=1, 2, or 3;
each of $Y_1$, $Y_2$, $Y_3$, and $Y_4$ is independently selected from the group consisting of —O—, —S—, —C(R)$_2$—, —N(R)—, —S(=O)$_2$—, —S(=O)—, —C(=O)—, and —C(=S)—;
$X_1$ is $CR_{X1}$, or N;
$X_2$ is $CR_{X2}$, or N;
$X_3$ is $CR_{X3}$, or N;
each of $R_{X1}$, $R_{X2}$, $R_{X3}$ is independently selected from H, F, Cl, Br, I, CN, OH, SH, or NH$_2$, or each of $R_{X1}$, $R_{X2}$, $R_{X3}$ is independently selected from the group consisting of $C_{1-6}$ alkyl and $C_{1-6}$ heteroalkyl, and the aforesaid group is optionally substituted by one, two, three, or four R(s);
$R_1$ is H, F, Cl, Me, CN, or CF$_3$;
$R_2$ is $R_{02}$, $OR_{02}$, or $SR_{02}$;
$R_{02}$ is independently selected from the group consisting of $C_{1-4}$ alkyl, $C_{1-4}$ heteroalkyl, and $C_{3-5}$ cycloalkyl-(CH$_2$)$_{0-3}$—, and the aforesaid group is optionally substituted by one, two, three, or four R(s);
$R_3$ is selected from the group consisting of $C_{1-6}$ alkyl, $C_{1-6}$ heteroalkyl, $C_{2-4}$ alkynyl, 3 to 7 membered cycloalkyl, 3 to 7 membered cycloalkyl-L-, 3 to 7 membered heterocycloalkyl, and 3 to 7 membered heterocycloalkyl-L-, and the aforesaid group is optionally substituted by one, two, three, or four R(s);
L is —O—, —S—, —C(=O)—, —S(=O)$_2$—, or —S(=O)—, or L is selected from the group consisting of NH, $C_{1-4}$ alkyl, and $C_{1-4}$ heteroalkyl, and the aforesaid group is optionally substituted by one, two, three, or four R(s);
the "hetero" represents a heteroatom or a hetero-atomic group, which is —C(=O)NH—, —NH—, —O—, —S—, N, =O, =S, —C(=O)O—, —C(=O)—, —C(=S)—, —S(=O)—, or —S(=O)$_2$—;
the number of the heteroatom or the hetero-atomic group is independently selected from 0, 1, 2, or 3;
R is H, F, Cl, Br, I, OH, or CN, or R is selected from the group consisting of NH$_2$, $C_{1-4}$ alkyl, $C_{1-4}$ heteroalkyl, 3 to 7 membered cycloalkyl, and 3 to 7 membered heterocycloalkyl, and the aforesaid group is optionally substituted by one, two, three or four R'(s);
R' is F, Cl, Br, I, CN, OH, NH$_2$, CF$_3$, NHCH$_3$, CH$_2$OCH$_3$, or N(CH$_3$).

In one embodiment of the present invention, R is H, F, Cl, Br, I, OH, NH$_2$, CN, Me, Et, CF$_3$, N(CH$_3$)$_2$, N(CD$_3$)$_2$, NHCH$_3$,

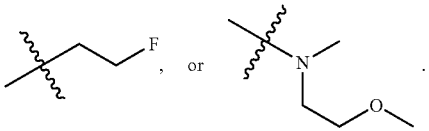

In one embodiment of the present invention, each of $Y_1$, $Y_2$, $Y_3$ and $Y_4$ is independently selected from —O—, —S—, —CH$_2$—, —CF$_2$—, —CHF—, —C(Me)$_2$-, —CH(Me)-, —CH(OH)—, —C(=O)—, —S(=O)$_2$—, or —S(=O)—.

In one embodiment of the present invention, each of $Y_1$ and $Y_3$ is independently selected from —CH$_2$—, —C(Me)$_2$-, —CH(Me)-, —C(=O)—, —CF$_2$—, —CHF—, or —CH(OH)—.

In one embodiment of the present invention, each of $Y_2$ and $Y_4$ is independently selected from a single bond, —O—, —S—, —S(=O)$_2$—, —CH$_2$—, —C(Me)$_2$-, —C(=O)—, —CF$_2$—, —CH(OH)—, —CH(Me)-, or —CHF—.

In one embodiment of the present invention, the moiety

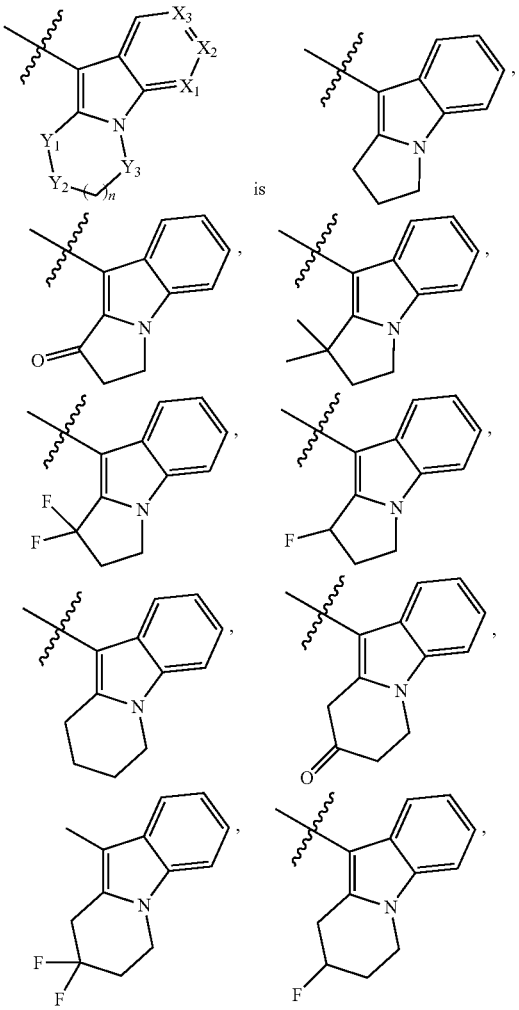

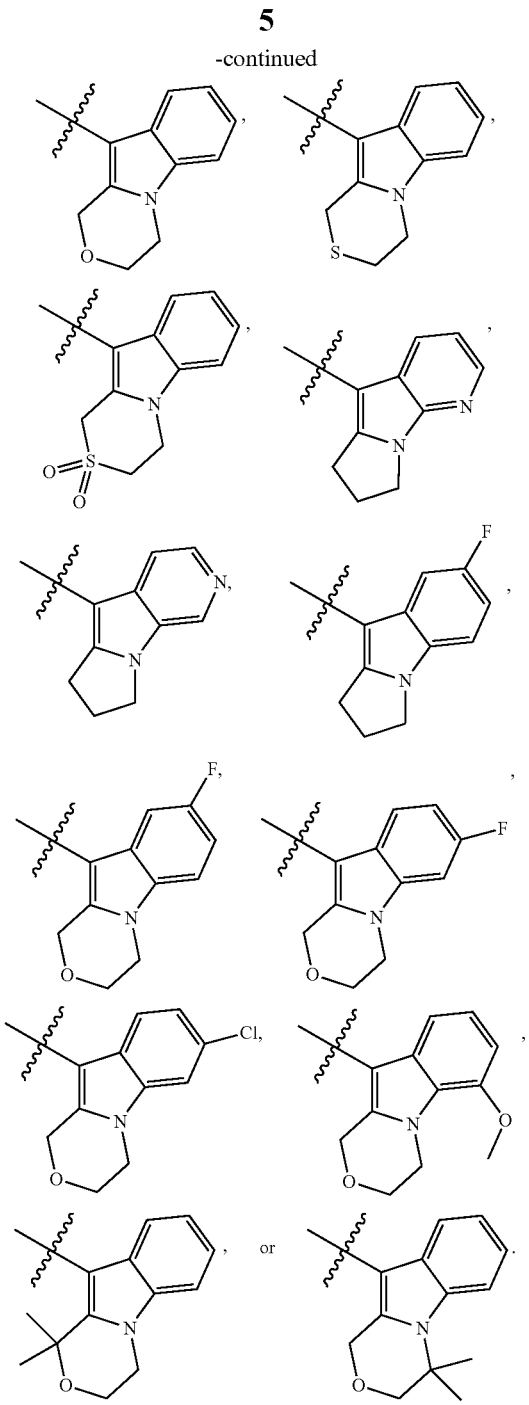

In one embodiment of the present invention, the moiety

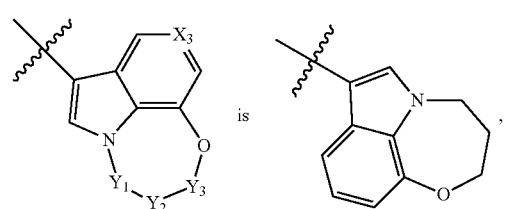

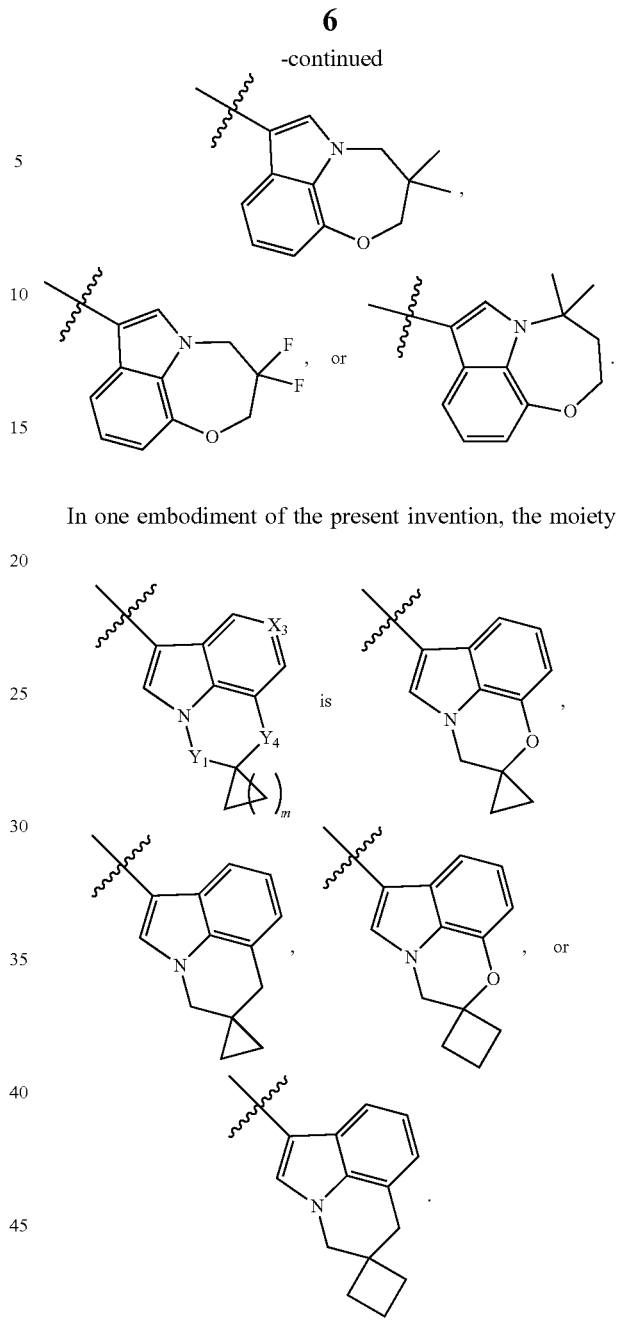

In one embodiment of the present invention, L is —O—, —S—, —C(=O)—, —S(=O)$_2$—, or —S(=O)—, or L is selected from the group consisting of NH, C$_{1-3}$ alkyl, —O—C$_{1-3}$ alkyl, —S-alkyl, and —NH—C$_{1-3}$ alkyl, and the aforesaid group is optionally substituted by one, two, or three R(s).

In one embodiment of the present invention, L is —O—, —S—, —C(=O)—, —S(=O)$_2$—, or —S(=O)—, or L is selected from the group consisting of —NH—, —CH$_2$—,

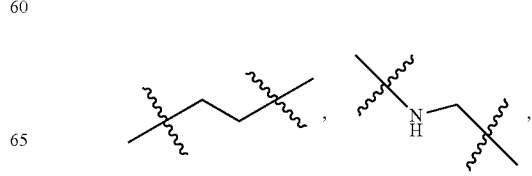

-continued

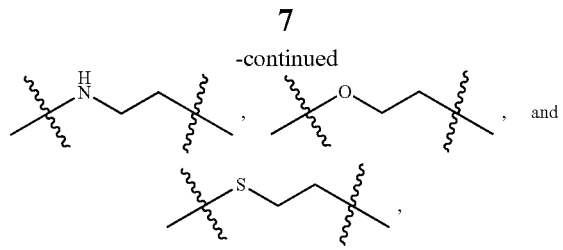

and the aforesaid group is optionally substituted by one, two, or three R(s).

In one embodiment of the present invention, L is —O—, —S—, —C(=O)—, —NH—, —N(CH$_3$)—, —CH$_2$—,

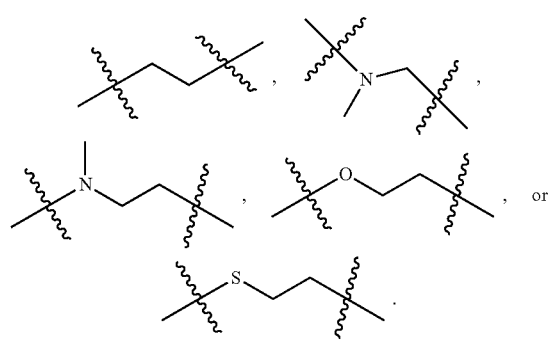

, or

In one embodiment of the present invention, R$_3$ is selected from the group consisting of —C$_{1-4}$ alkyl, —NH—C$_{1-4}$ alkyl, —NH—C(=O)—C$_{1-4}$ alkyl, —O—C$_{1-4}$ alkyl, —S-alkyl, —S(=O)—C$_{1-4}$ alkyl, —S(=O)$_2$—C$_{1-4}$ alkyl, C$_{2-3}$ alkynyl, 3 to 6 membered cycloalkyl, 3 to 6 membered cycloalkyl-L-, 3 to 6 membered heterocycloalkyl, and 3 to 6 membered heterocycloalkyl-L-, and the aforesaid group is optionally substituted by one, two, three, or four R(s), and the "hetero" represents a heteroatom or a hetero-atomic group, which is —C(=O)NH—, —NH—, —O—, —S—, N, =O, =S, —C(=O)O—, —C(=O)—, —C(=S)—, —S(=O)—, or —S(=O)$_2$—, the number of the heteroatom or the hetero-atomic group is independently selected from 0, 1, 2, or 3.

In one embodiment of the present invention, R$_3$ is selected from the group consisting of

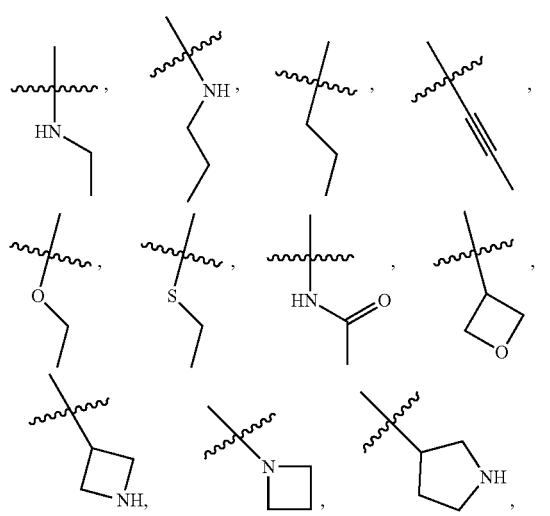

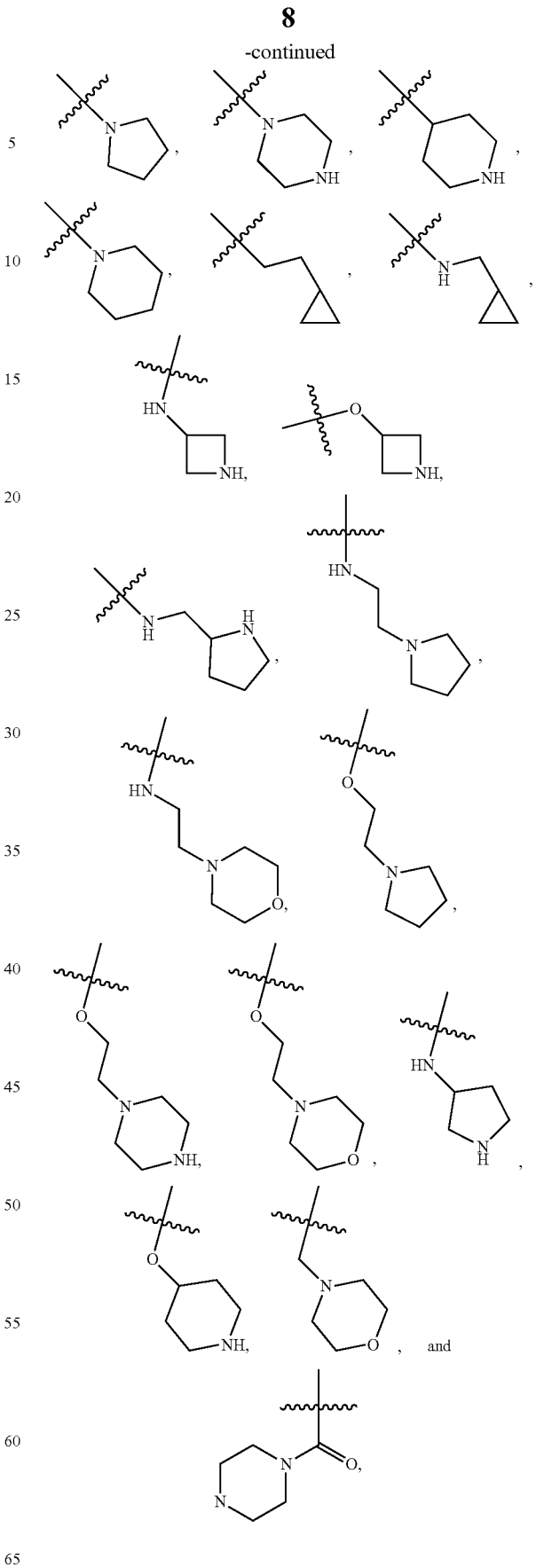

the aforesaid group is optionally substituted by one, two, three or four R(s).

In one embodiment of the present invention, $R_3$ is
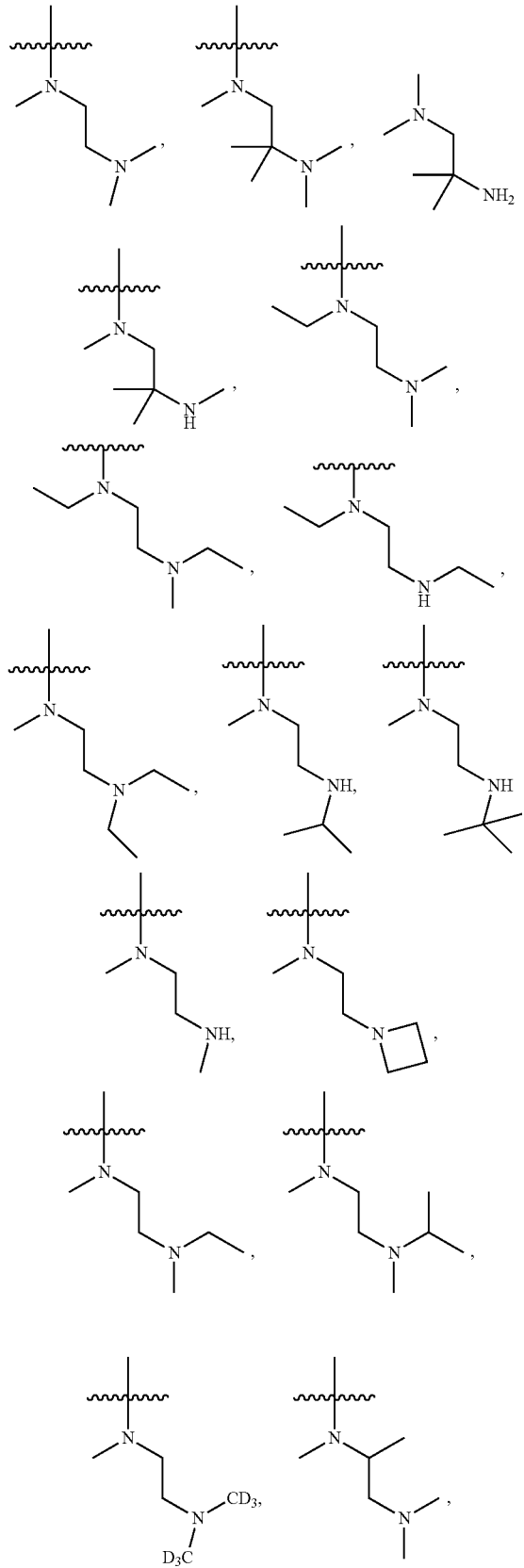
-continued
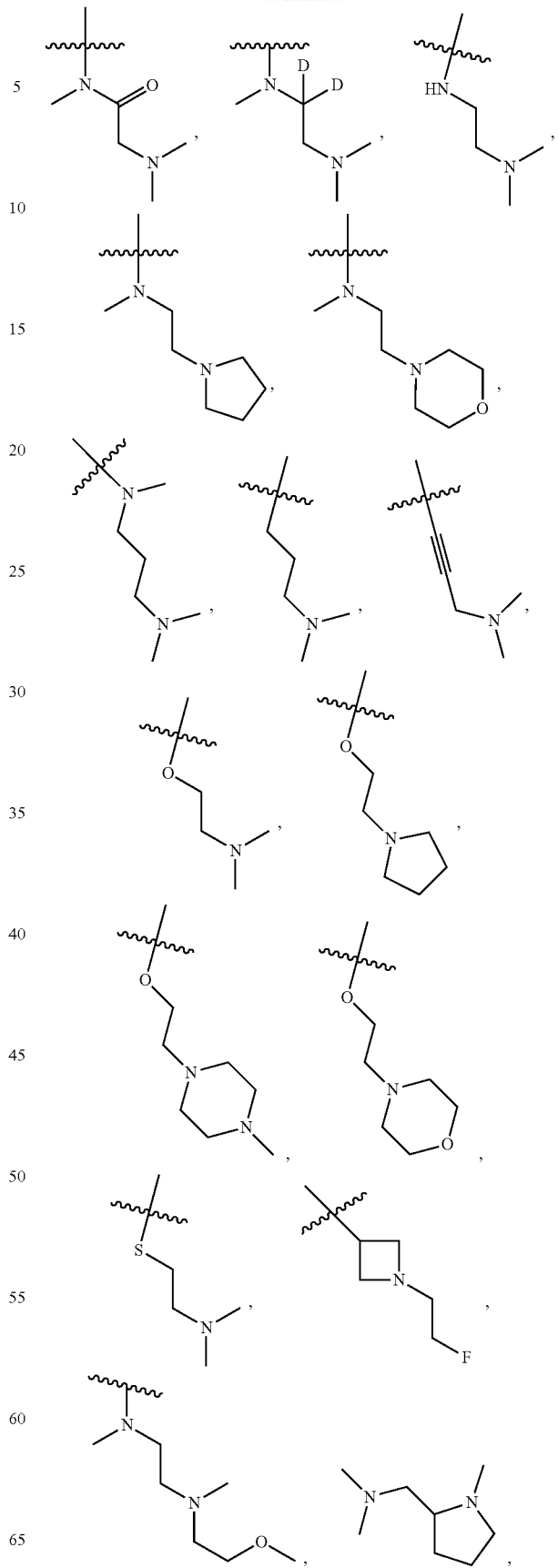

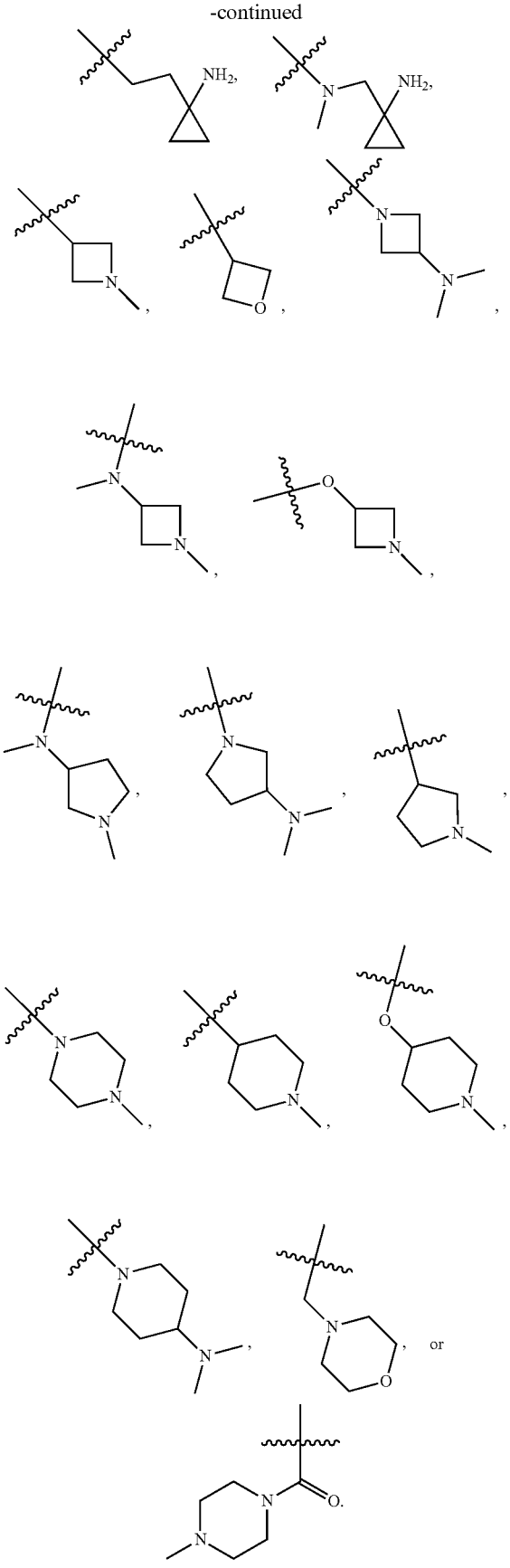
In one embodiment of the present invention, $R_{02}$ is Me, $CHF_2$, $CH_2CH_3$, or $CH(CH_3)_2$.
In one embodiment of the present invention, the above mentioned compound is selected from
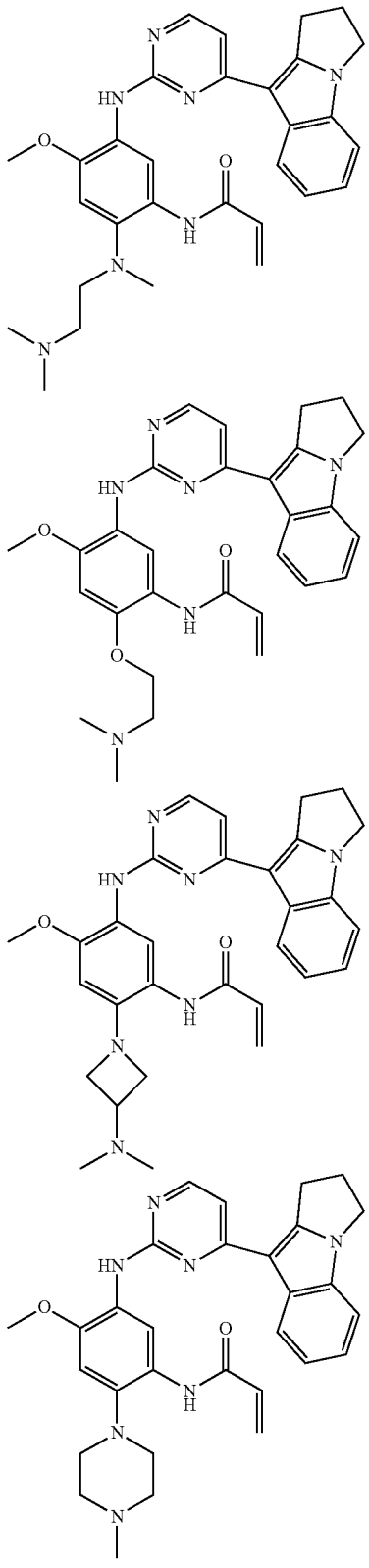

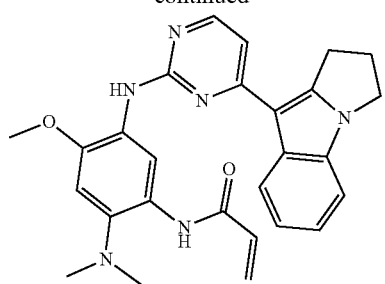
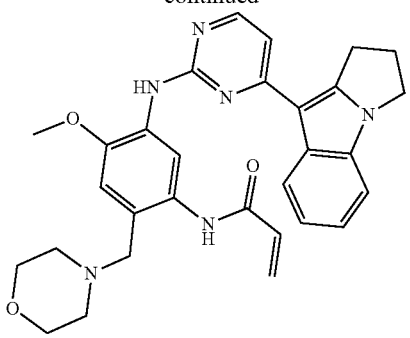
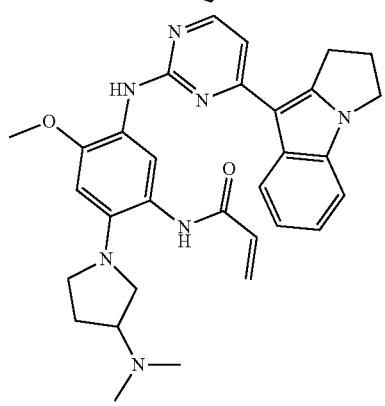
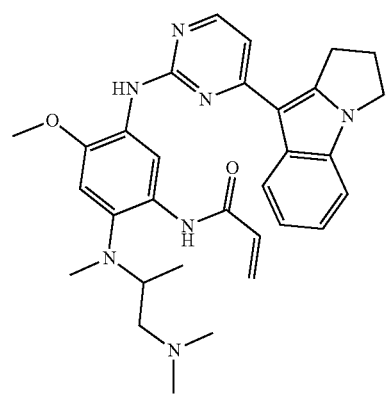
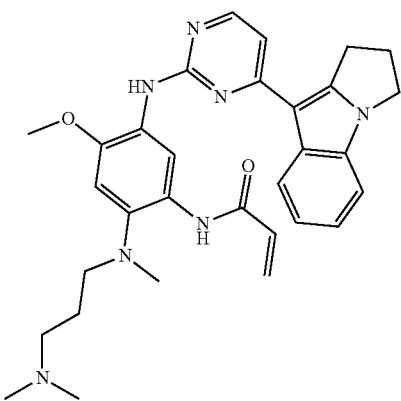
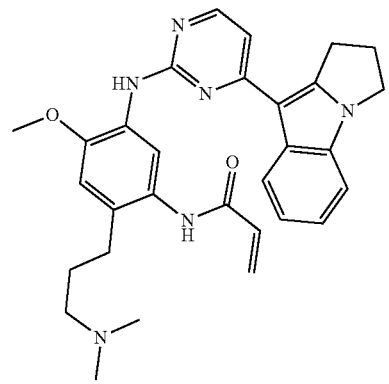
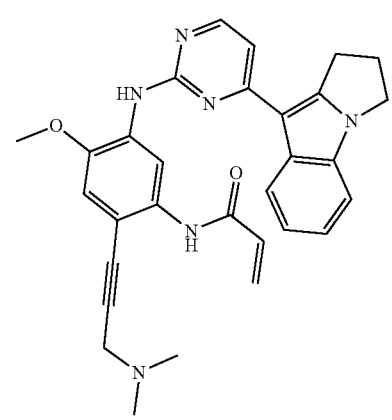
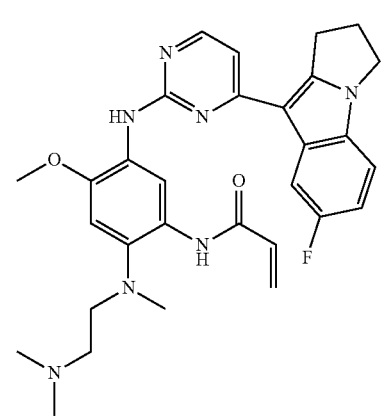

-continued
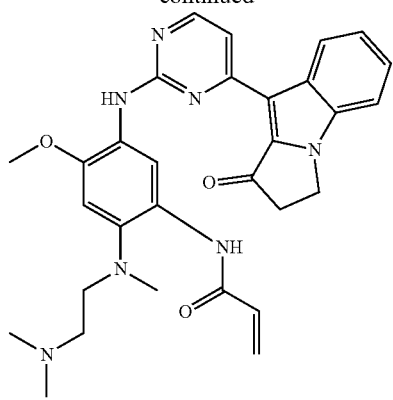
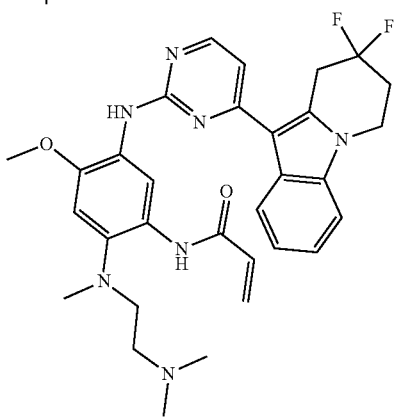
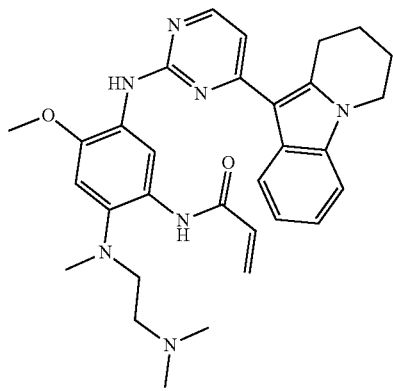
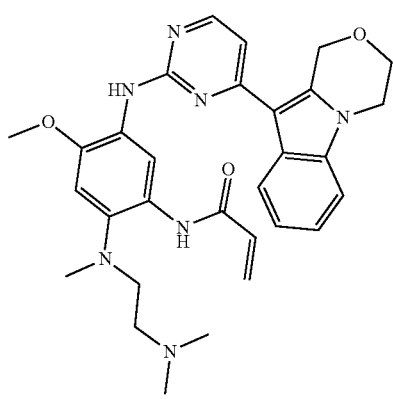
-continued
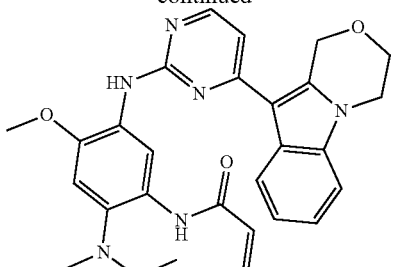
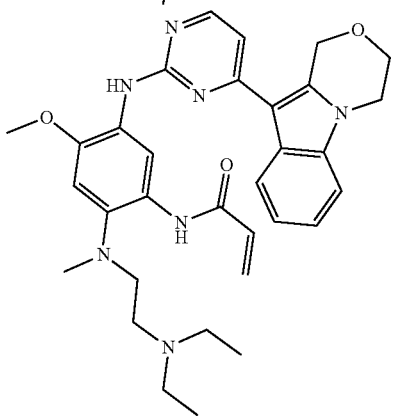
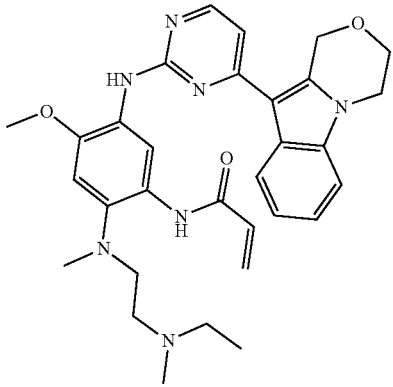
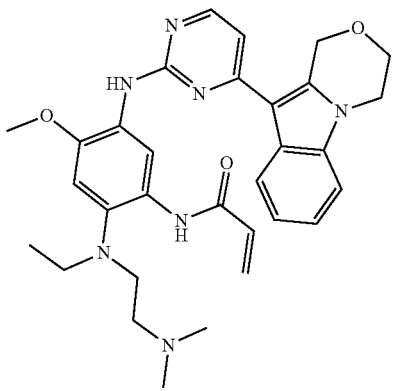

-continued
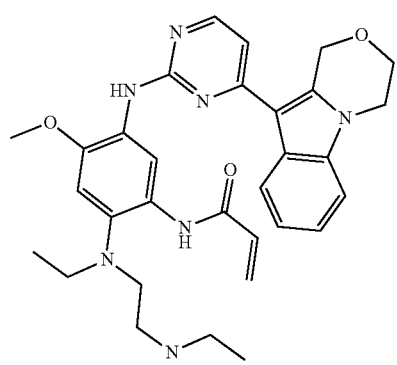
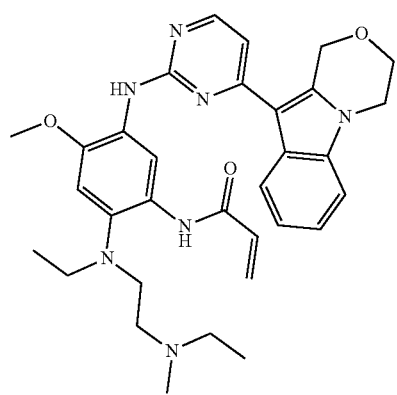
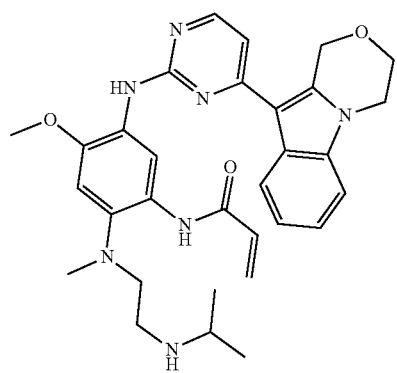
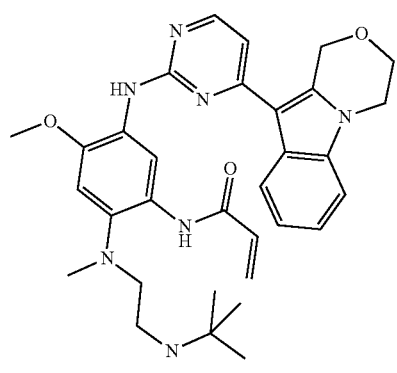
-continued
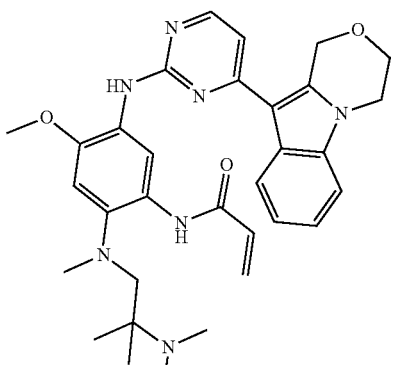
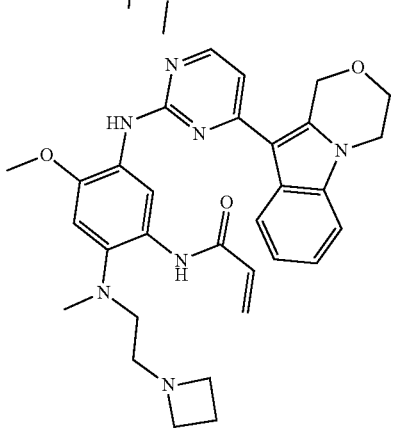
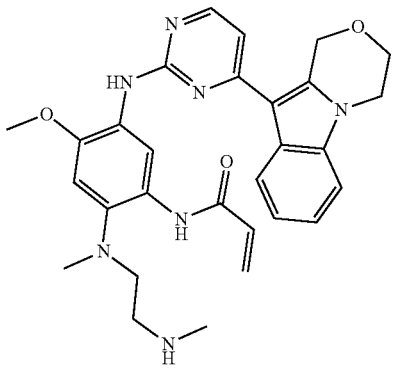
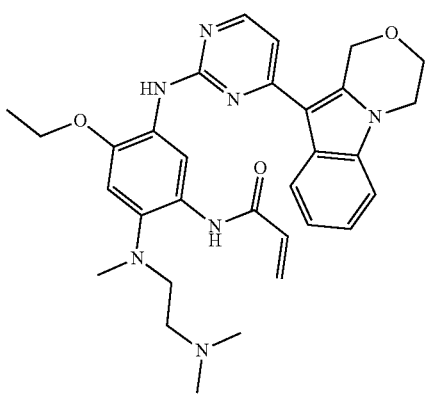

-continued
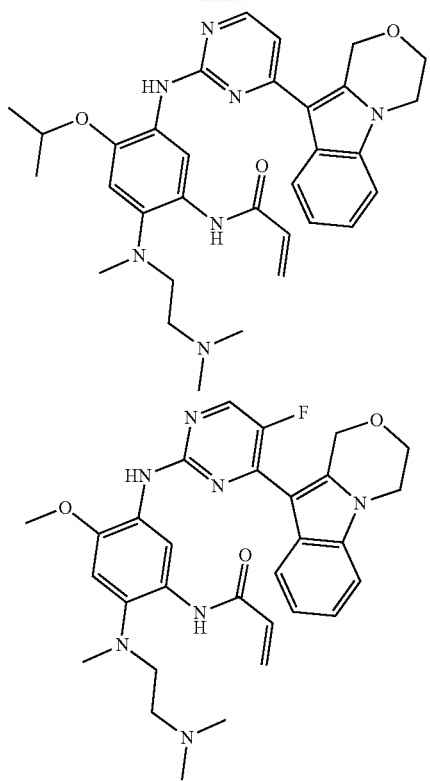
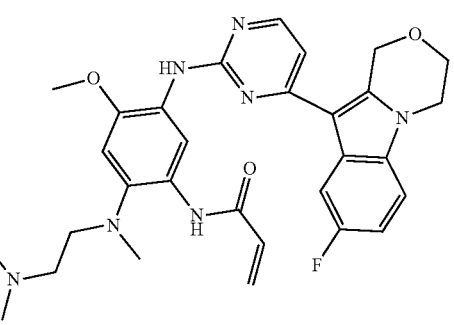
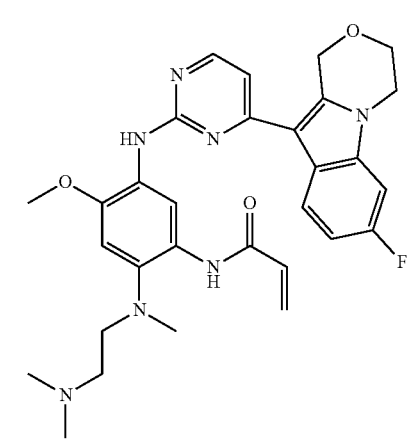
-continued
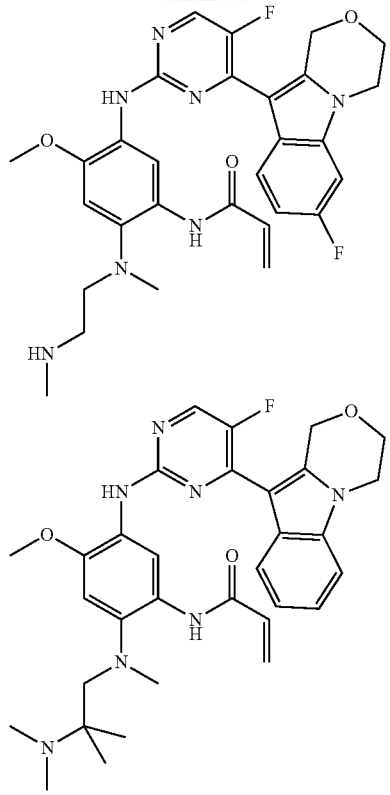
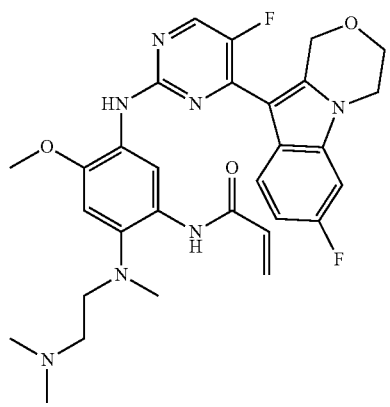
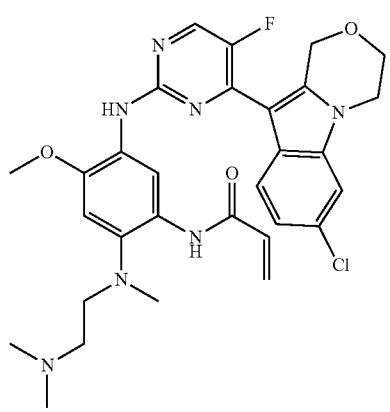

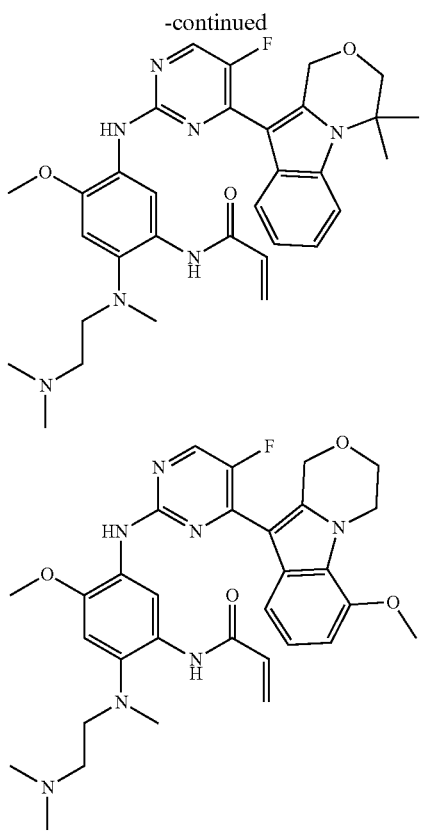

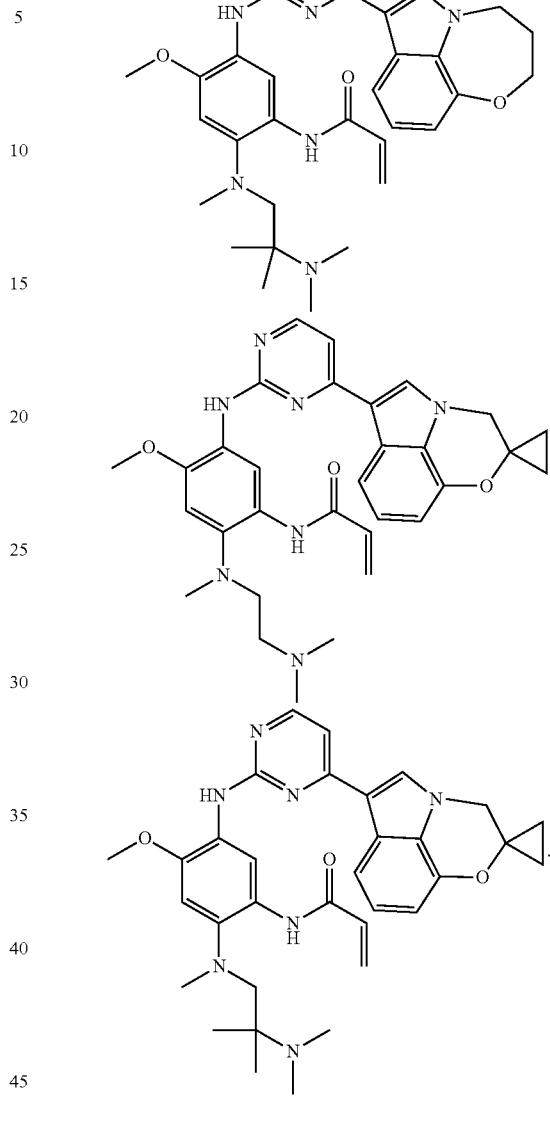

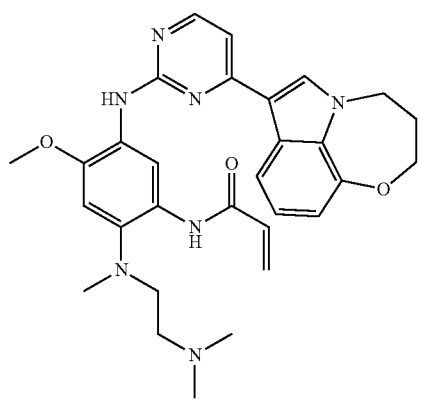

DEFINITIONS AND DESCRIPTIONS

Unless otherwise specified, the following terms and phrases used herein are intended to have the following meanings. A particular term or phrase should not be considered uncertain or unclear in the absence of a specific definition while should be understood according to the ordinary meaning. When a trade name appears herein, it refers to the corresponding commodity or its active ingredient.

$C_{1-6}$ is selected from $C_1$, $C_2$, $C_3$, $C_4$, $C_5$, and $C_6$; and 3 to 7 membered is selected from 3 membered, 4 membered, 5 membered, 6 membered, and 7 membered.

Herein, the term "pharmaceutically acceptable" is aimed at those compounds, materials, compositions and/or formulations, which are within the scope of reliable medical judgment and applicable for use in contact with human and animal tissues but without too much toxicity, irritation, allergic reactions or other problems or complications, also meet the reasonable benefit/risk ratio.

The term "pharmaceutically acceptable salt" refers to a salt of the compound of the present invention, which is prepared from the compound with specific substituent discovered by the present invention and relatively non-toxic acid or alkali. When the compound of the present invention contains a relatively acidic functional group, an alkali-addition salt can be obtained by contacting the compound in a neutral form with sufficient amount of alkali in a pure solution or suitable inert solvent. The pharmaceutically acceptable alkali-addition salt includes the salt of sodium, potassium, calcium, ammonium, organic ammonia or magnesium or the like. When the compound of the present invention contains a relatively alkaline functional group, an acid-addition salt can be obtained by contacting the compound in a neutral form with sufficient amount of acid in a pure solution or suitable inert solvent. Embodiments of the pharmaceutically acceptable acid-addition salt include a salt of inorganic acid, the inorganic acid includes such as hydrochloric acid, hydrobromic acid, nitric acid, carbonic acid, bicarbonate, phosphoric acid, hydrogen phosphate, dihydrogen phosphate, sulfuric acid, hydrogen sulfate, hydriodic acid, phosphorous acid etc; and salt of organic acid, the organic acid includes such as acetic acid, propionic acid, isobutyric acid, maleic acid, malonic acid, benzoic acid, succinic acid, suberic acid, fumaric acid, lactic acid, mandelic acid, phthalic acid, phenylsulfonic acid, p-toluene sulfonic acid, citric acid, tartaric acid, methylsulfonic acid and the like; and also includes salt of amino acid (e.g. arginine etc.), and salt of organic acid such as glucuronic acid and the like (see Berge et al., "Pharmaceutical Salts", Journal of Pharmaceutical Science 66: 1-19 (1977)). Some specific compound of the present invention contains both alkaline and acidic functional groups so as to be transformed to any alkali-addition or acid-addition salt.

Preferably, the neutral form of a compound is regenerated by contacting a salt with a base or an acid in a conventional manner and then separating the parent compound. The difference between a parent form of a compound and the various salt forms lies in some physical properties, such as that the solubility in a polar solvent is different.

The "pharmaceutically acceptable salt" in the present invention is the derivative of the compound of the present invention, wherein the parent compound is modified by salifying with an acid or an alkali. Embodiments of the pharmaceutically acceptable salt include but not limited to an inorganic acid or organic acid salt of an alkali such as amine, an alkali metal or organic salt of an acid radical such as carboxylic acid and so on. The pharmaceutically acceptable salt includes conventionally non-toxic salts or quaternary ammonium salts of the parent compound, such as a salt formed by a non-toxic inorganic acid or organic acid. The conventionally non-toxic salt includes but not limited to those salts derived from inorganic acids and organic acids, the inorganic acids or organic acids are selected from 2-acetoxybenzoic acid, 2-isethionic acid, acetic acid, ascorbic acid, phenylsulfonic acid, benzoic acid, bicarbonate, carbonic acid, citric acid, edetic acid, ethanedisulfonic acid, ethanesulfonic acid, fumaric acid, glucoheptose, gluconic acid, glutamic acid, glycolic acid, hydrobromic acid, hydrochloric acid, hydriodate, hydroxyl, hydroxynaphthalene, isethionic acid, lactic acid, lactose, dodecanesulfonic acid, maleic acid, malic acid, mandelic acid, methanesulfonic acid, nitric acid, oxalic acid, pamoic acid, pantothenic acid, phenylacetic acid, phosphoric acid, polygalactaldehyde aldehyde, propionic acid, salicylic acid, stearic acid, folinate acid, succinic acid, aminosulfonic acid, sulfanilic acid, sulphuric acid, tannic acid, tartaric acid and p-toluene sulfonic acid.

The pharmaceutically acceptable salt of the present invention can be prepared by a conventional method with a parent compound containing an acidic or alkaline group. Generally, the preparation method of the salt comprises reacting these compounds in forms of free acids or alkalis with stoichiometric amount of proper alkalis or acids in water or an organic solvent or the mixture of water and organic solvent. In general, non-aqueous media is preferably ether, ethyl acetate, ethanol, isopropanol or acetonitrile and so on.

Except for the form of salt, there is a form of prodrug for the compound in the present invention. The prodrug of the compound described in the present invention is easily transformed to the compound of the present invention via chemical changes under physiological conditions. Besides, the prodrug can be transformed to the compound of the present invention via chemical or biochemical method in vivo environment.

Some compounds of the present invention can exist in the form of non-solvate or solvate forms, including hydrate forms. In general, the solvate form is similar to the non-solvate form, both of which are included within the scope of the present invention. Some compounds of the present invention exist in the form of polycrystalline or amorphous.

Some compounds of the present invention can contain asymmetric carbon atoms (optical center) or double bonds. The racemic isomers, diastereomers, geometric isomers and single isomers are included within the scope of the present invention.

The diagrammatic representation of the racemic isomer, the ambiscalemic and scalemic or the enantiopure compound of the present invention is from Maehr, J. Chem. Ed. 1985, 62: 114-120. Unless otherwise indicated, the absolute configuration of a stereocenter is represented by the wedge and dashed lines. When the compound of the present invention contains a vinyl double bond or other geometric asymmetric center, unless otherwise specified, E, Z geometric isomers are included. Similarly, all tautomeric forms are included within the scope of the present invention.

The compound of the present invention may exist as a specific geometric or stereoisomeric isomer. The present invention envisages all of this class of compounds, including cis- and trans-isomers, (−)- and (+)-antimers, (R)- and (S)-antimers, diastereomers, (D)-isomer, (L)-isomer, as well as racemic mixtures and other mixtures, such as enantiomers- or diastereoisomers-enriched mixtures, all of these mixtures are within the scope of the present invention. Additional asymmetric carbon atoms may exist in substituents such as in an alkyl. All of these isomers and their mixtures are included within the scope of the present invention.

Optically active (R)- and (S)-isomers, (D)- and (L)-isomers can be prepared by asymmetric synthesis or chiral reagents or other conventional techniques. If an enantiomer of a compound of the present invention is desired, asymmetric synthesis or derivatization action of the chiral auxiliaries can be employed in preparation, in which the resulting diastereomer mixtures are isolated, and the auxiliary groups are cleaved to provide the pure desired enantiomer. Or, when a molecule contains an alkaline functional group (such as amino) or an acidic functional group (such as carboxyl), a salt of diastereomer is formed with an appropriate optical active acid or alkali, and then the pure enantiomer can be recycled after resolution on the salt of diastereomer by fractional crystallization or chromatography which is known in the art. In addition, the separation of an enantiomer and a diastereomer is usually realized by the chromatographic method, the chromatography method employs a chiral stationary phase, and optionally combined with chemical derivatization method (e.g. an amine generates a carbamate).

One or more atoms constituting the compound of the present invention may comprise an unnatural proportion of atomic isotopes. For Example, the compound can be labeled by a radioactive isotope, such as tritium ($^3$H), iodine-125 ($^{125}$I) or C-14 ($^{14}$C). All the variations in the isotopic composition of the compound disclosed in the present invention, whether radioactive or not, are included within the scope of the present invention.

The term "pharmaceutically acceptable carrier" refers to any formulation or carrier medium which is capable of delivering effective amount of the active substance disclosed in the present invention, does not interfere with the biological activity of the active substance, and is with no toxic side-effects on host or patient. Representative carrier includes water, oil, vegetables and minerals, cream base, lotion matrix, ointment matrix etc. The matrix comprises a suspension, a viscosity increaser, transdermal enhancers etc. Their formulations are well known to the person in cosmetic or topical drug art. Other information about the carrier can refer to Remington: The Science and Practice of Pharmacy, 21st Ed., Lippincott, Williams & Wilkins (2005), the content of which is incorporated into this article as reference.

The term "excipient" usually refers to a carrier, diluent and/or medium required for the preparation of an effective pharmaceutical composition.

In terms of drug or pharmacological active agent, the term "effective amount" or "therapeutically effective amount" refers to enough quantity of the drug or formulation that can achieve desired effects but is with no toxicity. For the oral formulation of the present invention, "an effective amount" of one active substance in the composition is the amount required to achieve desired effects in combination with another active substance in the composition. The determination of the effective amount varies from person to person, which depends on the age and the general situation of the recipient, also on the specific active substance. In one case, an appropriate effective amount can be determined by the person skilled in the art according to conventional tests.

The term "active ingredient", "therapeutic agent", "active substance" or "active agent" refers to a chemical entity, which can effectively treat disorder, disease or condition of a target subject.

The term "substituted" refers to one or more hydrogen atoms in a specific atom optionally substituted by a substituent, including a deuterium and a variant of hydrogen, as long as the valence state of the specific atom is normal and the compound obtained after substitution is stable. When the substituent is a ketone group (i.e. =O), it means that two hydrogen atoms are substituted. A substitution of ketone group does not occur in an aryl. The term "optionally substituted" means that it may be substituted or not be substituted, unless otherwise specified, the type and number of substituents can be arbitrary under the premise of stability available in chemistry.

When any parameter (e.g. R) shows an occurrence for more than one time in the composition or structure of the compound, the definition of each occurrence is independent. Therefore, for example, if a group is substituted by 0 to 2 of R(s), the group may optionally be substituted by at most two R(s), and R has an independent option in each case. In addition, the combination of substituents and/or their variants is allowed only if such a combination will lead to a stable compound.

When one of the parameters is selected from a single bond, it indicates that the two groups which it is attached are directly connected, for example, when the L in A-L-Z represents a single bond, it indicates that the structure actually is A-Z.

When bonds of a substituent can be crossly connected to two atoms of a ring, the substituent can be bonded to arbitrary atoms in the ring. When the listed substituent does not specify through which atom it is connected to the general structure formula including the compound that is not specifically mentioned, the substituent can be bonded through any of its atoms. The combination of substituents and/or their variants is allowed only if such a combination will lead to a stable compound. For example, the structural unit

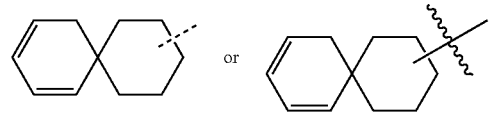

represents that the connection can occur on any atom in the cyclohexyl or cyclohexadiene.

The substituent in alkyl and heteroalkyl group is generally called "alkyl substituent", which can be selected from but not limited to the group consisting of —R', —OR', =O, =NR', =N—OR', —NR'R", —SR', halogen, —SiR'R"R'", OC(O)R', —C(O)R', —CO$_2$R', —CONR'R", —OC(O)NR'R", —NR"C(O)R', NR'C(O)NR"R'", —NR"C(O)$_2$R', —NR''''—C(NR'R"R''')=NR'''', NR''''C(NR'R")=NR''', —S(O)R', —S(O)$_2$R', —S(O)$_2$NR'R", NR"SO$_2$R', —CN, —NO$_2$, —N$_3$, —CH(Ph)$_2$ and fluoro(C$_1$-C$_4$)alkyl, the number of the substituent is between 0 and (2m'+1), wherein m' is the total number of the carbon atoms in the group. R', R", R''', R'''' and R''''' are independently selected from H, substituted or unsubstituted heteroalkyl, substituted or unsubstituted aryl (e.g. aryl substituted by 1~3 of halogen), substituted or unsubstituted alkyl, alkoxy, thioalkoxy or aralkyl. When the compound of the present invention includes more than one R group, for example, each of the R group is independently selected, as each of R', R", R''', R'''' and R''''' group is when more than one of them are included. When R' and R" are attached to the same nitrogen atom, they can form 5-, 6-, or 7-membered ring together with the nitrogen atom. For example, —NR'R" includes but not limited to 1-pyrrolidinyl and 4-morpholinyl. According to the above discussion on substituent, the person skilled in the art can understand, the term "alkyl" is intended to include a group formed by bonding a carbon atom to a non-hydrogen group, such as a halogenated alkyl (e.g. —CF$_3$, —CH$_2$CF$_3$) and an acyl (e.g. —C(O)CH$_3$, —C(O)CF$_3$, C(O)CH$_2$OCH$_3$, etc.).

Similar to the substituent in the alkyl group, the substituent in aryl and heteroaryl group is generally called "aryl substituent", which can be selected from such as —R', —OR', —NR'R", —SR', -halogen, —SiR'R"R'", OC(O)R', —C(O)R', —CO$_2$R', —CONR'R", —OC(O)NR'R", —NR"C(O)R', NR'C(O)NR"R'", —NR"C(O)$_2$R', —NR''''—C(NR'R"R''')=NR'''', NR''''C(NR'R")=NR''', —S(O)R', —S(O)$_2$R', —S(O)$_2$NR'R", NR"SO$_2$R', —CN, —NO$_2$, —N$_3$, —CH(Ph)$_2$, fluoro(C$_1$-C$_4$)alkoxy and fluoro(C$_1$-C$_4$)alkyl, etc., a number of the substituent ranges from 0 to the total opening valence of the aromatic ring; wherein R', R'', R''', R'''' and R''''' are independently and preferably selected from H, substituted or unsubstituted alkyl, substituted or unsubstituted heteroalkyl, substituted or unsubstituted aryl and substituted or unsubstituted heteroaryl. When the compound of the present invention includes more than one R group, for example, each of the R group is independently selected, as each of R', R'', R''', R'''' and R''''' group is when more than one of them are included.

Unless otherwise specified, two substituents attached to adjacent atoms in an aryl or a heteroaryl ring can optionally be substituted by a substituent with a general formula as -T-C(O)—(CRR')q-U—, wherein T and U are independently selected from —NR—, —O—, CRR'— or a single bond, q is an integer from 0 to 3. As an alternative, two substituents attached to adjacent atoms in an aryl or a heteroaryl ring can optionally be substituted by a substituent with a general formula as -A (CH$_2$)r B—, wherein A and B are independently selected from —CRR'—, —O—, —NR—, —S—, —S(O)—, S(O)$_2$—, —S(O)$_2$NR'— or a single bond, r is an integer from 1 to 4. Optionally, a single bond in the new ring thereby formed can be replaced by a double bond. As an alternative, two substituents attached to adjacent atoms in an aryl or a heteroaryl ring can optionally be substituted by a substituent with a general formula as -A (CH$_2$)r B—, wherein s and d is independently selected from an integer from 0 to 3, X is —O—, —NR', —S—, —S(O)—, —S(O)$_2$— or —S(O)$_2$NR'—. The substituent R, R', R'' and R''' are respectively and preferably selected from hydrogen and substituted or unsubstituted ($C_1$-$C_6$) alkyl.

Unless otherwise specified, the term "halogenated" or "halogen" itself or as a part of another substituent refers to fluorine, chlorine, bromine or iodine atom. In addition, the term "halogenated alkyl" is intended to include monohalogenated alkyl and polyhalogenated alkyl. For example, the term "halogenated ($C_1$-$C_4$)alkyl" is intended to include but not limited to trifluoromethyl, 2,2,2-trifluoroethyl, 4-chlorobutyl and 3-bromopropyl, etc.

Embodiments of halogenated alkyl include but not limited to trifluoromethyl, trichloromethyl, pentafluoroethyl, and pentachloroethyl. The "alkoxy" represents that the alkyl group with a specific number of carbon atoms is connected through an oxygen bridge. The $C_{1-6}$ alkoxy includes $C_1$, $C_2$, $C_3$, $C_4$, $C_5$ and $C_6$ alkoxy. Embodiments of alkoxy include but not limited to methoxy, ethoxy, n-propoxy, iso-propoxy, n-butoxy, sec-butoxy, tert-butoxy, n-pentyloxy and S-pentyloxy. The "cycloalkyl" includes saturated cyclic group, such as cyclopropyl, cyclobutyl or cyclopentyl. The 3- to 7-membered cycloalkyl includes $C_3$, $C_4$, $C_5$, $C_6$ and $C_7$ cycloalkyl. The "alkenyl" includes linear or branched hydrocarbon chain, wherein any stable sites on the chain exists one or more than one C—C double bonds, such as vinyl and propenyl.

The term "halo" or "halogen" refers to fluorine, chlorine, bromine and iodine.

Unless otherwise specified, the term "hetero" refers to a heteroatom or a heteroatomic group (i.e. a group containing a heteroatom), including atoms except for carbon (C) and hydrogen (H) and groups containing these heteroatoms, such as including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and optionally substituted —C(=O)N(H)—, —N(H)—, —C(=NH)—, —S(=O)$_2$N(H)— or —S(=O)N(H)—.

Unless otherwise specified, the "ring" refers to substituted or unsubstituted cycloalkyl, heterocycloalkyl, cycloalkenyl, heterocycloalkenyl, cycloalkynyl, heterocycloalkynyl, aryl or heteroaryl. The ring includes a single ring, a joint ring, a spiro ring, a fused ring or a bridged ring. A number of the atoms in the ring is usually defined as the member of the ring, for example, "5- to 7-membered ring" is a ring looped with 5 to 7 atoms. Unless otherwise specified, the ring optionally contains 1~3 of heteroatoms. Therefore, "5- to 7-membered ring" includes, for example, phenyl pyridine and piperidinyl; on the other hand, the term "5- to 7-membered heterocycloalkyl ring" includes pyridyl and piperidinyl, but does not include phenyl. The term "ring" also includes a ring system containing at least one ring, wherein each ring is of the above definition independently.

Unless otherwise specified, the term "heterocycle" or "heterocyclyl" refers to a stable monocyclic, bicyclic or tricyclic ring containing a heteroatom and a heteroatomic group, they can be saturated, partially unsaturated or unsaturated (aromatic), they contain carbon atoms and 1, 2, 3 or 4 of heteroatom which is independently selected from the group consisting of N, O and S, wherein any of the heterocycle can be fused to a benzene ring to form a bicyclic ring. Nitrogen and sulfur atoms can be optionally oxidized (i.e., NO and S(O)$_p$). The nitrogen atom can be substituted or unsubstituted (i.e. N or NR, wherein R is H or other substituent that has been defined herein). The heterocycle can be attached to the side group of any heteroatom or carbon atom to form a stable structure. If the formed compound is stable, the heterocycle described herein can be substituted on its carbon or nitrogen atom. The nitrogen atom in the heterocycle is optionally quaternized. As a preferred embodiment of the present invention, when the total number of S and O atoms contained in the heterocycle exceeds 1, these heteroatoms are not adjacent to each other. As another preferred embodiment of the present invention, the total number of S and O atoms in the heterocycle is no more than 1. As used herein, the term "aromatic heterocyclic group" or "heteroaryl" refers to a stable 5-, 6-, 7-membered monocycle or bicycle or 7-, 8-, 9- or 10-membered bicyclic heteroaromatic ring, which contains carbon atoms and 1, 2, 3 or 4 of heteroatom which independently selected from the group consisting of N, O and S. The nitrogen atom can be substituted or unsubstituted (i.e. N or NR, wherein R is H or other substituent that has been defined herein). Nitrogen and sulfur atoms can be optionally oxidized (i.e., NO and S(O)$_p$). It is worth noting that the total number of S and O atoms in the heteroaromatic ring is no more than 1. Bridged rings are also included in the definition of the heterocycle. When one or more atoms (i.e. C, O, N, or S) are connected to two nonadjacent carbon atoms or nitrogen atoms, a bridged ring is formed. The preferred bridged ring includes but not limited to one carbon atom, two carbon atoms, one nitrogen atom, two nitrogen atoms and one carbon-nitrogen group. It is worth noting that a bridge always converts a monocyclic ring into a tricyclic ring. In the bridged ring, the substituent in the ring can also locate on the bridge.

Embodiments of heterocyclic compound include but not limited to acridinyl, azocinyl, benzimidazolyl, benzofuranyl, benzomercaptofuranyl, benzomercaptophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnolinyl decahydroquinolyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indazolyl, indoalkenyl, indolinyl, indolizinyl, indolyl, 3H-indolyl, isatino group, isobenzofuranyl, pyranyl, isoindolyl, isoindolinyl, isoindolyl, indolyl, isoquinolyl, isothiazolyl, isoxazolyl, methylenedioxyphenyl, morpholinyl, naphthyridinyl, octahydroisoquinolyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, isoxazolyl, hydroxyl indyl, pyrimidyl, phenanthridinyl, phenanthrolinyl, phenazine, phenothiazine, benzopurinyl, phenoxazinyl, phthalazinyl, piperazinyl, piperidyl, oxopiperidinyl, 4-oxopiperidinyl, piperonyl, pteridyl, purinyl, pyranyl, pyrazinyl, pyrazolidinyl, pyrazolinyl, pyrazolyl, pyridazinyl, oxazolopyridine, pyridinoimidazole, pyridinothiazole, pyridyl, pyrimidinyl, pyrrolidinyl, pyrrolinyl, 2H-pyrrolyl, pyrrolyl, pyrazolyl, quinazolinyl, quinolyl, 4H-quinolizinyl, quinoxalinyl, quinuclidinyl, tetrahydrofuryl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazyl, isothiazolylthienyl, thienyl, thiophenoxazolyl, thiophenothiazolyl, thiophenoimidazolyl, thienyl, triazinyl, 1,2,3-triazolyl, 1,2,4-triazolyl, 1,2,5-triazolyl, 1,3,4-triazolyl and xanthenyl. Fused ring and spiro ring compound are also included.

Unless otherwise specified, the term "hydrocarbonyl" or its specific concept (such as alkyl, alkenyl, alkynyl, phenyl, etc.) itself or as a part of another substituent represents a linear, branched or cyclic hydrocarbonyl or a combination thereof, which can be fully saturated, monocyclic or polycyclic unsaturated, can be monosubstituted, disubstituted or polysubstituted, can be univalent (such as methyl), bivalent (such as methylene) or multivalent (such as methenyl), can include bivalent or multivalent atomic groups, with a specified number of carbon atoms (such as that $C_1$-$C_{10}$ refers to having 1~10 carbon atoms). The term "alkyl" includes but not limited to an aliphatic hydrocarbonyl and aromatic hydrocarbonyl, the aliphatic hydrocarbonyl includes linear and cyclic structures, specifically includes but not limited to alkyl, alkenyl and alkynyl, the aromatic hydrocarbonyl includes but not limited to 6- to 12-membered aromatic hydrocarbonyl such as benzene, naphthalene and the like. In some embodiments, the term "hydrocarbonyl" refers to linear or branched groups or their combination, which can be completely saturated, monocyclic or polycyclic unsaturated, can include divalent and polyvalent groups. Embodiments of saturated hydrocarbonyl include but not limited to homologues or isomers of methyl, ethyl, n-propyl, iso-propyl, n-butyl, tert-butyl, iso-butyl, sec-butyl, iso-butyl, cyclohexyl, (cyclohexyl)methyl, cyclopropyl methyl, and n-amyl, n-hexyl, n-heptyl, n-octyl and the like. Unsaturated alkyl has one or more than one double or triple bond, embodiments of which includes but not limited to vinyl, 2-propenyl, butenyl, crotyl, 2-isopentenyl, 2-butadienyl, 2,4-(pentadienyl), 3-(1,4-pentadienyl), acetenyl, 1- and 3-propinyl, 3-butynyl, and more advanced homologues and isomers.

Unless otherwise specified, the term "heterohydrocarbonyl" or its specific concepts (such as heteroalkyl, heteroalkenyl, heteroalkynyl, heteroaryl, etc.) itself or the term combining with another term refers to a stable linear, branched or cyclic hydrocarbonyl or their combinations, which consists of a certain number of carbon atoms and at least one heteroatom. In some embodiments, the term "heterohydrocarbonyl" itself or the term combining with another term refers to a stable linear, branched hydrocarbonyl or their combinations, which consists of a certain number of carbon atoms and at least one heteroatom. In a typical embodiment, the heteroatom is selected from the group consisting of B, O, N and S, in which the nitrogen and sulfur atoms are optionally oxidized, and the nitrogen atom is optionally quaternized. The heteroatom or the hetero-atomic group can be located in any internal position of the heterohydrocarbonyl (including the position where the hydrocarbonyl is attached to the rest part of the molecule). Embodiments include but not limited to —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —CH$_2$—CH=N—OCH$_3$ and —CH=CH—N(CH$_3$)—CH$_3$. At most two heteroatoms are adjacent, such as —CH$_2$—NH—OCH$_3$.

Unless otherwise specified, the terms "alkoxy", "alkylamino" and "alkylthio" (or thioalkoxy) are the idiomatic expressions, which refers to the alkyl group attached to the rest moiety of the molecule through an oxygen, an amino, or a sulfur atom, respectively.

Unless otherwise specified, the term "cyclohydrocarbonyl", "heterocyclohydrocarbonyl" or its specific concepts (such as aryl, heteroaryl, cycloalkyl, heterocycloalkyl, cycloalkenyl, heterocyclovinyl, cycloalkynyl, heterocycloalkynyl, etc.) itself or the term combining with other terms respectively refers to a cyclic "hydrocarbonyl", "heterohydrocarbonyl". In addition, in terms of heterohydrocarbonyl or heterocyclohydrocarbonyl (such as heteroalkyl, heterocycloalkyl), heteroatoms can occupy the position where the heterocyclic ring is attached to the rest part of the molecule. Embodiments of the cycloalkyl include but not limited to cyclopentyl, cyclohexyl, 1-cyclohexenyl, 3-cyclohexenyl, cycloheptyl etc. Unrestricted embodiments of the heterocyclyl include 1-(1,2,5,6-tetrahydropyridinyl), 1-piperidyl, 2-piperidyl, 3-piperidyl, 4-morpholinyl, 3-morpholinyl, tetrahydrofuran-2-yl, tetrahydrofuranylindol-3-yl, tetrahydrothiophene-2-yl, tetrahydrothiophene-3-yl, 1-piperazinyl and 2-piperazinyl.

Unless otherwise specified, the term "aryl" refers to a polyunsaturated aromatic hydrocarbon substituent, which can be monosubstituted, disubstituted or multisubstituted, can be univalent, bivalent or multivalent. It can be monocyclic or polycyclic (such as 1 to 3 rings, at least one of which is aromatic). They fuse together or connect by a covalent linkage. The term "heteroaryl" refers to an aryl (or ring) containing 1 to 4 heteroatoms. In an exemplary embodiment, the heteroatom is selected from the group consisting of B, N, O, and S, in which the nitrogen and sulfur atoms are optionally oxidized, and the nitrogen atom is optionally quaternized. The heteroaryl group can be connected to the rest part of the molecule via a heteroatom. Unrestricted embodiments of an aryl or a heteroaryl include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-benzothiazolyl, purinyl, 2-benzoimidazolyl, 5-indolyl, 1-isoquinolyl, 5-isoquinolyl, 2-quinoxalyl, 5-quinoxalyl, 3-quinolyl and 6-quinolyl. Unless otherwise specified, when used in combination with other terms (e.g. aryloxy, arylthio, aralkyl), the aryl includes the definition of aryl and heteroaryl ring defined above. Therefore, the term "aralkyl" is intended to include the groups that an aryl is attached to an alkyl (e.g. benzyl, phenyl ethyl, pyridyl methyl etc.), including those alkyls where carbon atoms (such as methylene) has been replaced by such as oxygen atoms, such as phenoxy methyl, 2-pyridyloxymethyl-3-(1-naphthoxy) propyl, etc.

The term "leaving group" refers to a functional group or atom which can be replaced by another functional group or atom through a substitution reaction (e.g., nucleophilic substitution reaction). For example, representative leaving groups include triflate; chlorine, bromine, iodine; sulfonate, such as mesylate, tosylate, p-bromobenzene sulfonate, p-tosylate etc.; acyloxy, such as acetoxy, trifluoroacetoxy and so on.

The term "protecting group" includes but not limited to "protecting group of an amino", "protecting group of a hydroxyl", or "protecting group of a mercapto". The term "protecting group of an amino" refers to a protecting group that is suitable for preventing side reactions occurring at the nitrogen atom of an amino group. A representative protecting group of an amino includes but not limited to formyl; acyl, such as alkanoyl (such as acetyl, trichloroacetyl or trifluoroacetyl); alkoxycarbonyl, such as tert-butoxycarbonyl (Boc); aryl methoxycarbonyl, such as benzyloxycarbonyl (Cbz) and 9-fluorenylmethoxycarbonyl (Fmoc); aryl methyl, such as benzyl (Bn), triphenyl methyl (Tr), 1,1-bis-(4'-methoxyphenyl)methyl; silyl, such as trimethylsilyl (TMS) and tert-butyldimethylsilyl (TBS) and etc. The term "protecting group of a hydroxyl" refers to a protecting group that is suitable for preventing side reactions of a hydroxyl group. A representative protecting group of a hydroxyl includes but not limited to alkyl, such as methyl, ethyl and tert-butyl; acyl, such as alkanoyl (such as acetyl); aryl methyl, such as benzyl (Bn), p-methoxybenzyl (PMB), 9-fluorenylmethyl (Fm) and diphenylmethyl (diphenylmethyl, DPM); silyl, such as trimethylsilyl (TMS) and tert-butyldimethylsilyl (TBS) and etc.

The compound of the present invention can be prepared through many synthetic methods which are well-known to the person skilled in the art, including the specific embodiments listed below and its combination with other chemical synthetic methods and the equivalent alternative methods which are known to the person skilled in the art, the preferred embodiments include but not limited to the embodiments of the present invention.

The solvents used in the present invention are commercially available. The present invention adopts the following abbreviations: aq. is water; DCM is dichloromethane; PE is petroleum ether; DMF is N,N-dimethylformamide, DMA is N, N-dimethylacetamide; MeCN is acetonitrile; NMP is N-methyl-2-pyrrolidone; DME is 1,2-dimethoxyethane; TsOH is p-toluenesulfonic acid; DMSO is dimethyl sulfoxide; EtOH is ethanol; MeOH is methanol; HOAc is acetic acid; NaCNBH$_3$ is sodium cyanoborohydride; THF is tetrahydrofuran; Boc2O is di-tert-butyl dicarbonate; TFA is trifluoroacetic acid; DIEA is diisopropylethylamine; Pd(dppf)Cl$_2$ is [1,1'-bis (diphenylphosphino)ferrocene] dichloropalladium (II); NaH is sodium hydride; LAH is lithium aluminum hydride; Pd(OAc)$_2$ is palladium (II) acetate; Pd$_2$(dba)$_3$ is tris(dibenzylideneacetone)dipalladium (0); Xantphos is 4,5-bis(diphenylphosphino)-9,9-dimethylxanthene; MeSO$_3$H is methanesulfonic acid; t-BuOK is potassium tert-butoxide; MsCl is methanesulfonyl chloride; HATU is O-(7-azabenzotriazol-1-yl)-N,N,N',N'-tetramethyluronium hexafluorophosphate; Cs$_2$CO$_3$ is cesium carbonate; K$_2$CO$_3$ is potassium carbonate; NaHCO$_3$ is sodium bicarbonate; Na$_2$SO$_4$ is sodium sulfate; KOAc is potassium acetate; t-BuOH is t-butanol; TFAA is trifluoroacetic anhydride; FA is formic acid; DBU is 1,8-diazabicyclo[5.4.0]undec-7-ene; m-CPBA is 3-chloroperoxybenzoic acid; DAST is diethylaminosulfur trifluoride.

Compounds are named by manual work or software ChemDraw®, the commercially available compounds are named in accordance with suppliers' catalogue.

EMBODIMENTS

In some embodiments, the compound having a structure of formula (I) could be prepared according to the synthetic method described in Scheme A. Where W is selected from the following structures

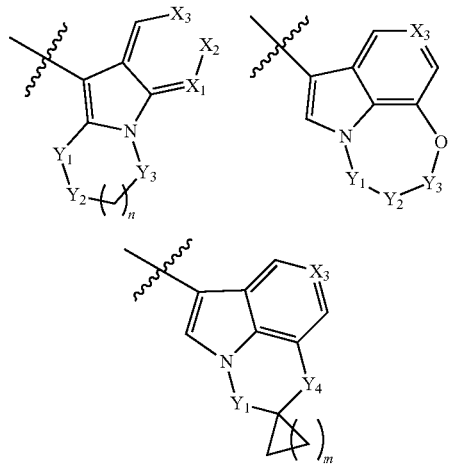

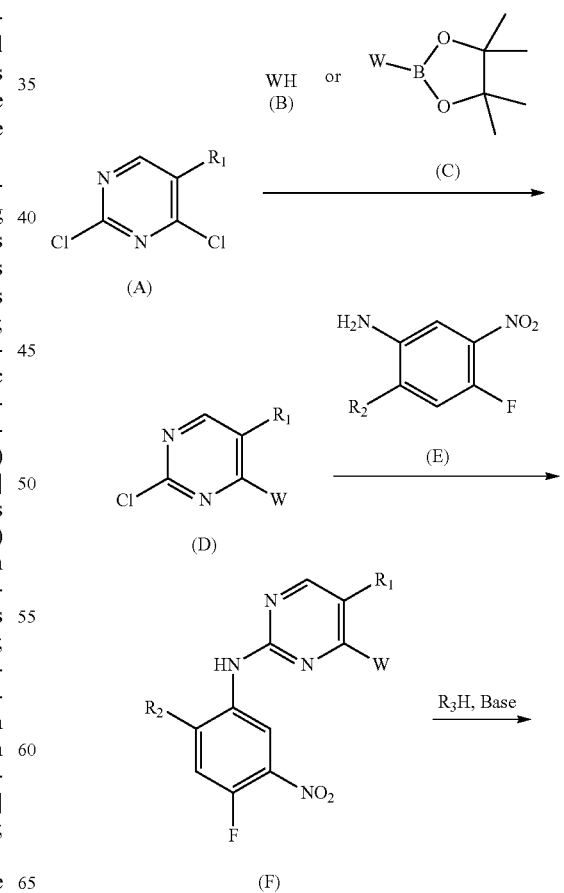

Scheme A

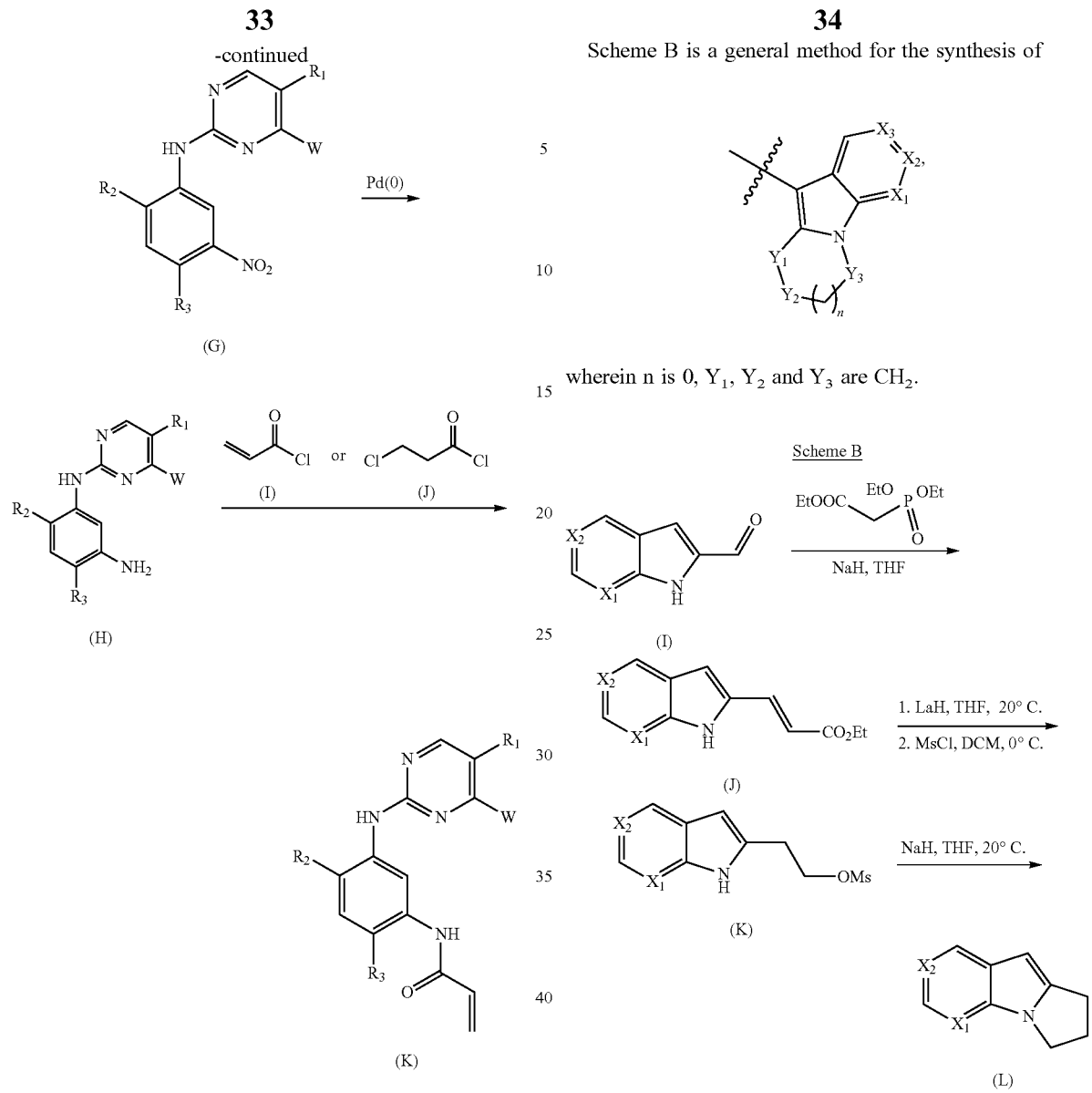

In the above scheme A, a reaction similar to the Friedel-Crafts reaction is carried out by a dichloropyrimidine derivative (A) with an electron rich tricyclic or bicyclic compound (B) in the presence of a Lewis acid such as $FeCl_3$ or $AlCl_3$, or a Suzuki coupling reaction is carried out with a borate (C) to deliver a compound (D). The compound (D) and arylamine (E) undergo the SNAr substitution in the presence of an acid such as TsOH or TfOH, or a coupling reaction is carried out under a catalysis of palladium, in the presence of a base such as anhydrous potassium phosphate, a ligand such as XPhos to deliver (F), and the yield is medium to excellent. (F) and a variety of nucleophilic reagents such as N1,N1-dimethylethane-1,2-diamine in the presence of a base such as DIEA can deliver a compound (G), which can be reduced by a reducing agent such as Pd/C, $NH_4Cl/Fe$ to deliver an amine (H). The amine (H) can be acylated directly with acryloyl chloride (I) in the presence of a base such as DIEA at low temperature such as −40 to 0° C. to deliver a compound of formula (K). The compound of formula (K) can also be delivered by acylating the amine (H) with 3-chloropropionyl chloride (J) in a single step, followed by carrying out an eliminate reaction in the presence of a base such as NaOH.

Scheme B is a general method for the synthesis of wherein n is 0, $Y_1$, $Y_2$ and $Y_3$ are $CH_2$.

An aldehyde (L) reacts with a phosphate ester to deliver (M) through a wittig reaction, (M) is then reduced by a reducing agent such as LAH, followed by being esterified with MsCl to deliver (N). (N) can be cyclized in the presence of a base such as NaH to deliver (O), which can react with the dichloropyrimidine derivative (A) according to scheme A to deliver (D).

Scheme C is a general method for the synthesis of

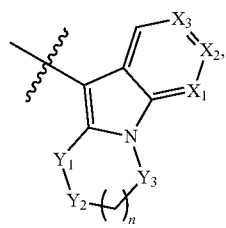

wherein n is 1, $Y_1$ and $Y_3$ are $CH_2$, $Y_2$ is O.

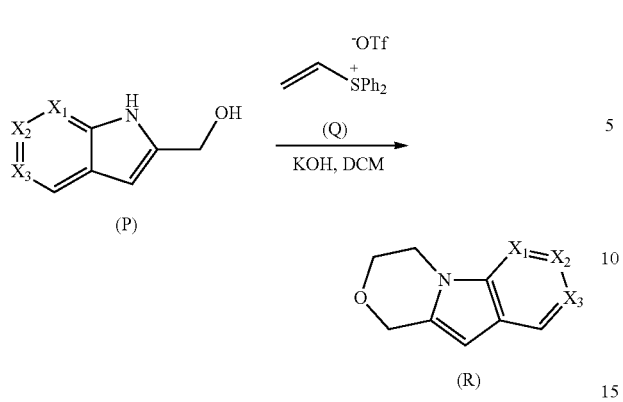

A substituted 2-hydroxymethylindole (P) reacts with diphenylvinylsulfonium salt (Q) in the presence of a base such as potassium hydroxide, and a solvent such as dichloromethane to deliver (R) through an addition reaction and an intramolecular cyclization reaction, (R) can react with the dichloropyrimidine derivative (A) according to scheme A to deliver (D).

Scheme D is a general method for the synthesis of

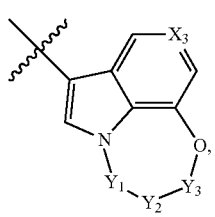

wherein $Y_1$, $Y_2$ and $Y_3$ are $CH_2$.

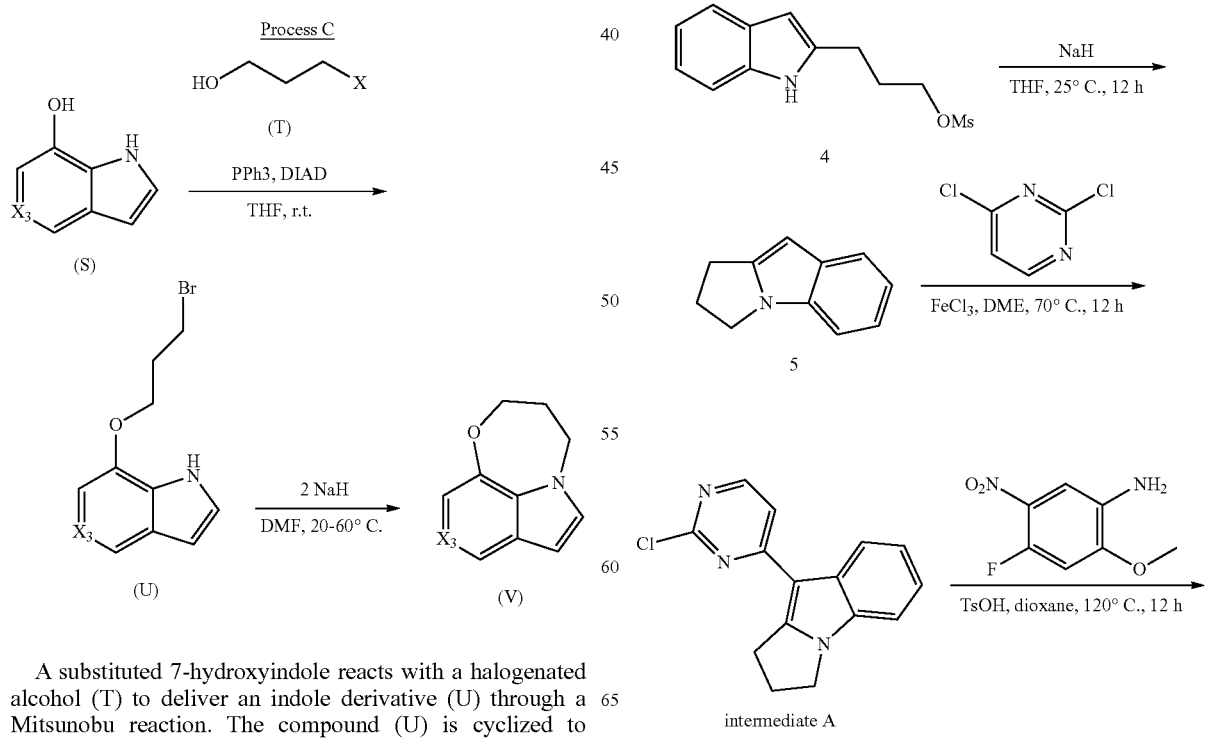

A substituted 7-hydroxyindole reacts with a halogenated alcohol (T) to deliver an indole derivative (U) through a Mitsunobu reaction. The compound (U) is cyclized to deliver a compound (V) in the presence of a base such as sodium hydride, compound (V) can react with the dichloropyrimidine derivative (A) according to scheme A to deliver (D).

The following illustrative embodiments have been prepared, separated and characterized by the methods disclosed herein. The following embodiments are delivered to illustrate the present invention in detail, but the scope of the present invention is not limited thereto.

Process 1

General preparation method of intermediates A and B intermediate A

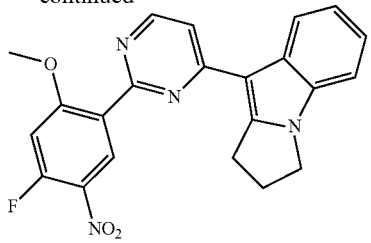

intermediate B

Embodiment A1

4-Fluoro-2-methoxyaniline

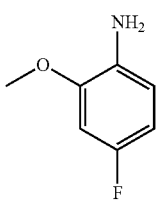

2-Methoxy-4-fluoronitrobenzene (100.00 g, 584.35 mmol) was dissolved in methanol (400 mL), Pd/C (10%, 10 g) was added after sweeping with nitrogen. The mixture was heated to 40° C. under $H_2$ (50 Psi) and stirred for 12 hours. TLC showed the reaction was complete, the reaction mixture was filtered and the filtrate was concentrated to dryness to deliver the title compound (red oil, 83.00 g, yield 93.28%). LCMS (ESI) (10-80CD): m/z: 142.1 [M+1].

Embodiment A2

4-Fluoro-2-methoxy-5-nitroaniline

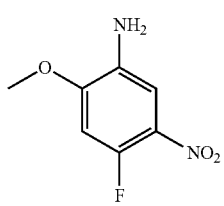

Embodiment A1 (83.00 g, 558.67 mmol) was slowly added dropwise to concentrated $H_2SO_4$ (415 mL) at 0° C. and then $KNO_3$ (56.48 g, 558.67 mmol) was added in batches. The mixture was stirred at 0 to 10° C. for 3 hours. TLC showed the reaction was complete, $NH_3.H_2O$ was added until the pH of the reaction mixture was 8, and the temperature was controlled below 10° C. The resulting mixture was filtered and the filter cake was washed with water (500 mL) and dissolved in DCM (1 L). The solution was dried over anhydrous sodium sulfate, concentrated and purified by column chromatography (PE:DCM=5:1, 1:10) to deliver the title compound (yellow solid, 60.00 g, yield 54.81%). $^1$H NMR (400 MHz, CDCl$_3$): δ 7.40 (d, J=7.2 Hz, 1H), 6.64 (d, J=12.4 Hz, 1H), 3.86-3.97 (m, 5H).

Embodiment A3

(E) Ethyl 3-(1H-indol-2-yl)acrylate

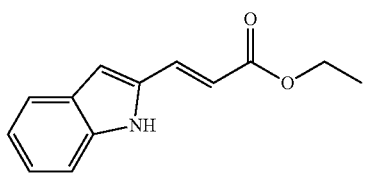 [SMILES: CCOC(=O)/C=C/c1cc2ccccc2[nH]1]

2-Diethyl phosphate-ethyl acetate (18.53 g, 82.67 mmol) was dissolved in THF (100 mL) at 0° C. and NaH (4.13 g, 60% w, 103.33 mmol) was added to the mixture and stirred for 1 hour. A solution of 1H-indole-2-carbaldehyde (10 g, 69.89 mmol) in THF (80 mL) was added dropwise and the reaction mixture was warmed to 20° C. and stirred for 10 hours. TLC showed the reaction was complete, saturated NH$_4$Cl solution (100 mL) was added to the reaction mixture, THF was removed by concentration, the mixture was extracted with EA (100 mL×3) and washed with saturated brine (100 mL×2), then dried over anhydrous sodium sulfate and concentrated to deliver the title compound (yellow solid, 12.20 g, yield 74.05%). $^1$H NMR (400 MHz, CDCl$_3$): δ, 8.60 (br. s., 1H), 7.71 (d, J=16.0 Hz, 1H), 7.64 (d, J=8.0 Hz, 1H), 7.39 (d, J=8.4 Hz, 1H), 7.30-7.26 (m, 1H), 7.15-7.14 (m, 1H), 6.84 (s, 1H), 6.28 (d, J=16.0 Hz, 1H), 4.33-4.28 (m, 2H), 1.39-1.35 (m, 3H).

Embodiment A4

3-(1H-Indol-2-yl)propan-1-ol

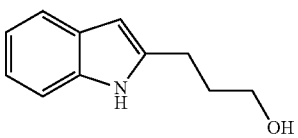 [SMILES: OCCCc1cc2ccccc2[nH]1]

LiAlH$_4$ (4.58 g, 120.79 mmol) was suspended in THF (100 mL) at 0° C. and a solution of embodiment A3 (13.00 g, 60.69 mmol) in THF (50 mL) was added to the mixture and stirred for 8 hours. TLC showed the reaction was complete, water (4.5 mL), 15% NaOH (4.5 mL) and water (13.5 mL) were added sequentially to the reaction mixture and stirred for 30 minutes, dried over anhydrous magnesium sulfate. The mixture was filtered and the filtrate was concentrated and purified by column chromatography (PE: EA=6:1, 1:1) to deliver the title compound (yellow oil, 9.00 g, yield 76.54%). $^1$H NMR (400 MHz, CDCl$_3$): δ 8.25 (s, 1H), 7.56 (d, J=7.6 Hz, 1H), 7.34-7.27 (m, 1H), 7.18-7.08 (m, 2H), 6.27 (s, 1H), 3.83-3.71 (m, 2H), 2.94-2.81 (m, 2H), 2.04-1.91 (m, 2H).

Embodiment A5

3-(1H-Indol-2-yl)propyl methanesulfonate

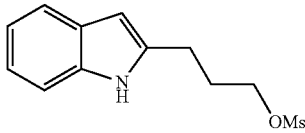 [SMILES: CS(=O)(=O)OCCCc1cc2ccccc2[nH]1]

Embodiment A4 (9.23 g, 42.12 mmol) and TEA (8.52 g, 84.24 mmol) were dissolved in DCM (100 mL) at 0° C. and methanesulfonyl chloride (7.24 g, 63.18 mmol) was added to the mixture and stirred for 10 hours. TLC showed the reaction was complete, water (30 mL) was added to the mixture, the mixture was extracted with DCM (30 mL×3), the organic layer was dried over anhydrous sodium sulfate, concentrated, and purified by column chromatography (PE:EA=20:1, 3:1) to deliver the title compound (brown solid, 4.50 g, yield 37.96%). $^1$H NMR (400 MHz, CDCl$_3$): δ 8.25 (s, 1H), 7.56 (d, J=7.6 Hz, 1H), 7.34-7.27 (m, 1H), 7.18-7.08 (m, 2H), 6.28 (s, 1H), 4.32-4.29 (m, 2H), 3.02 (s, 3H), 2.94-2.90 (m, 2H), 2.20-2.13 (m, 2H).

Embodiment A6

2,3-Dihydro-1H-pyrrolo[1,2-a]indole

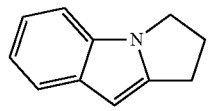 [SMILES: c1ccc2c(c1)cc1n2CCC1]

Embodiment A5 (4.50 g, 17.76 mmol) was dissolved in THF (150 mL) at 25° C. and NaH (852.48 mg, 60% w, 35.52 mmol) was added to the mixture and stirred for 12 hours. TLC showed the reaction was complete, saturated NH$_4$Cl solution was added to the mixture to neutral, concentrated to remove the THF, extracted with EA (30 mL×3). The organic layer was dried over anhydrous sodium sulfate, concentrated, and purified by column chromatography (PE: EA=200:1, 100:1) to deliver the title compound (yellow solid, 2.80 g, 95.27% yield). $^1$H NMR (400 MHz, CDCl$_3$): δ 7.57 (d, J=8.8 Hz, 1H), 7.28-7.24 (m, 1H), 7.14-7.11 (m, 1H), 7.10-7.04 (m, 1H), 6.19 (br. s., 1H), 4.12-4.06 (m, 2H), 3.09-3.00 (m, 2H), 2.69-2.59 (m, 2H).

Embodiment A 9-(2-Chloropyrimidin-4-yl)-2,3-dihydro-1H-pyrrolo[1,2-α]indole

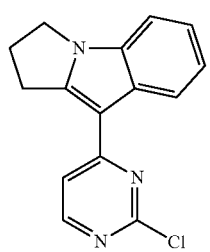 [SMILES: Clc1nccc(-c2c3n(c4ccccc24)CCC3)n1]

Embodiment A6 (3.50 g, 22.26 mmol) and 2,4-dichloropyrimidine (6.63 g, 44.53 mmol) were dissolved in DME (40 mL), FeCl$_3$ (3.61 g, 22.26 mmol) was added to the mixture, and the reaction mixture was warmed to 70° C. and stirred for 12 hours. TLC showed there were 60% of the title compound and 40% of embodiment 1F in the reaction solution. The mixture was filtered, concentrated, water (20 mL) was added thereto, the mixture was extracted with EA (20 mL×3), the organic layer was dried over anhydrous sodium sulfate, concentrated and purified by column chromatography (PE:EA=200:1, 100:1) to deliver the title compound (white solid, 3.00 g, yield 47.47%). $^1$H NMR (400 MHz, CDCl$_3$): δ 8.41 (d, J=5.2 Hz, 1H), 8.36-8.31 (m, 1H), 7.38 (d, J=5.6 Hz, 1H), 7.33-7.27 (m, 3H), 4.20-4.15 (m, 2H), 3.44-3.37 (m, 2H), 2.79-2.73 (m, 2H). LCMS (ESI) (5-95AB): m/z: 269.9 [M+1].

Embodiment B 4-(2,3-Dihydro-1H-pyrrolo[1,2-a]indole-9-yl)-N-(4-fluoro-2-methoxy-5-nitrophenyl)pyrimidin-2-amine

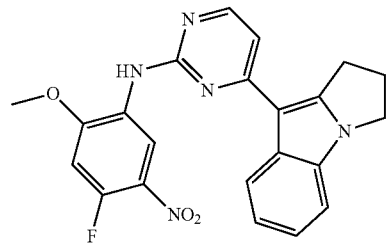 [SMILES: COc1cc(F)c([N+](=O)[O-])cc1Nc1nccc(-c2c3n(c4ccccc24)CCC3)n1]

Embodiment A (2.40 g, 8.90 mmol) and 2-methoxy-4-fluoro-5-nitroaniline (1.66 g, 8.90 mmol) were dissolved in 1,4-dioxane (40 mL), TsOH (1.53 g, 8.90 mmol) was added to the mixture and the reaction mixture was warmed to 120° C., stirred for 10 hours. LCMS showed the reaction was complete, saturated NaHCO$_3$ solution (30 mL) was added to the mixture, the 1,4-dioxane was removed by concentration and then water (50 mL) was added, the mixture was extracted with DCM (50 mL×3) and the organic layer was dried over anhydrous sodium sulfate, and concentrated to obtain a crude product. The product was washed with PE/EA (5:1, 20 mL×2) to deliver the title compound (yellow solid, 3.30 g, yield 83.99%). $^1$H NMR (400 MHz, CDCl$_3$): δ 9.46 (d, J=8.0 Hz, 1H), 8.41 (d, J=5.2 Hz, 1H), 8.33-8.23 (m, 1H), 7.58 (s, 1H), 7.35-7.30 (m, 1H), 7.28-7.24 (m, 2H), 7.15 (d, J=5.2 Hz, 1H), 6.78 (d, J=12.4 Hz, 1H), 4.22-4.16 (m, 2H), 4.06 (s, 3H), 3.47 (t, J=7.2 Hz, 2H), 2.78-2.73 (m, 2H). LCMS (ESI) (5-95AB): m/z: 420.0 [M+1].

Process 2

The general preparation method of Embodiment 1

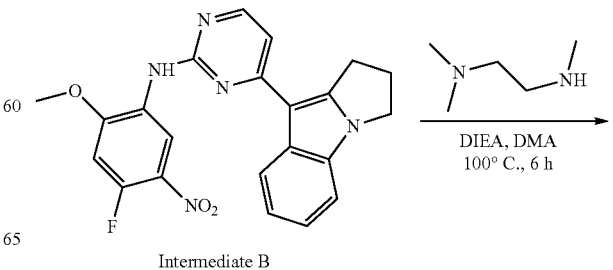

Intermediate B

-continued

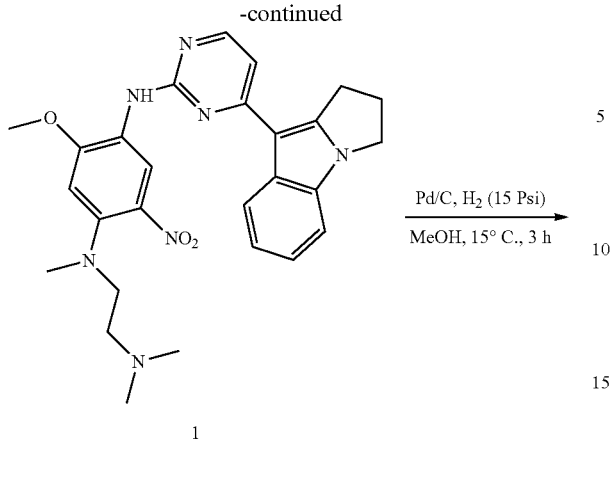

1

Pd/C, H₂ (15 Psi)
MeOH, 15° C., 3 h
→

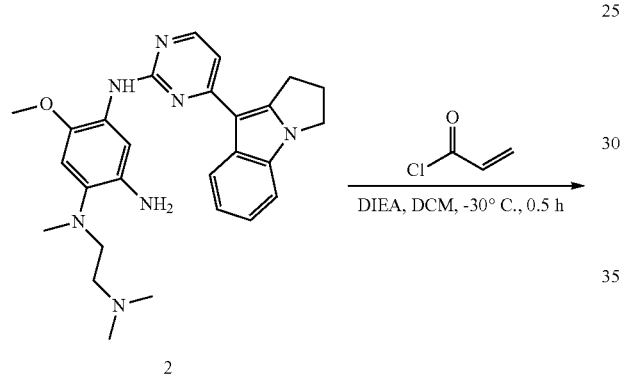

2

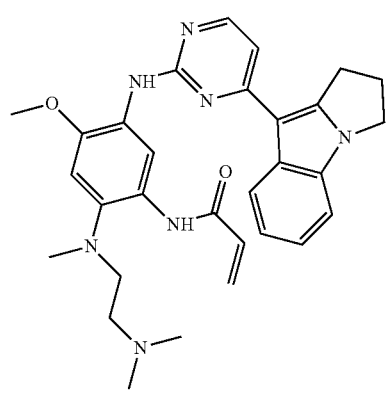

Embodiment 1

Embodiment 1

N-(5-((4-(2,3-Dihydro-1H-pyrrolo[1,2-a]indol-9-yl)pyrimidin-2-yl)amino)-2-((2-(dimethylamino)ethyl)amino)-4-methoxyphenyl)acrylamide

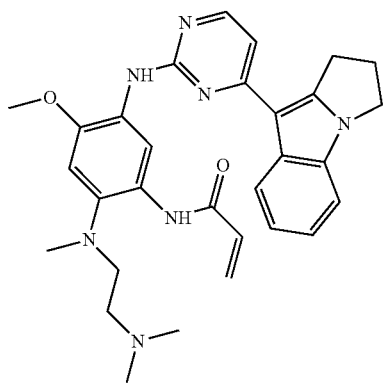 [SMILES: C=CC(=O)Nc1cc(Nc2nccc(-c3c4n(c5ccccc35)CCC4)n2)c(OC)cc1N(C)CCN(C)C]

Embodiment 1A

N1-(4-(2,3-Dihydro-1H-pyrrolo[1,2-a]indol-9-yl)pyrimidin-2-yl)-N4-(2-(dimethylamino)ethyl)-2-methoxy-N4-methyl-5-nitrobenzene-1,4-diamine

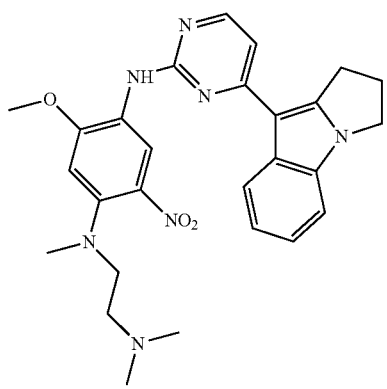

Embodiment B (2.80 g, 6.68 mmol) and N,N',N'-trimethyl-1,2-ethylenediamine (1.02 g, 10.01 mmol) were dissolved in DMA (50 mL), DIEA (1.29 g, 10.01 mmol) was added to the mixture and the reaction mixture was warmed to 90° C. and stirred for 2 hours. LCMS showed the reaction was complete, the mixture was concentrated to remove DMA, water (30 mL) was added and the mixture was extracted with DCM (50 mL×3). The organic layer was dried over anhydrous sodium sulfate and concentrated to give the crude product. The product was washed with PE/EA (5:1, 20 mL×2) to deliver the title compound (red solid, 3.20 g, 90.73% yield). $^1$H NMR (400 MHz, CDCl₃): δ 9.03 (s, 1H), 8.35-8.24 (m, 2H), 7.36 (d, J=7.2 Hz, 1H), 7.24-7.12 (m, 3H), 7.09 (s, 1H), 4.21-4.14 (m, 2H), 4.10 (s, 3H), 3.53-3.48 (m, 2H), 3.43-3.37 (m, 4H), 2.99 (s, 6H), 2.88 (s, 3H), 2.76-2.69 (m, 2H). LCMS (ESI) (0-60AB): m/z: 502.2 [M+1].

Embodiment 1B

N4-(4-(2,3-Dihydro-1H-pyrrolo[1,2-a]indol-9-yl)pyrimidin-2-yl)-N1-(2-(dimethylamino)ethyl)-5-methoxy-N1-methylbenzene-1,2,4-triamine

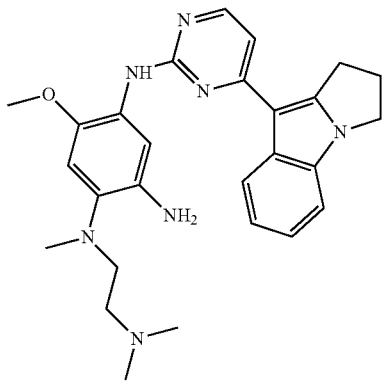 [SMILES: COc1cc(N(C)CCN(C)C)c([N+](=O)[O-])cc1Nc1nccc(-c2c3n(c4ccccc24)CCC3)n1]

Embodiment 1A (3.20 g, 6.38 mmol) was dissolved in MeOH (100 mL) at 25° C. and Pd/C (10%, 500 mg) was added after sweeping with nitrogen. The mixture was stirred under H$_2$ (15 psi) for 2 hours. LCMS showed the reaction was complete, the reaction mixture was filtered and the filtrate was concentrated to dryness to deliver the title compound (gray solid, 2.42 g, yield 76.41%). $^1$H NMR (400 MHz, CDCl$_3$): δ 8.53-8.48 (m, 1H), 8.33 (d, J=5.2 Hz, 1H), 8.16 (s, 1H), 7.56 (s, 1H), 7.33-7.29 (m, 1H), 7.28-7.23 (m, 2H), 6.95 (d, J=5.2 Hz, 1H), 6.70 (s, 1H), 4.17 (t, J=7.2 Hz, 2H), 3.87 (s, 3H), 3.39 (t, J=7.6 Hz, 2H), 3.22 (t, J=6.4 Hz, 2H), 2.83 (t, J=6.0 Hz, 2H), 2.78-2.71 (m, 5H), 2.63 (s, 6H). LCMS (ESI) (0-60AB): m/z: 472.2 [M+1].

Embodiment 1C

N-(5-((4-(2,3-Dihydro-1H-pyrrolo[1,2-a]indol-9-yl)pyrimidin-2-yl)amino)-2-((2-(dimethylamino)ethyl)amino)-4-methoxyphenyl)acrylamide

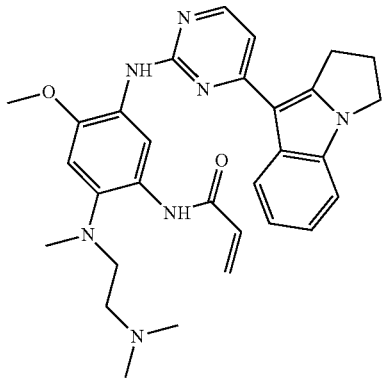 [SMILES: C=CC(=O)Nc1cc(Nc2nccc(-c3c4n(c5ccccc35)CCC4)n2)c(OC)cc1N(C)CCN(C)C]

Embodiment 1B (2.40 g, 5.09 mmol) and DIEA (789.40 mg, 6.11 mmol) were dissolved in DCM (150 mL) at −40° C. and acetyl chloride (460.00 mg, 5.09 mmol) was added to the mixture and stirred for 1 hour. LCMS showed the product was produced, water (100 mL) was added to the reaction mixture, the mixture was extracted with DCM (50 mL×3), the organic phase was separated, dried over anhydrous sodium sulfate and concentrated to give the crude product. The crude product was separated by preparative HPLC to deliver the title compound (Hydrochloride, 859.00 mg, yield 29.87%). $^1$H NMR (400 MHz, CD$_3$OD): δ 8.30 (br. s., 1H), 8.01 (d, J=7.2 Hz, 1H), 7.88 (br. s., 1H), 7.43-7.39 (m, 1H), 7.31-7.17 (m, 3H), 7.10 (s, 1H), 6.75-6.70 (m, 1H), 6.47 (dd, J$_1$=1.6 Hz, J$_2$=16.8 Hz, 1H), 5.89-5.84 (m, 1H), 4.22 (t, J=7.2 Hz, 2H), 3.98 (s, 3H), 3.65-3.54 (m, 2H), 3.41-3.39 (m, 4H), 2.93 (s, 6H), 2.83 (s, 3H), 2.75 (t, J=7.2 Hz, 2H). LCMS (ESI) (0-60AB): m/z: 526.2 [M+1].

Embodiment 2

N-(5-((4-(2,3-Dihydro-1H-pyrrolo[1,2-a]indol-9-yl)pyrimidin-2-yl)amino)-2-(3-(dimethylamino)azetidin-1-yl)-4-methoxyphenyl)acrylamide

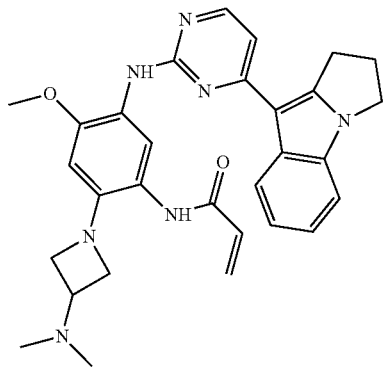 [SMILES: C=CC(=O)Nc1cc(Nc2nccc(-c3c4n(c5ccccc35)CCC4)n2)c(OC)cc1N1CC(N(C)C)C1]

Embodiment 2A 4-(2,3-Dihydro-1H-pyrrolo[1,2-a]-indol-9-yl)-N-(4-(3-(dimethylamino)azetidin-1-yl)-2-methoxy-5-nitrophenyl)pyrimidin-2-amine

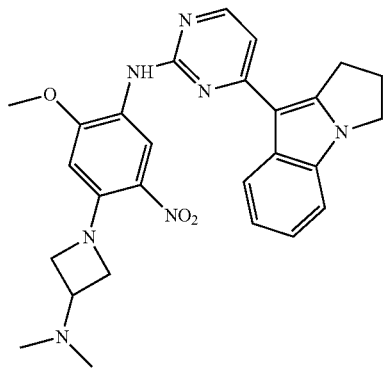

The embodiment was prepared according to the method of embodiment 1A except for replacing N,N',N'-trimethyl-1,2-ethylenediamine with 3-N,N-dimethyl cyclobutylamine hydrochloride to deliver the title compound (red solid, 180.00 mg, yield 90.67%). $^1$H NMR (400 MHz, CDCl$_3$): δ

9.01 (br. s., 1H), 8.30-8.12 (m, 2H), 7.28-7.24 (m, 1H), 7.19 (d, J=2.4 Hz, 2H), 7.04 (d, J=5.6 Hz, 1H), 6.09 (s, 1H), 4.19-4.09 (m, 4H), 3.98-3.96 (m, 5H), 3.60 (br. s., 1H), 3.19-3.12 (m, 2H), 2.69-2.67 (m, 2H), 2.51 (br. s., 6H). LCMS (ESI) (0-60AB): m/z: 500.2 [M+1].

Embodiment 2B

N1-(4-(2,3-Dihydro-1H-pyrrolo[1,2-a]indol-9-yl)pyrimidin-2-yl)-4-(3-(dimethylamino) azetidin-1-yl)-6-methylbenzene-1,3-diamine

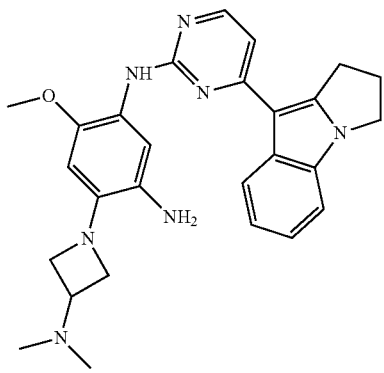 [SMILES: COc1cc(N2CC(N(C)C)C2)c([N+](=O)[O-])cc1Nc1nccc(-c2c3n(c4ccccc24)CCC3)n1]

The embodiment was prepared according to the method of embodiment 1B except for replacing embodiment 1A with embodiment 2A to deliver the title compound (brown solid, 170.00 mg, yield 94.50%). LCMS (ESI) (5-95AB): m/z: 470.2 [M+1].

Embodiment 2C

N-5-((4-(2,3-Dihydro-1H-pyrrolo[1,2-a]indol-9-yl)pyrimidin-2-yl)amino)-2-(3-(dimeth ylamino)azetidin-1-yl)-4-methoxyphenyl) acrylamide

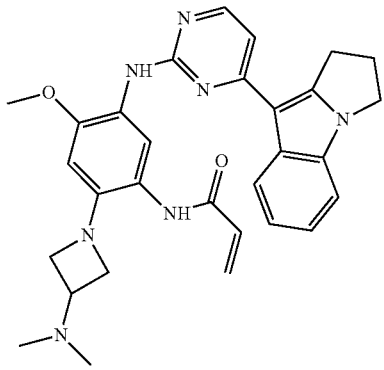 [SMILES: C=CC(=O)Nc1cc(Nc2nccc(-c3c4n(c5ccccc35)CCC4)n2)c(OC)cc1N1CC(N(C)C)C1]

The embodiment was prepared according to the method of embodiment 1C except for replacing embodiment 1B with embodiment 2B to deliver the title compound (TFA salt, 40.00 mg, yield 26.11%). $^1$H NMR (400 MHz, DMSO-d$_6$): δ 8.97 (br. s., 1H), 8.29-8.23 (m, 2H), 7.90 (s, 1H), 7.53 (s, 1H), 7.39-7.34 (m, 1H), 7.18-7.12 (m, 2H), 6.97 (d, J=5.6 Hz, 1H), 6.53-6.39 (m, 1H), 6.26 (s, 1H), 6.19 (dd, J=2.0 Hz, J$_2$=17.2 Hz, 1H), 5.65 (d, J=10.4 Hz, 1H), 4.15 (t, J=7.2 Hz, 2H), 3.97-3.94 (m, 2H), 3.87 (s, 3H), 3.64-3.62 (m, 2H), 3.31 (t, J=7.6 Hz, 2H), 2.66-2.62 (m, 3H), 2.14 (s, 6H). LCMS (ESI) (5-95AB): m/z: 524.2 [M+1].

Embodiment 3

N-(5-((4-(2,3-Dihydro-1H-pyrrolo[1,2-a]indol-9-yl)pyrimidin-2-yl)amino)-2-(2-(dimethylamino)ethoxy)-4-methoxyphenyl)acrylamide

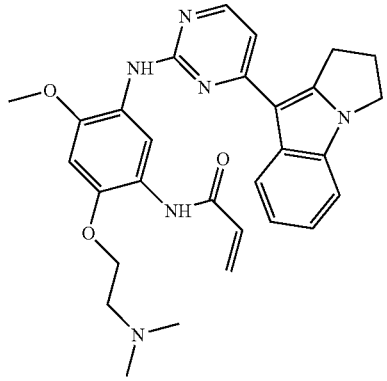 [SMILES: C=CC(=O)Nc1cc(Nc2nccc(-c3c4n(c5ccccc35)CCC4)n2)c(OC)cc1OCCN(C)C]

Embodiment 3A 4-(2,3-Dihydro-1H-pyrrolo[1,2-a]-indol-9-yl)-N-(4-(2-(dimethylamino)ethoxy)-2-meth oxy-5-nitrophenyl)pyrimidin-2-amine

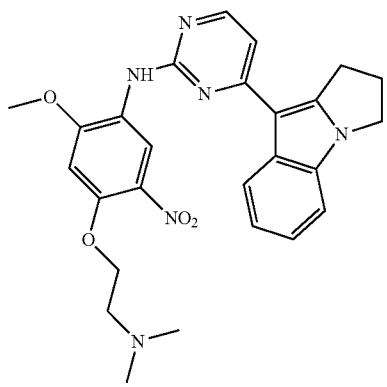 [SMILES: COc1cc(OCCN(C)C)c([N+](=O)[O-])cc1Nc1nccc(-c2c3n(c4ccccc24)CCC3)n1]

2-N,N-Dimethyl ethanol amine (47.82 mg, 536.47 mmol) was dissolved in DMA (3 mL) at 0 to 10° C., and the embodiment B (2.80 g, 6.68 mmol) and N,N',N'-trimethyl-1,2-ethylenediamine were added to the mixture, and then NaH (28.61 mg, 715.29 µmol) was added to the mixture, the reaction mixture was warmed to 20 to 30° C. and stirred for 30 minutes. After cooling to 0 to 10° C., a solution of embodiment B (150.00 mg, 357.65 µmol) in DMA (8 mL) was added and the reaction mixture was warmed to 40° C. and stirred for 12 hours. TLC showed the reaction was complete, the mixture was cooled to 0 to 10° C., and saturated NH$_4$Cl solution (8 mL) was added, the mixture was extracted with DCM (8 mL×3). The organic layer was dried over anhydrous sodium sulfate, concentrated and purified by preparative plate to deliver the title compound (yellow solid, 140.00 mg, yield 72.11%). LCMS (ESI) (10-80AB): m/z: 489.3 [M+1].

Embodiment 3B

N1-(4-(2,3-Dihydro-1H-pyrrolo[1,2-a]indol-9-yl)pyrimidin-2-yl)-4-(2-(dimethylamino) methoxy)-6-methylbenzene-1,3-diamine

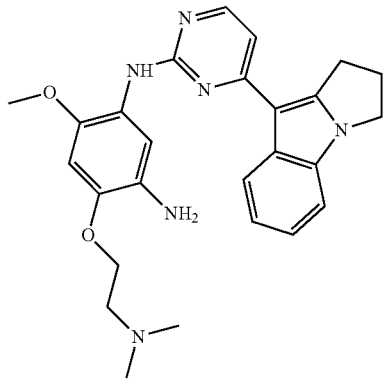

The embodiment was prepared according to the method of embodiment 1B except for replacing embodiment 1A with embodiment 3A to deliver the title compound (yellow solid, 70.00 mg, yield 34.80%). LCMS (ESI) (10-80AB): m/z: 459.2 [M+1].

Embodiment 3C

N-5-((4-(2,3-Dihydro-1H-pyrrolo[1,2-a]indol-9-yl)pyrimidin-2-yl)amino)-2-(2-(dimeth ylamino)ethoxy)-4-methoxyphenyl)acrylamide

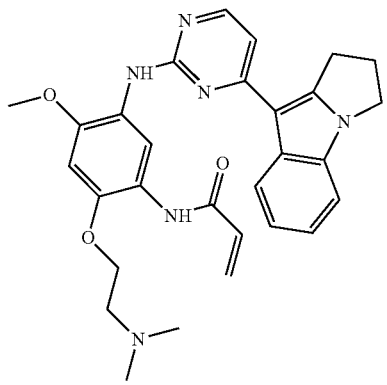

The embodiment was prepared according to the method of embodiment 1C except for replacing embodiment 1B with embodiment 3B to deliver the title compound (FA salt, 20.00 mg, yield 24.79%). $^1$H NMR (400 MHz, MeOH-d$_4$): δ 8.59-8.63 (m, 1H), 8.45-8.52 (m, 1H), 8.25-8.31 (m, 1H), 8.18-8.25 (m, 1H), 7.27-7.34 (m, 1H), 7.07-7.18 (m, 2H), 7.00-7.05 (m, 1H), 6.87-6.92 (m, 1H), 6.50-6.60 (m, 1H), 6.35-6.44 (m, 1H), 5.79-5.86 (m, 1H), 4.42-4.50 (m, 2H), 4.11 (s, 2H), 3.99 (s, 3H), 3.38-3.42 (m, 2H), 3.37 (s, 2H), 2.87 (s, 6H), 2.60-2.70 (m, 2H). LCMS (ESI) (5-95AB): m/z: 513.2 [M+1].

Embodiment 4

2-(2-Methoxy-4-(N-methyl)piperazine-5-acrylamidoanilino)-4-(3-(1,2,3-dihydropyrrol o[1,2-a]indol))pyrimidine

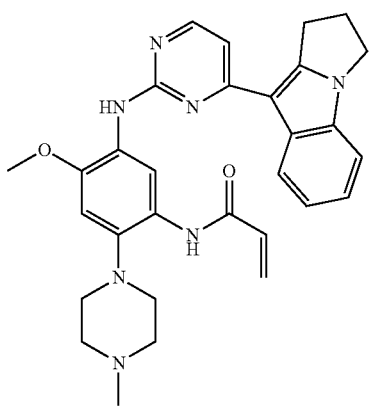 [SMILES: C=CC(=O)Nc1cc(Nc2nccc(-c3c4n(c5ccccc35)CCC4)n2)c(OC)cc1N1CCN(C)CC1]

Embodiment 4A 4-(2,3-Dihydro-1H-pyrrol o[1,2-a]indol-9-yl)-N-(2-methoxy-4-(4-methylpiperazin-1-yl)-5-nitrophenyl)pyrimidin-2-amine

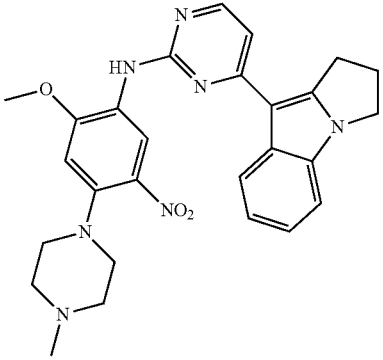 [SMILES: COc1cc(N2CCN(C)CC2)c([N+](=O)[O-])cc1Nc1nccc(-c2c3n(c4ccccc24)CCC3)n1]

The embodiment was prepared according to the method of embodiment 1A except for replacing N,N',N',N'-trimethyl-1,2-ethylenediamine with N-methylpiperazine to deliver the title compound (yellow solid, 80.00 mg, yield 43.88%). LCMS (ESI) (5-95AB): m/z: 500.1 [M+1].

Embodiment 4B

N1-(4-(2,3-Dihydro-1H-pyrrolo[1,2-a]indol-9-yl)pyrimidin-2-yl)-6-methoxy-4-(4-methylpiperazin-1-yl)benzene-1,3-diamine

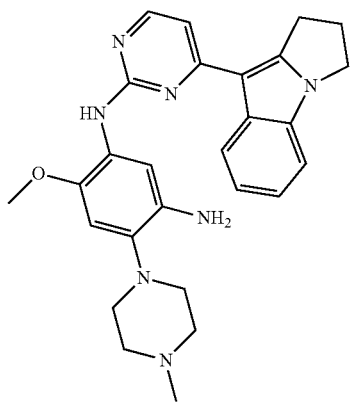 [SMILES: COc1cc(N2CCN(C)CC2)c(N)cc1Nc1nccc(-c2c3n(c4ccccc24)CCC3)n1]

The embodiment was prepared according to the method of embodiment 1B except for replacing embodiment 1A with embodiment 4A to deliver the title compound (yellow solid, 80.00 mg, yield 43.88%). LCMS (ESI) (5-95AB): m/z: 470.1 [M+1].

Embodiment 4C

N-5-((4-(2,3-Dihydro-1H-pyrrolo[1,2-a]indol-9-yl)pyrimidin-2-yl)amino)-4-methoxy-2-(4-methylpiperazin-1-yl)phenyl)acrylamide

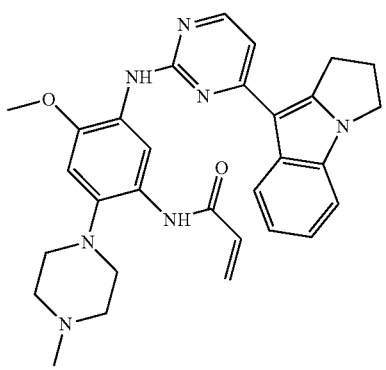 [SMILES: C=CC(=O)Nc1cc(Nc2nccc(-c3c4n(c5ccccc35)CCC4)n2)c(OC)cc1N1CCN(C)CC1]

The embodiment was prepared according to the method of embodiment 1C except for replacing embodiment 1B with embodiment 4B to deliver the title compound (FA salt, 17.60 mg, yield 19.33%). $^1$H NMR (400 MHz, METHANOL-$d_6$): δ 8.85 (s, 1H), 8.34 (br. s., 2H), 8.18-8.28 (m, 2H), 7.25-7.30 (m, 1H), 7.09-7.18 (m, 2H), 7.03 (d, J=4 Hz, 1H), 6.92 (s, 1H), 6.57 (dd, J=16, 12 Hz, 1H), 6.31 (d, J=20 Hz, 1H), 5.79 (d, J=8 Hz, 1H), 4.07 (t, J=8 Hz, 2H), 3.95 (s, 3H), 3.32-3.35 (m, 2H), 3.24-3.30 (m, 4H), 3.17 (m, 4H), 2.87 (s, 3H), 2.56-2.66 (m, 2H). LCMS (ESI) (0-60AB): m/z: 524.2 [M+1].

Embodiment 5

N-5-((4-(2,3-Dihydro-1H-pyrrolo[1,2-a]indol-9-yl)pyrimidin-2-yl)amino)-4-methoxy-2-(methyl(2-(pyrrolidin-1-yl)ethyl)amino)phenyl)acrylamide

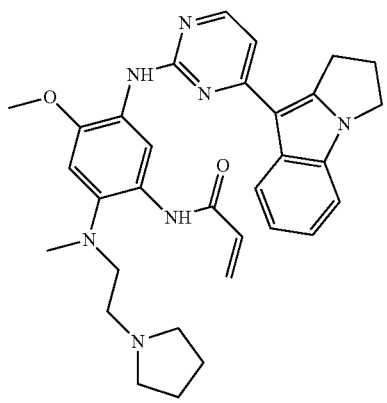 [SMILES: C=CC(=O)Nc1cc(Nc2nccc(-c3c4n(c5ccccc35)CCC4)n2)c(OC)cc1N(C)CCN1CCCC1]

Embodiment 5A tert-Butyl (2-(pyrrolidin-1-yl)ethyl)carbamate

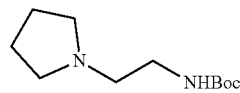 [SMILES: CC(C)(C)OC(=O)NCCN1CCCC1]

Pyrrole-2-ethanamine (2.50 g, 21.89 mmol) was dissolve in THF (50 mL) at 0° C., (Boc)$_2$O (4.78 g, 21.89 mmol) was added dropwise to the mixture and the reaction mixture was warmed to 15° C. and stirred for 12 hours. LCMS showed the reaction was complete and the mixture was concentrated to deliver the title compound (yellow oil, 4.50 g, 95.26% yield). $^1$H NMR (400 MHz, CDCl$_3$): δ 5.09 (br. s., 1H), 3.22 (m, 2H), 2.54 (t, J=6.0 Hz, 2H), 2.48 (br. s., 4H), 1.74 (m, 4H), 1.43 (s, 9H). LCMS (0-60CD): m/z: 215.2 [M+1].

Embodiment 5B

N-Methyl-2-(pyrrolidin-1-yl)ethanamine

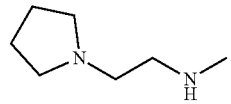

Embodiment 5A (2.00 g, 9.33 mmol) was dissolved in THF (100 mL) at 0° C. and LAH (1.06 g, 27.99 mmol) was added in batches to the mixture and the reaction mixture was warmed to 70° C. and stirred for 12 hours. TLC showed the reaction was complete and the reaction mixture was warmed to 0° C. NaOH solution (1N, 2 mL) and water (2 mL) were added to the mixture sequentially, the mixture was filtered and the filtrate was diluted with DCM (50 mL), dried over anhydrous sodium sulfate, concentrated to deliver the title compound (yellow oil, 1.00 g, yield 79.42%). $^1$H NMR (400

MHz, CDCl₃): δ 2.67-2.72 (m, 2H), 2.57-2.61 (m, 2H), 2.48-2.53 (m, 4H), 2.44 (s, 3H), 1.74-1.80 (m, 4H).

Embodiment 5C

N1-(4-(2,3-Dihydro-1H-pyrrolo[1,2-a]indol-9-yl)pyrimidin-2-yl)-2-methoxy-N4-methyl-5-nitro-N-4-(2-(pyrrolidin-1-yl)ethyl)benzene-1,4-diamine

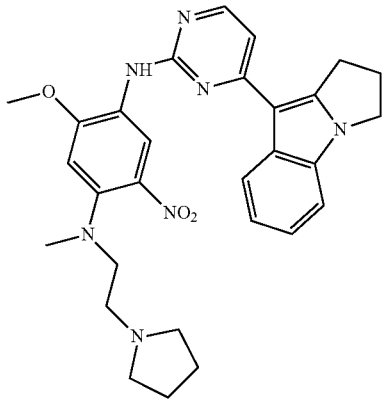 [SMILES: COc1cc(N(C)CCN2CCCC2)c([N+](=O)[O-])cc1Nc1nccc(-c2c3n(c4ccccc24)CCC3)n1]

The embodiment was prepared according to the method of embodiment 1A except for replacing N,N',N'-trimethyl-1,2-ethylenediamine with embodiment 5B to deliver the title compound (yellow solid, 200.00 mg, yield 79.49%). LCMS (5-95AB): m/z: 528.2 [M+1].

Embodiment 5D

N4-(4-(2,3-Dihydro-1H-pyrrolo[1,2-a]indol-9-yl)pyrimidin-2-yl)-5-methoxy-N1-methyl-N1-(2-(pyrrolidin-1-yl)ethyl)benzene-1,2,4-triamine

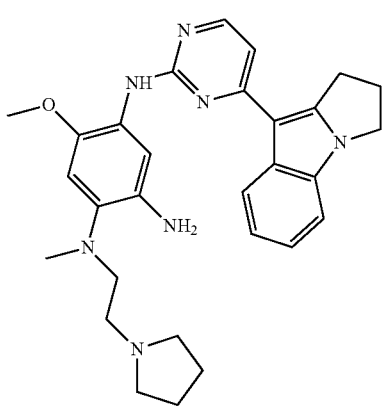 [SMILES: COc1cc(N(C)CCN2CCCC2)c(N)cc1Nc1nccc(-c2c3n(c4ccccc24)CCC3)n1]

The embodiment was prepared according to the method of embodiment 1B except for replacing embodiment 1A with embodiment 5C to deliver the title compound (white solid, 160.00 mg, yield 81.43%). LCMS (5-95AB): m/z: 498.2 [M+1].

Embodiment 5E

N-(5-((4-(2,3-Dihydro-1H-pyrrolo[1,2-a]indol-9-yl)pyrimidin-2-yl)amino)-4-methoxy-2-(methyl (2-(pyrrolidin-1-yl)ethyl)amino)phenyl)acrylamide

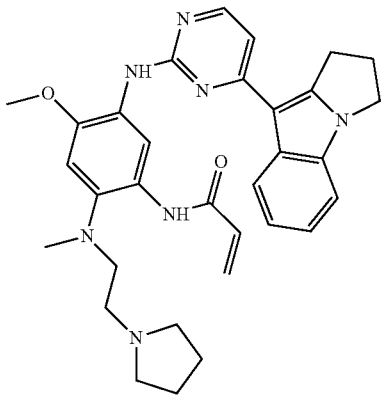 [SMILES: C=CC(=O)Nc1cc(Nc2nccc(-c3c4n(c5ccccc35)CCC4)n2)c(OC)cc1N(C)CCN1CCCC1]

The embodiment was prepared according to the method of embodiment 1C except for replacing embodiment 1B with embodiment 5D to deliver the title compound (FA salt, 16.20 mg, yield 7.34%). ¹H NMR (400 MHz, CD₃OD): δ 8.47 (s, 1H), 8.43 (br. s., 1H), 8.25-8.29 (m, 1H), 8.23 (d, J=4 Hz, 1H), 7.27-7.32 (m, 1H), 7.07-7.15 (m, 2H), 7.03 (d, J=8.0 Hz, 1H), 6.95 (s, 1H), 6.36-6.57 (m, 2H), 5.87 (dd, J=10, 2.0 Hz, 1H), 4.06-4.12 (m, 2H), 4.00 (s, 3H), 3.44-3.53 (m, 2H), 3.32-3.38 (m, 4H), 3.23-3.31 (m, 4H), 2.73 (s, 3H), 2.60-2.68 (m, 2H), 2.09-2.22 (m, 4H). LCMS (0-60AB): m/z: 552.3 [M+1].

Embodiment 6

N-(5-((4-(2,3-Dihydro-1H-pyrrolo[1,2-a]indol-9-yl)pyrimidin-2-yl)amino)-2-(3-(dimethylamino)pyrrolidin-1-yl)-4-methoxyphenyl)acrylamide

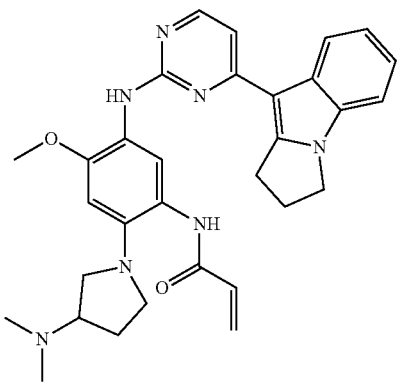 [SMILES: C=CC(=O)Nc1cc(Nc2nccc(-c3c4n(c5ccccc35)CCC4)n2)c(OC)cc1N1CCC(N(C)C)C1]

Embodiment 6A

N,N-Dimethylpyrrolidin-3-amine

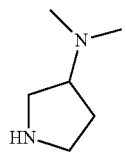

Tert-butyl 3-(N,N-dimethylamino)pyrrole carboxylate (300.00 mg, 1.40 mmol) was dissolved in DCM (20 mL) at 25° C. and TFA (1.60 g, 14.00 mmol) was added to the mixture and stirred for 30 minutes. TLC showed the reaction was complete and the reaction mixture was concentrated to deliver the title compound (1.50 g, crude).

Embodiment 6B 4-(2,3-Dihydro-1H-pyrrolo[1,2-a]indol-9-yl)-N-(4-(3-(dimethylamino)pyrrolidin-1-yl)-2-methoxy-5-nitrophenyl)pyrimidin-2-amine

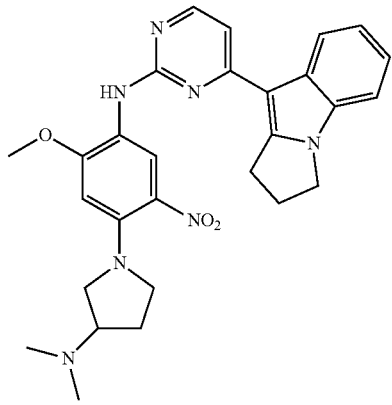

The embodiment was prepared according to the method of embodiment 1A except for replacing N,N',N'-trimethyl-1,2-ethylenediamine with embodiment 6A to deliver the title compound (yellow solid, 250.00 mg, yield 75.95%). LCMS (0-60AB): m/z: 514.2 [M+1].

Embodiment 6C

N1-(4-(2,3-Dihydro-1H-pyrrolo[1,2-a]indol-9-yl)pyrimidin-2-yl)-4-(3-(dimethylamino)pyrrolidin-1-yl)-6-methylbenzene-1,3-diamine

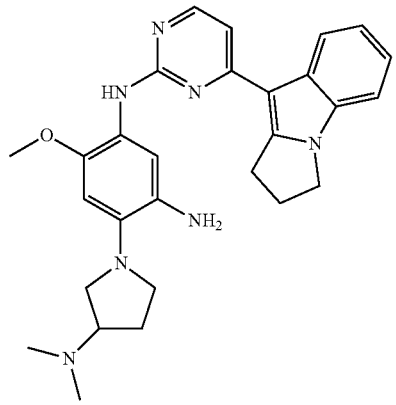 [SMILES: COc1cc(N2CCC(N(C)C)C2)c([N+](=O)[O-])cc1Nc1nccc(-c2c3n(c4ccccc24)CCC3)n1]

The embodiment was prepared according to the method of embodiment 1B except for replacing embodiment 1A with embodiment 6B to deliver the title compound (white solid, 200.00 mg, yield 80.54%). LCMS (5-95AB): m/z: 484.2 [M+1].

Embodiment 6D

N-(5-((4-(2,3-Dihydro-1H-pyrrolo[1,2-a]indol-9-yl)pyrimidin-2-yl)amino)-2-(3-(dimethylamino)pyrrolidin-1-yl)-4-methoxyphenyl)acrylamide

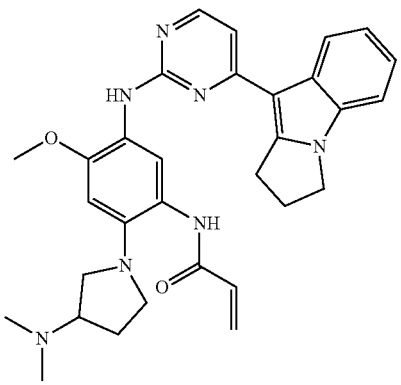 [SMILES: C=CC(=O)Nc1cc(Nc2nccc(-c3c4n(c5ccccc35)CCC4)n2)c(OC)cc1N1CCC(N(C)C)C1]

The embodiment was prepared according to the method of embodiment 1C except for replacing embodiment 1B with embodiment 6C to deliver the title compound (FA salt, 17.75 mg, yield 6.17%). $^1$H NMR (400 MHz, CD$_3$OD): δ 8.46 (s, 1H), 8.26-8.15 (m, 2H), 7.28 (dd, J=2.0, 8.0 Hz, 1H), 7.17-7.10 (m, 2H), 7.00 (d, J=6.0 Hz, 1H), 6.71 (s, 1H), 6.59-6.49 (m, 1H), 6.31 (dd, J=2.0, 16.0 Hz, 1H), 5.76 (dd, J=2.0, 12.0 Hz, 1H), 4.08 (t, J=8.0 Hz, 2H), 3.93 (s, 3H), 3.37-3.32 (m, 2H), 3.29-3.23 (m, 4H), 3.16-3.06 (m, 1H), 2.67-2.56 (m, 2H), 2.45 (s, 6H), 2.31-2.20 (m, 1H), 2.00-1.90 (m, 1H). LCMS (0-60AB): m/z: 538.3 [M+1].

Embodiment 7

N-(5-((4-(2,3-Dihydro-1H-pyrrolo[12-a]indol-9-yl)pyrimidin-2-yl)amino)-2-((3-(dimethylamino)propyl)(methyl)amino)-4-methoxyphenyl)acrylamide

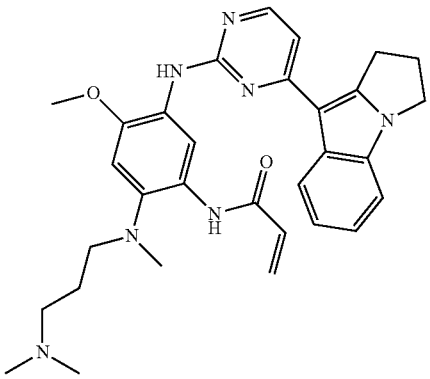 [SMILES: C=CC(=O)Nc1cc(Nc2nccc(-c3c4n(c5ccccc35)CCC4)n2)c(OC)cc1N(C)CCCN(C)C]

Embodiment 7A

N1-(4-(2,3-Dihydro-1H-pyrrolo[1,2-a]indol-9-yl)pyrimidin-2-yl)-N4-(3-(dimethylamino)propyl)-2-methoxy-N-4-methyl-5-nitrobenzene-1,4-diamine

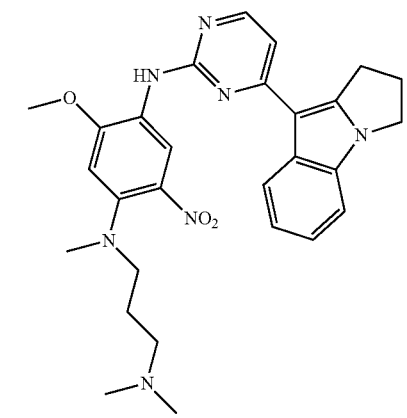 [SMILES: COc1cc(N(C)CCCN(C)C)c([N+](=O)[O-])cc1Nc1nccc(-c2c3n(c4ccccc24)CCC3)n1]

The embodiment was prepared according to the method of embodiment 1A except for replacing N,N',N'-trimethyl-1,2-ethylenediamine with N,N',N'-trimethyl-1,2-propanediamine to deliver the title compound (200.00 mg, crude). LCMS (ESI) (0-60AB): m/z: 516.2 [M+1].

Embodiment 7B

N4-(4-(2,3-Dihydro-1H-pyrrolo[12-a]indol-9-yl)pyrimidin-2-yl)-N-(3-(dimethylamino)propyl)-5-methoxy-N-methylbenzene-1,2,4-triamine

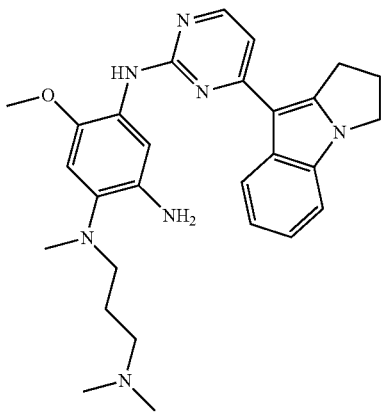 [SMILES: COc1cc(N(C)CCCN(C)C)c(N)cc1Nc1nccc(-c2c3n(c4ccccc24)CCC3)n1]

The embodiment was prepared according to the method of embodiment 1B except for replacing embodiment 1A with embodiment 7A to deliver the title compound (white solid, 200.00 mg, crude). LCMS (ESI) (0-60AB): m/z: 486.2 [M+1].

Embodiment 7C

N-(5-((4-(2,3-Dihydro-1H-pyrrolo[1,2-a]indol-9-yl)pyrimidin-2-yl)amino)-2-((3-(dimethylamino)propyl)(methyl)amino)-4-methoxyphenyl)acrylamide

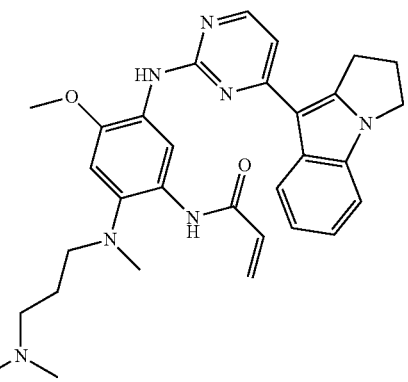

The embodiment was prepared according to the method of embodiment 1C except for replacing embodiment 1B with embodiment 7B to deliver the title compound (FA salt, 40.00 mg, yield 17.58%). $^1$H NMR (400 MHz, CD$_3$OD): δ 8.78 (s, 1H), 8.45 (br. s., 1H), 8.19-8.33 (m, 2H), 7.30 (d, J=5.09 Hz, 1H), 6.99-7.19 (m, 3H), 6.96 (s, 1H), 6.49-6.71 (m, 1H), 6.33 (d, J=16.95 Hz, 1H), 5.80 (d, J=10.55 Hz, 1H), 4.12 (t, J=6.88 Hz, 2H), 3.96 (s, 3H), 2.99-3.20 (m, 4H), 2.54-2.93 (m, 11H), 1.76-2.00 (m, 2H). LCMS (ESI) (0-60AB): m/z: 540.2 [M+1].

Process 3
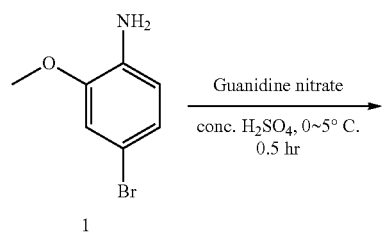
1
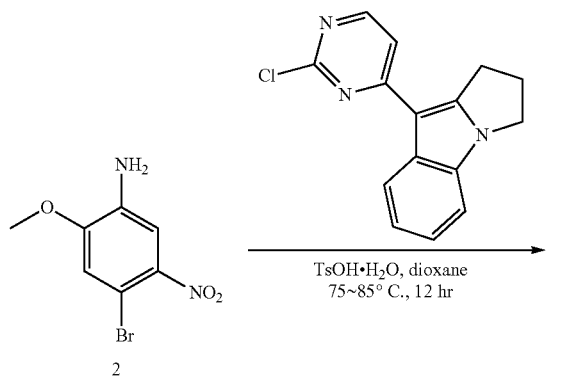
2
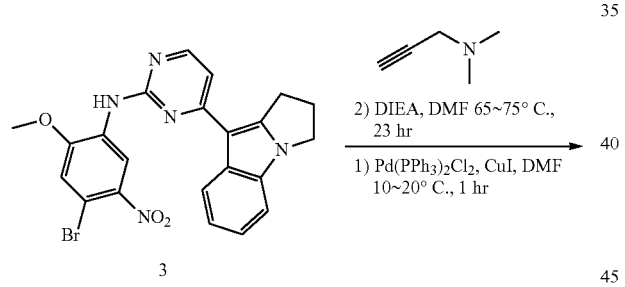
3
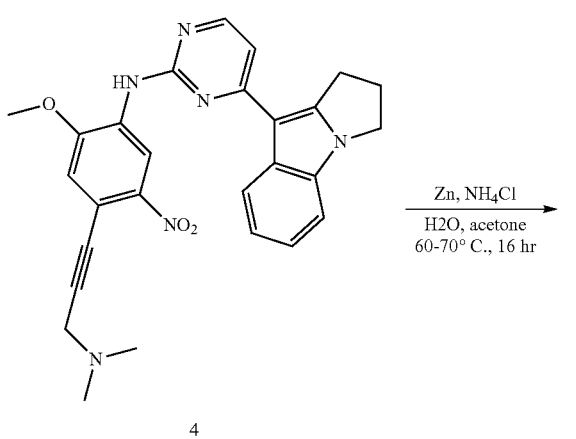
4
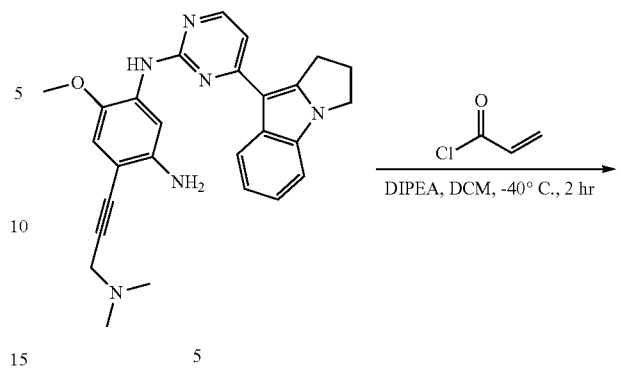
5
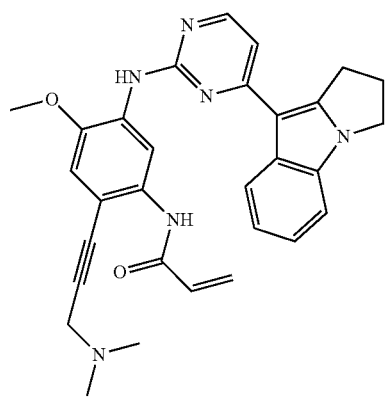 [SMILES: C=CC(=O)Nc1cc(Nc2nccc(-c3c4n(c5ccccc35)CCC4)n2)c(OC)cc1C#CCN(C)C]
Embodiment 8
Embodiment 8
N-(5-((4-(2,3-Dihydro-1H-pyrrolo[1,2-a]indol-9-yl)
pyrimidin-2-yl)amino)-2-(3-(dimethylamino)prop-1-
yn-1-yl)-4-methoxyphenyl)acrylamide
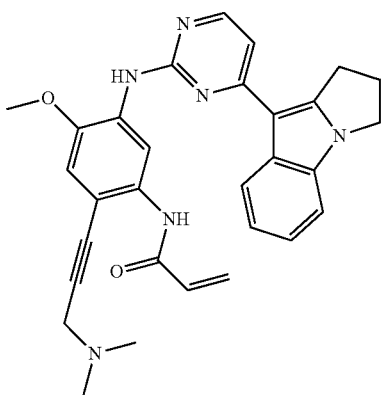

Embodiment 8A

4-Bromo-2-methoxy-5-nitroaniline

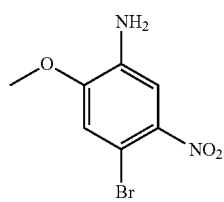

2-Methoxy-4-bromoaniline (5.00 g, 24.75 mmol) was added to concentrated $H_2SO_4$ (50 mL) at 0 to 5° C. and then guanidine nitrate (3.02 g, 24.75 mmol) was added in batches. The mixture was stirred at 0 to 5° C. for 30 minutes. TLC showed the reaction was complete and the reaction mixture was slowly added dropwise to a solution of $NaHCO_3$ (100 g) in water (1 L), the temperature was controlled below 15° C. The resulting mixture was filtered to deliver the title compound (yellow solid, 5.40 g, yield 83.90%). $^1$H NMR (400 MHz, $CDCl_3$): δ, 7.39 (s, 1H), 7.01 (s, 1H), 4.09 (br. s., 2H), 3.96 (s, 3H).

Embodiment 8B

N-(4-Bromo-2-methoxy-5-nitrophenyl)-4-(2,3-dihydro-1H-pyrrolo[1,2-a]indol-9-yl)pyrimidin-2-amine

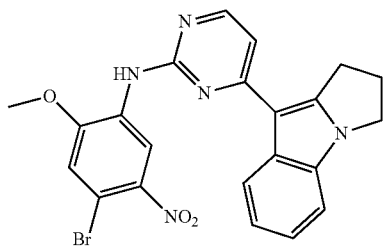 [SMILES: COc1cc(Br)c([N+](=O)[O-])cc1Nc1nccc(-c2c3n(c4ccccc24)CCC3)n1]

Embodiment 8A (1.51 g, 5.56 mmol) and embodiment A (1.50 g, 5.56 mmol) were added to 1,4-dioxane (20 mL), TsOH.$H_2O$ (1.27 g, 6.67 mmol) was added to the mixture and the reaction mixture was warmed to 75 to 85° C. and stirred for 12 hours. TLC showed the reaction was complete, the reaction mixture was concentrated, dissolved in DCM (20 mL), washed with saturated $NaHCO_3$ (20 mL), and the organic phase was concentrated and purified by column chromatography (DCM/MeOH=100:0 to 100:1) to deliver the title compound (yellow solid, 2.40 g, yield 85.38%). $^1$H NMR (400 MHz, DMSO-$d_6$): δ, 9.08 (s, 1H), 8.42 (d, J=5.2 Hz, 1H), 8.35 (d, J=8 Hz, 1H), 8.30 (s, 1H), 7.53 (s, 1H), 7.42 (d, J=7.6 Hz, 1H), 7.12-7.21 (m, 3H), 4.18 (t, J=7.2 Hz, 2H), 4.05 (s, 3H), 3.23-3.33 (m, 2H), 2.64-2.67 (m, 2H).

Embodiment 8C 4-(2,3-Dihydro-1H-pyrrolo[1,2-a]indol-9-yl)-N-(4-(3-(dimethylamino)prop-1-yn-1-yl)-2-methoxy-5-nitrophenyl)pyrimidin-2-amine

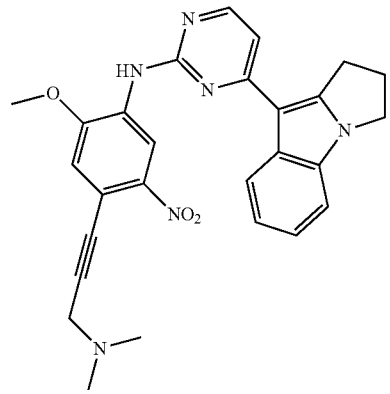 [SMILES: COc1cc(C#CCN(C)C)c([N+](=O)[O-])cc1Nc1nccc(-c2c3n(c4ccccc24)CCC3)n1]

Embodiment 8B (1.00 g, 2.08 mmol), CuI (39.65 mg, 208.00 mol) and Pd(PPh$_3$)$_2$Cl$_2$ (73.07 mg, 104.00 mol) were added to DMF (20 mL) at 10 to 20° C. and stirred for 1 hour. 1-Dimethylamino-2-propyne (345.82 mg, 4.16 mmol) and DIEA (537.64 mg, 4.16 mmol) were added to the mixture and the reaction mixture was warmed to 65 to 75° C. and stirred for 23 hours. TLC showed the reaction was complete, the reaction mixture was filtered, concentrated, and purified by column chromatography (DCM/MeOH=100:0 to 100:5) to deliver the title compound (yellow solid, 500.00 g, yield 45.33%). LCMS (ESI) (0-60AB): m/z: 483.1 [M+1].

Embodiment 8D

N1-(4-(2,3-Dihydro-1H-pyrrolo[1,2-a]indol-9-yl)pyrimidin-2-yl)-4-(3-(dimethylamino)prop-1-yn-1-yl)-6-methoxybenzene-1,3-diamine

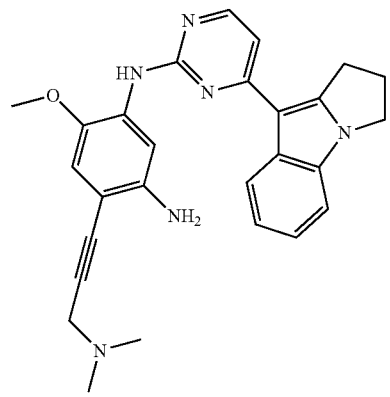 [SMILES: COc1cc(C#CCN(C)C)c(N)cc1Nc1nccc(-c2c3n(c4ccccc24)CCC3)n1]

Embodiment 8C (200.00 mg, 414.48 mmol) and NH$_4$Cl (110.85 mg, 2.07 mmol) were added to acetone (9 mL) and water (1 mL). Zinc powder (110.85 mg, 2.07 mmol) was added to the mixture, and the reaction mixture was warmed to 60 to 70° C. and stirred for 16 hours. TLC showed the reaction was complete, the reaction mixture was filtered and saturated Na₂CO₃ was added to adjust pH=9. The mixture was extracted with DCM (10 mL×2), the organic layer was concentrated, and purified by preparative (DCM/MeOH=20: 1) to deliver the title compound (yellow solid, 20.00 mg, yield 10.12%). LCMS (ESI) (0-60AB): m/z: 453.1 [M+1].

Embodiment 8E

N-(5-((4-(2,3-Dihydro-1H-pyrrolo[1,2-a]indol-9-yl)pyrimidin-2-yl)amino)-2-(3-(dimethylamino)prop-1-yn-1-yl)-4-methoxyphenyl)acrylamide

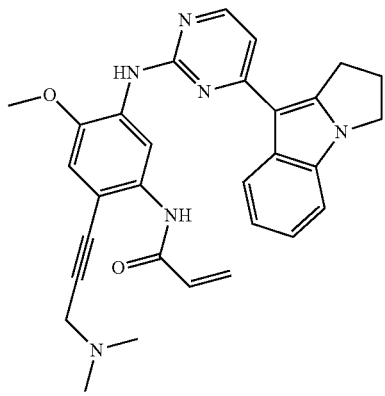 [SMILES: C=CC(=O)Nc1cc(Nc2nccc(-c3c4n(c5ccccc35)CCC4)n2)c(OC)cc1C#CCN(C)C]

The embodiment was prepared according to the method of embodiment 1C except for replacing embodiment 1B with embodiment 8D to deliver the title compound (FA salt, 7.00 mg, yield 20.84%). ¹H NMR (400 MHz, CD₃OD): δ 8.88 (s, 1H), 8.43 (br. s., 1H), 8.27-8.29 (m, 2H), 7.30-7.32 (m, 1H), 7.08-7.18 (m, 4H), 6.50-6.54 (m, 1H), 6.34-6.39 (m, 1H), 5.81 (dd, J=1.13, 10 Hz, 1H), 4.07-4.09 (m, 2H), 3.99 (s, 3H), 3.90 (s, 2H), 3.29-3.30 (m, 2H), 2.55-2.72 (m, 8H). LCMS (ESI) (0-60AB): m/z: 507.2 [M+1].

Embodiment 9

N-(5-((4-(2,3-Dihydro-1H-pyrrolo[12-a]indol-9-yl)pyrimidin-2-yl)amino)-4-methoxy-2-(morpholinomethyl)phenyl)acrylamide

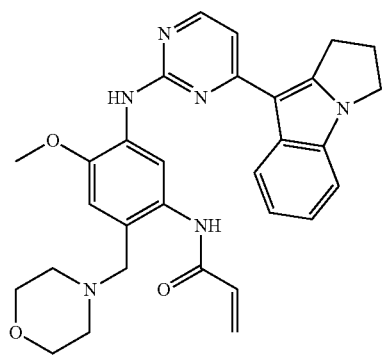 [SMILES: C=CC(=O)Nc1cc(Nc2nccc(-c3c4n(c5ccccc35)CCC4)n2)c(OC)cc1CN1CCOCC1]

Embodiment 9A

3-Methoxy-4-(2,2,2-trifluoroethyl)benzoic acid

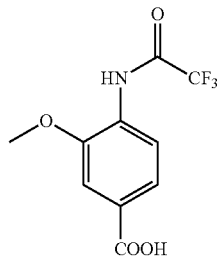 [SMILES: COc1cc(C(=O)O)ccc1NC(=O)C(F)(F)F]

4-Amino-3-methoxybenzoic acid (10.00 g, 59.82 mmol) was added to TFA (60 mL) at 0 to 5° C., and TFAA (31.41 g, 59.82 mmol) was added dropwise and stirred for 30 minutes. TLC showed the reaction was complete, the reaction mixture was poured into ice water (1 L), stirred for 30 minutes and then filtered. The filter cake was dried to deliver the title compound (14.50 g, yield 87.50%). ¹H NMR (400 MHz, CDCl3): δ 8.74 (br. s., 1H), 8.49 (d, J=8.4 Hz, 1H), 7.87 (dd, J=1.2, 7.2 Hz, 1H), 7.68 (d, J=1.2 Hz, 1H), 4.05 (s, 3H).

Embodiment 9B

5-Methoxy-2-nitro-4-(2,2,2-trifluoroethyl)benzoic acid

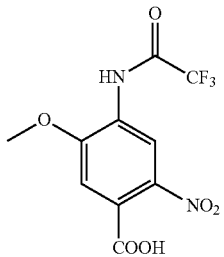 [SMILES: COc1cc(C(=O)O)c([N+](=O)[O-])cc1NC(=O)C(F)(F)F]

Embodiment 9A (13.50 g, 51.30 mmol) was added to fuming nitric acid (100 mL) at 0° C. in batches. TFAA (31.41 g, 59.82 mmol) was added to the mixture dropwise and stirred for 30 minutes. TLC showed the reaction was complete, the reaction mixture was poured into ice water (1 L), stirred for 30 minutes and filtered, and the filter cake was dried to deliver the title compound (off-white solid, 13.50 g, yield 76.85%). ¹H NMR (400 MHz, CDCl₃): δ 9.01 (s, 1H), 8.65 (br. s., 1H), 7.36 (s, 1H), 4.13 (s, 3H).

Embodiment 9C 2,2,2-Trifluoro-N-(2-methoxy-4-(morpholine-4-carbonyl)-5-nitrophenyl)acetamide

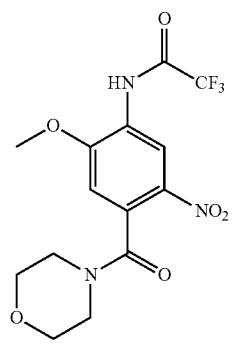 [SMILES: COc1cc(C(=O)N2CCOCC2)c([N+](=O)[O-])cc1NC(=O)C(F)(F)F]

Embodiment 9B (5.00 g, 16.22 mmol) and morpholine (1.70 g, 19.46 mmol) were added to DMF (50 mL) at 10 to 20° C. HATU (7.40 g, 19.46 mmol) and DIEA (3.14 g, 24.33 mmol) were added to the mixture and stirred for 3 hours. TLC showed the reaction was complete, the reaction mixture was slowly added to water (200 mL), filtered and the filter cake was dried to deliver the title compound (yellow solid, 13.50 g, yield 76.85%). $^1$H NMR (400 MHz, CDCl$_3$): δ 9.22 (s, 1H), 8.60 (br. s., 1H), 6.90 (s, 1H), 4.09 (s, 3H), 3.60-3.94 (m, 6H), 3.22 (t, J=4.8 Hz, 2H).

Embodiment 9D (4-Amino-5-methoxy-2-nitrophenyl)(morpholino)methanone

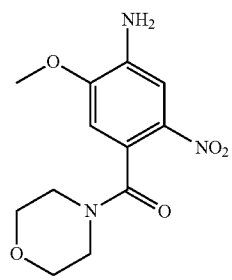 [SMILES: COc1cc(C(=O)N2CCOCC2)c([N+](=O)[O-])cc1N]

Embodiment 9C (4.00 g, 10.60 mmol) was added to MeOH/H$_2$O (1:1, 40 mL), K$_2$CO$_3$ (7.33 g, 53.00 mmol) was added to the mixture and the reaction mixture was warmed to 65° C. and stirred for 5 hours. TLC showed the reaction was complete, the reaction mixture was concentrated to remove MeOH, then extracted with EA (15 mL×2), and the organic phase was dried over anhydrous sodium sulfate and concentrated to deliver the title compound (yellow solid, 2.50 g, crude).

Embodiment 9E

2-Methoxy-4-(morpholino)-5-nitroaniline

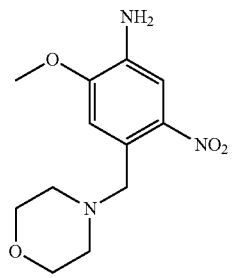 [SMILES: COc1cc(CN2CCOCC2)c([N+](=O)[O-])cc1N]

Embodiment 9D (1.00 g, 3.56 mmol) was added to THF (10 mL) at 5 to 15° C. BH$_3$-Me$_2$S (10M, 1.78 mL) was added to the mixture and the reaction mixture was warmed to 66° C. and stirred for 2 hours. TLC showed the reaction was complete, MeOH (5 mL) was slowly added dropwise to the reaction mixture and stirred at 66° C. for 1 hour. The reaction mixture was concentrated to deliver the title compound (yellow solid, 700.00 mg, yield 72.83%). LCMS (ESI) (0-60AB): m/z: 268.0 [M+1].

Embodiment 9F 4-(2,3-Dihydro-1H-pyrrolo[1,2-a]indol-9-yl)-N-(2-methoxy-4-(morpholinomethyl)-5-nitrophenyl)pyrimidin-2-amine

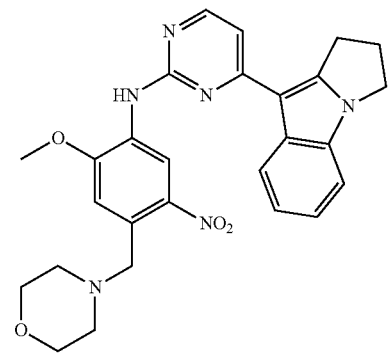 [SMILES: COc1cc(CN2CCOCC2)c([N+](=O)[O-])cc1Nc1nccc(-c2c3n(c4ccccc24)CCC3)n1]

Embodiment 9E (435.13 mg, 1.63 mmol) and embodiment A (400.00 mg, 1.48 mmol) was added to t-BuOH (10 mL). Methanesulfonic acid (170.69 mg, 1.78 mmol) was added to the mixture, and the reaction mixture was warmed to 75 to 85° C. for 48 hours. TLC showed the reaction was complete and the reaction mixture was concentrated, dissolved with DCM (10 mL), washed with NaHCO$_3$ (5 mL) and brine (5 mL) respectively, concentrated and purified by column chromatography (DCM/MeOH=100:0 to 100:1) to deliver the title compound (yellow oil, 400.00 mg, yield 43.74%). LCMS (ESI) (0-60AB): m/z: 501.2 [M+1].

Embodiment 9G

N1-(4-(2,3-dihydro-1H-pyrrolo[1,2-a]indol-9-yl)pyrimidin-2-yl)-6-methoxy-4-(morpholinomethyl)benzene-1,3-diamine

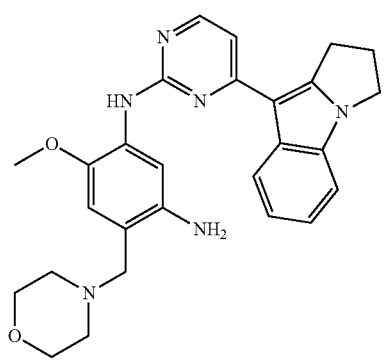 [SMILES: COc1cc(CN2CCOCC2)c(N)cc1Nc1nccc(-c2c3n(c4ccccc24)CCC3)n1]

The embodiment was prepared according to the method of embodiment 1B except for replacing embodiment 1A with embodiment 9F to deliver the title compound (red oil, 300.00 mg, crude). LCMS (ESI) (0-60AB): m/z: 471.2 [M+1].

Embodiment 9H

N-(5-((4-(2,3-Dihydro-1H-pyrrolo[1,2-a]indol-9-yl)pyrimidin-2-yl)amino)-4-methoxy-2-(morpholinomethyl)phenyl)acrylamide

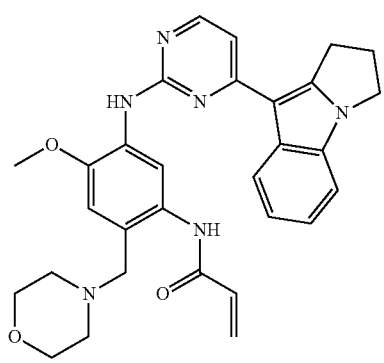 [SMILES: C=CC(=O)Nc1cc(Nc2nccc(-c3c4n(c5ccccc35)CCC4)n2)c(OC)cc1CN1CCOCC1]

The embodiment was prepared according to the method of embodiment 1C except for replacing embodiment 1B with embodiment 9G to deliver the title compound (FA salt, 37.00 mg, yield 11.02%). $^1$H NMR (400 MHz, CD$_3$OD): δ 8.84 (s, 1H), 8.18-8.37 (m, 4H), 7.34 (d, J=7.6 Hz, 1H), 7.05-7.23 (m, 3H), 6.34-6.52 (m, 2H), 5.86 (dd, J=2.38, 9.16 Hz, 1H), 4.13 (t, J=7.1 Hz, 2H), 4.00 (s, 3H), 3.85 (d, J=12.8 Hz, 6H), 2.84 (br. s., 4H), 2.53-2.73 (m, 3H). LCMS (ESI) (0-60AB): m/z: 525.2 [M+1].

Embodiment 10

N-(5-((4-(2,3-Dihydro-1H-pyrrolo[1,2-a]indol-9-yl)pyrimidin-2-yl)amino)-2-(3-(dimethylamino)propyl)-4-methylphenyl)acrylamide

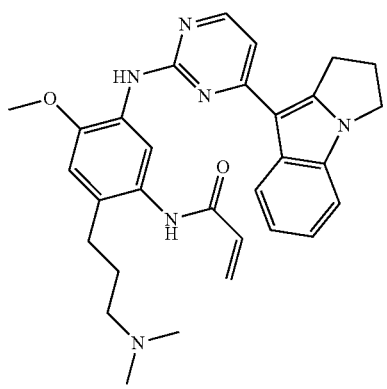 [SMILES: C=CC(=O)Nc1cc(Nc2nccc(-c3c4n(c5ccccc35)CCC4)n2)c(OC)cc1CCCN(C)C]

Embodiment 10A

3-Methoxy-4-nitrobenzaldehyde

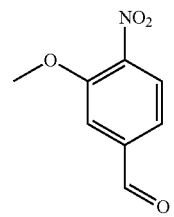

3-Methoxy-4-nitrobenzyl alcohol (4.70 g, 25.66 mmol) was added to DCM (50 mL), and MnO$_2$ (13.39 g, 153.96 mmol) was added to the mixture and the reaction mixture was warmed to 40° C. and stirred for 12 hours. TLC showed the reaction was complete, the reaction mixture was filtered and the filtrate was concentrated to deliver the title compound (yellow solid, 3.90 g, yield 79.71%). $^1$H NMR (300 MHz, CDCl$_3$): δ 10.0-10.20 (m, 1H), 7.87-8.05 (m, 1H), 7.47-7.72 (m, 2H), 3.96-4.14 (m, 3H).

Embodiment 10B (Z)-Ethyl 3-(3-methoxy-4-nitrophenyl)acrylate

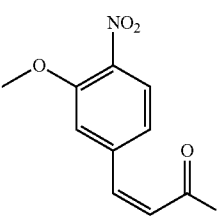

Embodiment 10A (3.90 g, 21.53 mmol) was added to THF (20 mL) at 5° C. and NaH (60%, 1.29 g, 32.30 mmol) was added in batches to the mixture and stirred for 30 minutes. And then triethyl phosphonoacetate (7.24 g, 32.30 mmol) was added dropwise to the mixture and the reaction mixture was warmed to 20° C. and stirred for 2.5 hours. TLC showed the reaction was complete, saturated NH₄Cl aqueous solution (5 mL) was added to the reaction mixture, and THF was removed by concentration. The resulting mixture was dissolved in DCM (20 mL) and washed with H₂O (30 mL×3). The organic phase was dried over anhydrous sodium sulfate, concentrated, and purified by column chromatography (PE/EA=10:1-5:1) to deliver the title compound (yellow solid, 2.95 g, yield 53.89%). LCMS (ESI) (5-95AB): m/z: 252.1 [M+1].

Embodiment 10C

Ethyl 3-(4-amino-3-methoxyphenyl)propanoate

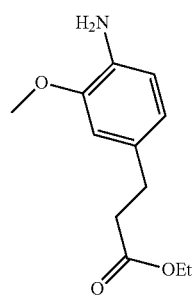 [SMILES: CCOC(=O)CCc1ccc(N)c(OC)c1]

Embodiment 10B (2.75 g, 10.95 mmol) was dissolved in MeOH (25 mL) at 16° C. and Pd/C (10%, 300 mg) was added after replacing with nitrogen. The mixture was stirred in H₂ (the pressure was 15 Psi) for 5 hours. LCMS showed the reaction complete, the reaction mixture was filtered and the filtrate was concentrated to dryness to deliver the title compound (pale red solid, 2.30 g, 96.40% yield). LCMS (ESI) (5-95AB): m/z: 224.2 [M+1].

Embodiment 10D 3-(4-Amino-3-methoxyphenyl)propan-1-ol

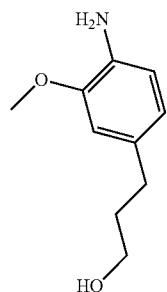

Embodiment 10C (1.90 g, 8.51 mmol) was added to THF (10 mL) at 20° C., LAH (322.95 g, 8.51 mmol) was added to the mixture and stirred for 5 hours. LCMS showed the reaction was complete and water (0.3 mL) and NaOH (1 M, 1 mL) were added successively to the reaction mixture. The resulting mixture was filtered, the filter cake was washed with DCM (20 mL) and the filtrate was concentrated to deliver the title compound (yellow oil, 1.4 g, crude). LCMS (ESI) (5-95AB): m/z: 182.0 [M+1].

Embodiment 10E tert-Butyl (4-(3-hydroxypropyl)-2-methoxyphenyl)carbamate

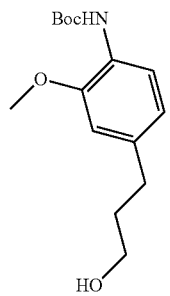 [SMILES: COc1cc(CCCO)ccc1NC(=O)OC(C)(C)C]

Embodiment 10D (1.50 g, 8.28 mmol) was added to THF (10 mL). Boc₂O (1.81 g, 8.28 mmol) was added in batches to the mixture and the reaction mixture was warmed to 60 to 70° C. and stirred for 5 hours. TLC showed the reaction was complete, the reaction mixture was concentrated and purified by column chromatography (PE/EA=10:1-5:1) to deliver the title compound (1.20 g, crude). LCMS (ESI) (5-95AB): m/z: 282.0 [M+1].

Embodiment 10F tert-Butyl (2-methoxy-4-(3-oxopropyl)phenyl)carbamate

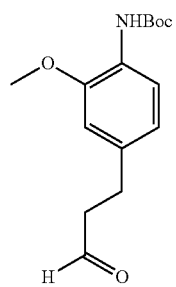 [SMILES: COc1cc(CCC=O)ccc1NC(=O)OC(C)(C)C]

Embodiment 10E (1.20 g, crude) was added to DCM (10 mL) at 20° C. and DMP (1.81 g, 4.27 mmol) was added in batches to the mixture and stirred for 3 hours. TLC showed the reaction was complete, saturated Na₂CO₃ aqueous solution (5 mL) was added to the reaction mixture, extracted with DCM (10 mL×6), washed with organic water (20 mL), dried over anhydrous sodium sulfate and concentrated to deliver the title compound (red oil, 1.23 g, crude). LCMS (ESI) (5-95AB): m/z: 180.1 [M+1-100].

Embodiment 10G tert-Butyl (4-(3-(dimethylamino)propyl)-2-methoxyphenyl)carbamate

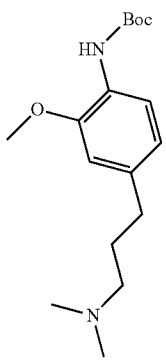 [SMILES: COc1cc(CCCN(C)C)ccc1NC(=O)OC(C)(C)C]

Embodiment 10F (1.2 g, crude) was added to MeOH (20 mL) at 20° C. and dimethylamine hydrochloride (701.24 mg, 8.60 mmol) and NaBH$_3$CN (810.64 mg, 12.90 mmol) were added to the mixture and stirred for 5 hours. LCMS showed the reaction was complete, and saturated aqueous Na$_2$CO$_3$ solution (5 mL) was added to the reaction mixture. And the reaction mixture was extracted with DCM (20 mL), the organic layer was dried over anhydrous sodium sulfate and concentrated to deliver the title compound (yellow oil, 750.00 mg, crude). LCMS (ESI) (5-95AB): m/z: 309.2 [M+1].

Embodiment 10H 4-(3-(Dimethylamino)propyl)-2-methoxy-5-nitroaniline

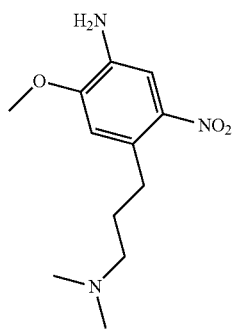 [SMILES: COc1cc(CCCN(C)C)c([N+](=O)[O-])cc1N]

Embodiment 10G (720.00 mg, 2.33 mmol) was added to H$_2$SO$_4$ (3 mL) at 0° C., guanidine nitrate (284.45 mg, 2.33 mmol) was added to the mixture and stirred for 2 hours, and then the reaction mixture was warmed to 20° C. and stirred for 1 hour. TLC showed the reaction was complete, saturated aqueous Na$_2$CO$_3$ solution was added to the reaction mixture until the pH was 7 to 8, extracted with DCM (10 mL×2), the organic layer was dried over anhydrous sodium sulfate, concentrated, and purified by column chromatography (DCM/MeOH=10:1) to deliver the title compound (yellow solid, 270.00 mg, yield 40.08%). LCMS (ESI) (5-95AB): m/z: 254.2 [M+1].

Embodiment 10I 4-(2,3-Dihydro-1H-pyrrolo[1,2-a]indol-9-yl)-N-(4-(3-(dimethylamino)propyl)-2-methoxy-5-nitrophenyl)pyrimidin-2-amine

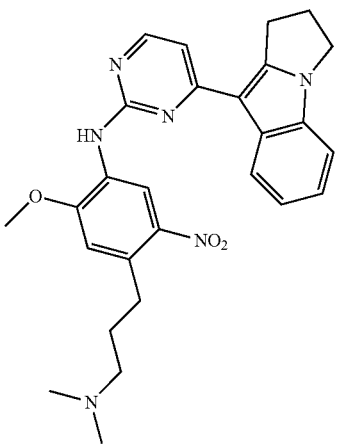 [SMILES: COc1cc(CCCN(C)C)c([N+](=O)[O-])cc1Nc1nccc(-c2c3n(c4ccccc24)CCC3)n1]

The Embodiment was prepared according to the method of Embodiment 1A except for replacing N,N',N'-trimethyl-1,2-ethylenediamine with Embodiment 10H to deliver the title compound (red solid, 300.00 mg, crude). LCMS (ESI) (5-95AB): m/z: 487.3 [M+1].

Embodiment 10J

N$^1$-(4-(2,3-Dihydro-1H-pyrrolo[1,2-a]indol-9-yl)pyrimidin-2-yl)-4-(3-(dimethylamino) propyl)-6-methoxybenzene-1,3-diamine

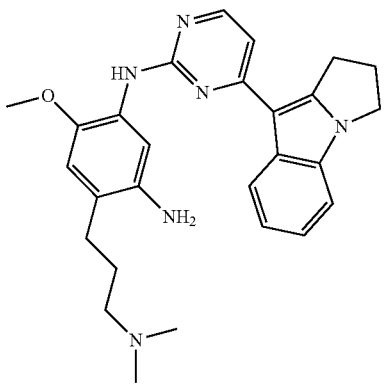 [SMILES: COc1cc(CCCN(C)C)c(N)cc1Nc1nccc(-c2c3n(c4ccccc24)CCC3)n1]

The Embodiment was prepared according to the method of Embodiment 1B except for replacing Embodiment 1A with Embodiment 10I to deliver the title compound (yellow solid, 200.00 mg, yield 66.21%). LCMS (ESI) (5-95AB): m/z: 457.2 [M+1].

Embodiment 10K

N-(5-((4-(2,3-Dihydro-1H-pyrrolo[1,2-a]indol-9-yl)pyrimidin-2-yl)amino)-2-(3-(dimethylamino)propyl)-4-methoxyphenyl)acrylamide

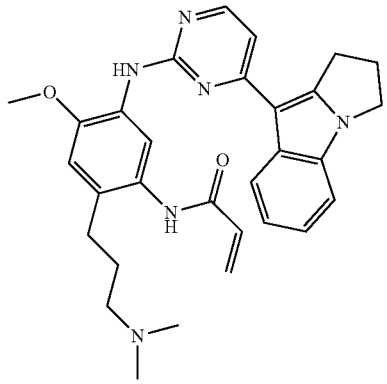 [SMILES: C=CC(=O)Nc1cc(Nc2nccc(-c3c4n(c5ccccc35)CCC4)n2)c(OC)cc1CCCN(C)C]

The Embodiment was prepared according to the method of Embodiment 1C except for replacing Embodiment 1B with Embodiment 10J to deliver the title compound (FA salt, 30.00 mg, yield 11.80%). $^1$H NMR (400 MHz, CDCl$_3$) ppm δ 9.22 (br. s., 1H), 8.58-8.78 (m, 1H), 8.50 (s, 1H), 8.19-8.37 (m, 2H), 7.65-7.79 (m, 1H), 7.16-7.26 (m, 2H), 7.00 (d, J=5.40 Hz, 1H), 6.63-6.72 (m, 1H), 6.35-6.52 (m, 2H), 5.63-5.78 (m, 1H), 4.10 (t, J=7.15 Hz, 2H), 3.82-3.92 (m, 3H), 3.28-3.43 (m, 2H), 2.53-2.78 (m, 12H), 1.88-2.18 (m, 2H). LCMS (ESI) (5-95AB): m/z: 511.3 [M+1].

Embodiment 11

N-(5-((4-(2,3-Dihydro-1H-pyrrolo[12-a]indol-9-yl)pyrimidin-2-yl)amino)-2-((1-(dimethylamino)propan-2-yl)(methyl)amino)-4-methoxyphenyl)acrylamide

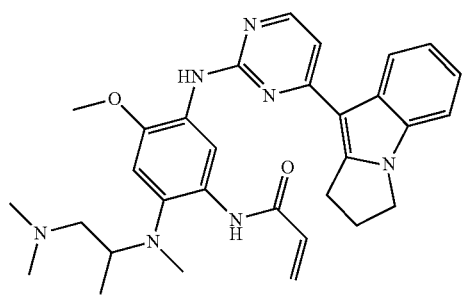 [SMILES: C=CC(=O)Nc1cc(Nc2nccc(-c3c4n(c5ccccc35)CCC4)n2)c(OC)cc1N(C)C(C)CN(C)C]

Embodiment 11A 2-((4-Amino-5-methoxy-2-nitrophenyl)(methyl)amino)-N,N-dimethylpropanamide

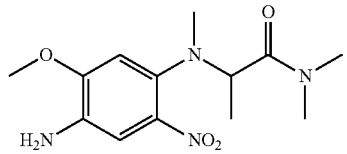

N,N-Dimethyl-2-(methylamino)propanamide (4.80 g, 36.87 mmol) and 4-fluoro-2-methoxy-5-nitroaniline (6.86 g, 36.87 mmol) were added to MeCN (10 mL), Cs$_2$CO$_3$ (48.05 g, 147.48 mmol) was added to the mixture, and the reaction mixture was warmed to 100° C. and stirred for 12 hours. TLC showed the reaction was complete, water (25 mL) was added to the reaction mixture and extracted with DCM (60 mL×3). The organic phase was washed with saturated brine (15 mL), dried over anhydrous sodium sulfate, concentrated and purified by column chromatography (PE/EA=5:1 to 1:2) to deliver the title compound (red oil, 1.00 g, yield 6.49%). $^1$H NMR (400 MHz, CDCl$_3$): δ 7.25 (s, 1H), 6.71 (s, 1H), 4.11-4.17 (m, 1H), 3.92 (s, 3H), 2.93 (d, J=8.0 Hz, 6H), 2.82 (s, 3H), 1.42 (d, J=6.8 Hz, 3H). LCMS (ESI) (10-80_CD): m/z: 297.2 [M+1].

Embodiment 11B

N1-(1-(Dimethylamino)propan-2-yl)-5-methoxy-N1-methyl-2-nitrobenzene-1,4-diamine

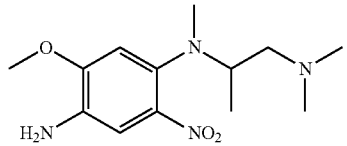

Embodiment 11A (1.00 g, 3.37 mmol) was added to THF (40 mL), BH$_3$/Me$_2$S (10M, 1.69 mL) was added to the mixture and the reaction mixture was warmed to 80° C. for 3 hours. After cooling to room temperature, MeOH (40 mL) was added to the reaction mixture and stirred for 30 minutes and then the reaction mixture was warmed to 80° C. for 1 hour. TLC showed the reaction was complete and the reaction mixture was concentrated and purified by preparative plate (DCM/MeOH=10:1) to deliver the title compound (red oil, 480.00 mg, yield 37.09%). $^1$H NMR (400 MHz, CDCl$_3$): δ 7.20 (s, 1H), 6.59 (s, 1H), 3.84 (s, 3H), 3.55-3.72 (m, 2H), 3.38-3.42 (m, 1H), 2.61 (s, 3H), 2.45-2.48 (m, 1H), 2.23-2.32 (m, 1H), 2.15 (s, 6H), 1.14 (d, J=6.4 Hz, 3H). LCMS (ESI) (10-80_CD): m/z: 283.2 [M+1].

Embodiment 11C

N1-(4-(2,3-Dihydro-1H-pyrrolo[1,2-a]indol-9-yl)pyrimidin-2-yl)-N4-(1-(dimethylamino)propan-2-yl)-2-methoxy-N4-methyl-5-nitrobenzene-1,4-diamine

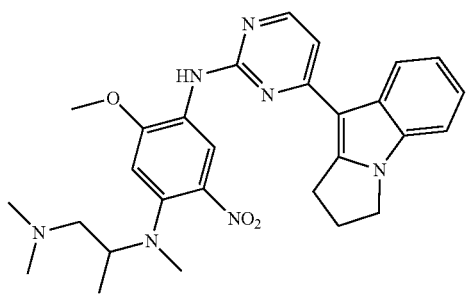 [SMILES: COc1cc(N(C)C(C)CN(C)C)c([N+](=O)[O-])cc1Nc1nccc(-c2c3n(c4ccccc24)CCC3)n1]

Embodiment 11B (165.00 mg, 584.40 mol) and Embodiment A (173.39 mg, 642.84 mol) were added to dioxane (10 mL), Pd(OAc)$_2$ (13.12 mg, 58.44 mol), Xantphos (33.81 mg, 58.44 mol) and K$_3$PO$_4$ (248.10 mg, 1.17 mmol) were added to the mixture and after replacing with nitrogen, the reaction mixture was warmed to 100° C. and stirred for 12 hours. LCMS showed the reaction was complete, the reaction mixture was concentrated, saturated aqueous Na$_2$CO$_3$ solution (10 mL) was added and extracted with DCM (30 mL×3). The organic phase was washed with saturated brine (10 mL), dried over anhydrous sodium sulfate, concentrated and purified by preparative plate (DCM/MeOH=10:1) to deliver the title compound (red oil, 220.00 mg, yield 66.25%). LCMS (ESI) (0-60_AB): m/z: 516.2 [M+1].

Embodiment 11D

N4-(4-(2,3-Dihydro-1H-pyrrolo[1,2-a]indol-9-yl)pyrimidin-2-yl)-N1-(1-(dimethylamino)propan-2-yl)-5-methoxy-N1-methylbenzene-1,2,4-triamine

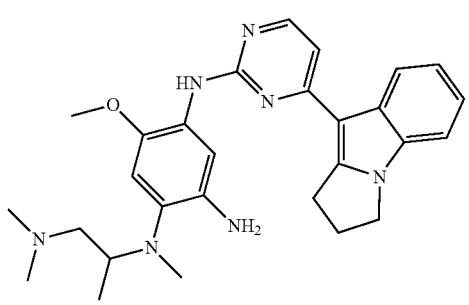 [SMILES: COc1cc(N(C)C(C)CN(C)C)c(N)cc1Nc1nccc(-c2c3n(c4ccccc24)CCC3)n1]

The Embodiment was prepared according to the method of Embodiment 1B except for replacing Embodiment 1A with Embodiment 11C to deliver the title compound (brown oil, 200.00 mg, yield 92.81%). LCMS (ESI) (0-60_AB): m/z: 486.3 [M+1].

Embodiment 11E

N-(5-((4-(2,3-Dihydro-1H-pyrrolo[12-a]indol-9-yl)pyrimidin-2-yl)amino)-2-((1-(dimethylamino)propan-2-yl)(methyl)amino)-4-methoxyphenyl)acrylamide

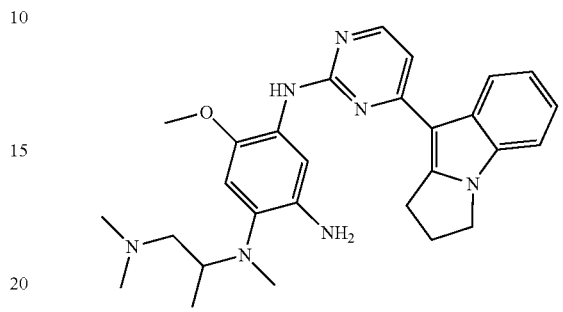

The Embodiment was prepared according to the method of Embodiment 1C except for replacing Embodiment 1B with Embodiment 11D to deliver the title compound (FA salt, 75.92 mg, yield 30.52%). $^1$H NMR (400 MHz, CD$_3$OD) δ 8.51 (s, 1H), 8.26-8.31 (m, 2H), 7.32-7.35 (m, 1H), 6.87-7.17 (m, 3H), 6.88 (s, 1H), 6.47-6.51 (m, 2H), 5.85-5.88 (m, 1H), 4.16 (t, J=7.2 Hz, 2H), 3.91-4.07 (m, 4H), 3.35-3.42 (m, 2H), 3.12-3.15 (m, 1H), 2.83-2.97 (m, 7H), 2.67-2.74 (m, 5H), 1.40 (d, J=6.4 Hz, 3H). LCMS (ESI) (0-60_AB): m/z: 540.3 [M+1].

Process 4

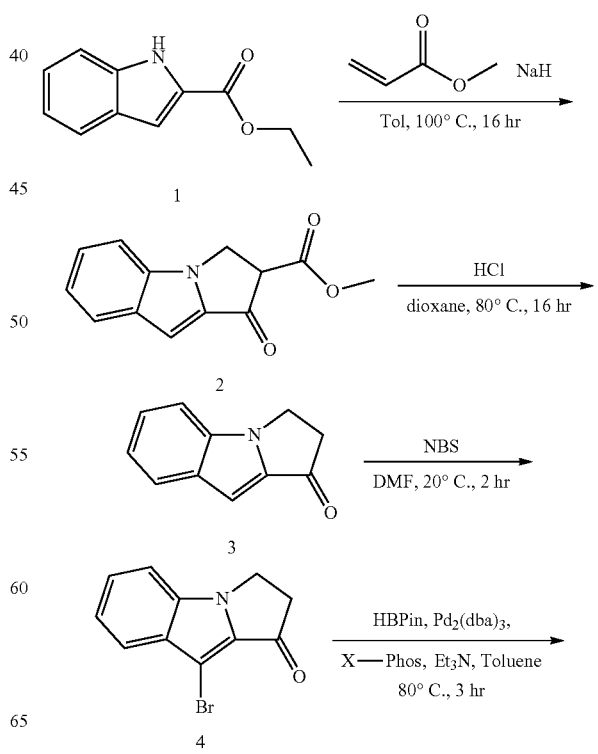

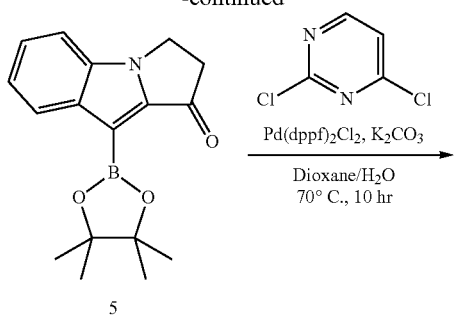
5
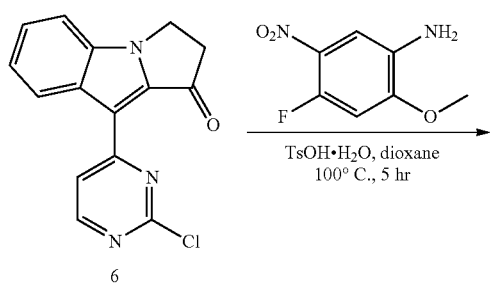
6
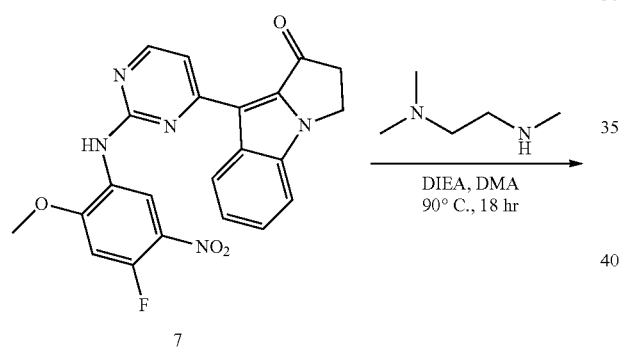
7
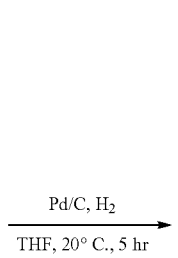
8
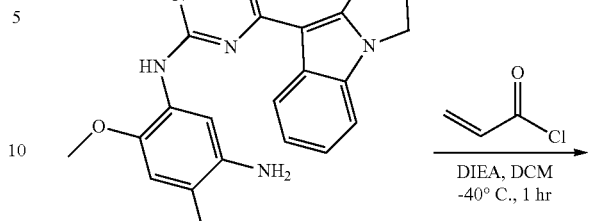
9
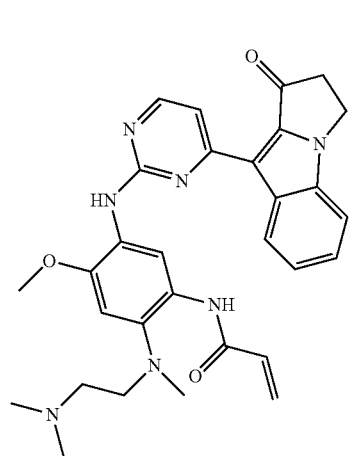
Embodiment 12
Embodiment 12
N-(2-((2-(Dimethylamino)ethyl)(methyl)amino)-4-methoxy-5-((4-(1-oxo-2,3-dihydro-1H-pyrrolo[1,2-a]indol-9-yl)pyrimidin-2-yl)amino)phenyl)acrylamide

Embodiment 12A

Methyl 1-oxo-2,3-dihydro-1H-pyrrolo[1,2-a]indole-2-carboxylate

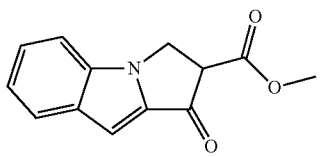 [SMILES: COC(=O)C1Cn2c(cc3ccccc32)C1=O]

Ethyl indole 2-carboxylate (4.00 g, 21.14 mmol) and methyl acrylate (3.28 g, 38.05 mmol) were added to toluene (200 mL). NaH (60%, 974.13 mg, 40.59 mmol) was added to the mixture and the reaction mixture was warmed to 100° C. and stirred for 16 hours. LCMS showed the reaction was complete and saturated aqueous NH$_4$Cl solution (100 mL) was added to the reaction mixture. The resulting reaction mixture was extracted with EA (300 mL×3), the organic phase was dried over anhydrous sodium sulfate and concentrated to deliver the title compound (yellow oil, 3.73 g, yield 76.97%). LCMS (ESI) (5-95AB): m/z: 229.9 [M+1].

Embodiment 12B 2,3-Dihydro-1H-pyrrolo[1,2-a]indol-1-one

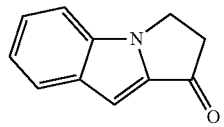 [SMILES: O=C1CCn2c1cc1ccccc12]

Embodiment 12A (3.73 g, 16.27 mmol) was added to dioxane (150 mL), hydrochloric acid (2M, 40 mL) was added to the mixture and the reaction mixture was warmed to 80° C. and stirred for 16 hours. LCMS showed the reaction was complete and sodium hydroxide solution (2M, 100 mL) was added to the reaction mixture. The resulting mixture was extracted with EA (100 mL×3) and the organic phase was concentrated and purified by column chromatography (PE/EA=100:1 to 5:1) to deliver the title compound (yellow solid, 1.52 g, 51.84%). $^1$H NMR (400 MHz, CDCl$_3$): δ, 7.80-7.78 (m, 1H), 7.47-7.39 (m, 2H), 7.39-7.22 (m, 1H), 7.04 (d, J=0.8 Hz, 1H), 4.49-4.46 (m, 2H), 3.27-3.24 (m, 2H). LCMS (ESI) (5-95AB): m/z: 171.9 [M+1].

Embodiment 12C

9-Bromo-2,3-dihydro-1H-pyrrolo[1,2-a]indol-1-one

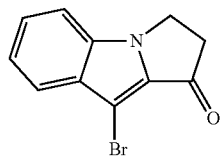 [SMILES: O=C1CCn2c1c(Br)c1ccccc12]

Embodiment 12B (6.00 g, 35.05 mmol) was added to DMF (100 mL) at 20° C. and NBS (6.24 g, 35.05 mmol) was added to the mixture and stirred for 2 hours. The reaction mixture was filtered, the filtrate was concentrated, and purified by column chromatography (PE/EA=20:1 to 3:1) to deliver the title compound (yellow solid, 7.98 g, yield 591.04%). $^1$H NMR (400 MHz, CDCl$_3$): δ, 7.74 (d, J=8.4 Hz, 1H), 7.47-7.42 (m, 2H), 7.31-7.27 (m, 1), 4.46-4.43 (m, 2H), 3.26-3.29 (m, 2H). LCMS (ESI) (5-95AB): m/z: 251.9 [M+3].

Embodiment 12D 9-(4,4,5,5-Tetramethyl-1,3,2-dioxaborolan-2-yl)-2,3-dihydro-1H-pyrrolo[1,2-a]indol-1-one

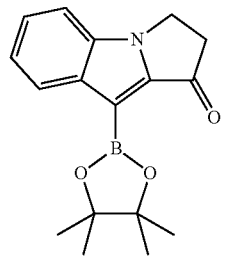 [SMILES: CC1(C)OB(c2c3n(c4ccccc24)CCC3=O)OC1(C)C]

Embodiment 12C (7.80 g, 31.19 mmol) and B$_2$Pin$_2$ (11.98 g, 93.57 mmol) were added to toluene (150 mL). Pd$_2$(dba)$_3$ (571.23 mg, 623.80 μmol), X-phos (1.19 g, 2.50 mmol) and TEA (9.47 g, 93.57 mmol) were added to the mixture and after replacing with nitrogen, the reaction mixture was warmed to 80° C. and stirred for 3 hours. LCMS showed the reaction was complete, the reaction mixture was filtered and the filtrate was concentrated to deliver the title compound (brown oil, 10.00 g, crude). LCMS (ESI) (5-95AB): m/z: 298.0 [M+1].

Embodiment 12E 9-(2-Chloropyrimidin-4-yl)-2,3-dihydro-1H-pyrrolo[1,2-a]indol-1-one

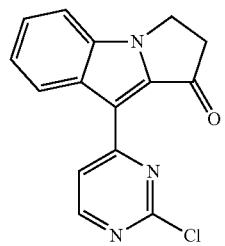 [SMILES: O=C1CCn2c1c(-c1ccnc(Cl)n1)c1ccccc12]

Embodiment 12D (11.00 g, 37.02 mmol) and 2,4-dichloropyrimidine (11.03 g, 74.03 mmol) were added to dioxane/water (15:1, 160 mL) and Pd(dppf)Cl$_2$ (812.56 mg, 1.11 mmol), K$_2$CO$_3$ (10.23 g, 74.03 mmol) were added to the mixture, and after replacing with nitrogen, the reaction mixture was warmed to 70° C. and stirred for 10 hours. LCMS showed the reaction was complete, the reaction mixture was filtered, the filtrate was concentrated, and purified by column chromatography (PE/DCM/EA=10:1:0 to 0:1:3) to deliver the title compound (yellow solid, 1.80 g, yield 12.00%). ¹H NMR (400 MHz, CDCl₃): δ, 9.00 (d, J=8.8 Hz, 1H), 8.73-8.80 (m, 1H), 8.61 (d, J=5.2 Hz, 1H), 7.53-7.40 (m, 3H), 4.55 (t, J=6.4 Hz, 2H), 3.43-3.36 (m, 2H). LCMS (ESI) (5-95AB): m/z: 283.9 [M+1].

Embodiment 12F 9-(2-((4-Fluoro-2-methoxy-5-nitrophenyl)amino)pyrimidin-4-yl)-2,3-dihydro-1H-pyrrolo[1,2-a]indol-1-one

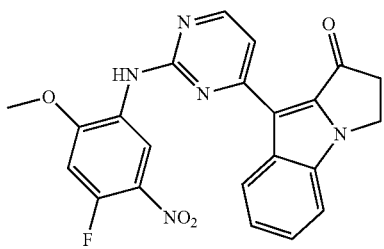 [SMILES: COc1cc(F)c([N+](=O)[O-])cc1Nc1nccc(-c2c3n(c4ccccc24)CCC3=O)n1]

The Embodiment was prepared according to the method of Embodiment B except for replacing Embodiment A with Embodiment 12E to deliver the title compound (yellow solid, 280.00 mg, yield 8.31%). LCMS (ESI) (5-95AB): m/z: 434.0 [M+1].

Embodiment 12G 9-(2-((4-((2-(Dimethylamino)ethyl)(methyl)amino)-2-methoxy-5-nitrophenyl)amino)pyrimidin-4-yl)-2,3-dihydro-1H-pyrrolo[1,2-a]indol-1-one

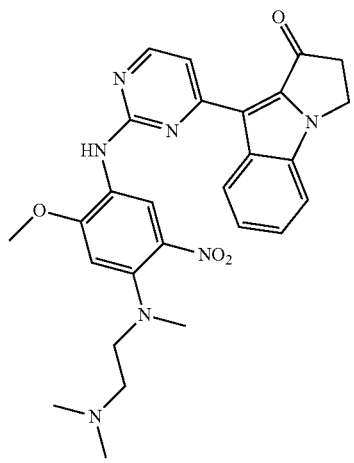 [SMILES: COc1cc(N(C)CCN(C)C)c([N+](=O)[O-])cc1Nc1nccc(-c2c3n(c4ccccc24)CCC3=O)n1]

The Embodiment was prepared according to the method of Embodiment 1A by replacing Embodiment B with Embodiment 12F to deliver the title compound (brown solid, 140.00 mg, yield 54.04%). ¹H NMR (400 MHz, CDCl₃): δ, 9.03 (s, 1H), 8.35-8.24 (m, 2H), 7.36 (d, J=7.2 Hz, 1H), 7.24-7.12 (m, 3H), 7.09 (s, 1H), 4.21-4.14 (m, 2H), 4.10 (s, 3H), 3.53-3.48 (m, 2H), 3.43-3.37 (m, 4H), 2.99 (s, 6H), 2.88 (s, 3H), 2.76-2.69 (m, 2H). LCMS (ESI) (0-60AB): m/z: 516.2 [M+1].

Embodiment 12H 9-(2-((5-Amino-4-((2-(dimethylamino)ethyl)(methyl)amino)-2-methoxyphenyl)amino)pyrimidin-4-yl)-2,3-dihydro-1H-pyrrolo[1,2-a]indol-1-one

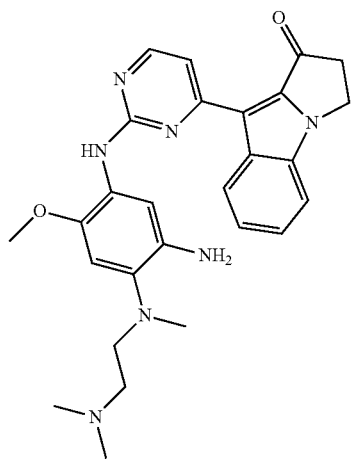

The Embodiment was prepared according to the method of Embodiment 1B except for replacing Embodiment 1A with Embodiment 12G to deliver the title compound (brown solid, 140.00 mg, crude). 1H NMR (400 MHz, CDCl₃): δ, 8.98 (d, J=8.4 Hz, 1H), 8.51 (d, J=5.2 Hz, 1H), 8.20 (s, 1H), 8.06-8.01 (m, 1H), 7.68 (s, 1H), 7.50-7.48 (m, 2H), 7.02-6.99 (m, 1H), 6.74-6.69 (m, 1H), 4.55 (t, J=6.0 Hz, 2H), 3.89 (s, 3H), 3.38-3.37 (m, 2H), 3.28-3.26 (m, 2H), 3.11 (s, 3H), 2.95-2.94 (m, 2H), 2.75 (s, 6H). LCMS (ESI) (0-60AB): m/z: 486.1 [M+1].

Embodiment 12I

N-(2-((2-(Dimethylamino)ethyl)(methyl)amino)-4-methoxy-5-((4-(1-oxo-2,3-dihydro-1H-pyrrolo[1,2-a]indol-9-yl)pyrimidin-2-yl)amino)phenyl)acrylamide

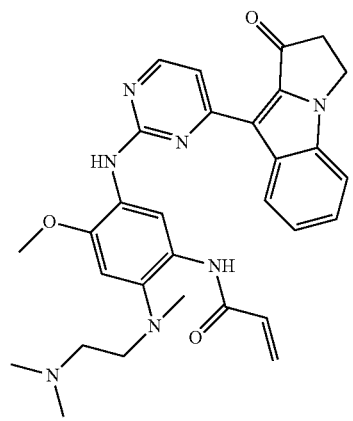 [SMILES: C=CC(=O)Nc1cc(Nc2nccc(-c3c4n(c5ccccc35)CCC4=O)n2)c(OC)cc1N(C)CCN(C)C]

The Embodiment was prepared according to the method of Embodiment 1C except for replacing Embodiment 1B with Embodiment 12H to deliver the title compound (FA salt, 50.00 mg, yield 28.78%). 1H NMR (400 MHz, CD$_3$OD): δ 8.75-8.64 (m, 2H), 8.21 (d, J=6.4 Hz, 1H), 7.82-7.68 (m, 2H), 7.52 (t, J=8.0 Hz, 1H), 7.38-7.35 (m, 1H), 7.11 (s, 1H), 6.71-6.60 (m, 1H), 6.53-6.43 (m, 1H), 5.87 (dd, J=1.6, J$_2$=10.4 Hz, 1H), 4.6-4.63 (m, 2H), 3.97 (s, 3H), 3.64-3.56 (m, 2H), 3.46-3.36 (m, 4H), 2.94 (s, 6H), 2.84 (s, 3H). LCMS (ESI) (5-95AB): m/z: 540.2 [M+1].
Process 5
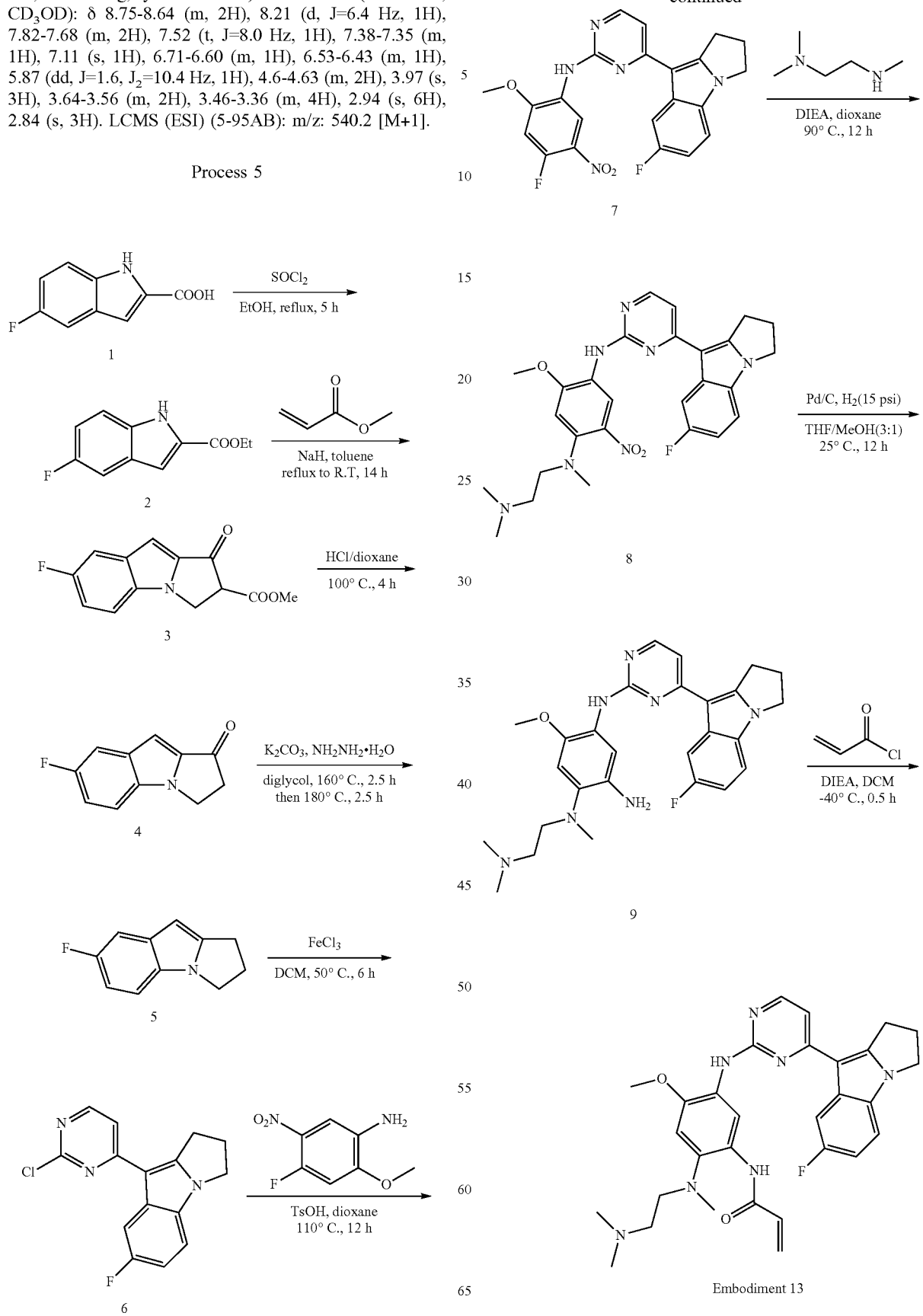
Embodiment 13

Embodiment 13

N-(2-((2-(Dimethylamino)ethyl)(methyl)amino)-5-((4-(7-fluoro-2,3-dihydro-1H-pyrrolo[1,2-a]indol-9-yl)pyrimidin-2-yl)amino)-4-methoxyphenyl)acrylamide

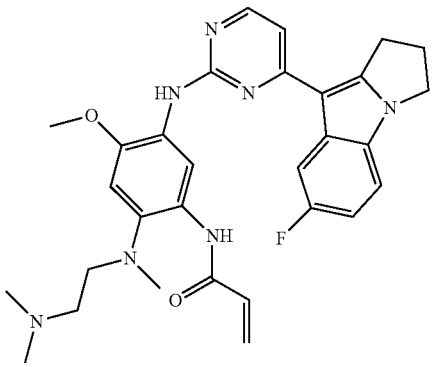 [SMILES: C=CC(=O)Nc1cc(Nc2nccc(-c3c4n(c5ccc(F)cc35)CCC4)n2)c(OC)cc1N(C)CCN(C)C]

Embodiment 13A

Ethyl 5-fluoro-1H-indole-2-carboxylate

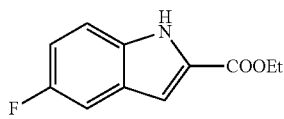 [SMILES: CCOC(=O)c1cc2cc(F)ccc2[nH]1]

5-Fluorondole-2-carboxylic acid (5.00 g, 27.91 mmol) was added to ethanol (50 mL) at 0° C. SOCl$_2$ (9.84 g, 82.71 mmol) was added to the mixture and the reaction mixture was warmed to reflux and stirred for 5 hours. TLC showed the reaction was complete, the reaction mixture was concentrated, and saturated aqueous NaHCO$_3$ solution (15 mL) was added thereto. The resulting mixture was extracted with DCM (100 mL×2) and the organic phase was dried over anhydrous sodium sulfate and concentrated to deliver the title compound (light yellow solid, 5.50 g, yield 85.60%). $^1$H-NMR (400 MHz, CDCl$_3$) δ 9.00 (br. s., 1H), 7.31-7.39 (m, 2H), 7.19 (d, J=1.2 Hz, 1H), 7.10 (td, J=9.0, 2.4 Hz, 1H), 4.43 (q, J=7.1 Hz, 2H), 1.43 (t, J=7.1 Hz, 3H).

Embodiment 13B

Methyl 6-fluoro-3-oxo-1,2-dihydropyrrolo[1,2-a]indole-2-carboxylate

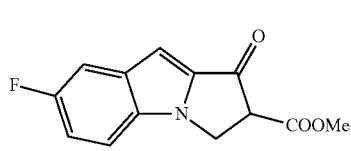 [SMILES: COC(=O)C1Cn2c(cc3cc(F)ccc32)C1=O]

The Embodiment was prepared according to the method of Embodiment 12A except for replacing ethyl indole 2-carboxylate with Embodiment 13A to deliver the title compound (yellow oil, 8.20 g, crude). LCMS (ESI) (5-95 AB): m/z: 270.0 [M+23] RT: 0.658 min/2 min.

Embodiment 13C

6-Fluoro-1,2-dihydropyrrolo[1,2-a]indol-3-one

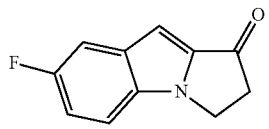 [SMILES: O=C1CCn2c1cc1cc(F)ccc12]

The Embodiment was prepared according to the method of Embodiment 12B except for replacing Embodiment 12A with Embodiment 13B to deliver the title compound (yellow solid, 3.08 g, yield 48.43%). $^1$H-NMR (400 MHz, CDCl$_3$) δ 7.35-7.45 (m, 1H), 7.10-7.20 (m, 1H), 6.96 (s, 1H), 4.44 (t, J=6.1 Hz, 2H), 3.23 (t, J=6.0 Hz, 2H).

Embodiment 13D

6-Fluoro-2,3-dihydro-1H-pyrrolo[1,2-α]indole

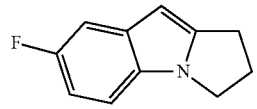 [SMILES: Fc1ccc2c(c1)cc1n2CCC1]

Embodiment 13C (3.04 g, 16.07 mmol) was added to diethylene glycol (50 mL), K$_2$CO$_3$ (15.00 g, 108.53 mmol) and N$_2$H$_4$.H$_2$O (5.96 g, 119.07 mmol) were added to the mixture. And after replacing with nitrogen, the reaction mixture was warmed to 160° C. and stirred for 2.5 hours, and then the reaction mixture was warmed to 180° C. and stirred for 2.5 hours. TLC showed the reaction was complete and EA (100 mL) was added to the reaction mixture. After washing with water (30 mL×2), the organic phase was concentrated and purified by preparative plate (PE/EA=3:1) to deliver the title compound (white solid, 1.02 g, yield 32.81%). $^1$H-NMR (400 MHz, CDCl$_3$) δ 7.21 (dd, J=10.0, 2.5 Hz, 1H), 7.14 (dd, J=8.7, 4.5 Hz, 1H), 6.87 (td, J=9.1, 2.5 Hz, 1H), 6.15 (s, 1H), 4.07 (t, J=7.0 Hz, 2H), 3.04 (t, J=7.4 Hz, 2H), 2.56-2.70 (m, 2H).

Embodiment 13E 4-(2-Chloropyrimidin-4-yl)-6-fluoro-2,3-dihydro-1H-pyrrolo[1,2-a]indole

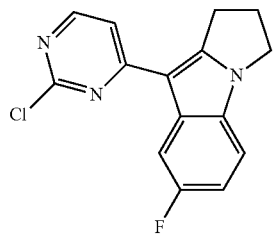 [SMILES: Fc1ccc2c(c1)c(-c1ccnc(Cl)n1)c1n2CCC1]

The Embodiment was prepared according to the method of Embodiment A except for replacing Embodiment A6 with Embodiment 13D to deliver the title compound (yellow solid, 716.00 mg, yield 38.35%). $^1$H-NMR (400 MHz, CDCl$_3$) δ 8.41 (d, J=5.5 Hz, 1H), 8.08 (dd, J=10.3, 2.4 Hz, 1H), 7.28 (s, 1H), 7.27 (s, 1H), 7.20 (dd, J=8.7, 4.5 Hz, 1H), 7.00 (td, J=8.9, 2.5 Hz, 1H), 4.17 (t, J=7.2 Hz, 2H), 3.40 (t, J=7.5 Hz, 2H), 2.77 (quin, J=7.3 Hz, 2H).

Embodiment 13F 4-(6-Fluoro-2,3-dihydro-1H-pyrrolo[12-a]indol-4-yl)-N-(4-fluoro-2-methoxy-5-nitrophenyl)pyrimidin-2-amine

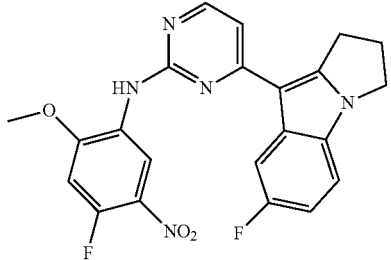 [SMILES: COc1cc(F)c([N+](=O)[O-])cc1Nc1nccc(-c2c3n(c4ccc(F)cc24)CCC3)n1]

The Embodiment was prepared according to the method of Embodiment B except for replacing Embodiment A with Embodiment 13E to deliver the title compound (yellow solid, 378.00 mg, crude). LCMS (ESI) (5-95 AB): m/z: 438.1 [M+1] RT: 0.672 min/2 min.

Embodiment 13G

N4-(2-(dimethylamino)ethyl)-N1-(4-(6-fluoro-2,3-dihydro-1H-pyrrolo[1,2-a]indol-4-yl)pyrimidin-2-yl)-2-methoxy-N4-methyl-5-nitrobenzene-1,4-diamine

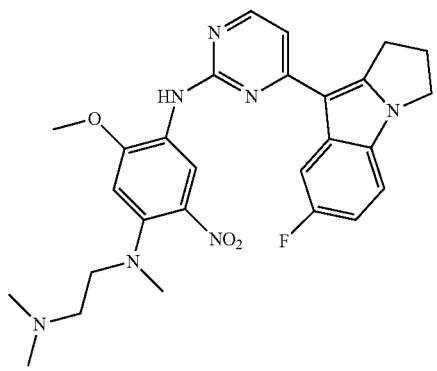 [SMILES: COc1cc(N(C)CCN(C)C)c([N+](=O)[O-])cc1Nc1nccc(-c2c3n(c4ccc(F)cc24)CCC3)n1]

The Embodiment was prepared according to the method of Embodiment 1A except for replacing Embodiment B with Embodiment 13F to deliver the title compound (brown solid, 373.00 mg, yield 69.78%). $^1$H-NMR (400 MHz, CDCl$_3$) δ 9.09 (s, 1H), 8.36 (d, J=4.0 Hz, 1H), 7.99 (d, J=8.91 Hz, 1H), 7.44 (s, 1H), 7.20 (dd, J=8.72, 4.58 Hz, 1H), 6.92-7.01 (m, 2H), 6.72 (s, 1H), 4.15 (t, J=7.15 Hz, 2H), 4.01 (s, 3H), 3.42 (t, J=7.47 Hz, 2H), 3.32 (t, J=7.03 Hz, 2H), 2.90 (s, 3H), 2.74 (quin, J=7.31 Hz, 2H), 2.66 (d, J=6.65 Hz, 2H), 2.34 (s, 6H).

Embodiment 13H

N1-(2-(dimethylamino)ethyl)-N4-(4-(6-fluoro-2,3-dihydro-1H-pyrrolo[1,2-a]indol-4-yl)pyrimidin-2-yl)-5-methoxy-N1-methylbenzene-1,2,4-triamine

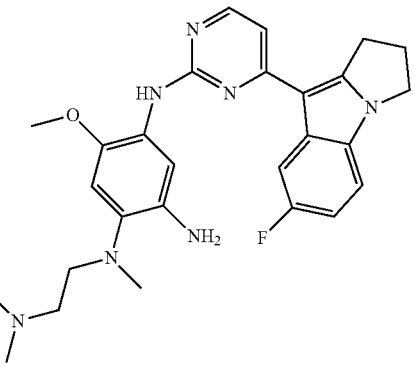

The Embodiment was prepared according to the method of Embodiment 1B except for replacing Embodiment 1A with Embodiment 12G to deliver the title compound (pink solid, 306.00 mg, yield 64.46%). $^1$H-NMR (400 MHz, CDCl$_3$) δ 8.21-8.29 (m, 2H), 8.05 (s, 1H), 7.52 (s, 1H), 7.15 (dd, J=8.6, 4.5 Hz, 1H), 6.89-6.99 (m, 1H), 6.78 (d, J=5.4 Hz, 1H), 6.73 (s, 1H), 4.09 (t, J=7.2 Hz, 2H), 3.83-3.90 (m, 3H), 3.30 (t, J=7.4 Hz, 2H), 2.98 (t, J=6.9 Hz, 2H) 2.65-2.73 (m, 4H), 2.38-2.48 (m, 2H), 2.23-2.30 (m, 6H).

Embodiment 13I

N-(2-((2-(Dimethylamino)ethyl)(methyl)amino)-5-((4-(6-fluoro-2,3-dihydro-1H-pyrrolo[1,2-a]indol-4-yl)pyrimidin-2-yl)amino)-4-methoxyphenyl)acrylamide

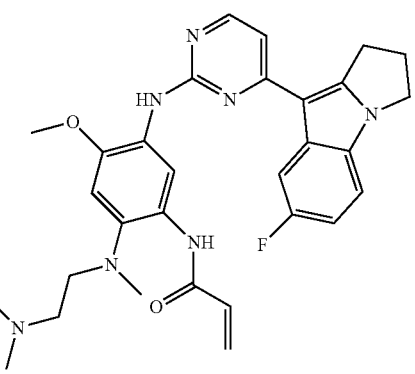

The Embodiment was prepared according to the method of Embodiment 1C except for replacing Embodiment 1B with Embodiment 13H to deliver the title compound (FA salt, 13.60 mg, yield 7.53%). LCMS (ESI) (0-60 AB): m/z: 544.2 [M+1] RT: 2.075 min/4 min; $^1$H-NMR (400 MHz, DMSO) δ 10.08 (s, 1H), 8.61 (s, 1H), 8.27 (br. s., 1H), 8.24 (d, J=5.4 Hz, 1H), 8.17 (s, 1H), 8.01 (d, J=10.9 Hz, 1H), 7.34

(dd, J=8.7, 4.7 Hz, 1H), 7.00 (s, 1H), 6.93 (td, J=9.1, 2.64 Hz, 1H), 6.89 (d, J=5.5 Hz, 1H), 6.43 (dd, J=17.0, 10.1 Hz, 1H), 6.15 (dd, J=17.0, 1.88 Hz, 1H), 5.66-5.72 (m, 1H), 4.12 (t, J=7.1 Hz, 2H), 3.78 (s, 3H), 3.27 (t, J=7.4 Hz, 3H), 2.93 (t, J=5.5 Hz, 2H), 2.69 (s, 3H), 2.59 (quin, J=7.2 Hz, 2H), 2.44 (t, J=5.6 Hz, 2H).
Process 6
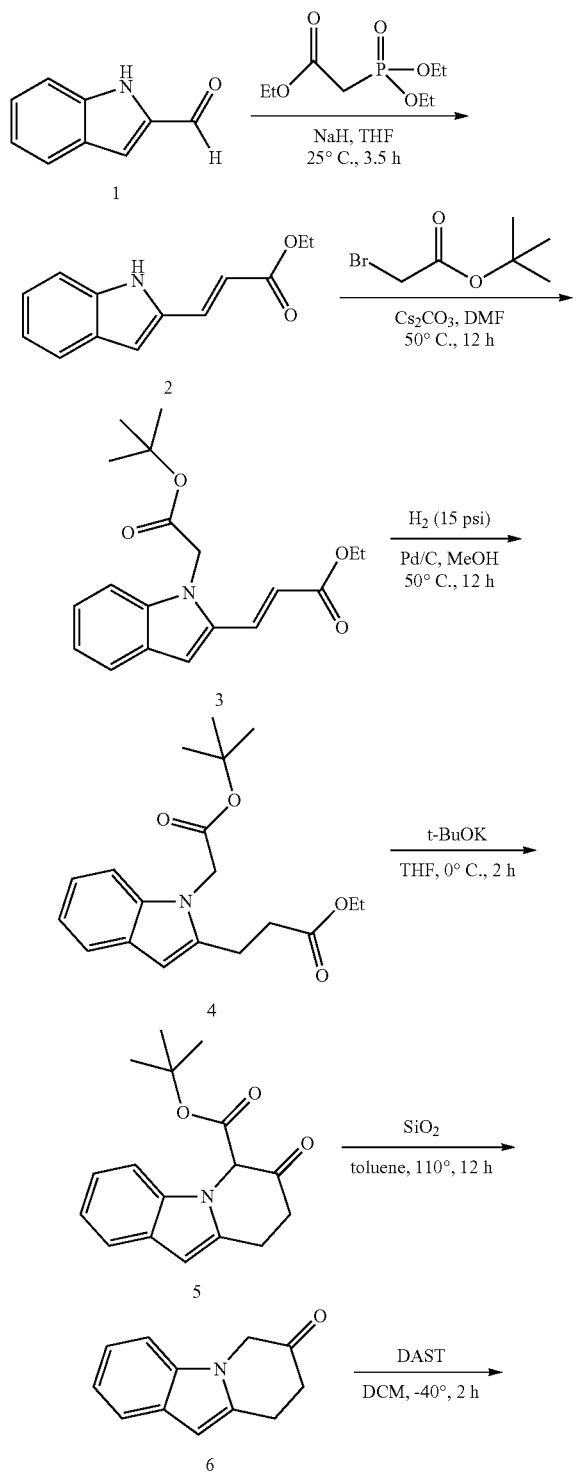
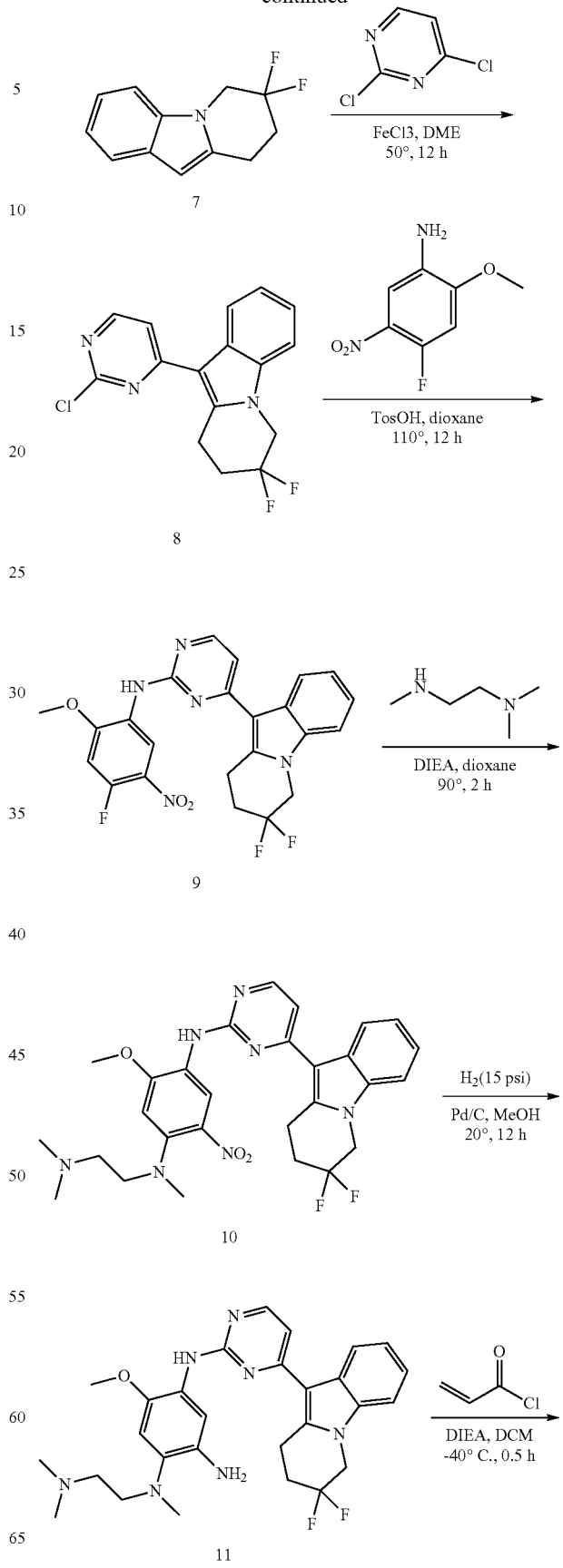

Embodiment 14

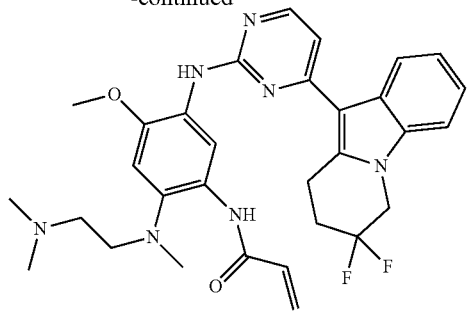

Embodiment 14

N-(5-((4-(7,7-Difluoro-8,9-dihydro-6H-pyrido[1,2-a]indol-10-yl)pyrimidin-2-yl)amino)-2-((2-(dimethylamino)ethyl)(methyl)amino)-4-methoxyphenyl)acrylamide

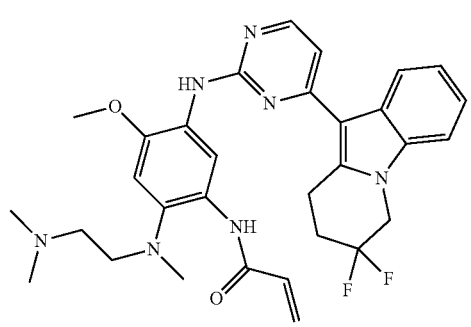 [SMILES: C=CC(=O)Nc1cc(Nc2nccc(-c3c4n(c5ccccc35)CC(F)(F)CC4)n2)c(OC)cc1N(C)CCN(C)C]

Embodiment 14A (E)-Ethyl 3-(1H-indol-2-yl)acrylate

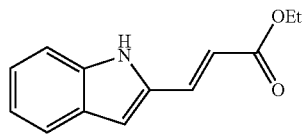 [SMILES: CCOC(=O)/C=C/c1cc2ccccc2[nH]1]

Indole-2-carboxaldehyde (5.00 g, 51.66 mmol) was added to THF (30 mL) at 25° C. Triethyl phosphonoacetate (11.58 g, 51.66 mmol) and NaH (2.76 g, 68.88 mmol) were slowly added to the mixture and stirred for 3 hours after replacing with nitrogen. TLC showed the reaction was complete and the reaction mixture was slowly added to saturated aqueous NH₄Cl solution (15 mL), extracted with DCM (20 mL×3). The organic phase was washed with saturated brine (10 mL), dried over anhydrous sodium sulfate, concentrated and purified by column chromatography (PE/EA=20:1 to 10:1) to deliver the title compound (pale yellow solid, 5.20 g, yield 70.15%). ¹H NMR (400 MHz, CDCl₃) δ 8.33 (br. s., 1H), 7.69 (d, J=16.0 Hz, 1H), 7.62 (d, J=8.0 Hz, 1H), 7.34-7.39 (m, 1H), 7.26-7.30 (m, 1H), 7.09-7.15 (m, 1H), 6.82 (d, J=1.6 Hz, 1H), 6.22 (d, J=16.0 Hz, 1H), 4.28 (q, J=7.2 Hz, 2H), 1.35 (t, J=7.2 Hz, 3H), 1.35 (t, J=7.15 Hz, 3H).

Embodiment 14B (E)-Ethyl 3-(1-(2-(tert-butoxy)-2-oxoethyl)-indol-2-yl)-2-acrylate

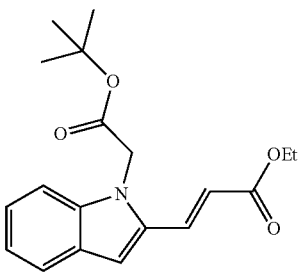 [SMILES: CCOC(=O)/C=C/c1cc2ccccc2n1CC(=O)OC(C)(C)C]

Embodiment 14A (7.00 g, 32.52 mmol) was added to DMF (100 mL) and tert-butyl 2-bromoacetate (12.69 g, 65.04 mmol) and Cs₂CO₃ (21.19 g, 65.04 mmol) were added to the mixture, and the reaction mixture was warmed to 50° C. and stirred for 12 hours. TLC showed the reaction was complete and the reaction mixture was filtered. The filter cake was washed with EA (150 mL), the filtrate was concentrated and purified by column chromatography (PE/EA=10:1) to deliver the title compound (pale yellow solid, 8.50 g, yield 73.80%). ¹H-NMR (400 MHz, CDCl₃): δ 7.61-7.73 (m, 2H), 7.29-7.31 (m, 1H), 7.24-7.28 (m, 1H), 7.16 (ddd, J=7.9, 6.0, 1.8 Hz, 1H), 7.03 (s, 1H), 6.49 (d, J=15.8 Hz, 1H), 4.25-4.34 (m, 2H), 1.46 (s, 9H), 1.36 (t, J=7.1 Hz, 3H).

Embodiment 14C

Ethyl 3-(1-(2-(tert-butoxy)-2-oxoethyl) indol-2-yl) propanoate

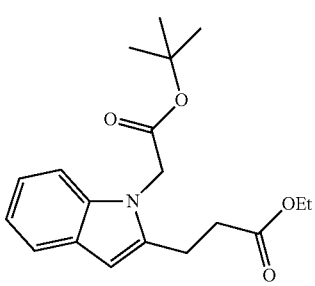 [SMILES: CCOC(=O)CCc1cc2ccccc2n1CC(=O)OC(C)(C)C]

Embodiment 14B (8.50 g, 25.81 mmol) was dissolved in MeOH (100 mL) at 20° C. and Pd/C (10%, 800 mg) was added after replacing with nitrogen. The mixture was stirred in H₂ (the pressure was 15 psi) for 12 hours. LCMS showed the reaction was complete and the reaction mixture was filtered and the filtrate was concentrated to dryness to deliver the title compound (yellow oil, 8.00 g, crude).

Embodiment 14D 7-oxo-8,9-dihydro-6H-pyrido[1,2-a]indole-6-carboxylate

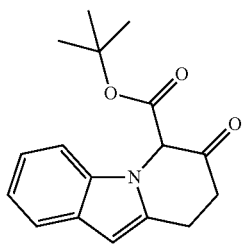 [SMILES: CC(C)(C)OC(=O)C1C(=O)CCc2cc3ccccc3n21]

Embodiment 14C (8.00 g, 24.14 mmol) was added to THF (60 mL) at 0° C., t-BuOK (5.42 g, 48.28 mmol) was added to the mixture and stirred for 2 hours. TLC showed the reaction was complete and dilute hydrochloric acid (0.5 M) was added to the reaction mixture until the pH was 6 to 7. EA (150 mL) and water (30 mL) were added and the organic phase was concentrated and purified by column chromatography (PE/EA=60:1 to 20:1) to deliver the title compound (brown solid, 7.00 g, yield 98.59%). $^1$H-NMR (400 MHz, CDCl$_3$): δ 7.59 (d, J=7.1 Hz, 1H), 7.13-7.26 (m, 3H), 6.39 (s, 1H), 5.42 (s, 1H), 3.25-3.41 (m, 2H), 2.95 (dt, J=16.3, 4.1 Hz, 1H), 2.62-2.75 (m, 1H), 1.41 (s, 9H).

Embodiment 14E 8,9-Dihydro-6H-pyrido[1,2-a]indol-7-one

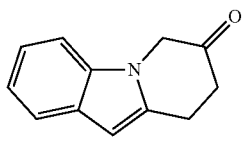 [SMILES: O=C1CCc2cc3ccccc3n2C1]

Embodiment 14D (7.00 g, 24.53 mmol) was added to toluene (100 mL), SiO$_2$ (7.00 g, 116.52 mmol) was added to the mixture and the mixture was replaced with nitrogen and the reaction mixture was warmed to 110° C. and stirred for 12 hours. The reaction mixture was filtered and the filtrate was concentrated and purified by column chromatography (PE/EA=50:1) to deliver the title compound (yellow solid, 1.75 g, yield 35.82%). $^1$H-NMR (400 MHz, CDCl$_3$): δ 7.60 (d, J=7.6 Hz, 1H), 7.19-7.26 (m, 2H), 7.13-7.19 (m, 1H), 6.38 (s, 1H), 4.69 (s, 2H), 3.28 (t, J=6.5 Hz, 2H), 2.74-2.86 (m, 2H).

Embodiment 14F 7,7-Dichloro-6,7,8,9-tetrahydropyrido[1,2-a]indole

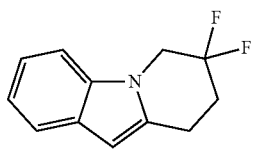 [SMILES: FC1(F)CCc2cc3ccccc3n2C1]

Embodiment 14E (1.70 g, 9.18 mmol) was added to DCM (20 mL) at −40° C. and DAST (5.92 g, 36.72 mmol) was added to the mixture and stirred for 2 hours. TLC showed the reaction was complete, saturated aqueous NaHCO$_3$ solution (10 mL) was added to the reaction mixture, and then extracted with DCM (50 mL). The organic phase was washed with water (15 mL), concentrated and purified by column chromatography (PE/EA=30:1 to 10:1) to deliver the title compound (yellow solid, 1.17 g, yield 59.66%). $^1$H-NMR (400 MHz, CDCl$_3$): δ 7.56 (d, J=7.6 Hz, 1H), 7.12-7.26 (m, 3H), 6.31 (s, 1H), 4.35 (t, J=12.7 Hz, 2H), 3.20 (t, J=6.8 Hz, 2H), 2.38 (tt, J=13.4, 6.7 Hz, 2H).

Embodiment 14G 10-(2-Chloropyrimidin-4-yl)-7,7-difluoro-8,9-dihydro-6H-pyrido[1,2-a]indole

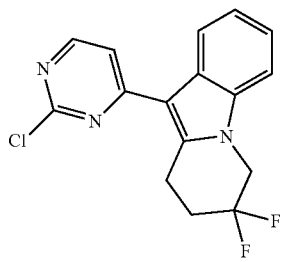 [SMILES: FC1(F)CCc2c(-c3ccnc(Cl)n3)c3ccccc3n2C1]

The Embodiment was prepared according to the method of Embodiment A by replacing Embodiment A6 with Embodiment 14F to deliver the title compound (yellow solid, 600.00 mg, yield 49.25%). $^1$H-NMR (400 MHz, CDCl$_3$): δ 8.52-8.56 (m, 1H), 8.03-8.10 (m, 1H), 7.58 (d, J=5.4 Hz, 1H), 7.30-7.37 (m, 3H), 4.43 (t, J=12.3 Hz, 2H), 3.69 (t, J=6.8 Hz, 2H), 2.47 (tt, J=13.4, 6.7 Hz, 2H).

Embodiment 14H 4-(7,7-Dichloro-8,9-dihydro-6H-pyrido[1,2-a]indol-10-yl)-N-(4-fluoro-2-methoxy-5-nitrophenyl)pyrimidin-2-amine

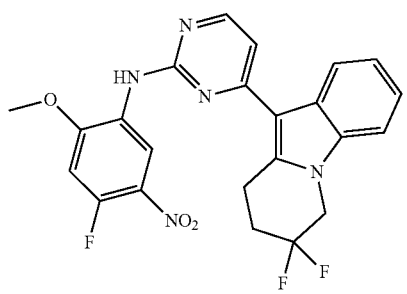 [SMILES: COc1cc(F)c([N+](=O)[O-])cc1Nc1nccc(-c2c3n(c4ccccc24)CC(F)(F)CC3)n1]

The Embodiment was prepared according to the method of Embodiment B except for replacing Embodiment A with Embodiment 14G to deliver the title compound (yellow solid, 1.06 g, yield 78.01%). $^1$H-NMR (400 MHz, DMSO-d$_6$): δ 8.96 (m, 1H), 8.26-8.60 (m, 2H), 8.08 (m, 1H), 7.54 (m, 1H), 7.12-7.44 (m, 4H), 4.65 (m, 2H), 4.02 (m, 3H), 3.49 (m, 2H), 2.52 (m, 2H).

Embodiment 14I

N[1]-(4-(7,7-Difluoro-8,9-dihydro-6H-pyrido[1,2-a]indol-10-yl)pyrimidin-2-yl)-4-(2-(dimethylamino)ethyl)-2-methoxy-N4-methyl-5-nitrobenzene-1,4-diamine

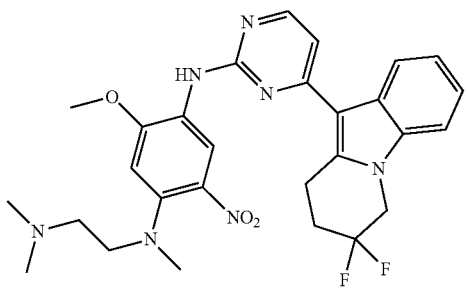 [SMILES: COc1cc(N(C)CCN(C)C)c([N+](=O)[O-])cc1Nc1nccc(-c2c3n(c4ccccc24)CC(F)(F)CC3)n1]

The Embodiment was prepared according to the method of Embodiment 1A except for replacing Embodiment B with Embodiment 14I to deliver the title compound (brown solid, 1.05 g, 75.98% yield). LCMS (ESI) (5-95 AB): m/z: 552.2 [M+1].

Embodiment 14J

N4-(4-(7,7-Difluoro-8,9-dihydro-6H-pyrido[1,2-a]indol-10-yl)pyrimidin-2-yl)-N-(2-(dimethylamino)ethyl)-5-methoxy-N[1]-methylbenzene-1,2,4-triamine

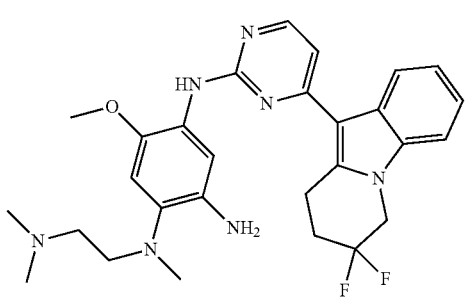

The Embodiment was prepared according to the method of Embodiment 1B except for replacing Embodiment 1A with Embodiment 14I to deliver the title compound (pink solid, 491.00 mg, crude). LCMS (ESI) (5-95 AB): m/z: 522.3 [M+1].

Embodiment 14K

N-(5-((4-(7,7-Difluoro-8,9-dihydro-6H-pyrido[1,2-a]indol-10-yl)pyrimidin-2-yl)amino)-2-((2-(dimethylamino)ethyl)(methyl)amino)-4-methoxyphenyl)acrylamide

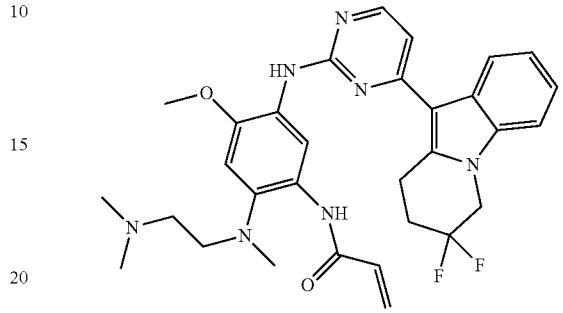

The Embodiment was prepared according to the method of Embodiment 1C except for replacing Embodiment 1B with Embodiment 14J to deliver the title compound (FA salt, 141.90 mg, yield 23.81%). $^1$H-NMR (400 MHz, MeOD): δ 8.56 (s, 2H), 8.39 (d, J=5.4 Hz, 1H), 8.07 (d, J=7.15 Hz, 1H), 7.43 (d, J=7.1 Hz, 1H), 7.15-7.28 (m, 3H), 6.96 (s, 1H), 6.38-6.54 (m, 2H), 5.85 (dd, J=9.0, 2.7 Hz, 1H), 4.50 (t, J=12.6 Hz, 2H), 4.00 (s, 3H), 3.54 (t, J=6.8 Hz, 2H), 3.43 (t, J=5.5 Hz, 2H), 3.17 (d, J=5.2 Hz, 2H), 2.79 (s, 6H) 2.71 (s, 3H), 2.42 (tt, J=13.5, 6.9 Hz, 2H). LCMS (ESI) (0-60 AB): m/z: 576.3 [M+1].

Embodiment 15

N-(2-((2-(Dimethylamino)ethyl)(methyl)amino)-4-methoxy-5-((4-(6,7,8,9-tetrahydropyrido[1,2-a]indol-10-yl)pyrimidin-2-yl)amino)phenyl)acrylamide

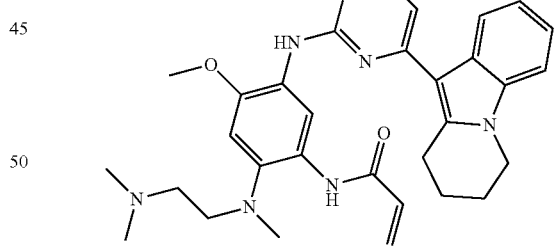

Embodiment 15A 6,7,8,9-Tetrahydropyrido[1,2-a]indole

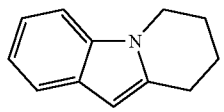 [SMILES: c1ccc2c(c1)cc1n2CCCC1]

The Embodiment was prepared according to the method of Embodiment 13D except for replacing Embodiment 13C with 8,9-dihydropyrido[1,2-a]indole-7 (6H)one to deliver the title compound (brown solid, 182.00 mg, yield 26.24%). $^1$H NMR (400 MHz, CD$_3$OD): δ 7.57-7.60 (m, 1H), 7.31-7.33 (m, 1H), 7.13-7.19 (m, 2H), 6.25 (s, 1H), 4.06-4.11 (m, 2H), 3.01-3.04 (m, 2H), 2.11-2.15 (m, 2H), 1.92-1.97 (m, 2H).

Embodiment 15B 10-(2-Chloropyrimidin-4-yl)-6,7,8,9-tetrahydro-pyrido[1,2-a]indole

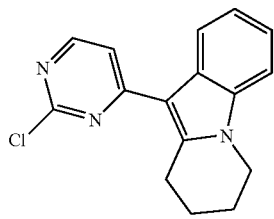 [SMILES: Clc1nccc(-c2c3n(c4ccccc24)CCCC3)n1]

The Embodiment was prepared according to the method of Embodiment A except for replacing Embodiment A6 with Embodiment 15A to deliver the title compound (brown oil, 100.00 mg, yield 18.44%). LCMS (ESI) (5-95_AB): m/z: 284.1 [M+1].

Embodiment 15C

N-(4-Fluoro-2-methoxy-5-nitrophenyl)-4-(6,7,8,9-tetrahydropyrido[1,2-a]indol-10-yl)pyrimidin-2-amine

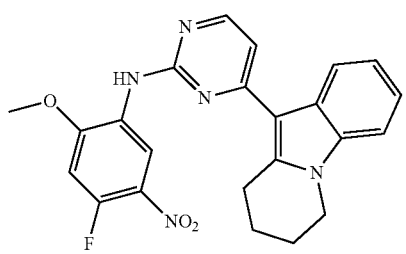 [SMILES: COc1cc(F)c([N+](=O)[O-])cc1Nc1nccc(-c2c3n(c4ccccc24)CCCC3)n1]

The Embodiment was prepared according to the method of Embodiment B except for replacing Embodiment A with Embodiment 15B to deliver the title compound (yellow solid, (150.00 mg, yield 37.43%). LCMS (ESI) (5-95_AB): m/z: 434.0 [M+1].

Embodiment 15D

N$^1$-(2-(Dimethylamino)ethyl)-5-methoxy-N$^1$-methyl-2-nitro-N$^4$-(4-(6,7,8,9-tetrahydropyrido[1,2-a]indol-10-yl)pyrimidin-2-yl)benzene-1,4-diamine

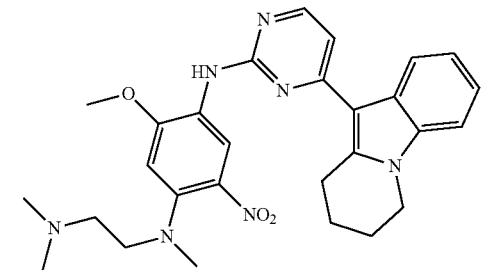

The Embodiment was prepared according to the method of Embodiment 1A except for replacing Embodiment B with Embodiment 15C to deliver the title compound (brown solid, 300.00 mg, yield 79.26%). LCMS (ESI) (5-95_AB): m/z: 516.2 [M+1].

Embodiment 15E

N$^1$-(2-(Dimethylamino)ethyl)-5-methoxy-N$^1$-methyl-N$^4$-(4-(6,7,8,9-tetrahydropyrido[1,2-a]indol-10-yl)pyrimidin-2-yl)benzene-1,2,4-triamine

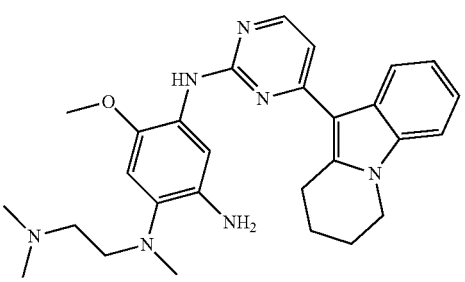 [SMILES: COc1cc(N(C)CCN(C)C)c([N+](=O)[O-])cc1Nc1nccc(-c2c3n(c4ccccc24)CCCC3)n1]

The Embodiment was prepared according to the method of Embodiment 1B except for replacing Embodiment 1A with Embodiment 15D to deliver the title compound (pink solid, 250.00 mg, crude).

Embodiment 15F

N-(2-((2-(Dimethylamino)ethyl)(methyl)amino)-4-methoxy-5-((4-(6,7,8,9-tetrahydropyrido[1,2-a]indol-10-yl)pyrimidin-2-yl)amino)phenyl)acrylamide

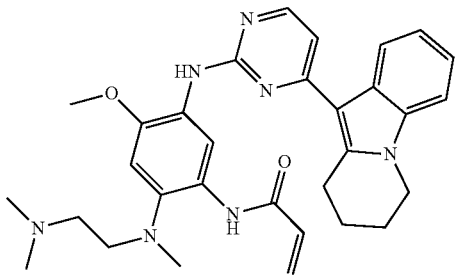 [SMILES: C=CC(=O)Nc1cc(Nc2nccc(-c3c4n(c5ccccc35)CCCC4)n2)c(OC)cc1N(C)CCN(C)C]

The Embodiment was prepared according to the method of Embodiment 1C except for replacing Embodiment 1B with Embodiment 15E to deliver the title compound (FA salt, 46.00 mg, yield 11.64%). $^1$H NMR (400 MHz, CD$_3$OD): δ 8.60 (s, 1H), 8.48 (s, 1H), 8.35 (d, J=5.2 Hz, 1H), 8.11 (d, J=7.6 Hz, 1H), 7.41 (d, J=8.0 Hz, 1H), 7.12-7.20 (m, 3H), 6.97 (s, 1H), 6.48-6.50 (m, 2H), 5.88 (t, J=5.8 Hz, 1H), 4.16 (t, J=5.8 Hz, 2H), 4.03 (s, 3H), 3.49 (t, J=5.4 Hz, 2H), 3.24-3.30 (m, 4H), 2.86 (s, 6H), 2.72 (s, 3H), 2.08-2.19 (m, 2H), 1.98-1.88 (m, 2H). LCMS (ESI) (5-95AB): m/z: 540.3 [M+1].

Process 7

General Preparation Methods for Intermediates C and D

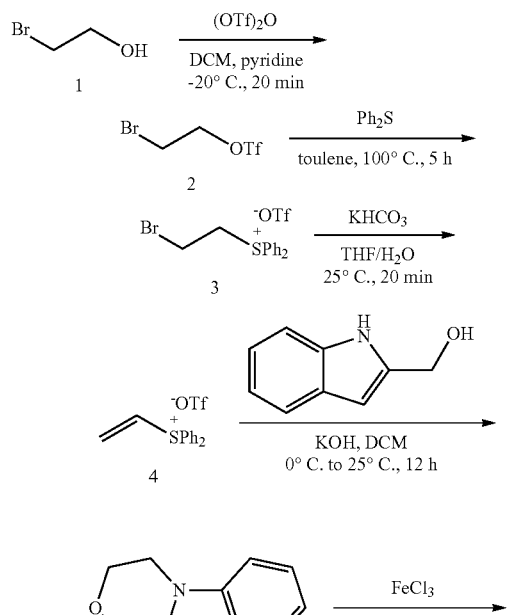

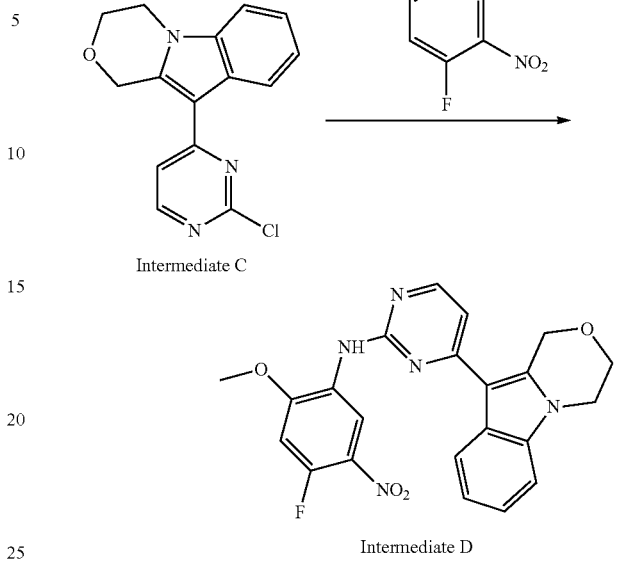

Embodiment C1

2-Bromoethyl trifluoromethanesulfonate

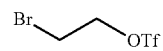

Trifluoromethanesulfonic anhydride (20.06 g, 63.86 mmol) was added dropwise to pyridine (20 mL) and DCM (70 mL) at −20° C. After stirring for 10 minutes, 2-bromoethanol (7.60 g, 60.82 mmol) was added dropwise to the mixture and stirred for 10 minutes and the reaction mixture was warmed to 10° C. The reaction mixture was filtered and the filtrate was concentrated (below 20° C.). The resulting crude product was dissolved in petroleum ether (60 mL), vigorously stirred, filtered and the filtrate was concentrated to deliver the title compound (17.90 g, crude). $^1$H NMR (300 MHz, CDCl$_3$): δ 3.61 (t, J=6.0 Hz, 2H) 4.75 (t, J=6.0 Hz, 2H).

Embodiment C2

(2-Bromoethyl)diphenylsulfonium

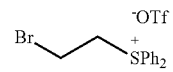

Embodiment C1 (17.90 g, 69.64 mmol) was added to toluene (40 mL) at 25° C., diphenyl sulfide (13.81 g, 69.64 mmol) was added to the mixture and the reaction mixture was warmed to 100° C., and stirred for 5 hours in nitrogen. The reaction mixture was cooled to 25° C., added with ether (80 mL), filtered and the filter cake was dried to deliver the title compound (11.90 g, 34.69% yield). $^1$H NMR (400

MHz, CDCl₃): δ 3.64-3.74 (t, J=6.0 Hz 2H) 4.87 (t, J=6.0 Hz, 2H) 7.69-7.82 (m, 6H) 8.09 (d, J=8.0 Hz, 4H).

Embodiment C3

Diphenyl(vinyl)sulfonium

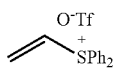

Embodiment C2 (11.20 g, 25.27 mmol) was added to THF/H₂O (2:1, 36 mL) at 25° C., KHCO₃ (3.04 g, 30.32 mmol) was added to the mixture and stirred for 20 minutes. The reaction mixture was concentrated immediately (the temperature was not higher than 20° C.), DCM (40 mL) was added, dried over anhydrous magnesium sulfate, the organic layer was concentrated and purified by column chromatography (DCM:MeOH=20:1, 10:1) To deliver the title compound (brown oil, 6.20 g, yield 54.16%). ¹H NMR (400 MHz, CDCl₃): δ 6.50 (dd, J=16.0, 4 Hz, 1H) 6.71 (dd, J=8.0, 4 Hz, 1H) 7.53 (dd, J=16.0, 8.0 Hz, 1H) 7.65-7.78 (m, 2H) 7.83-7.93 (m, 1H).

Embodiment C4

3,4-Dihydro-1H-[1,4]oxazino[4,3-a]indole

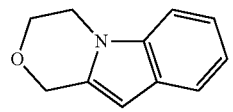 [SMILES: c1ccc2c(c1)cc1n2CCOC1]

2-Hydroxymethyl-indole (2.50 g, 16.99 mmol) was added to DCM (250 mL) at 0° C., KOH (1.14 g, 20.39 mmol) was added to the mixture and stirred for 30 minutes. And then a solution of Embodiment C3 (6.16 g, 16.99 mmol) in DCM (50 mL) was added dropwise to the mixture and the reaction mixture was warmed to 20° C. and stirred for 11.5 hours. The reaction mixture was concentrated and purified by column chromatography (PE/EA=20:1) to deliver the title compound (yellow solid, 1.50 g, yield 48.42%). ¹H NMR (400 MHz, CDCl₃): δ07.59 (d, J=8.0 Hz, 1H), 7.34-7.29 (m, 1H), 7.21 (dt, J=1.2, 7.6 Hz, 1H), 7.17-7.12 (m, 1H), 6.24 (d, J=0.8 Hz, 1H), 5.01 (d, J=0.8 Hz, 2H), 4.22-4.17 (m, 2H), 4.13-4.08 (m, 2H).

Embodiment C 10-(2-Chloropyrimidin-4-yl)-3,4-dihydro-1H-[1,4]oxazino[4,3-a]indole

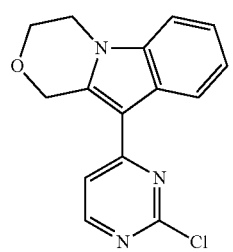 [SMILES: Clc1nccc(-c2c3n(c4ccccc24)CCOC3)n1]

The Embodiment was prepared according to the method of Embodiment A except for replacing Embodiment A6 with Embodiment C4 to deliver the title compound (brown solid, 1.30 g, crude). LCMS (ESI) (10-80 AB): m/z: 286.1 [M+1].

Embodiment D 4-(3,4-Dihydro-1H-[1,4]oxazino[4,3-a]indol-10-yl)-N-(4-fluoro-2-methoxy-5-nitrophenyl)pyrimidin-2-amine

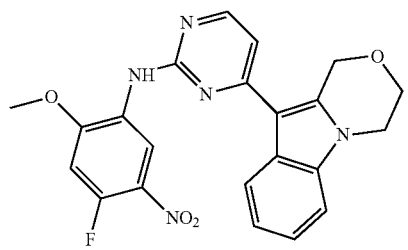 [SMILES: COc1cc(F)c([N+](=O)[O-])cc1Nc1nccc(-c2c3n(c4ccccc24)CCOC3)n1]

The Embodiment was prepared according to the method of Embodiment B by replacing Embodiment A with Embodiment C to deliver the title compound (yellow solid, 311.00 mg, crude). LCMS (ESI) (5-95 AB): m/z: 436.0 [M+1].

Process 8

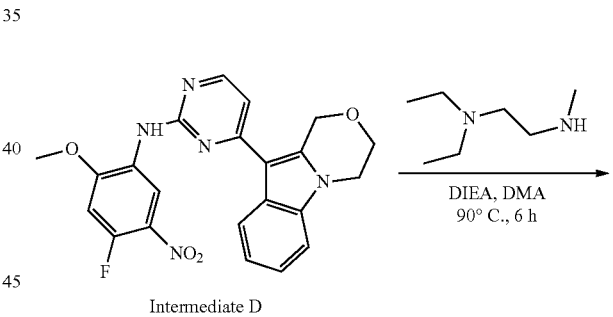

Intermediate D

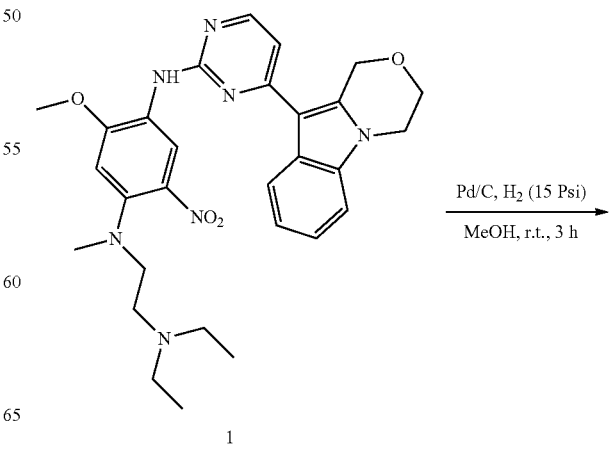

-continued

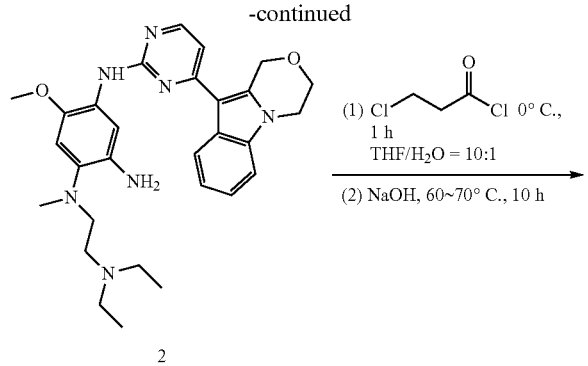

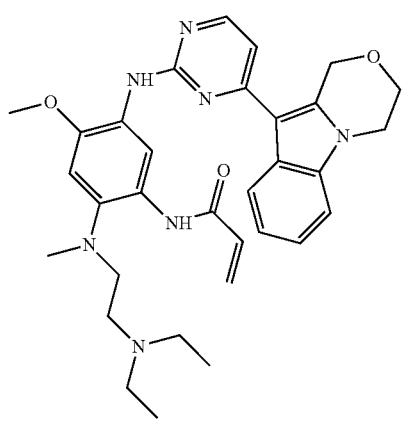

Embodiment 16

N-(2-((2-(Diethyl amino)ethyl)(methyl)amino)-5-((4-(3,4-dihydro-1H-[1,4]oxazino[4,3-a]indol-10-yl)pyrimidin-2-yl)amino)-4-methoxyphenyl)acrylamide

Embodiment 16A $N^1$-(2-(Diethylamino)ethyl)-$N^4$-(4-(3,4-dihydro-1H-[1,4]oxazino[4,3-a]indol-10-yl)pyrimidin-2-yl)-5-methoxy-$N^1$-methyl-2-nitrobenzene-1,4-diamine

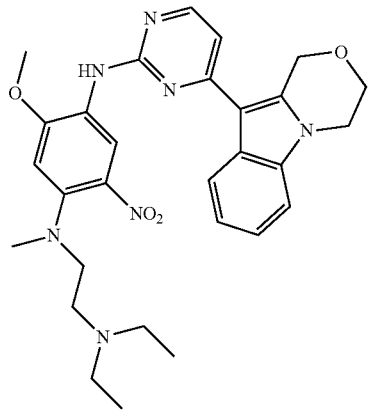

Under the protection of nitrogen atmosphere, intermediate D (150.00 mg, 344.50 μmol) and N,N-diethyl-N-methyl-ethane-1,2-diamine (134.59 mg, 1.03 mmol) were dissolved in DMA (5 mL), DIEA (133.57 mg, 1.03 mmol) was added to the mixture and the reaction mixture was warmed to 90° C. and stirred for 12 hours. LCMS showed the reaction was complete and the reaction mixture was diluted with water (5 mL) and extracted with DCM (10 mL*2). The organic phases were combined and dried over anhydrous sodium sulfate, filtered and the filtrate was concentrated to deliver the title compound (yellow solid, 300.00 mg, crude). LCMS (ESI) (0-60AB): m/z: 546.3 [M+1].

Embodiment 16B $N^1$-(2-(Diethylamino)ethyl)-$N^4$-(4-(3,4-dihydro-1H-[1,4]oxazino[4,3-a]indol-10-yl)pyrimidin-2-yl)-5-methoxy-$N^1$-methylbenzene-1,2,4-triamine

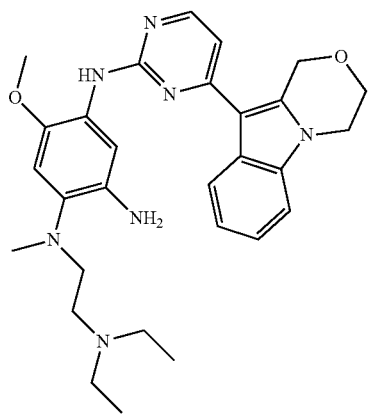 [SMILES: CCN(CC)CCN(C)c1cc(OC)c(Nc2nccc(-c3c4n(c5ccccc35)CCOC4)n2)cc1[N+](=O)[O-]]

Embodiment 16A (300.00 mg, 549.82 μmol) was dissolved in MeOH (5 mL) at 25° C., and Pd/C (10%, 0.20 g) was added after replacing with nitrogen. The mixture was replaced with $H_2$ three times and stirred at 15 psi for 2 hours.

TLC (DCM:MeOH=20:1) showed the reaction was complete and the reaction mixture was filtered and the filtrate was concentrated to dryness to deliver the title compound (yellow solid, 200.00 mg, yield 70.54%). LCMS (ESI)(0-60AB): m/z: 516.3 [M+1].

Embodiment 16C

N-(2-((2-(Diethylamino)ethyl)(methyl)amino)-5-((4-(3,4-dihydro-1H-[1,4]oxazino[4,3-a]indol-10-yl)pyrimidin-2-yl)amino)-4-methoxyphenyl)acrylamide

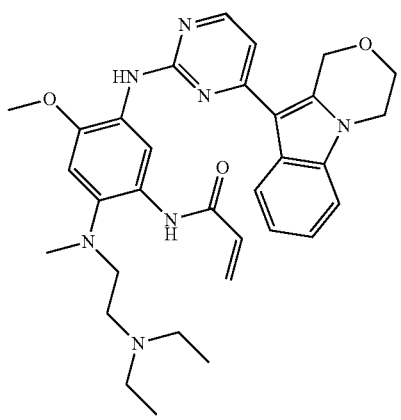 [SMILES: C=CC(=O)Nc1cc(Nc2nccc(-c3c4n(c5ccccc35)CCOC4)n2)c(OC)cc1N(C)CCN(CC)CC]

Embodiment 16B (200.00 mg, 387.86 μmol) was dissolved in a mixed solvent of tetrahydrofuran (3 mL) and water (1 mL) at 0° C. 3-Chloropropionyl chloride (73.87 mg, 581.79 μmol) was added to the mixture and stirred for 0.5 hour, then sodium hydroxide (62.06 mg, 1.55 mmol) was added to the mixture and the reaction mixture was warmed to 70° C. for 12 hours. LCMS showed the reaction was complete, water (2 mL) was added to the mixture, extracted with DCM (10*2) and the organic phase was concentrated. The crude product was purified by preparative HPLC to deliver the title compound (FA salt, 45.80 mg, yield 19.14%). $^1$H NMR (400 MHz, CD$_3$OD): δ 8.53 (br. s., 1H), 8.28-8.30 (m, 2H), 8.01-8.03 (m, 1H), 7.39-7.40 (m, 1H), 7.21-7.23 (m, 2H), 7.09 (d, J=5.20 Hz, 1H), 6.95 (s, 1H), 6.53-6.55 (m, 1H), 6.40-6.44 (m, 1H), 5.84-5.87 (m, 1H), 5.14 (s, 2H), 4.09 (s, 4H), 4.00 (s, 3H), 3.29-3.51 (m, 2H), 3.27 (t, J=5.60 Hz, 2H), 3.20 (q, J=7.20 Hz, 4H), 2.74 (s, 3H), 1.25 (t, J=7.20 Hz, 6H). LCMS (ESI) (0-60AB): m/z: 570.3 [M+1].

Embodiment 17

N-(5-((4-(3,4-Dihydro-1H-[1,4]oxazino[4,3-a]indol-10-yl)pyrimidin-2-yl)amino)-2-((2-(dimethylamino)ethyl)(methyl)amino)-4-methoxyphenyl)acrylamide

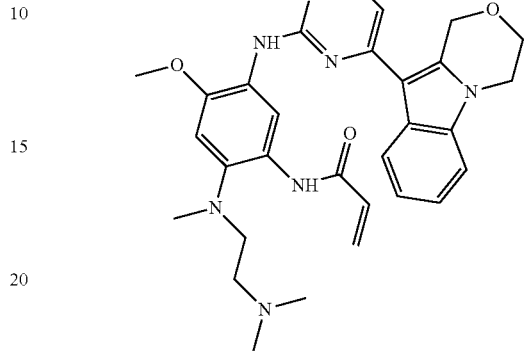

Embodiment 17A

N$^1$-(4-(3,4-Dihydro-1H-[1,4]oxazino[4,3-a]indol-10-yl)pyrimidin-2-yl)-N-(2-(dimethylamino)ethyl)-2-methoxy-N$^4$-methyl-5-nitrobenzene-1,4-diamine

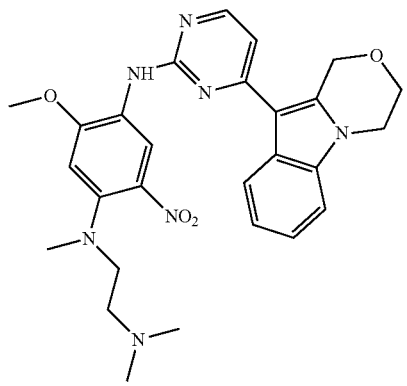 [SMILES: COc1cc(N(C)CCN(C)C)c([N+](=O)[O-])cc1Nc1nccc(-c2c3n(c4ccccc24)CCOC3)n1]

The Embodiment was prepared according to the method of Embodiment 16A except for replacing N,N-diethyl-N-methylethane-1,2-diamine with N,N',N'-trimethyl-1,2-ethylenediamine to deliver the title compound (yellow solid, 230.00 mg, yield 87.95%). LCMS (0-60AB): m/z: 518.2 [M+1].

Embodiment 17B

N$^4$-(4-(3,4-Dihydro-1H-[1,4]oxazino[4,3-a]indol-10-yl)pyrimidin-2-yl)-N$^1$-(2-(dimethylamino)ethyl)-5-methoxy-N$^1$-methylbenzene-1,2,4-triamine

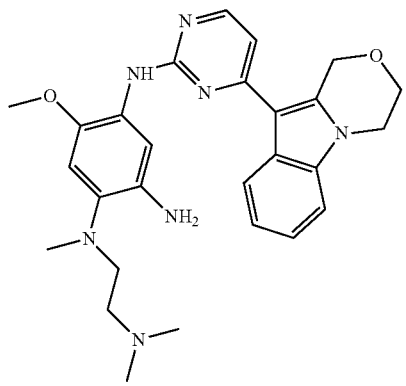 [SMILES: COc1cc(N(C)CCN(C)C)c(N)cc1Nc1nccc(-c2c3n(c4ccccc24)CCOC3)n1]

The Embodiment was prepared according to the method of Embodiment 16B except for replacing Embodiment 16A with Embodiment 17A to deliver the title compound (yellow solid, 170.00 mg, yield 72.96%). LCMS (0-60AB): m/z: 488.2 [M+1].

Embodiment 17C

N-(5-((4-(3,4-Dihydro-1H-[1,4]oxazino[4,3-a]indol-10-yl)pyrimidin-2-yl)amino)-2-((2-(dimethylamino)ethyl)(methyl)amino)-4-methoxyphenyl)acrylamide

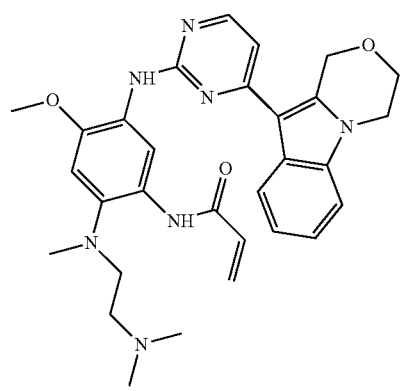 [SMILES: C=CC(=O)Nc1cc(Nc2nccc(-c3c4n(c5ccccc35)CCOC4)n2)c(OC)cc1N(C)CCN(C)C]

The Embodiment was prepared according to the method of Embodiment 16C except for replacing Embodiment 16B with Embodiment 17B to deliver the title compound (FA salt, 20.00 mg, yield 10.29%). $^1$H NMR (400 MHz, CD$_3$OD): δ 8.49 (br. s., 1H), 8.33 (d, J=4.0 Hz, 1H), 8.29 (s, 1H), 8.08-8.01 (m, 1H), 7.46-7.40 (m, 1H), 7.26-7.20 (m, 2H), 7.17 (d, J=4.0 Hz, 1H), 6.95 (s, 1H), 6.59-6.38 (m, 2H), 5.84 (dd, J=2.0, 8.0 Hz, 1H), 5.18 (s, 2H), 4.17-4.11 (m, 4H), 3.97 (s, 3H), 3.45 (t, J=6.0 Hz, 2H), 3.20 (t, J=6.0 Hz, 2H), 2.81 (s, 6H), 2.72 (s, 3H). LCMS (0-60AB): m/z: 542.2 [M+1].

Embodiment 18

N-(5-((4-(3,4-Dihydro-1H-[1,4]oxazino[4,3-a]indol-10-yl)pyrimidin-2-yl)amino)-2-((2-(ethyl(methyl)amino)ethyl)(methyl)amino)-4-methoxyphenyl)acrylamide

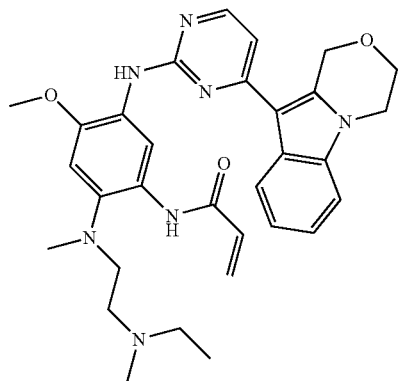 [SMILES: C=CC(=O)Nc1cc(Nc2nccc(-c3c4n(c5ccccc35)CCOC4)n2)c(OC)cc1N(C)CCN(C)CC]

Embodiment 18A

N$^1$-(4-(3,4-Dihydro-1H-[1,4]oxazino[4,3-a]indol-10-yl)pyrimidin-2-yl)-2-methoxy-N$^4$-methyl-N$^4$-(2-(methylamino)ethyl)-5-nitrobenzene-1,4-diamine

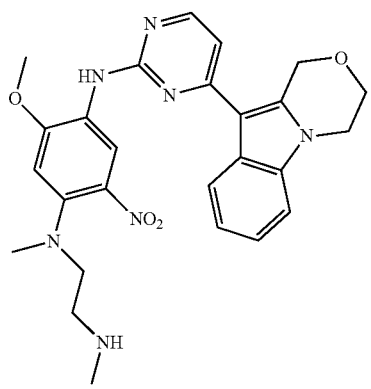 [SMILES: CNCCN(C)c1cc(OC)c(Nc2nccc(-c3c4n(c5ccccc35)CCOC4)n2)cc1[N+](=O)[O-]]

The Embodiment was prepared according to the method of Embodiment 16A except for replacing N,N-diethyl-N-methylethane-1,2-diamine with N$^1$,N$^2$-dimethylethane-1,2-amine to deliver the title compound (yellow solid, 160.00 mg, yield 85.24%). LCMS (ESI)(0-60AB): m/z: 504.3 [M+1].

Embodiment 18B

N$^1$-(4-(3,4-Dihydro-1H-[1,4]oxazino[4,3-a]indol-1-yl)pyrimidin-2-yl)-N$^4$-(2-(ethyl(methyl)amino)ethyl)-2-methoxy-N$^4$-methyl-5-nitrobenzene-1,4-diamine

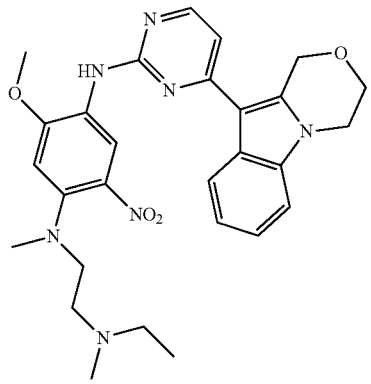 [SMILES: CCN(C)CCN(C)c1cc(OC)c(Nc2nccc(-c3c4n(c5ccccc35)CCOC4)n2)cc1[N+](=O)[O-]]

Embodiment 18A (100.00 mg, 198.59 μmol), MeCHO (26.24 mg, 595.77 μmol) and acetic acid (5.96 mg, 99.30 μmol) were dissolved in DCE (5 mL) and the temperature of the resulting mixture was raised to 40° C. and stirred for 2 hours. Then, NaBH(OAc)$_3$ (126.27 mg, 595.77 μmol) was added to the reaction solution, after the addition, the resulting mixture was stirred at 40° C. for 2 hours. LCMS showed the reaction was complete and the reaction mixture was diluted with water (5 mL) and extracted with DCM (10 mL×3). The organic layer was dried over anhydrous sodium sulfate and concentrated to deliver the title compound (yellow solid, 140.00 mg, crude). LCMS (ESI)(0-60AB): m/z: 532.3 [M+1].

Embodiment 18C 4-(4-(3,4-Dihydro-1H-[1,4]oxazino[4,3-a]indol-10-yl)pyrimidin-2-yl)-N$^1$-(2-(ethyl(methyl)amino)ethyl)-5-methoxy-N$^1$-methylbenzene-1,2,4-triamine

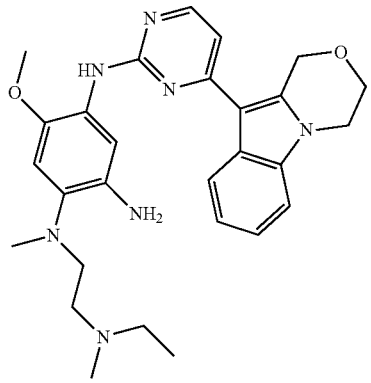 [SMILES: CCN(C)CCN(C)c1cc(OC)c(Nc2nccc(-c3c4n(c5ccccc35)CCOC4)n2)cc1N]

The Embodiment was prepared according to the method of Embodiment 16B except for replacing Embodiment 16A with Embodiment 18B to deliver the title compound (yellow solid, 100.00 mg, crude). LCMS (ESI)(0-60AB): m/z: 502 [M+1].

Embodiment 18D

N-(5-((4-(3,4-Dihydro-1H-[1,4]oxazino[4,3-a]indol-10-yl)pyrimidin-2-yl)amino)-2-((2-(ethyl(methyl)amino)ethyl)(methyl)amino)-4-methoxyphenyl)acrylamide

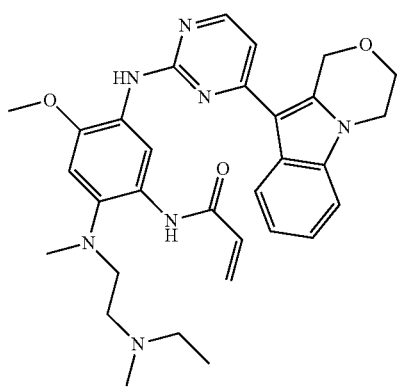 [SMILES: C=CC(=O)Nc1cc(Nc2nccc(-c3c4n(c5ccccc35)CCOC4)n2)c(OC)cc1N(C)CCN(C)CC]

The Embodiment was prepared according to the method of Embodiment 16C by replacing Embodiment 16B with Embodiment 18C to deliver the title compound (FA salt, 38.3 mg, yield 31.89%). $^1$H NMR (400 MHz, CD$_3$OD): δ 8.46 (br. s., 1H), 8.34 (s, 1H), 8.23 (br. s., 1H), 7.96 (d, J=4.80 Hz, 1H), 7.33-7.34 (m, 1H), 7.17-7.19 (m, 2H), 7.01 (d, J=5.20 Hz, 1H), 6.94 (s, 1H), 6.56-6.63 (m, 1H), 6.41-6.45 (m, 1H), 5.85 (d, J=10.40 Hz, 1H), 5.06 (br. s., 2H), 4.01 (br. S., 4H), 3.98 (s, 3H), 3.48 (br. s., 2H), 3.26 (br. s., 2H), 3.12-3.21 (m, 2H), 2.82 (s, 3H), 2.72 (s, 3H), 1.25 (t, J=7.20 Hz, 3H). LCMS (ESI) (0-60AB): m/z: 556.4 [M+1].

Embodiment 19

N-(5-((4-(3,4-Dihydro-1H-[1,4]oxazino[4,3-a]indol-10-yl)pyrimidin-2-yl)amino)-2-((2-(dimethylamino)ethyl)(ethyl)amino)-4-methoxyphenyl)acrylamide

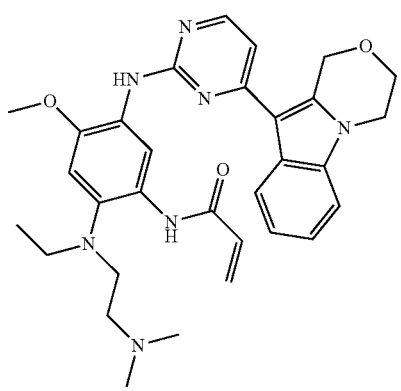 [SMILES: C=CC(=O)Nc1cc(Nc2nccc(-c3c4n(c5ccccc35)CCOC4)n2)c(OC)cc1N(CC)CCN(C)C]

Embodiment 19A

N-(4-(3,4-Dihydro-1H-[1,4]oxazino[4,3-a]indol-10-yl)pyrimidin-2-yl)-N$^4$-(2-(dimethylamino)ethyl)-N$^4$-ethyl-2-methoxy-5-nitrobenzene-1,4-diamine

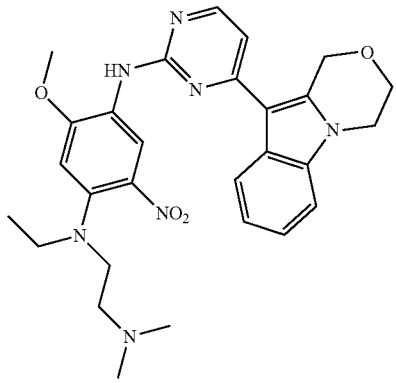 [SMILES: CCN(CCN(C)C)c1cc(OC)c(Nc2nccc(-c3c4n(c5ccccc35)CCOC4)n2)cc1[N+](=O)[O-]]

The Embodiment was prepared according to the method of Embodiment 16A except for replacing N,N-diethyl-N-methylethane-1,2-diamine with N$^1$-ethyl-N$^2$,N$^2$-dimethyl-ethane-1,2-diamine to deliver the title compound (yellow solid, 80 mg, crude). LCMS (ESI) (0-60AB): m/z: 532.3 [M+1].

Embodiment 19B N$^4$-(4-(3,4-Dihydro-1H-[1,4]oxazino[4,3-a]indol-10-yl)pyrimidin-2-yl)-N$^1$-(2-(dimethylamino)ethyl)-N$^1$-ethyl-5-methoxybenzene-1,2,4-triamine

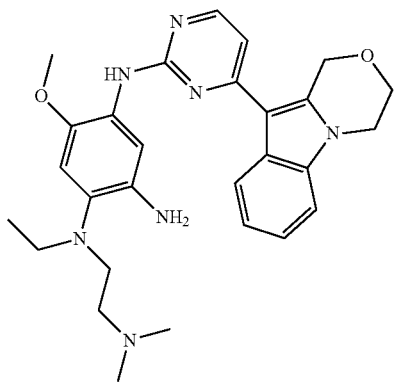

The Embodiment was prepared according to the method of Embodiment 16B except for replacing Embodiment 16A with Embodiment 19A to deliver the title compound (yellow solid, 80 mg, crude). LCMS (ESI) (0-60AB): m/z: 502.3 [M+1].

Embodiment 19C

N-(5-((4-(3,4-Dihydro-1H-[1,4]oxazino[4,3-a]indol-10-yl)pyrimidin-2-yl)amino)-2-((2-(dimethylamino)ethyl)(ethyl)amino)-4-methoxyphenyl)acrylamide

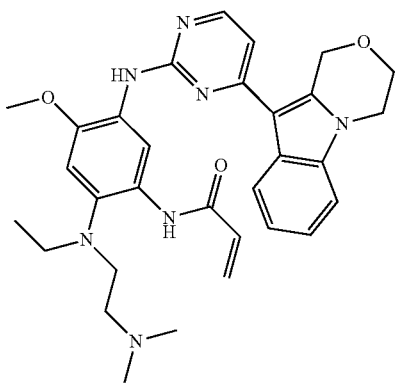 [SMILES: C=CC(=O)Nc1cc(Nc2nccc(-c3c4n(c5ccccc35)CCOC4)n2)c(OC)cc1N(CC)CCN(C)C]

The Embodiment was prepared according to method of Embodiment 16C except for replacing Embodiment 16B with Embodiment 19B to deliver the title compound (FA salt, 13.40 mg, yield 13.79%). $^1$H NMR (400 MHz, CD$_3$OD): δ 8.49 (br. s., 1H), 8.32 (d, J=5.60 Hz, 1H), 8.28 (s, 1H), 8.04 (d, J=8.80 Hz, 1H), 7.41-7.44 (m, 1H), 7.23-7.25 (m, 2H), 7.14 (d, J=5.60 Hz, 1H), 6.96 (s, 1H), 6.48-6.54 (m, 2H), 5.83-5.92 (m, 1H), 5.16 (s, 2H), 4.12 (s, 3H), 3.99 (s, 2H), 3.52 (t, J=5.80 Hz, 1H), 3.25 (t, J=5.60 Hz, 1H), 3.08 (d, J=6.80 Hz, 1H), 2.85 (s, 2H), 1.06 (t, J=7.20 Hz, 1H). LCMS (ESI)(0-60AB): m/z: 556.3 [M+1].

Embodiment 20

N-(5-((4-(3,4-Dihydro-1H-[1,4]oxazino[4,3-a]indol-10-yl)pyrimidin-2-yl)amino)-2-((1-(dimethylamino)propan-2-yl)(methyl)amino)-4-methoxyphenyl)acrylamide

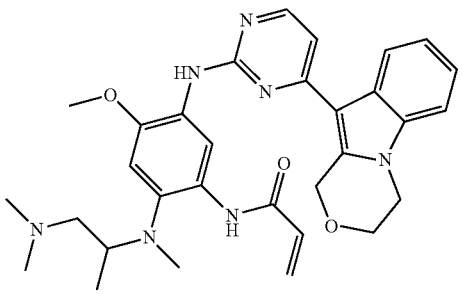 [SMILES: C=CC(=O)Nc1cc(Nc2nccc(-c3c4n(c5ccccc35)CCOC4)n2)c(OC)cc1N(C)C(C)CN(C)C]

Embodiment 20A

N[1]-(4-(3,4-Dihydro-1H-[1,4]oxazino[4,3-a]indol-10-yl)pyrimidin-2-yl)-N[4]-(1-(dimethylamino)propan-2-yl)-2-methoxy-N4-methyl-5-nitrobenzene-1,4-diamine

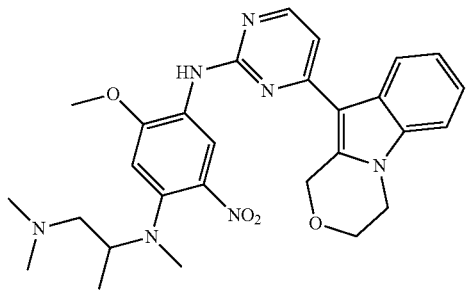 [SMILES: COc1cc(N(C)C(C)CN(C)C)c([N+](=O)[O-])cc1Nc1nccc(-c2c3n(c4ccccc24)CCOC3)n1]

The Embodiment was prepared according to the method of Embodiment 16A except for replacing N,N-diethyl-N-methylethane-1,2-diamine with N,N',N'-trimethyl-1,2-ethylenediamine to deliver the title compound (red oil, 270.00 mg, yield 48.90%). LCMS (ESI) (0-60AB): m/z: 532.3 [M+1].

Embodiment 20B

N[4]-(4-(3,4-Dihydro-1H-[1,4]oxazino[4,3-a]indol-10-yl)pyrimidin-2-yl)-N[1]-(1-(dimethylamino)propan-2-yl)-5-methoxy-N[1]-methylbenzene-1,2,4-triamine

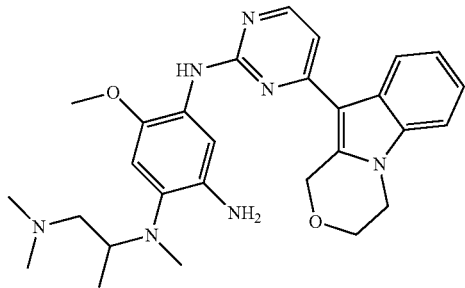 [SMILES: COc1cc(N(C)C(C)CN(C)C)c(N)cc1Nc1nccc(-c2c3n(c4ccccc24)CCOC3)n1]

The Embodiment was prepared according to the method of Embodiment 16B except for replacing Embodiment 16A with Embodiment 20A to deliver the title compound (brown oil, 227.00 mg, yield 75.03%). LCMS (ESI) (0-60AB): m/z: 502.3 [M+1].

Embodiment 20C

N-(5-((4-(3,4-Dihydro-1H-[1,4]oxazino[4,3-a]indol-10-yl)pyrimidin-2-yl)amino)-2-((1-(dimethylamino)propan-2-yl)(methyl)amino)-4-methoxyphenyl)acrylamide

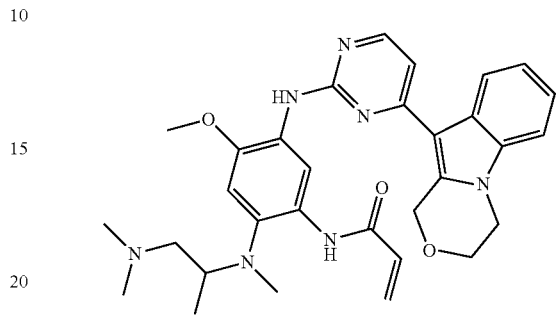

The Embodiment was prepared according to the method of Embodiment 16C except for replacing Embodiment 16B with Embodiment 20B to deliver the title compound (FA salt, 7.71 mg, yield 2.83%). $^1$H NMR (400 MHz, CD$_3$OD): δ 8.29 (s, 2H), 8.22 (d, J=5.2 Hz, 1H), 8.08 (s, 1H), 7.94-7.97 (m, 1H), 7.32-7.34 (m, 1H), 7.12-7.16 (m, 2H), 7.06 (d, J=5.2 Hz, 1H), 6.71-6.74 (m, 1H), 6.36-6.43 (m, 2H), 5.73-5.76 (m, 1H), 5.06-5.08 (m, 2H), 3.97-4.07 (m, 5H), 3.85-3.87 (m, 3H), 3.10-3.16 (m, 1H), 2.91-2.95 (m, 1H), 2.77 (s, 6H), 2.55-2.58 (m, 3H), 1.29-1.33 (m, 3H), 1.12-1.16 (m, 1H). LCMS (ESI) (0-60AB): m/z: 556.4 [M+1].

Process 9

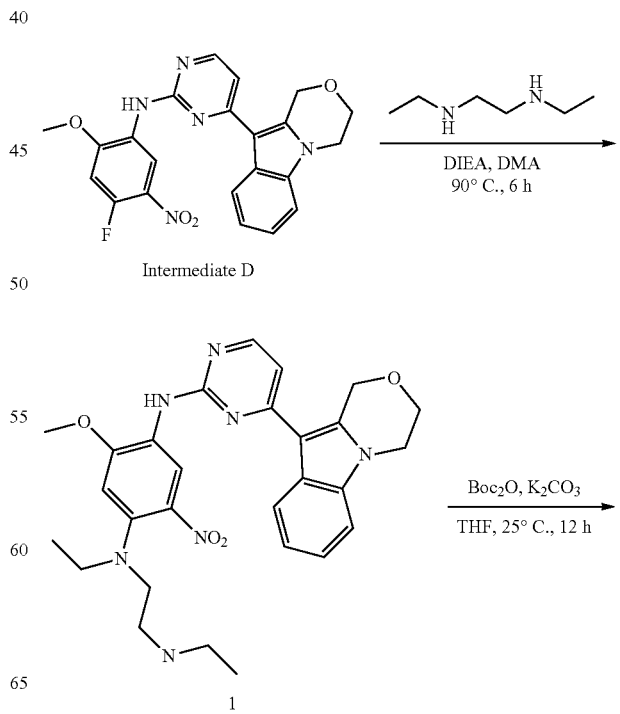

-continued

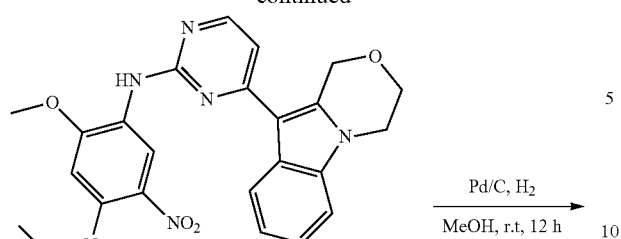

2

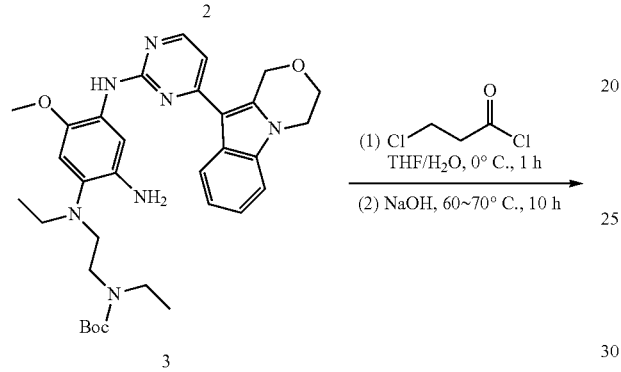

3

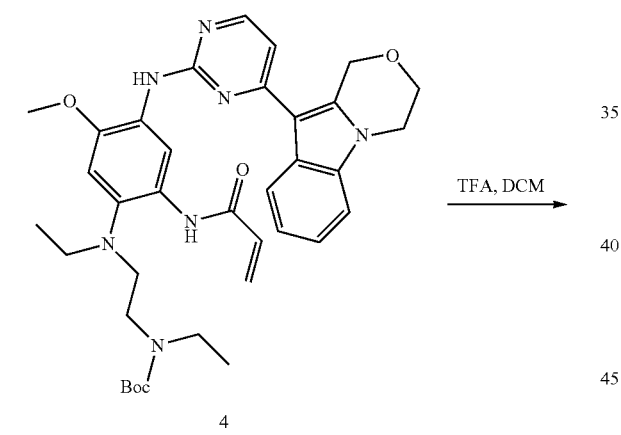

4

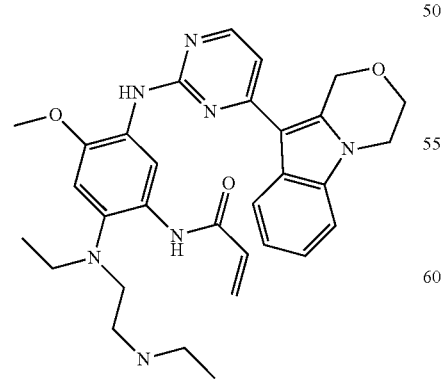

Embodiment 21

Embodiment 21

N-(5-((4-(3,4-Dihydro-1H-[1,4]oxazino[4,3-a]indol-10-yl)pyrimidin-2-yl)amino)-2-(ethyl(2-(ethylamino)ethyl)amino)-4-methoxyphenyl)acrylamide

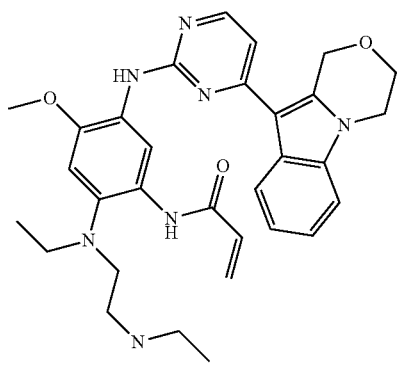 [SMILES: C=CC(=O)Nc1cc(Nc2nccc(-c3c4n(c5ccccc35)CCOC4)n2)c(OC)cc1N(CC)CCNCC]

Embodiment 21A $N^1$-(4-(3,4-Dihydro-1H-[1,4]oxazino[4,3-a]indol-1-yl)pyrimidin-2-yl)-$N^4$-ethyl-$N^4$-(2-(ethylamino)ethyl)-2-methoxy-5-nitrobenzene-1,4-diamine

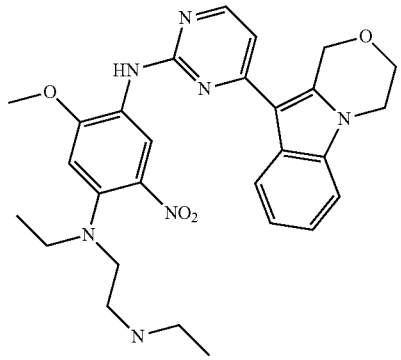 [SMILES: CCNCCN(CC)c1cc(OC)c(Nc2nccc(-c3c4n(c5ccccc35)CCOC4)n2)cc1[N+](=O)[O-]]

The Embodiment was prepared according to the method of Embodiment 16A except for replacing N,N-diethyl-N-methylethane-1,2-diamine with $N^1,N^2$-diethylethane-amine to deliver the title compound (red oil, 520 mg, crude). LCMS (ESI) (0-60AB): m/z: 532.2 [M+1].

Embodiment 21B tert-Butyl (2-((4-((4-(3,4-dihydro-1H-[1,4]oxazino[4,3-a]indol-10-yl)pyrimidin-2-yl)amino)-5-methoxy-2-nitrophenyl)(ethyl)amino)ethyl)(ethyl)carbamate

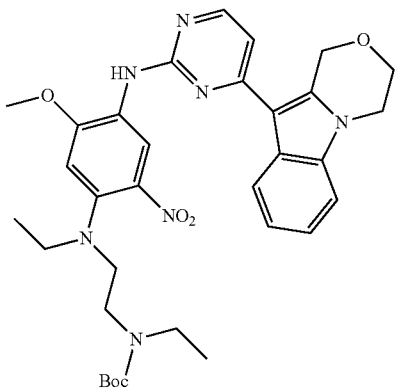

Embodiment 21A (260.00 mg, 489.09 μmol), (Boc)₂O (260.00 mg, 489.09 μmol) and potassium carbonate (101.40 mg, 733.63 μmol) were dissolved in THF (5 mL) and water (1 mL). The mixture was stirred at 25° C. for 12 hours. LCMS showed the reaction was complete and the reaction mixture was diluted with water (10 mL), extracted with EtOAc (30 mL×2) and the organic layer was concentrated. The crude product was purified by preparative plate (DCM/MeOH=20:1) to deliver the title compound, 230 mg, yield 71.98%). LCMS (ESI) (0-60AB): m/z: 632.3 [M+1].

Embodiment 21C tert-Butyl (2-((2-amino-4-((4-(3,4-dihydro-1H-[1,4]oxazino[4,3-a]indol-10-yl)pyrimidin-2-yl)amino)-5-methoxyphenyl)(ethyl)amino)ethyl)(ethyl)carbamate

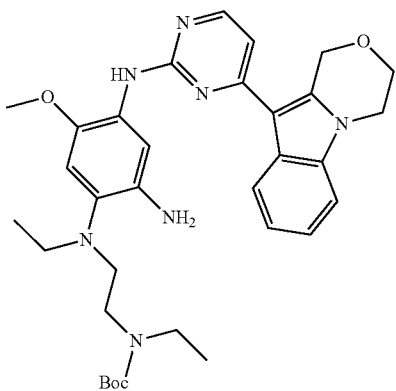 [SMILES: CCN(CCN(CC)c1cc(OC)c(Nc2nccc(-c3c4n(c5ccccc35)CCOC4)n2)cc1[N+](=O)[O-])C(=O)OC(C)(C)C]

The Embodiment was prepared according to the method of Embodiment 16B except for replacing Embodiment 16A with Embodiment 21B to deliver the title compound (brown oil, 180 mg, crude). LCMS (ESI) (0-60AB): m/z: 602.3[M+1].

Embodiment 21D tert-Butyl (2-((2-acrylamido-4-((4-(3,4-dihydro-1H-[1,4]oxazino[4,3-a]indol-10-yl)pyrimidin-2-yl)amino)-5-methoxyphenyl)(ethyl)amino)ethyl)(ethyl)carbamate

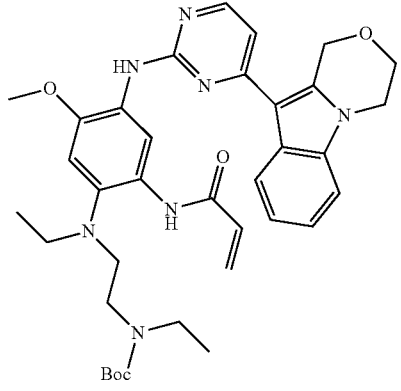 [SMILES: C=CC(=O)Nc1cc(Nc2nccc(-c3c4n(c5ccccc35)CCOC4)n2)c(OC)cc1N(CC)CCN(CC)C(=O)OC(C)(C)C]

The Embodiment was prepared according to the method of Embodiment 16C except for replacing Embodiment 16B with Embodiment 21C to deliver the title compound (brown oil, 180 mg, crude). LCMS (ESI) (0-60AB): m/z: 656.3[M+1].

Embodiment 21E

N-(5-((4-(3,4-Dihydro-1H-[1,4]oxazino[4,3-a]indol-10-yl)pyrimidin-2-yl)amino)-2-(ethyl(2-(ethylamino)ethyl)amino)-4-methoxyphenyl)acrylamide

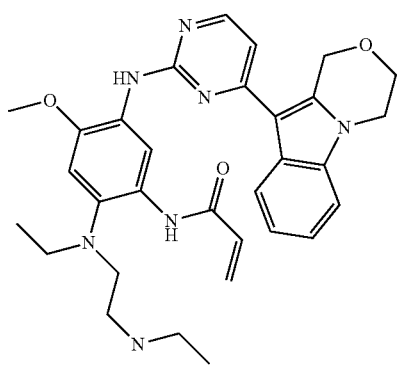 [SMILES: C=CC(=O)Nc1cc(Nc2nccc(-c3c4n(c5ccccc35)CCOC4)n2)c(OC)cc1N(CC)CCNCC]

Embodiment 21D (180 mg, 273.64 μmol) was dissolved in DCM (5 mL) at 0° C. and TFA (1.54 g, 13.51 mmol) was slowly added to the mixture. After the addition was complete, the reaction solution was stirred at 25° C. for 12 hours. LCMS showed the reaction was complete. The reaction solution was concentrated and the crude product was dissolved in DCM (20 mL) and the pH was adjusted to 9 to 10 with saturated NaHCO₃. The organic phase was separated and concentrated to give the crude product which was purified by preparative HPLC (FA) to deliver the title compound (yellow solid FA salt, 32.23 mg, yield 19.51%). ¹H NMR (400 MHz, CD₃OD): δ 8.23 (d, J=5.5 Hz, 1H), 8.09 (s, 1H), 7.95 (d, J=8.2 Hz, 1H), 7.31-7.37 (m, 1H), 7.10-7.18 (m, 2H), 7.07 (d, J=5.5 Hz, 1H), 6.82 (s, 1H), 6.38-6.48 (m, 1H), 6.26-6.34 (m, 1H), 5.74 (d, J=10.1 Hz, 1H), 5.07 (s, 2H), 4.04 (br. s., 4H), 3.87 (s, 3H), 3.38 (br. s., 2H), 3.04 (d, J=5.0 Hz, 2H), 2.87-3.01 (m, 4H), 1.22-1.33 (m, 3H), 0.94 (t, J=7.0 Hz, 3H). LCMS (ESI) (0-60AB): m/z: 556.3[M+1].

Embodiment 22

N-(5-((4-(3,4-Dihydro-1H-[1,4]oxazino[4,3-a]indol-10-yl)pyrimidin-2-yl)amino)-2-(ethyl(2-(ethyl(methyl)amino)ethyl)amino)

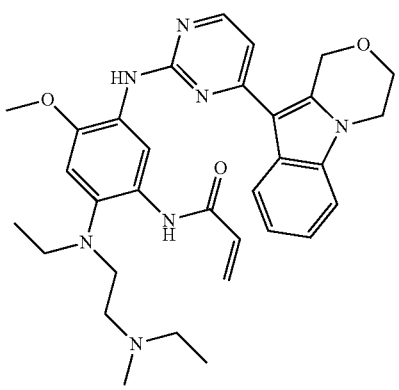 [SMILES: C=CC(=O)Nc1cc(Nc2nccc(-c3c4n(c5ccccc35)CCOC4)n2)c(OC)cc1N(CC)CCN(C)CC]

Embodiment 22A $N^1$-(4-(3,4-Dihydro-1H-[1,4]oxazino[4,3-a]indol-10-yl)pyrimidin-2-yl)-$N^4$-ethyl-$N^4$-(2-(ethyl(methyl)amino)ethyl)-2-methoxy-5-nitrobenzene-1,4-diamine

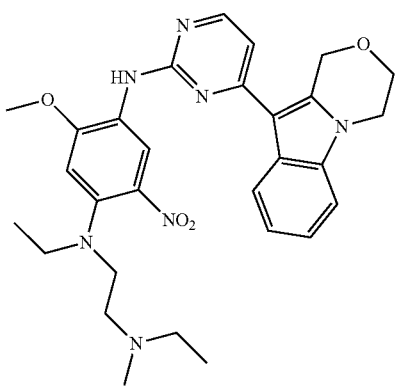

$N^1$-(4-(3,4-Dihydro-1H-[1,4]oxazino[4,3-a]indol-10-yl)pyrimidin-2-yl)-$N^4$-ethyl-$N^4$-(2-(methylamino)ethyl)-2-methoxy-5-nitrobenzene-1,4-diamine (260.00 mg, 489.09 μmol), HCHO (44.06 mg, 1.47 mmol, 40.42 uL) and HOAc (2.94 mg, 2.80 uL) were dissolved in MeOH (5 mL) and stirred for 0.5 h. NaBH(OAc)$_3$ (310.97 mg, 1.47 mmol) was added to the reaction solution, and the resulting reaction solution was stirred at 25° C. for 12 hours. LCMS showed the reaction was complete. Aqueous NaHCO$_3$ (10 mL) was added to the reaction solution, extracted with DCM (30 mL*2), and the organic phase was separated and concentrated. The crude product was purified by column chromatography (DCM, DCM:MeOH=60:1; DCM:MeOH=30:1) to deliver the title compound (yellow oil, 184.00 mg, yield 61.71%). LCMS (ESI) (0-60AB): m/z: 546.3 [M+1].

Embodiment 22B $N^4$-(4-(3,4-Dihydro-1H-[1,4]oxazino[4,3-a]indol-10-yl)pyrimidin-2-yl)-$N^1$-ethyl-$N^1$-(2-(ethyl(methyl)amino)ethyl)-5-methoxybenzene-1,2,4-triamine

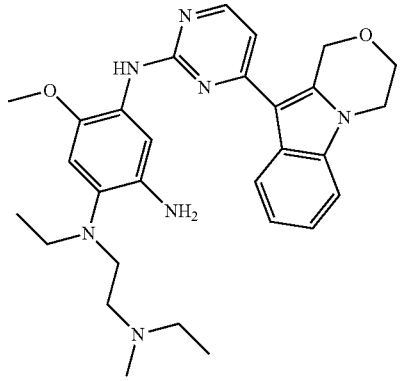 [SMILES: CCN(C)CCN(CC)c1cc(OC)c(Nc2nccc(-c3c4n(c5ccccc35)CCOC4)n2)cc1N]

The Embodiment was prepared according to the method of Embodiment 16B except for replacing Embodiment 16A with Embodiment 22A to deliver the title compound (brown oil, 155 mg, crude). LCMS (ESI) (0-60AB): m/z: 516.3 [M+1].

Embodiment 22C

N-(5-((4-(3,4-Dihydro-1H-[1,4]oxazino[4,3-a]indol-10-yl)pyrimidin-2-yl)amino)-2-(ethyl(2-(ethyl(methyl)amino)ethyl)amino)-4-methoxyphenyl)acrylamide

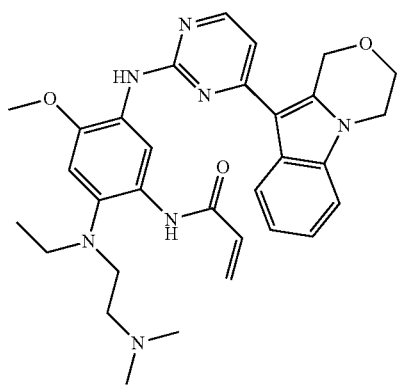 [SMILES: C=CC(=O)Nc1cc(Nc2nccc(-c3c4n(c5ccccc35)CCOC4)n2)c(OC)cc1N(CC)CCN(C)C]

The Embodiment was prepared according to the method of Embodiment 16C except for replacing Embodiment 16B with Embodiment 22B to deliver the title compound (FA salt, 38.72 mg, yield 19.93%). $^1$H NMR (400 MHz, CD$_3$OD): δ 8.50 (br. s., 1H), 8.21-8.29 (m, 2H), 7.93-7.99 (m, 1H), 7.31-7.36 (m, 1H), 7.14-7.22 (m, 2H), 7.02 (d, J=5.4 Hz, 1H), 6.92 (s, 1H), 6.48-6.59 (m, 1H), 6.37-6.45 (m, 1H), 5.84 (dd, J=10.0, 1.6 Hz, 1H), 5.07 (s, 2H), 4.02 (s, 4H), 3.92-3.99 (m, 3H), 3.51 (t, J=5.33 Hz, 2H), 3.23 (br. s., 2H), 2.99-3.18 (m, 4H), 2.79 (s, 3H), 1.21 (t, J=7.2 Hz, 3H), 1.03 (t, J=7.0 Hz, 3H). LCMS(ESI)(0-60AB): m/z: 570.4 [M+1].

Embodiment 23

N-(5-((4-(3,4-Dihydro-1H-[1,4]oxazino[4,3-a]indol-10-yl)pyrimidin-2-yl)amino)-2-((2-(isopropylamino)ethyl)(methyl)amino)-4-methoxyphenyl)acrylamide

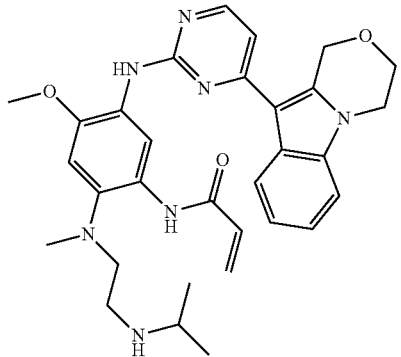 [SMILES: C=CC(=O)Nc1cc(Nc2nccc(-c3c4n(c5ccccc35)CCOC4)n2)c(OC)cc1N(C)CCNC(C)C]

Embodiment 23A tert-Butyl (2-hydroxyethyl)(isopropyl)carbamate

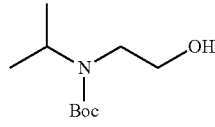

2-(Isopropylamino)ethanol (18.30 g, 177.39 mmol) and K$_2$CO$_3$ (49.04 g, 354.78 mmol) were dissolved in THF (100 mL) and H$_2$O (20 mL) at 25° C., (Boc)$_2$O (58.07 g, 266.09 mmol) was added to the mixture and stirred for 3 hours. TLC (PE:EtOAc=2:1) showed the reaction was complete. Water (50 mL) was added to the reaction solution and extracted with EtOAc (50 mL*2). The organic phases were combined and dried over anhydrous Na$_2$SO$_4$, filtered and concentrated. The crude product was purified by column chromatography (SiO$_2$, PE:EtOAc=50:1 to 2:1) to deliver the title compound (yellow oil, 24.00 g, yield 59.90%). $^1$H NMR (400 MHz, CDCl$_3$): δ 4.28-4.06 (m, 1H), 3.78-3.65 (m, 2H), 3.31 (br. s., 2H), 1.50-1.48 (s, 9H), 1.14 (d, J=6.8 Hz, 6H).

Embodiment 23B tert-Butyl isopropyl(2-oxoethyl)carbamate

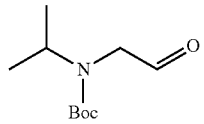

Embodiment 23A (10.00 g, 49.19 mmol) was dissolved in DCM (100 mL) at 20° C. Dess-martin reagent (31.30 g, 73.79 mmol) was added to the reaction solution and stirred for 2 hours. TLC (PE:EtOAc=3:1) showed the reaction was complete. The reaction solution was filtered and the filtrate was concentrated and the resulting residue was dissolved in EtOAc (50 mL), washed with saturated aqueous NaHCO$_3$ solution (50 mL×2), dried over anhydrous Na$_2$SO$_4$, filtered and concentrated. The crude product was purified by column chromatography (SiO$_2$:PE:EtOAc: 100:1 to 10:1) to deliver the title compound (yellow oil, 7.90 g, 71.82% yield). $^1$H NMR (400 MHz, CDCl$_3$): δ 9.53 (br. s., 1H), 4.63-4.21 (m, 1H), 3.86-3.61 (m, 2H), 1.50-1.39 (m, 9H), 1.12 (d, J=6.8 Hz, 6H).

Embodiment 23C tert-Butyl isopropyl(2-(methylamino)ethyl)carbamate

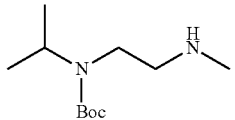

Embodiment 23B (1.80 g, 8.94 mmol) and methylamine hydrochloride (1.21 g, 17.89 mmol) were dissolved in MeOH (200 mL) and Pd/C (10%, 100.00 mg) was added after replacing with argon, and the reaction mixture was replaced with H$_2$ 3 times. The reaction solution was heated to 50° C. under the pressure of 50 psi and stirred for 24 hours. TLC (DCM:MeOH=20:1) showed the reaction was complete, the reaction mixture was filtered and the filtrate was concentrated to dryness to deliver the crude product in DCM (20 mL) and washed with 6N NaOH (10 mL×2), the organic phase was dried over anhydrous Na$_2$SO$_4$, filtered and concentrated to deliver the title compound (yellow oil, 600.00 mg, yield 26.37%). $^1$H NMR (300 MHz, CDCl$_3$): δ 4.24-4.07 (m, 1H), 3.20-3.15 (m, 2H), 2.77-2.66 (m, 2H), 2.52-2.42 (m, 3H), 1.48 (s, 9H), 1.13 (d, J=6.8 Hz, 6H).

Embodiment 23D tert-Butyl (2-((4-((4-(3,4-dihydro-1H-[1,4]oxazino[4,3-a]indol-10-yl)pyrimidin-2-yl)amino)-5-methoxy-2-nitrophenyl)(methyl)amino)ethyl)(isopropyl)carbamate

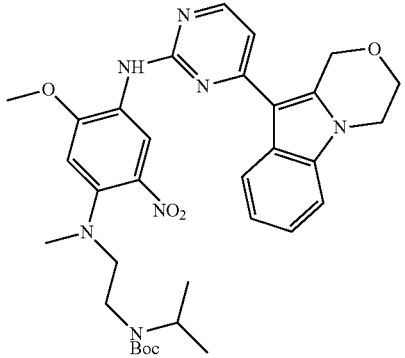 [SMILES: COc1cc(N(C)CCN(C(=O)OC(C)(C)C)C(C)C)c([N+](=O)[O-])cc1Nc1nccc(-c2c3n(c4ccccc24)CCOC3)n1]

The Embodiment was prepared according to the method of Embodiment 16A except for replacing N,N-diethyl-N-methylethane-1,2-diamine with Embodiment 23C to deliver the title compound (yellow solid, 200 mg, Rate of 88.4%). LCMS (ESI) (5-95AB): m/z: 632.2 [M+1].

Embodiment 23E tert-Butyl (2-((2-amino-4-((4-(3,4-dihydro-1H-[1,4]oxazino[4,3-a]indol-10-yl)pyrimidin-2-yl)amino)-5-methoxyphenyl)(methyl)amino)ethyl)(isopropyl)carbamate

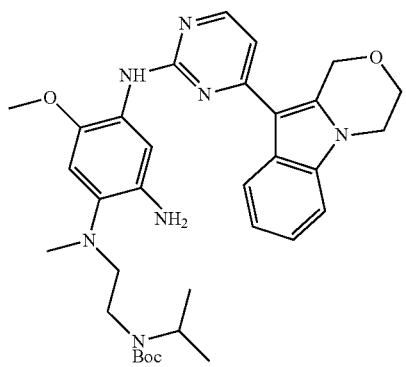 [SMILES: COc1cc(N(C)CCN(C(=O)OC(C)(C)C)C(C)C)c(N)cc1Nc1nccc(-c2c3n(c4ccccc24)CCOC3)n1]

The Embodiment was prepared according to the method of Embodiment 16B except for replacing Embodiment 16A with Embodiment 23D to deliver the title compound (brown solid, 180 mg, crude). LCMS (ESI) (5-95AB): m/z: 602.4 [M+1].

Embodiment 23F tert-Butyl (2-((2-acrylamido-4-((4-(3,4-dihydro-1H-[1,4]oxazino[4,3-a]indol-1-yl)pyrimidin-2-yl)amino)-5-methoxyphenyl)(methyl)amino)ethyl)(isopropyl)carbamate

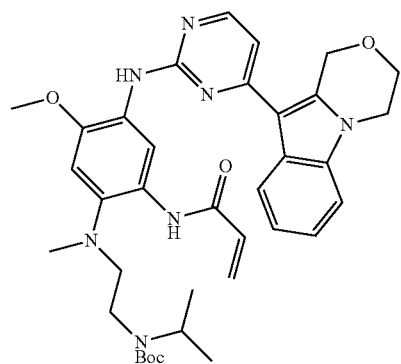 [SMILES: C=CC(=O)Nc1cc(Nc2nccc(-c3c4n(c5ccccc35)CCOC4)n2)c(OC)cc1N(C)CCN(C(=O)OC(C)(C)C)C(C)C]

The Embodiment was prepared according to the method of Embodiment 16C except for replacing Embodiment 16B with Embodiment 23E to deliver the title compound (180 mg, crude) which was used directly in the next step.

Embodiment 23G

N-(5-((4-(3,4-Dihydro-1H-[1,4]oxazino[4,3-a]indol-10-yl)pyrimidin-2-yl)amino)-2-((2-(isopropylamino)ethyl)(methyl)amino)-4-methoxyphenyl)acrylamide

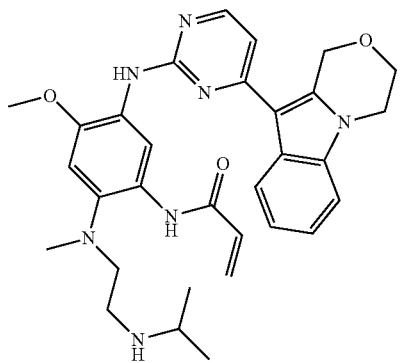 [SMILES: C=CC(=O)Nc1cc(Nc2nccc(-c3c4n(c5ccccc35)CCOC4)n2)c(OC)cc1N(C)CCNC(C)C]

The Embodiment was prepared according to the method of Embodiment 21E except for replacing Embodiment 21D with Embodiment 23F to deliver the title compound (FA salt, yellow solid, 24.30 mg, yield 14.34%). $^1$H NMR (400 MHz, CD$_3$OD): δ 8.33 (d, J=4.0 Hz, 1H), 8.27 (s, 1H), 8.08-8.03 (m, 1H), 7.46-7.42 (m, 1H), 7.28-7.20 (m, 2H), 7.15 (d, J=4.0 Hz, 1H), 6.92 (s, 1H), 6.58-6.49 (m, 1H), 6.44-6.37 (m, 1H), 5.84 (dd, J=2.0, 8.0 Hz, 1H), 5.19 (s, 2H), 4.14 (s, 4H), 3.98 (s, 3H), 3.44 (t, J=6.0 Hz, 2H), 3.39-3.33 (m, 1H), 3.15 (t, J=6.0 Hz, 2H), 2.72 (s, 3H), 1.35 (d, J=8.0 Hz, 6H). LCMS (ESI) (0-60AB): m/z: 556.4 [M+1].

Embodiment 24

N-(2-((2-(tert-Butylamino)ethyl)(methyl)amino)-5-((4-(3,4-dihydro-1H-[1,4]oxazino[4,3-a]indol-10-yl)pyrimidin-2-yl)amino)-4-methoxyphenyl)acrylamide

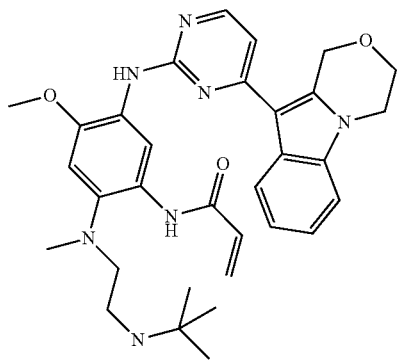 [SMILES: C=CC(=O)Nc1cc(Nc2nccc(-c3c4n(c5ccccc35)CCOC4)n2)c(OC)cc1N(C)CCNC(C)(C)C]

Embodiment 24A tert-Butyl (2-(tert-butylamino)ethyl)(methyl)carbamate

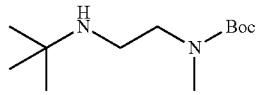 [SMILES: CN(CCNC(C)(C)C)C(=O)OC(C)(C)C]

2-Methylpropan-2-amine (844.04 mg, 11.54 mmol) and tert-butyl-N-methyl-N-(2-oxoethyl)carbamic acid (1.00 g, 5.77 mmol) were dissolved in MeOH (30 mL) and Pd/C (10%, 200.00 mg) was added after replacing with argon and the reaction mixture was replaced with $H_2$. The reaction solution was stirred in $H_2$ under the pressure of 50 psi for 16 hours. LCMS showed that the reactants were completely consumed and the desired MS was detected. The reaction mixture was filtered and the filtrate was concentrated to dryness to deliver the crude product which was dissolved in DCM (30 mL), washed with water (30 mL×2) and the organic phase was concentrated to deliver the title compound (orange oil, 1.00 g, 71.48% yield). $^1$H NMR (400 MHz, CDCl$_3$): δ 3.28 (t, J=6.7 Hz, 2H), 2.92-2.82 (m, 3H), 2.75-2.65 (m, 2H), 1.53-1.39 (m, 10H), 1.08 (s, 9H).

Embodiment 24B $N^1$-(tert-Butyl)-$N^2$-methylethane-1,2-diamine

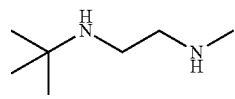

Embodiment 24A (200.00 mg, 868.24 μmol) was dissolved in EA (30 mL) at 20° C. and HCl/EtOAc (4 mol/L, 2.17 mL) was added to the mixture, and the resulting reaction was stirred for 4 hours. TLC (DCM/MeOH=10/1) showed starting materials were completely consumed. The reaction solution was concentrated to deliver the title compound (white powder hydrochloride, 160 mg, yield 86.18%). $^1$H NMR (400 MHz, D$_2$O): δ 3.60-3.39 (m, 4H), 3.00-2.79 (m, 3H), 1.60-1.37 (m, 9H).

Embodiment 24C $N^4$-(2-(tert-Butylamino)ethyl)-$N^1$-(4-(3,4-dihydro-1H-[1,4]oxazino[4,3-a]indol-10-yl)pyrimidin-2-yl)-2-methoxy-$N^4$-methyl-5-nitrobenzene-1,4-diamine

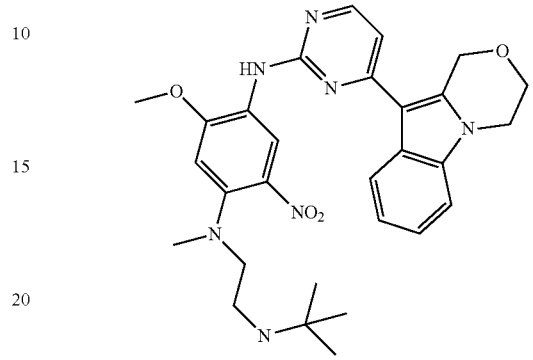

The Embodiment was prepared according to the method of Embodiment 16A except for replacing N,N-diethyl-N-methylethane-1,2-diamine with Embodiment 24B to deliver the title compound (120.00 mg, crude). LCMS (ESI) (5-95AB): m/z: 546.3 [M+1].

Embodiment 24D $N^1$-(2-(tert-Butylamino)ethyl)-$N^4$-(4-(3,4-dihydro-1H-[1,4]oxazino[4,3-a]indol-10-yl)pyrimidin-2-yl)-5-methoxy-N-methylbenzene-1,2,4-triamine

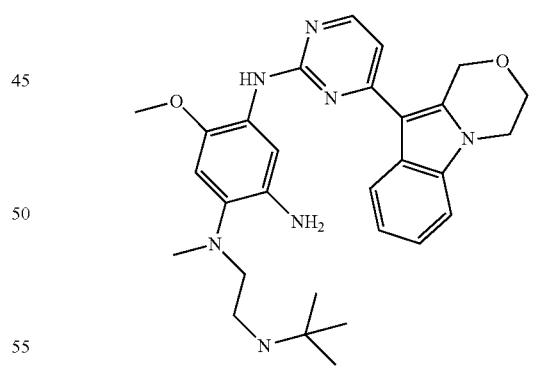

The Embodiment was prepared according to the method of Embodiment 16B except for replacing Embodiment 16A with Embodiment 24C to deliver the title compound (orange powder, 100 mg, crude). LCMS (ESI) (5-95AB): m/z: 516.3 [M+1].

Embodiment 24E

N-(2-((2-(tert-Butyl amino)ethyl)(methyl)amino)-5-((4-(3,4-dihydro-1H-[1,4]oxazino[4,3-a]indol-10-yl)pyrimidin-2-yl)amino)-4-methoxyphenyl)acrylamide

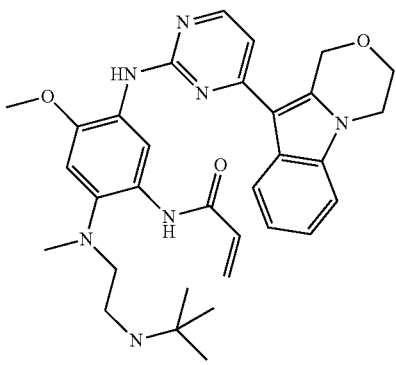 [SMILES: C=CC(=O)Nc1cc(Nc2nccc(-c3c4n(c5ccccc35)CCOC4)n2)c(OC)cc1N(C)CCNC(C)(C)C]

The Embodiment was prepared according to the method of Embodiment 16C except for replacing Embodiment 16B with Embodiment 24D to deliver the title compound (FA salt, 46.82 mg, yield 39.41%). $^1$H NMR (400 MHz, DMSO-$d_6$): δ 9.73 (s, 1H), 8.50 (s, 1H), 8.40 (s, 1H), 8.36 (d, J=5.3 Hz, 1H), 8.13-8.00 (m, 2H), 7.50 (d, J=7.0 Hz, 1H), 7.29-7.16 (m, 2H), 7.10 (d, J=5.5 Hz, 1H), 6.94 (s, 1H), 6.80 (dd, J=10.3, 16.8 Hz, 1H), 6.22 (d, J=16.8 Hz, 1H), 5.72 (d, J=11.0 Hz, 1H), 5.13 (s, 2H), 4.15 (d, J=4.8 Hz, 2H), 4.08 (d, J=4.8 Hz, 2H), 3.85 (s, 3H), 3.22 (br. s., 2H), 2.93 (br. s., 2H), 2.60 (s, 3H), 1.35-1.03 (m, 9H). LCMS (ESI) (5-95AB): m/z: 570.4 [M+1].

Embodiment 25

N-(5-((4-(3,4-Dihydro-1H-[1,4]oxazino[4,3-a]indol-10-yl)pyrimidin-2-yl)amino)-2-((2-(dimethylamino)-2-methylpropyl)(methyl)amino)-4-methoxyphenyl)acrylamide

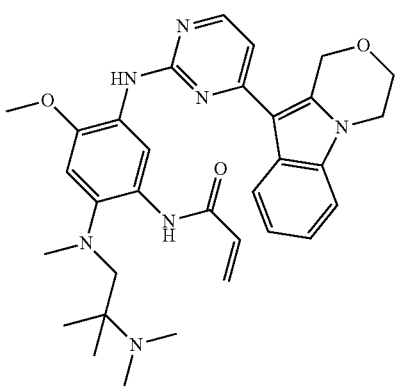 [SMILES: C=CC(=O)Nc1cc(Nc2nccc(-c3c4n(c5ccccc35)CCOC4)n2)c(OC)cc1N(C)CC(C)(C)N(C)C]

Embodiment 25A

1-Chloro-N,N,2-trimethylpropan-2-amine

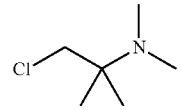

2-(Dimethylamino)-2-methylpropan-1-ol (10.00 g, 85.33 mmol) was dissolved in toluene (100 mL), SOCl$_2$ (20.30 g, 170.66 mmol) was added to the mixture. After the addition, the reaction solution was heated to 100° C. and stirred for 3 hours. TLC (DCM/MeOH=10/1) showed the starting materials were completely consumed. The reaction solution was concentrated to deliver the title compound (orange powder, hydrochloride, 12.00 g, crude). $^1$H NMR (400 MHz, CD$_3$OD): δ 3.65-3.56 (m, 2H), 3.05 (s, 6H), 1.77-1.68 (m, 6H).

Embodiment 25B

N$^1$,N$^2$,N$^2$,2-Tetramethylpropane-1,2-diamine

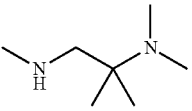

1-Chloro-N,N,2-trimethylpropan-2-amine (1.00 g, 5.81 mmol, hydrochloride) was dissolved in H$_2$O (10 mL) at 20° C., methylamine (1.80 g, 17.43 mmol) was added to the mixture and stirred for 2 hours. LCMS showed the reaction was complete, the NaOH solid (2 g) was slowly added to the reaction mixture, the reaction solution was extracted with MTBE (20 mL×2) after cooling. The separated organic phase was concentrated to 5 mL and then HCl/EA (5 mL) was added and concentrated to deliver the title The compound (orange powder, 1.00 g, crude, hydrochloride). $^1$H NMR (400 MHz, D$_2$O): δ 3.57-3.48 (m, 2H), 3.01 (s, 6H), 2.81-2.75 (m, 3H), 1.53 (s, 6H).

Embodiment 25C

N[1]-(4-(3,4-Dihydro-1H-[1,4]oxazino[4,3-a]indol-10-yl)pyrimidin-2-yl)-N[4]-(2-(dimethylamino)-2-methylpropyl)-2-methoxy-N[4]-methyl-5-nitrobenzene-1,4-diamine

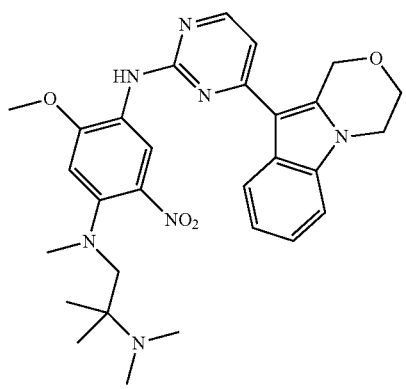 [SMILES: COc1cc(N(C)CC(C)(C)N(C)C)c([N+](=O)[O-])cc1Nc1nccc(-c2c3n(c4ccccc24)CCOC3)n1]

The Embodiment was prepared according to the method of Embodiment 16A except for replacing N,N-diethyl-N-methylethane-1,2-diamine with Embodiment 25B to deliver the title compound (red powder, 100.00 mg, crude). LCMS (ESI) (5-95AB): m/z: 546.4 [M+1].

Embodiment 25D

N[4]-(4-(3,4-Dihydro-1H-[1,4]oxazino[4,3-a]indol-10-yl)pyrimidin-2-yl)-N[1]-(2-(dimethylamino)-2-methylpropyl)-5-methoxy-N[1]-methylbenzene-1,2,4-triamine

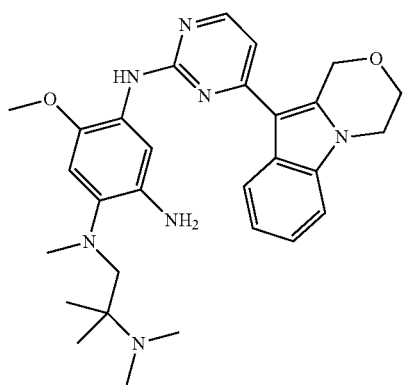 [SMILES: COc1cc(N(C)CC(C)(C)N(C)C)c(N)cc1Nc1nccc(-c2c3n(c4ccccc24)CCOC3)n1]

The Embodiment was prepared according to the method of Embodiment 16B except for replacing Embodiment 16A with Embodiment 25C to deliver the title compound (orange gum, 70 mg, crude). LCMS (ESI) (5-95AB): m/z: 516.4 [M+1].

Embodiment 25E

N-(5-((4-(3,4-Dihydro-1H-[1,4]oxazino[4,3-a]indol-10-yl)pyrimidin-2-yl)amino)-2-((2-(dimethylamino)-2-methylpropyl)(methyl)amino)-4-methoxyphenyl)acrylamide

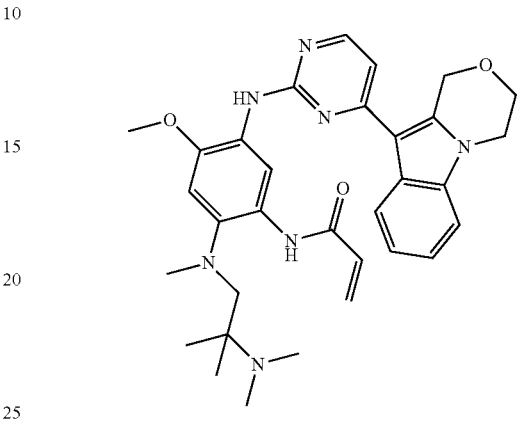

The Embodiment was prepared according to the method of Embodiment 16C except for replacing Embodiment 16B with Embodiment 25D to deliver the title compound (formate, 50.92 mg, yield 58.97%). $^1$H NMR (400 MHz, DMSO-$d_6$): δ 10.59 (br. s., 1H), 8.53 (s, 1H), 8.36 (d, J=5.3 Hz, 1H), 8.28 (s, 2H), 8.12-8.03 (m, 2H), 7.54-7.45 (m, 1H), 7.26-7.19 (m, 2H), 7.15-7.06 (m, 2H), 6.48 (dd, J=10.0, 16.8 Hz, 1H), 6.23 (dd, J=1.4, 16.9 Hz, 1H), 5.75 (d, J=11.5 Hz, 1H), 5.06 (s, 2H), 4.24-4.14 (m, 2H), 4.05 (d, J=4.8 Hz, 2H), 3.87-3.83 (m, 3H), 3.12 (br. s., 2H), 2.69 (s, 3H), 2.35 (s, 6H), 1.07-0.89 (m, 6H). LCMS (ESI) (5-95AB): m/z: 570.4 [M+1].

Embodiment 26

N-(2-((2-(Azetidin-1-yl)ethyl)(methyl)amino)-5-((4-(3,4-dihydro-1H-[1,4]oxazino[4,3-a]indol-10-yl)pyrimidin-2-yl)amino)-4-methoxyphenyl)acrylamide

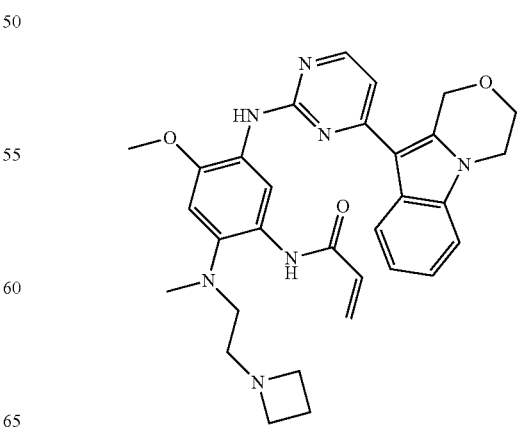

Embodiment 26A

N4-(2-(Azetidin-1-yl)ethyl)-N1-(4-(3,4-dihydro-1H-[1,4]oxazino[4,3-a]indol-10-yl)pyrimidin-2-yl)-2-methoxy-N4-methyl-5-nitrobenzene-1,4-diamine

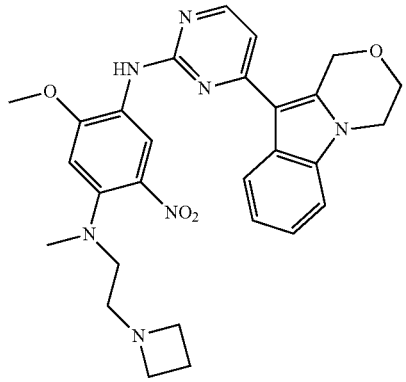 [SMILES: COc1cc(N(C)CCN2CCC2)c([N+](=O)[O-])cc1Nc1nccc(-c2c3n(c4ccccc24)CCOC3)n1]

The Embodiment was prepared according to the method of Embodiment 16A except for replacing N,N-diethyl-N-methylethane-1,2-diamine with 2-(aziridin-1-yl)-N-methylamine to deliver the title compound (red powder, 150.00 mg, crude). LCMS (ESI) (5-95AB): m/z: 530.2 [M+1].

Embodiment 26B

N1-(2-(Azetidin-1-yl)ethyl)-N4-(4-(3,4-dihydro-1H-[1,4]oxazino[4,3-a]indol-10-yl)pyrimidin-2-yl)-5-methoxy-N1-methylbenzene-1,2,4-triamine

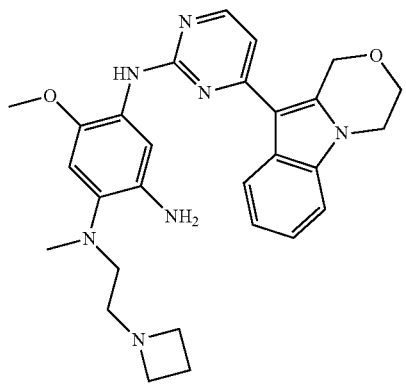

The Embodiment was prepared according to the method of Embodiment 16B except for replacing Embodiment 16A with Embodiment 26A to deliver the title compound (brown powder, 130.00 mg, crude).

Embodiment 26C

N-(2-((2-(Azetidin-1-yl)ethyl)(methyl)amino)-5-((4-(3,4-dihydro-1H-[1,4]oxazino[4,3-a]indol-10-yl)pyrimidin-2-yl)amino)-4-methoxyphenyl)acrylamide

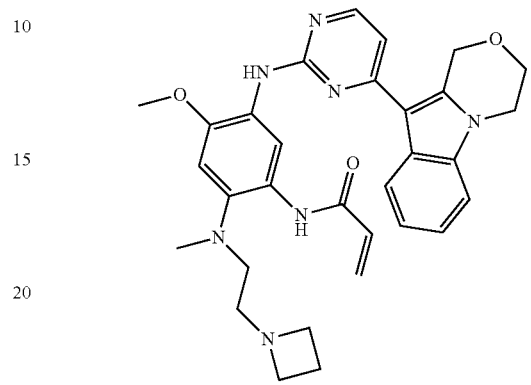

The Embodiment was prepared according to the method of Embodiment 16C except for replacing Embodiment 16B with Embodiment 26B to deliver the title compound (FA salt, 57.26 mg, yield 39.64%). $^1$H NMR (400 MHz, DMSO-$d_6$): δ 9.28 (s, 1H), 8.36-8.31 (m, 2H), 8.30 (s, 1H), 8.11-7.98 (m, 2H), 7.55-7.44 (m, 1H), 7.27-7.16 (m, 2H), 7.11-7.05 (m, 1H), 6.88 (s, 1H), 6.68 (dd, J=10.2, 16.9 Hz, 1H), 6.20 (dd, J=1.3, 17.1 Hz, 1H), 5.72 (d, J=10.8 Hz, 1H), 5.11 (s, 2H), 4.15 (d, J=5.0 Hz, 2H), 4.08 (d, J=4.8 Hz, 2H), 3.82 (s, 3H), 3.23 (br. s., 2H), 3.10 (t, J=5.3 Hz, 2H), 3.00 (br. s., 4H), 2.55 (s, 3H), 1.97 (br. s., 2H). LCMS (ESI) (5-95AB): m/z: 554.2 [M+1].

Embodiment 27

N-(5-((4-(3,4-Dihydro-1H-[1,4]oxazino[4,3-a]indol-10-yl)pyrimidin-2-yl)amino)-4-methoxy-2-(methyl (2-(methylamino)ethyl)amino)phenyl)acrylamide

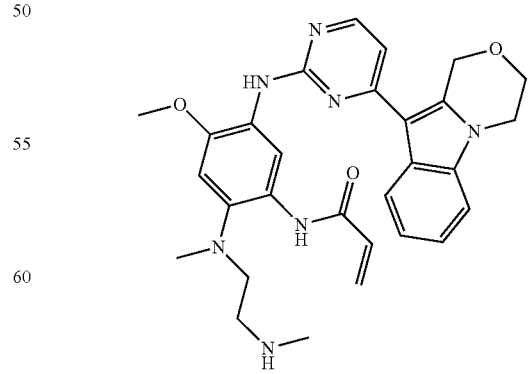

The synthetic process of the Embodiment is the same as the process 9.

Embodiment 27A tert-Butyl (2-((4-((4-(3,4-dihydro-1H-[1,4]oxazino[4,3-a]indol-10-yl)pyrimidin-2-yl)amino)-5-methoxy-2-nitrophenyl)(methyl)amino)ethyl)(methyl)carbamate

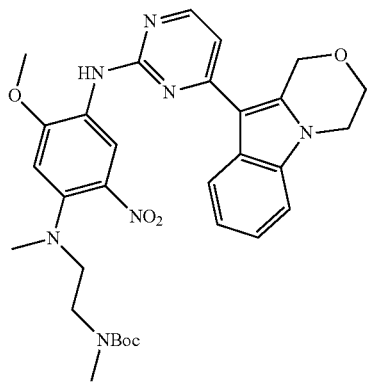 [SMILES: COc1cc(N(C)CCN(C)C(=O)OC(C)(C)C)c([N+](=O)[O-])cc1Nc1nccc(-c2c3n(c4ccccc24)CCOC3)n1]

The Embodiment was prepared according to the method of Embodiment 21B except for replacing Embodiment 21A with $N^1$-(4-(3,4-dihydro-1H-[1,4]oxazino[4,3-a]indol-10-yl)pyrimidin-2-yl)-2-methoxy-$N^4$-methyl-$N^4$-(2-(methylamino)ethyl)-5-nitrobenzene-1,4-diamine to deliver the title compound (yellow solid, 150.00 mg, crude). LCMS (ESI) (0-60AB): m/z: 604.3 [M+1].

Embodiment 27B tert-Butyl (2-((2-amino-4-((4-(3,4-dihydro-1H-[1,4]oxazino[4,3-a]indol-10-yl)pyrimidin-2-yl)amino)-5-methoxyphenyl)(methyl)amino)ethyl)(methyl)carbamate

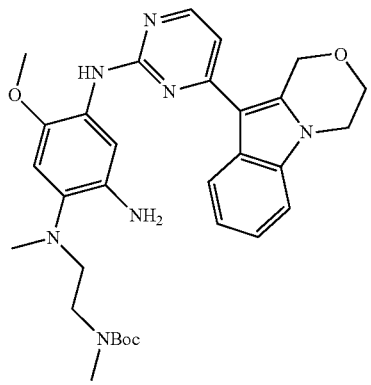 [SMILES: COc1cc(N(C)CCN(C)C(=O)OC(C)(C)C)c(N)cc1Nc1nccc(-c2c3n(c4ccccc24)CCOC3)n1]

The Embodiment was prepared according to the method of Embodiment 16B except for replacing Embodiment 16A with Embodiment 27A to deliver the title compound (yellow solid, 100.00 mg, crude). LCMS (ESI) (0-60AB): m/z: 574.3 [M+1].

Embodiment 27C tert-Butyl (2-((2-acrylamido-4-((4-(3,4-dihydro-1H-[1,4]oxazino[4,3-a]indol-10-yl)pyrimidin-2-yl)amino)-5-methoxyphenyl)(methyl)amino)ethyl)(methyl)carbamate

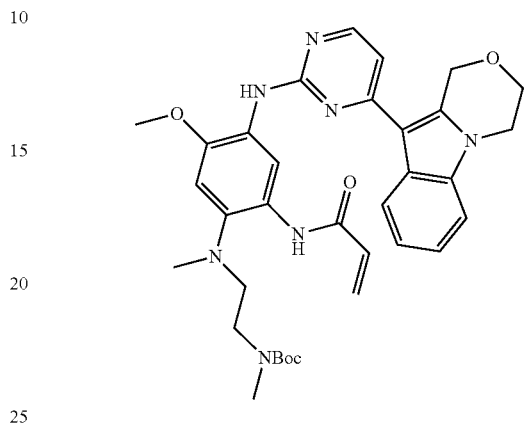

The Embodiment was prepared according to the method of Embodiment 16C except for replacing Embodiment 16B with Embodiment 27B to deliver the title compound (yellow solid, 150.00 mg, crude). LCMS (ESI) (0-60AB): m/z: 628.4 [M+1].

Embodiment 27D

N-(5-((4-(3,4-Dihydro-1H-[1,4]oxazino[4,3-a]indol-10-yl)pyrimidin-2-yl)amino)-4-methoxy-2-(methyl(2-(methylamino)ethyl)amino)phenyl)acrylamide

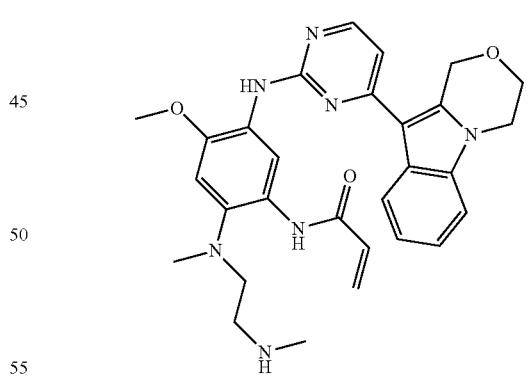

The Embodiment was prepared according to the method of Embodiment 21E except for replacing Embodiment 21D with Embodiment 27C to deliver the title compound (formate, 9.26 mg, yield 6.65%). $^1$H NMR (400 MHz, CD$_3$OD): δ 8.44 (br. s., 1H), 8.31-8.35 (m, 2H), 8.03-8.06 (m, 1H), 7.42 (s, 1H), 7.21-7.28 (m, 2H), 7.16 (d, J=5.60 Hz, 1H), 6.94 (s, 1H), 6.54-6.60 (m, 1H), 6.40-6.45 (m, 1H), 5.84-5.87 (m, 1H), 5.17 (s, 2H), 4.13 (s, 4H), 3.98 (s, 3H), 3.43 (t, J=5.20 Hz, 2H), 3.17 (t, J=5.20 Hz, 2H), 2.72 (d, J=1.20 Hz, 6H). LCMS (ESI) (0-60AB): m/z: 528.4 [M+1].

Embodiment 28

N-(5-((4-(3,4-Dihydro-1H-[1,4]oxazino[4,3-a]indol-10-yl)pyrimidin-2-yl)amino)-2-((2-(dimethyl amino)ethyl)(methyl)amino)-4-ethoxyphenyl)acrylamide

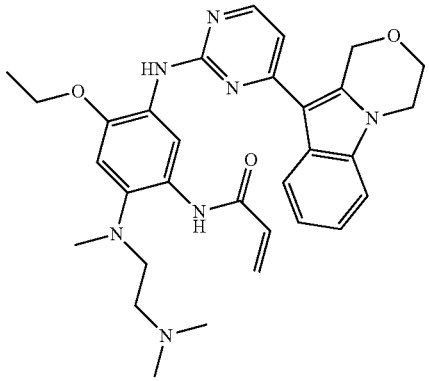 [SMILES: C=CC(=O)Nc1cc(Nc2nccc(-c3c4n(c5ccccc35)CCOC4)n2)c(OCC)cc1N(C)CCN(C)C]

Embodiment 28A 4-(3,4-Dihydro-1H-[1,4]oxazino[4,3-a]indol-1O-yl)-N-(2-ethoxy-4-fluoro-5-nitrophenyl)pyrimidin-2-amine

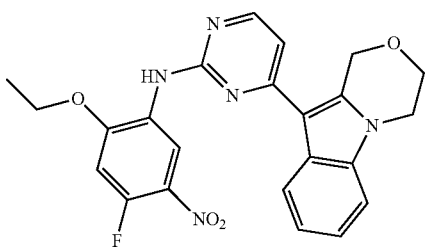 [SMILES: CCOc1cc(F)c([N+](=O)[O-])cc1Nc1nccc(-c2c3n(c4ccccc24)CCOC3)n1]

The Embodiment was prepared according to the method of Embodiment D except for replacing 4-fluoro-2-methoxy-5-nitroaniline with 2-ethyl-4-fluoro-5-nitroaniline to deliver the title compound (yellow solid, 300.00 mg, crude).

Embodiment 28B $N^1$-(4-(3,4-Dihydro-1H-[1,4]oxazino[4,3-a]indol-10-yl)pyrimidin-2-yl)-$N^4$-(2-(dimethylamino)ethyl)-2-ethoxy-$N^4$-methyl-5-nitrobenzene-1,4-diamine

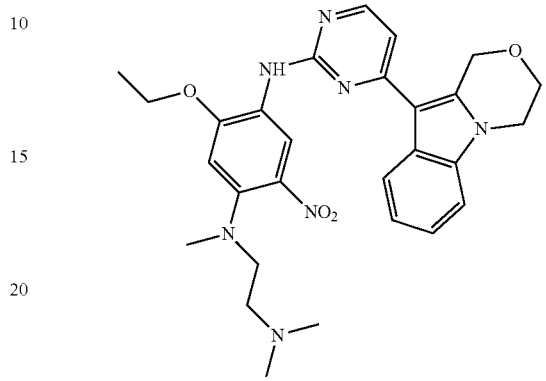

The Embodiment was prepared according to the method of Embodiment 16A except for replacing Embodiment D and N,N-diethyl-N-methylethane-1,2-diamine with Embodiment 28A and N,N',N'-trimethyl-1,2-ethanediamine respectively to deliver the title compound (yellow solid, 230.00 mg, crude). LCMS (ESI) (5-95AB): m/z: 532.2 [M+1].

Embodiment 28C $N^4$-(4-(3,4-Dihydro-1H-[1,4]oxazino[4,3-a]indol-10-yl)pyrimidin-2-yl)-$N^1$-(2-(dimethylamino)ethyl)-5-ethoxy-$N^1$-methylbenzene-1,2,4-triamine

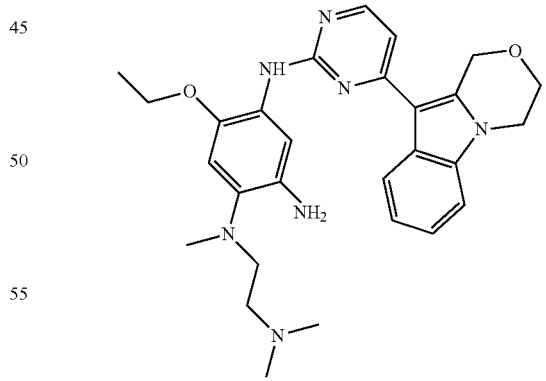

The Embodiment was prepared according to the method of Embodiment 16B except for replacing Embodiment 16A with Embodiment 28B to deliver the title compound (brown powder, 200.00 mg, crude). LCMS (ESI) (5-95AB): m/z: 502.3 [M+1].

Embodiment 28D

N-(5-((4-(3,4-Dihydro-1H-[1,4]oxazino[4,3-a]indol-10-yl)pyrimidin-2-yl)amino)-2-((2-(dimethylamino)ethyl)(methyl)amino)-4-ethoxyphenyl)acrylamide

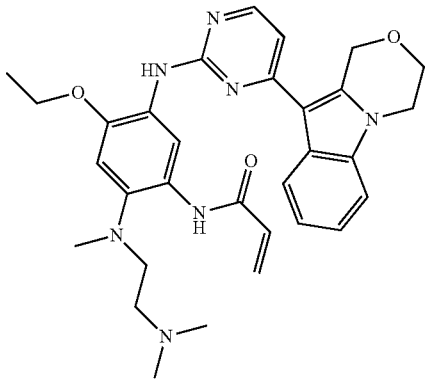 [SMILES: C=CC(=O)Nc1cc(Nc2nccc(-c3c4n(c5ccccc35)CCOC4)n2)c(OCC)cc1N(C)CCN(C)C]

The Embodiment was prepared according to the method of Embodiment 16C except for replacing Embodiment 16B with Embodiment 28C to deliver the title compound (FA salt, 125.00 mg, yield 50.65%). $^1$H NMR (400 MHz, CD$_3$OD): δ 8.46 (br. s., 1H), 8.35 (d, J=4.0 Hz, 1H), 8.32 (s, 1H), 8.09-8.05 (m, 1H), 7.49-7.42 (m, 1H), 7.28-7.21 (m, 2H), 7.19 (d, J=4.0 Hz, 1H), 6.95 (s, 1H), 6.57-6.42 (m, 2H), 5.86 (dd, J=2.0, 8.0 Hz, 1H), 5.20 (s, 2H), 4.22 (q, J=8.0 Hz, 2H), 4.16 (br. s., 4H), 3.46 (t, J=6.0 Hz, 1H), 3.25-3.20 (m, 1H), 2.84 (s, 2H), 2.73 (s, 1H), 1.49 (t, J=8.0 Hz, 1H). LCMS (ESI) (0-60AB): m/z: 556.4 [M+1].

Embodiment 29

N-(5-((4-(3,4-Dihydro-1H-[1,4]oxazino[4,3-a]indol-10-yl)pyrimidin-2-yl)amino)-2-((2-(dimethylamino)ethyl)(methyl)amino)-4-isopropoxyphenyl)acrylamide

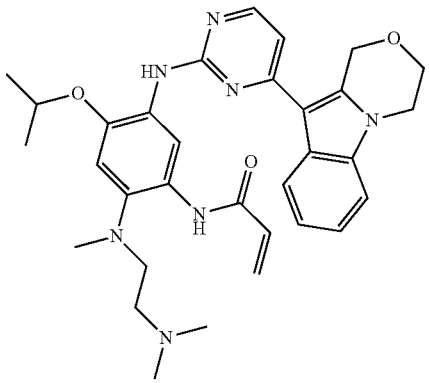 [SMILES: C=CC(=O)Nc1cc(Nc2nccc(-c3c4n(c5ccccc35)CCOC4)n2)c(OC(C)C)cc1N(C)CCN(C)C]

Embodiment 29A

N-(4-(3,4-Dihydro-1H-[1,4]oxazino[4,3-a]indol-10-yl)pyrimidin-2-yl)-N$^4$-(2-(dimethylamino)ethyl)-2-isopropoxy-N$^4$-methyl-5-nitrobenzene-1,4-diamine

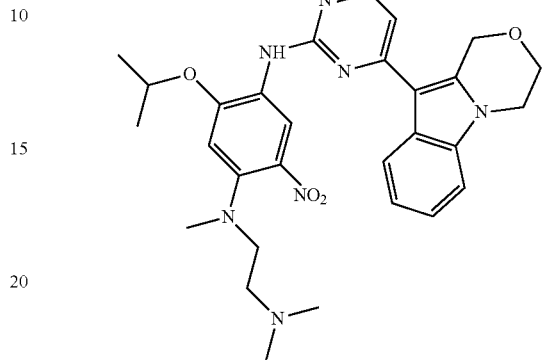

Under the protection of nitrogen, Pd(OAc)$_2$ (15.71 mg, 70.00 μmol), K$_3$PO$_4$ (297.16 mg, 1.40 mmol) and XPhos (33.37 mg, 70.00 μmol) were added to 10 mL of a solution of intermediate C (200 mg, 699.96 μmol) and N$^4$-[2-(dimethylamino)ethyl]-2-isopropoxy-N$^4$-methyl-5-nitro-benzene-1,4-diamine (207.44 mg, 699.96 μmol) in 1,4-dioxane, the reaction mixture was warmed to 90° C. and stirred for 10 hours. LCMS showed the reaction was complete, the mixture was filtered and concentrated, the crude product was purified by preparative plate (SiO$_2$, DCM:MeOH=10:1) to deliver the title compound (yellow solid, 130.00 mg, yield 26.45%). LCMS (ESI) (5-95AB): m/z: 546.4 [M+1].

Embodiment 29B

N$^4$-(4-(3,4-dihydro-1H-[1,4]oxazino[4,3-a]indol-10-yl)pyrimidin-2-yl)-N$^r$-(2-(dimethylamino)ethyl)-5-isopropoxy-N-methylbenzene-1,2,4-triamine

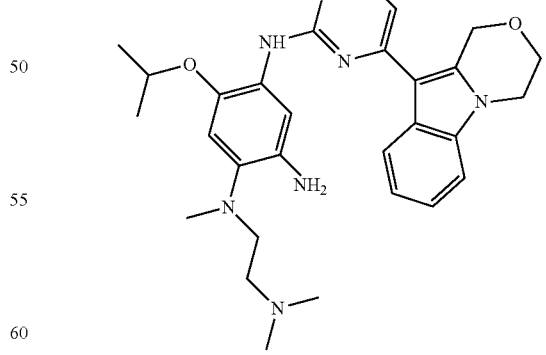

The Embodiment was prepared according to the method of Embodiment 16B except for replacing Embodiment 16A with Embodiment 29A to deliver the title compound (pale yellow solid, 120.00 mg, crude). LCMS (ESI) (5-95AB): m/z: 516.2 [M+1].

Embodiment 29C

N-(5-((4-(3,4-Dihydro-1H-[1,4]oxazino[4,3-a]indol-10-yl)pyrimidin-2-yl)amino)-2-((2-(dimethylamino)ethyl)(methyl)amino)-4-isopropoxyphenyl)acrylamide

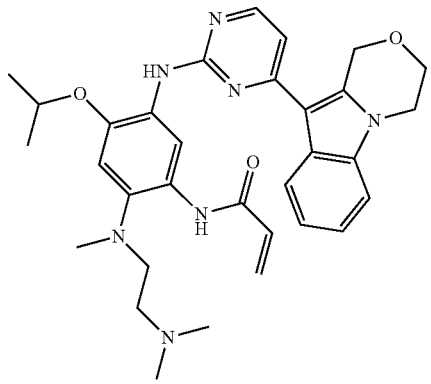 [SMILES: C=CC(=O)Nc1cc(Nc2nccc(-c3c4n(c5ccccc35)CCOC4)n2)c(OC(C)C)cc1N(C)CCN(C)C]

The Embodiment was prepared according to the method of Embodiment 16C except for replacing Embodiment 16B with Embodiment 29B to deliver the title compound (FA salt, 20.00 mg, yield 13.96%). $^1$H NMR (400 MHz, CDCl$_3$): δ 9.44 (br. s., 1H), 9.37 (s, 1H), 8.42 (d, J=4.0 Hz, 1H), 8.07-7.99 (m, 1H), 7.60 (s, 1H), 7.38-7.33 (m, 1H), 7.31-7.27 (m, 2H), 7.19 (d, J=4.0 Hz, 1H), 6.80 (dd, J=4.0, 16.0 Hz, 1H), 6.72 (s, 1H), 6.41 (dd, J=4.0, 16.0 Hz, 1H), 5.74-5.65 (m, 1H), 5.39 (s, 2H), 4.50 (spt, J=6.0 Hz, 1H), 4.16 (s, 4H), 3.18 (t, J=6.0 Hz, 2H), 2.95 (t, J=6.0 Hz, 2H), 2.67-2.64 (m, 9H), 1.39 (d, J=6.0 Hz, 6H). LCMS (ESI) (0-60AB): m/z: 570.3 [M+1].

Process 10

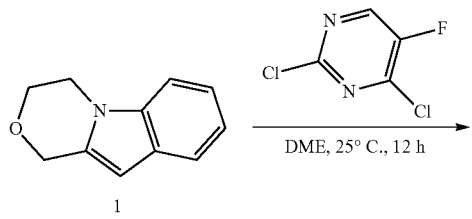

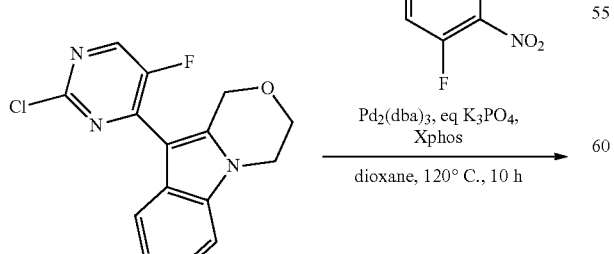

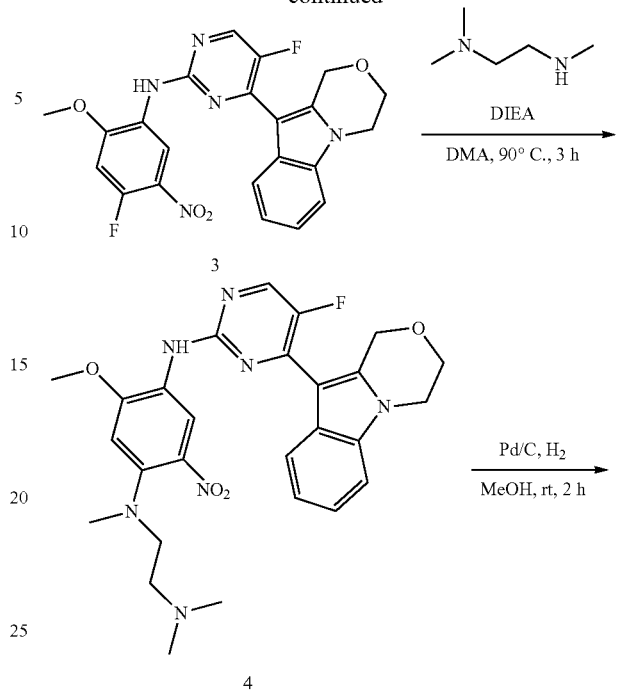

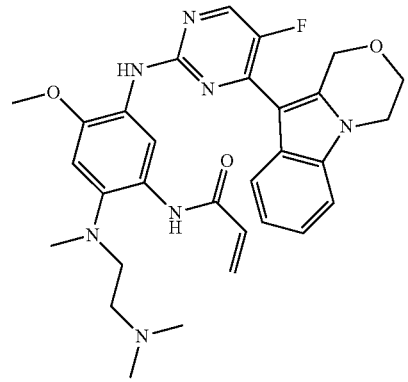

Embodiment 30

139

Embodiment 30

N-(5-((4-(3,4-Dihydro-1H-[1,4]oxazino[4,3-a]indol-10-yl)-5-fluoropyrimidin-2-yl)amino)-2-((2-(dimethylamino)ethyl)(methyl)amino)-4-methoxyphenyl)acrylamide

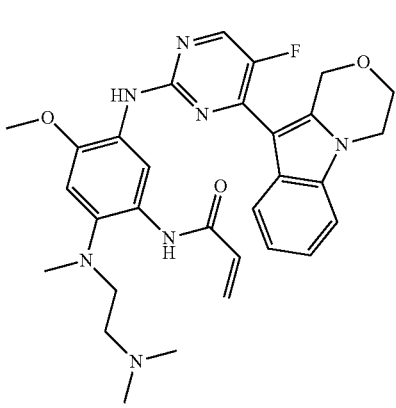 [SMILES: C=CC(=O)Nc1cc(Nc2ncc(F)c(-c3c4n(c5ccccc35)CCOC4)n2)c(OC)cc1N(C)CCN(C)C]

Embodiment 30A 10-(2-Chloro-5-fluoropyrimidin-4-yl)-3,4-dihydro-1H-[1,4]oxazino[4,3-a]indole

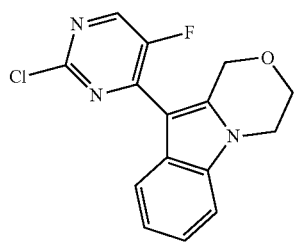 [SMILES: Fc1cnc(Cl)nc1-c1c2n(c3ccccc13)CCOC2]

2,3-Dichloro-5-fluoropyrimidine (23.14 g, 138.56 mmol) was dissolved in DME (400 mL) at 25° C. and AlCl₃ (30.79 g, 230.94 mmol) was added in batches to the mixture, and then 3,4-dihydro-1H-[1,4]oxazino[4,3-a]indole (20.00 g, 115.47 mmol) was added in batches and stirred for 12 hours. TLC showed the reaction was complete. The reaction solution was poured into stirred water (1200 mL) to precipitate a solid which was filtered and slurry with methanol (100 mL). The resulting solid was dried in vacuo to deliver the title compound (yellow solid, 31.10 g, yield 84.61%). $^1$H NMR (400 MHz, CDCl₃): δ 8.41 (d, J=2.80 Hz, 1H), 7.94-7.98 (m, 1H), 7.30-7.41 (m, 3H), 5.26 (s, 2H), 4.17-4.29 (m, 4H).

140

Embodiment 30B 4-(3,4-Dihydro-1H-[1,4]oxazino[4,3-a]indol-10-yl)-5-fluoro-N-(4-fluoro-2-methoxy-5-nitrophenyl)pyrimidin-2-amine

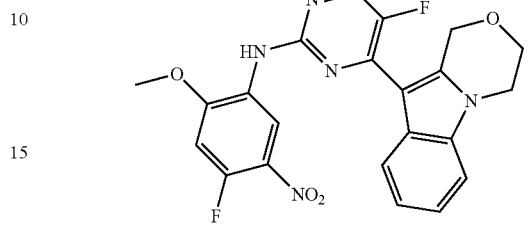

Under the protection of nitrogen, Embodiment 30A (28.00 g, 92.19 mmol) and 4-fluoro-2-methoxy-5-nitroaniline (18.02 g, 96.80 mmol) were dissolved in 1,4-dioxane (300 mL), K₃PO₄ (39.14 g, 184.38 mmol), XPhos (4.39 g, 9.22 mmol) and Pd₂(dba)₃ (8.44 g, 9.22 mmol) were added to the mixture and the reaction mixture was warmed to 120° C. for 10 hours. LCMS showed the reaction was complete and the mixture was filtered and the filter cake was washed with water (300 mL) and dried in vacuo to deliver the title compound (yellow solid, 32.06 g, 75.73% yield). $^1$H NMR (400 MHz, DMSO-d₆): δ 8.89 (d, J=8.40 Hz, 1H), 8.59 (d, J=3.20 Hz, 1H), 8.50 (s, 1H), 7.78 (dd, J=7.60, 3.51 Hz, 1H), 7.55 (d, J=8.00 Hz, 1H), 7.37 (d, J=13.20 Hz, 1H), 7.25 (d, J=7.20 Hz, 1H), 7.20 (d, J=7.20 Hz, 1H), 5.11 (s, 2H), 4.20 (d, J=8.00 Hz, 4H), 4.02 (s, 3H). LCMS (ESI) (5-95AB): m/z: 454.3 [M+1].

Embodiment 30C

N-(4-(3,4-Dihydro-1H-[1,4]oxazino[4,3-a]indol-10-yl)-5-fluoropyrimidin-2-yl)-N⁴-(2-(dimethylamino)ethyl)-2-methoxy-N4-methyl-5-nitrobenzene-1,4-diamine

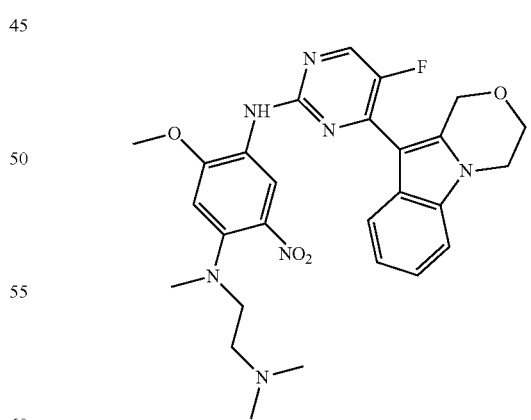

The Embodiment was prepared according to the method of Embodiment 16A except for replacing Embodiment D and N,N-diethyl-N-methylethane-1,2-diamine with Embodiment 30B and N,N',N'-trimethyl-1,2-ethanediamine respectively to deliver the title compound (red solid, 35.50 g, yield 87.43%). $^1$H NMR (400 MHz, CDCl₃): δ 9.06 (s, 1H), 8.35 (d, J=2.80 Hz, 1H), 7.88-7.93 (m, 1H), 7.54 (s, 1H), 7.38 (s, 1H), 7.32 (s, 2H), 6.69 (s, 1H), 5.29 (s, 2H), 4.30 (d, J=5.60 Hz, 2H), 4.23 (d, J=5.60 Hz, 2H), 4.00 (s, 3H), 3.25-3.31 (m, 2H), 2.89 (s, 3H), 2.53-2.61 (m, 2H), 2.28 (s, 6H). LCMS (ESI) (0-60AB): m/z: 536.4 [M+1].

Embodiment 30D

N$^4$-(4-(3,4-Dihydro-1H-[1,4]oxazino[4,3-a]indol-10-yl)-5-fluoropyrimidin-2-yl)-N$^1$-(2-(dimethylamino)ethyl)-5-methoxy-N$^1$-methylbenzene-1,2,4-triamine

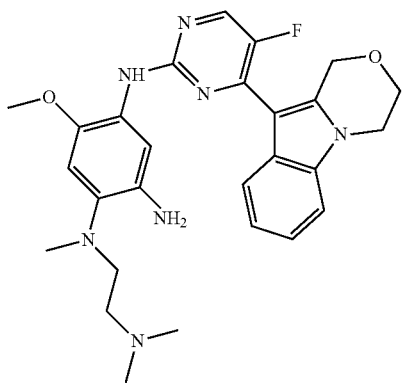 [SMILES: COc1cc(N(C)CCN(C)C)c(N)cc1Nc1ncc(F)c(-c2c3n(c4ccccc24)CCOC3)n1]

The Embodiment was prepared according to the method of Embodiment 16B except for replacing Embodiment 16A with Embodiment 30C to deliver the title compound (red solid, 26.50 g, yield 79.32%). $^1$H NMR (400 MHz, CDCl$_3$): δ 8.31 (d, J=2.80 Hz, 1H), 8.06-8.10 (m, 1H), 8.03 (s, 1H), 7.62 (s, 1H), 7.39 (d, J=4.80 Hz, 1H), 7.29-7.34 (m, 2H), 6.72 (s, 1H), 5.20 (s, 2H), 4.24 (dd, J=16.40, 5.20 Hz, 4H), 3.86 (s, 3H), 2.98 (s, 2H), 2.69 (s, 3H), 2.39-2.46 (m, 2H), 2.29 (s, 6H). LCMS (ESI) (0-60AB): m/z: 506.1 [M+1].

Embodiment 30E

N-(5-((4-(3,4-Dihydro-1H-[1,4]oxazino[4,3-a]indol-10-yl)-5-fluoropyrimidin-2-yl)amino)-2-((2-(dimethylamino)ethyl)(methyl)amino)-4-methoxyphenyl)acrylamide

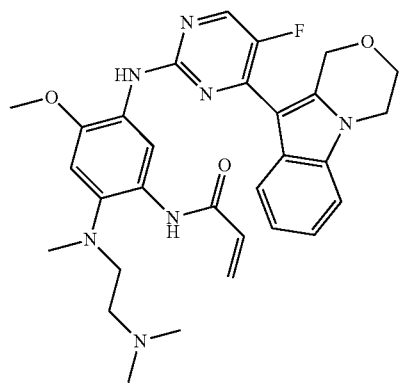 [SMILES: C=CC(=O)Nc1cc(Nc2ncc(F)c(-c3c4n(c5ccccc35)CCOC4)n2)c(OC)cc1N(C)CCN(C)C]

The Embodiment was prepared according to the method of Embodiment 16C except for replacing Embodiment 16B with Embodiment 30D to deliver the title compound (23.20 g, yield 79.02%). $^1$H NMR (400 MHz, CDCl$_3$): δ 10.09-10.17 (m, 1H), 9.46 (s, 1H), 8.39 (d, J=3.20 Hz, 1H), 7.89-7.94 (m, 1H), 7.55 (s, 1H), 7.34-7.38 (m, 1H), 7.29 (s, 1H), 7.24-7.28 (m, 1H), 6.81 (s, 1H), 6.26-6.43 (m, 2H), 5.65-5.71 (m, 1H), 5.31 (s, 2H), 4.22-4.27 (m, 2H), 4.20 (d, J=5.60 Hz, 2H), 3.90 (s, 3H), 2.86-2.94 (m, 2H), 2.73 (s, 3H), 2.23-2.33 (m, 8H). LCMS (ESI) (0-60AB): m/z: 560.2 [M+1].

Embodiment 31

N-(5-((4-(3,4-Dihydro-1H-[1,4]oxazino[4,3-a]indol-10-yl)-5-fluoropyrimidin-2-yl)amino)-4-methoxy-2-(methyl(2-(methylamino)ethyl)amino)phenyl)acrylamide

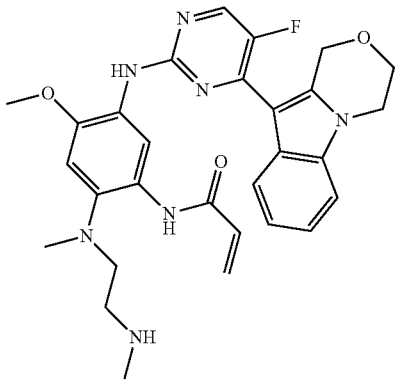 [SMILES: C=CC(=O)Nc1cc(Nc2ncc(F)c(-c3c4n(c5ccccc35)CCOC4)n2)c(OC)cc1N(C)CCNC]

The synthetic process of the Embodiment is the same as the process 9.

Embodiment 31A

N$^1$-(4-(3,4-Dihydro-1H-[1,4]oxazino[4,3-a]indol-10-yl)-5-fluoropyrimidin-2-yl)-2-methoxy-N$^4$-methyl-N$^4$-(2-(methylamino)ethyl)-5-nitrobenzene-1,4-diamine

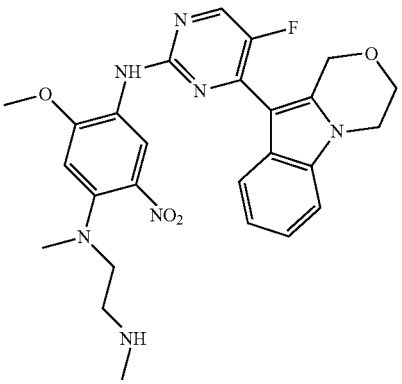 [SMILES: CNCCN(C)c1cc(OC)c(Nc2ncc(F)c(-c3c4n(c5ccccc35)CCOC4)n2)cc1[N+](=O)[O-]]

The Embodiment was prepared according to the method of Embodiment 16A except for replacing Embodiment D and N,N-diethyl-N-methylethane-1,2-diamine with 4-(3,4-dihydro-1H-[1,4]oxazino[4,3-a]indole-10-yl)-5-fluoro-N-

(4-fluoro-2-methoxy-5-nitro-phenyl)pyrimidin-2-amine and N¹,N²-dimethylethane-1,2-diamine respectively to deliver the title compound (yellow solid, 1.50 g, yield 93.08%). ¹H NMR (400 MHz, CDCl₃): δ 9.07 (s, 1H), 8.35 (d, J=2.80 Hz, 1H), 7.90 (m, 1H), 7.56 (s, 1H), 7.36-7.42 (m, 1H), 7.29-7.35 (m, 2H), 6.67 (s, 1H), 5.29 (s, 2H), 4.18-4.35 (m, 5H), 4.00 (s, 2H), 3.37 (t, J=6.00 Hz, 2H), 2.78-2.87 (m, 4H), 2.46 (s, 3H). LCMS (ESI) (5-95AB): m/z: 522.3 [M+1].

Embodiment 31B tert-Butyl N-(2-(4-((4-(3,4-dihydro-1H-[1,4]oxazino[4,3-a]indol-10-yl)-5-fluoropyrimidin-2-yl)amino)-5-methoxy-N-methyl-2-nitroaniline)ethyl)-N-methylcarbamate

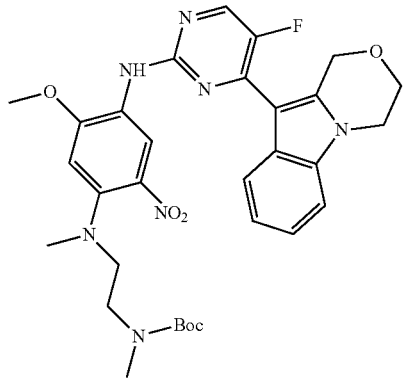 [SMILES: COc1cc(N(C)CCN(C)C(=O)OC(C)(C)C)c([N+](=O)[O-])cc1Nc1ncc(F)c(-c2c3n(c4ccccc24)CCOC3)n1]

The Embodiment was prepared according to the method of Embodiment 21B except for replacing Embodiment 21A with Embodiment 31A to deliver the title compound (yellow solid, 1.45 g, yield 80.99%). ¹H NMR (400 MHz, CDCl₃): δ 9.07 (s, 1H), 8.35 (d, J=2.80 Hz, 1H), 7.90 (m, 1H), 7.56 (s, 1H), 7.36-7.42 (m, 1H), 7.29-7.35 (m, 2H), 6.67 (s, 1H), 5.29 (s, 2H), 4.18-4.35 (m, 5H), 4.00 (s, 2H), 3.37 (t, J=6.00 Hz, 2H), 2.78-2.87 (m, 4H), 2.46 (s, 3H). LCMS (ESI) (5-95AB): m/z: 522.3 [M+1].

Embodiment 31C tert-Butyl N-(2-((2-amino-4-((4-(3,4-dihydro-1H-[1,4]oxazino[4,3-a]indol-10-yl)-5-fluoropyrimidin-2-yl)amino)-5-methoxy-N-methylanilino)ethyl)-N-methylcarbamate

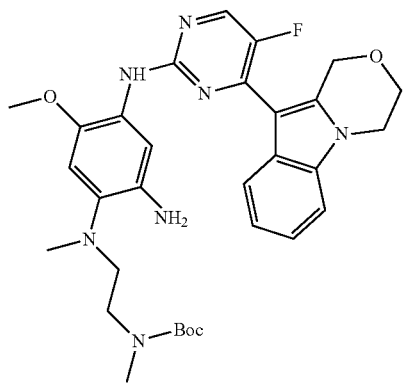

The Embodiment was prepared according to the method of Embodiment 16B except for replacing Embodiment 16A with Embodiment 31B to deliver the title compound (yellow solid, 1.30 g, 94.30% yield). LCMS (ESI) (5-95AB): m/z: 516.2 [M+1].

Embodiment 31D tert-Butyl N-(2-(4-((4-(3,4-dihydro-1H-[1,4]oxazino[4,3-a]indol-10-yl)-5-fluoropyrimidin-2-yl)amino)-5-methoxy-N-methyl-2-(pro-2-enoylamino)anilino)ethyl)-N-methylcarbamate

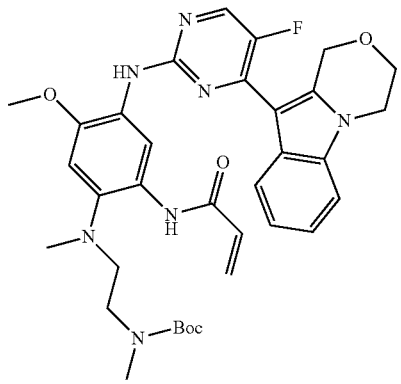 [SMILES: C=CC(=O)Nc1cc(Nc2ncc(F)c(-c3c4n(c5ccccc35)CCOC4)n2)c(OC)cc1N(C)CCN(C)C(=O)OC(C)(C)C]

The Embodiment was prepared according to the method of Embodiment 16C except for replacing Embodiment 16B with Embodiment 31C to deliver the title compound (yellow solid, 1.2 g, 84.47% yield). ¹H NMR (400 MHz, CDCl₃): δ 9.28-9.47 (m, 1H), 8.29 (d, J=2.80 Hz, 1H), 7.82 (d, J=5.20 Hz, 1H), 7.47 (s, 1H), 7.27-7.30 (m, 1H), 7.15-7.22 (m, 3H), 6.69 (s, 1H), 6.30 (d, J=4.40 Hz, 2H), 5.60-5.67 (m, 1H), 5.22 (d, J=2.80 Hz, 2H), 4.07-4.21 (m, 4H), 3.82 (s, 3H), 3.24-3.34 (m, 2H), 2.90 (br. s., 2H), 2.77 (s, 3H), 2.61 (s, 3H), 1.39 (s, 8H). LCMS (ESI) (5-95AB): m/z: 645.5 [M+1].

Embodiment 31 E

N-(5-((4-(3,4-Dihydro-1H-[1,4]oxazino[4,3-a]indol-10-yl)-5-fluoropyrimidin-2-yl)amino)-4-methoxy-2-(methyl(2-(methylamino)ethyl)amino)phenyl)acrylamide

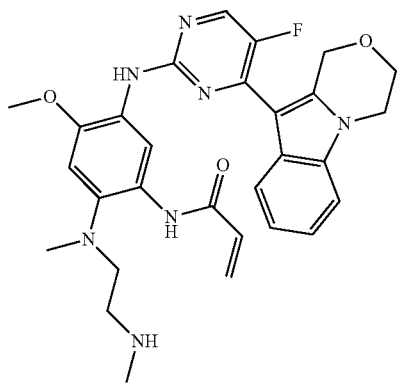 [SMILES: C=CC(=O)Nc1cc(Nc2ncc(F)c(-c3c4n(c5ccccc35)CCOC4)n2)c(OC)cc1N(C)CCNC]

The Embodiment was prepared according to the method of Embodiment 21E except for replacing Embodiment 21D with Embodiment 31D to deliver the title compound (formate, 235.20 mg, yield 20.76%). ¹H NMR (400 MHz, CD₃OD): δ 8.51-8.55 (m, 1H), 8.42 (s, 1H), 8.36-8.40 (m, 1H), 7.84-7.92 (m, 1H), 7.47 (d, J=7.60 Hz, 1H), 7.13-7.30 (m, 2H), 6.93 (s, 1H), 6.37-6.53 (m, 2H), 5.80-5.88 (m, 1H), 5.10 (s, 2H), 4.21 (s, 4H), 4.00 (s, 3H), 3.39-3.45 (m, 3H), 3.15 (br. s., 2H), 2.71 (s, 3H), 2.70 (s, 3H). LCMS (ESI) (0-60AB): m/z: 546.2 [M+1].

Embodiment 32

N-(5-((4-(3,4-Dihydro-1H-[1,4]oxazino[4,3-a]indol-10-yl)-5-fluoropyrimidin-2-yl)amino)-2-((2-(dimethylamino)-2-methylpropyl)(methyl)amino)-4-methoxyphenyl)acrylamide

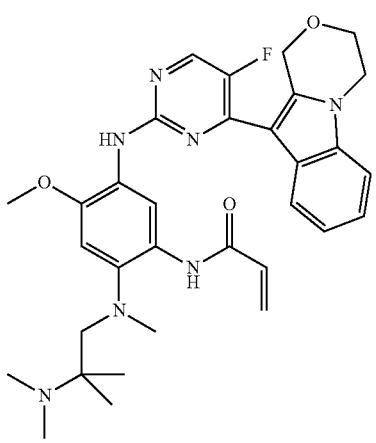 [SMILES: C=CC(=O)Nc1cc(Nc2ncc(F)c(-c3c4n(c5ccccc35)CCOC4)n2)c(OC)cc1N(C)CC(C)(C)N(C)C]

Embodiment 32A

N¹-(4-(3,4-Dihydro-1H-[1,4]oxazino[4,3-a]indol-10-yl)-5-fluoropyrimidin-2-yl)-N⁴-(2-(dimethylamino)-2-methylpropyl)-2-methoxy-N-methyl-5-nitrobenzene-1,4-diamine

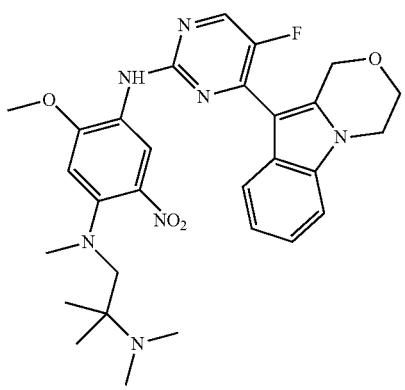 [SMILES: COc1cc(N(C)CC(C)(C)N(C)C)c([N+](=O)[O-])cc1Nc1ncc(F)c(-c2c3n(c4ccccc24)CCOC3)n1]

The Embodiment was prepared according to the method of Embodiment 16A except for replacing Embodiment D and N,N-diethyl-N-methylethane-1,2-diamine with 4-(3,4-dihydro-1H-[1,4]oxazino[4,3-a]indole-10-yl)-5-fluoro-N-(4-fluoro-2-methoxy-5-nitrophenyl)pyrimidin-2-amine and N¹,N²,N²,2-tetramethylpropane-1,2-diamine respectively to deliver the title compound (red solid, 200.00 mg, yield 80.44%). ¹H NMR (400 MHz, CDCl₃): δ 9.02 (s, 1H), 8.28 (d, J=4.0 Hz, 1H), 7.85-7.79 (m, 1H), 7.61 (s, 1H), 7.33-7.29 (m, 1H), 7.29-7.26 (m, 1H), 7.25-7.20 (m, 2H), 5.23 (s, 2H), 5.19 (s, 2H), 4.24-4.18 (m, 2H), 4.16-4.11 (m, 2H), 4.09 (s, 3H), 2.93 (s, 3H), 2.68 (s, 6H), 1.34 (s, 6H).

Embodiment 32B

N⁴-(4-(3,4-Dihydro-1H-[1,4]oxazino[4,3-a]indol-10-yl)-5-fluoropyrimidin-2-yl)-N¹-(2-(dimethylamino)-2-methylpropyl)-5-methoxy-N¹-methylbenzene-1,2,4-triamine

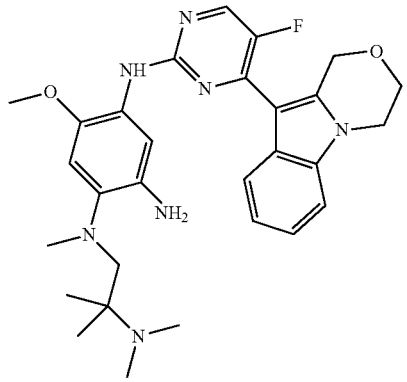

The Embodiment was prepared according to the method of Embodiment 16B except for replacing Embodiment 16A with Embodiment 32A to deliver the title compound (220.00 mg, yield 92.94%). ¹H NMR (400 MHz, CDCl₃): δ 8.23 (d, J=4.0 Hz, 1H), 8.02-7.94 (m, 1H), 7.91 (s, 1H), 7.54 (s, 1H), 7.32-7.27 (m, 1H), 7.26-7.20 (m, 2H), 6.57-6.54 (m, 1H), 5.08 (s, 2H), 4.22-4.15 (m, 2H), 4.14-4.09 (m, 2H), 3.77 (s, 3H), 3.21 (s, 2H), 2.72 (s, 3H), 2.67 (s, 6H), 1.33 (s, 6H). LCMS (ESI) (5-95AB): m/z: 534.3 [M+1].

Embodiment 32C

N-(5-((4-(3,4-Dihydro-1H-[1,4]oxazino[4,3-a]indol-10-yl)-5-fluoropyrimidin-2-yl)amino)-2-((2-(dimethylamino)-2-methylpropyl)(methyl)amino)-4-methoxyphenyl)acrylamide

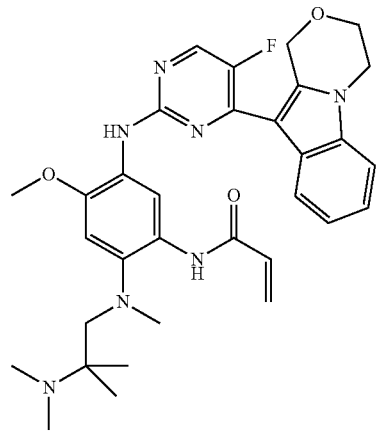 [SMILES: C=CC(=O)Nc1cc(Nc2ncc(F)c(-c3c4n(c5ccccc35)CCOC4)n2)c(OC)cc1N(C)CC(C)(C)N(C)C]

The Embodiment was prepared according to the method of Embodiment 16C except for replacing Embodiment 16B with Embodiment 32B to deliver the title compound (brown solid, 50.00 mg, yield 20.38%). ¹H NMR (400 MHz, CD₃OD): δ 8.39 (s, 1H), 8.22 (s, 1H), 8.16 (s, 1H), 7.75 (d, J=8.0 Hz, 1H), 7.32 (d, J=8.0 Hz, 1H), 7.15-7.09 (m, 1H), 7.09-7.03 (m, 1H), 7.01 (s, 1H), 6.43-6.33 (m, 2H), 5.82-5.72 (m, 1H), 4.92 (s, 2H), 4.06 (s, 4H), 3.89 (s, 3H), 3.66-3.27 (m, 2H), 2.67 (s, 3H), 2.63 (s, 6H), 1.22 (s, 6H). LCMS (ESI) (5-95AB): m/z: 588.3 [M+1].

Embodiment 33

N-(2-((2-(Dimethylamino)ethyl)(methyl)amino)-5-((5-fluoro-4-(7-fluoro-3,4-dihydro-1H-[1,4]oxazino[4,3-a]indol-10-yl)pyrimidin-2-yl)amino)-4-methoxyphenyl)acrylamide

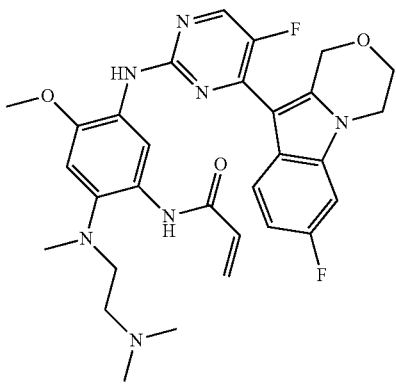 [SMILES: C=CC(=O)Nc1cc(Nc2ncc(F)c(-c3c4n(c5cc(F)ccc35)CCOC4)n2)c(OC)cc1N(C)CCN(C)C]

The synthetic process of the Embodiment is the same as the process 10.

Embodiment 33A

6-Fluoro-1-(p-toluenesulfonyl)indole

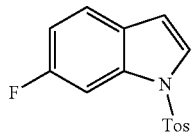

6-Fluoro-1H-indole (18.00 g, 133.20 mmol) was dissolved in N, N-dimethylformamide (400 mL) at 0° C. and NaH (6.39 g, 60% w, 159.84 mmol) was added to the mixture and stirred for 1 hour. 4-Methylbenzenesulfonyl chloride (30.47 g, 159.84 mmol) was slowly added to the mixture, and the reaction mixture was warmed to 15° C. and stirred for 11 hours. LCMS showed the reaction was complete, saturated NH₄Cl solution (500 mL) was added to the mixture, and the precipitated solid was filtered out and the filtrate was concentrated to deliver the title compound (yellow solid, 39.80 g, crude). ¹H NMR (400 MHz, CDCl₃): δ 7.71-7.81 (m, 3H), 7.56 (d, J=3.60 Hz, 1H), 7.46 (dd, J=8.40, 5.20 Hz, 1H), 7.26 (d, J=8.00 Hz, 2H), 7.00 (m, 1H), 6.64 (d, J=3.60 Hz, 1H), 2.37 (s, 3H).

Embodiment 33B

6-Fluoro-1-(p-toluenesulfonyl)indole-2-carboxylic acid

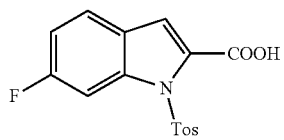

6-Fluoro-1-(p-toluenesulfonyl) indole (39.80 g, 132.06 mmol) was dissolved in tetrahydrofuran (400 mL) at −70° C., and n-butyllithium (2.5 mol, 52.82 mL) was added to the mixture and stirred for 1 hour. Dry ice (58.11 g, 1.32 mmol) was slowly added to the mixture and stirred for 1.5 hours. TLC showed the reaction was complete, saturated NH₄Cl solution (200 mL) was added to the mixture, extracted with EA (200 mL×2), the pH of the aqueous phase was adjusted to 1 with concentrated hydrochloric acid, and then extracted with DCM (200 mL×3) and concentrated to deliver the title compound (yellow solid, 32.75 g, yield 74.40%). ¹H NMR (400 MHz, DMSO-d₆): δ 7.96 (d, J=8.40 Hz, 1H), 7.80 (d, J=10.40 Hz, 1H), 7.72 (dd, J=8.80, 6.00 Hz, 1H), 7.44 (d, J=8.00 Hz, 2H), 7.34 (s, 1H), 7.23 (br. s., 1H), 2.37 (s, 3H).

Embodiment 33C (6-Fluoro-1H-indol-2-yl)methanol

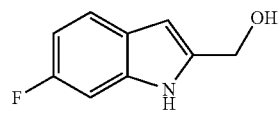 [SMILES: OCc1cc2ccc(F)cc2[nH]1]

6-Fluoro-1-(p-toluenesulfonyl)indole-2-carboxylic acid (32.75 g, 98.25 mmol) was dissolved in tetrahydrofuran (400 mL) at 0° C. Lithium aluminum hydride (9.32 g, 245.63 mmol) was added to the mixture in batches and stirred at 25° C. for 16 hours. TLC showed the reaction was complete, water (9.5 mL), 15% NaOH (9.5 mL) and water (28 mL) were added successively to the reaction mixture, and the mixture was filtered and the filtrate was concentrated to give the crude product. The product was purified by column chromatography (DCM:MeOH=20:1, 3:1) to deliver the title compound (white solid, 5.11 g, yield 31.49%). ¹H NMR (400 MHz, CDCl₃): δ 8.37 (br. s., 1H), 7.50 (dd, J=8.40, 5.20 Hz, 1H), 7.06 (dd, J=9.60, 1.60 Hz, 1H), 6.90 (td, J=9.20, 2.00 Hz, 1H), 6.41 (s, 1H), 4.84 (s, 2H).

Embodiment 33D

7-Fluoro-3,4-dihydro-1H-[1,4]oxazino[4,3-a]indole

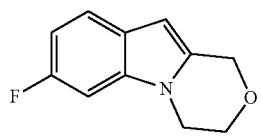 [SMILES: Fc1ccc2cc3n(c2c1)CCOC3]

(6-Fluoro-1H-indol-2-yl)methanol (5.11 g, 30.94 mmol) and potassium hydroxide (4.34 g, 77.35 mmol) were dissolved in dichloromethane (300 mL) at 0° C. Phenylvinylsulfone (14.02 g, 37.13 mmol) was added dropwise to the mixture and stirred at 20° C. for 12 hours. TLC showed the reaction was complete, the reaction mixture was washed with water (200 mL×2), the organic phase was concentrated to give the crude product. The product was purified by column chromatography (PE:EA=500:1, 200:1) to deliver the title compound (white solid, 3.65 g, yield 61.70%). $^1$H NMR (400 MHz, CDCl$_3$): δ 7.49 (dd, J=8.40, 5.20 Hz, 1H), 6.99 (dd, J=9.20, 2.00 Hz, 1H), 6.91 (ddd, J=9.60, 8.40, 2.00 Hz, 1H), 6.22 (s, 1H), 4.98 (s, 2H), 4.16-4.24 (m, 2H), 4.01-4.09 (m, 2H).

Embodiment 33E 10-(2-Chloro-5-fluoropyrimidin-4-yl)-7-fluoro-3,4,5a,9a-tetrahydro-1H-[1,4]oxazino[4,3-a]indole

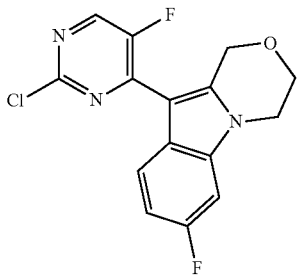 [SMILES: Fc1ccc2c(-c3nc(Cl)ncc3F)c3n(c2c1)CCOC3]

The Embodiment was prepared according to the method of Embodiment 30A except for replacing 3,4-dihydro-1H-[1,4]oxazino[4,3-a]indole with Embodiment 33D to deliver the title compound (yellow solid, 3.40 g, yield 64.79%). $^1$H NMR (400 MHz, CDCl$_3$): δ 8.44 (d, J=2.80 Hz, 1H), 7.85-7.96 (m, 1H), 6.98-7.13 (m, 2H), 5.24 (s, 2H), 4.22-4.30 (m, 2H), 4.10-4.20 (m, 2H).

Embodiment 33F

5-Fluoro-4-(7-fluoro-3,4-dihydro-1H-[1,4]oxazino[4,3-a]indol-10-yl)-N-(4-fluoro-2-methoxy-5-nitrophenyl)-pyrimidin-2-amine

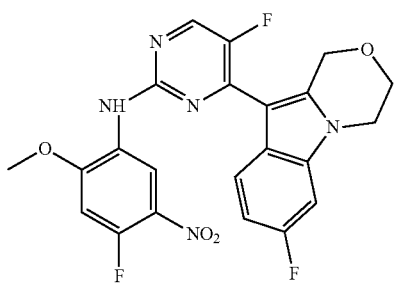

The Embodiment was prepared according to the method of Embodiment 30B except for replacing Embodiment 30A with Embodiment 33E to deliver the title compound (yellow solid, 5.10 g, crude). $^1$H NMR (400 MHz, CDCl$_3$): δ 9.37 (d, J=8.00 Hz, 1H), 8.40 (d, J=2.40 Hz, 1H), 7.81-7.88 (m, 1H), 7.67 (s, 1H), 7.44 (m, 1H), 7.05-7.11 (m, 2H), 6.79 (d, J=12.00 Hz, 1H), 5.25 (s, 2H), 4.27-4.33 (m, 2H), 4.15-4.20 (m, 3H), 4.06 (s, 3H).

Embodiment 33G

N$^4$-(2-(Dimethylamino)ethyl)-N$^1$-(5-fluoro-4-(7-fluoro-3,4-dihydro-1H-[1,4]oxazino[4,3-a]indol-10-yl)pyrimidin-2-yl)-2-methoxy-N$^4$-methyl-5-nitrobenzene-1,4-diamine

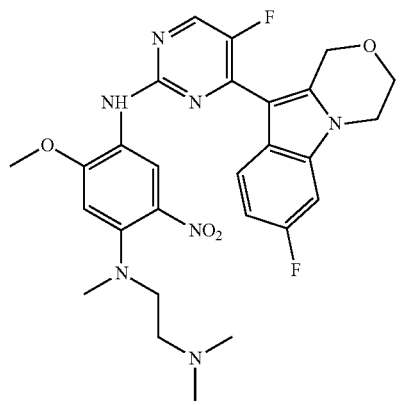 [SMILES: COc1cc(N(C)CCN(C)C)c([N+](=O)[O-])cc1Nc1ncc(F)c(-c2c3n(c4cc(F)ccc24)CCOC3)n1]

The Embodiment was prepared according to the method of Embodiment 16A except for replacing Embodiment D and N,N-diethyl-N-methylethane-1,2-diamine with Embodiment 33F and N,N',N'-trimethyl-1,2-ethanediamine respectively to deliver the title compound (yellow solid, 4.20 g, crude). $^1$H NMR (400 MHz, CDCl$_3$): δ 9.01 (s, 1H), 8.33 (d, J=2.80 Hz, 1H), 7.76-7.86 (m, 1H), 7.53 (s, 1H), 6.97-7.08 (m, 2H), 6.68 (s, 1H), 5.23 (s, 2H), 4.24-4.30 (m, 2H), 4.10-4.17 (m, 2H), 3.99 (s, 3H), 3.26 (t, J=7.20 Hz, 2H), 2.88 (s, 3H), 2.55 (t, J=7.20 Hz, 2H), 2.26 (s, 6H). LCMS (ESI) (5-95AB): m/z: 554.2 [M+1].

Embodiment 33H

N$^1$-(2-(Dimethylamino)ethyl)-N$^4$-(5-fluoro-4-(7-fluoro-3,4-dihydro-1H-[1,4]oxazino[4,3-a]indol-10-yl)pyrimidin-2-yl)-5-methoxy-N$^1$-methylbenzene-1,2,4-triamine

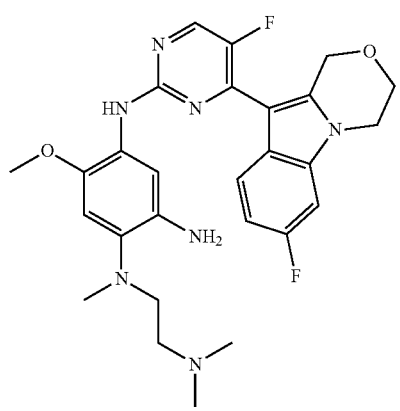

The Embodiment was prepared according to the method of Embodiment 16B except for replacing Embodiment 16A with Embodiment 33G to deliver the title compound (yellow solid, 1.23 g, yield 30.95%). ¹H NMR (400 MHz, CDCl₃): δ. 8.32 (d, J=2.40 Hz, 1H), 8.00 (s, 1H), 7.64 (s, 1H), 6.99-7.13 (m, 2H), 6.68 (s, 1H), 5.15 (s, 2H), 4.26 (d, J=5.20 Hz, 2H), 4.15 (d, J=5.20 Hz, 2H), 3.87 (s, 3H), 3.35 (br. s., 2H), 3.08 (br. s., 2H), 2.84 (s, 6H), 2.73 (s, 3H). LCMS (ESI) (0-60AB): m/z: 524.1 [M+1].

Embodiment 33I

N-(2-((2-(Dimethylamino)ethyl)(methyl)amino)-5-((5-fluoro-4-(7-fluoro-3,4-dihydro-1H-[1,4]oxazino[4,3-a]indol-10-yl)pyrimidin-2-yl)amino-4-methoxyphenyl)acrylamide

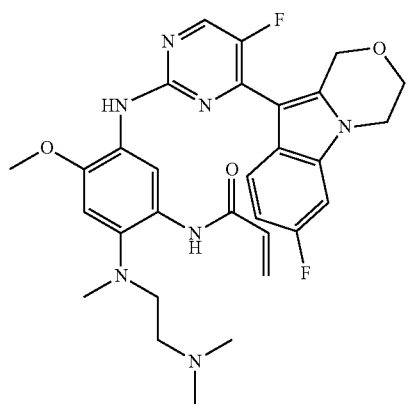 [SMILES: C=CC(=O)Nc1cc(Nc2ncc(F)c(-c3c4n(c5cc(F)ccc35)CCOC4)n2)c(OC)cc1N(C)CCN(C)C]

The Embodiment was prepared according to the method of Embodiment 16C except for replacing Embodiment 16B with Embodiment 33H to deliver the title compound (281.50 g, yield 24.41%). ¹H NMR (400 MHz, CD₃OD): δ 8.54 (br. s., 1H), 8.48 (br. s., 1H), 8.38 (br. s., 1H), 7.81-7.90 (m, 1H), 7.17-7.25 (m, 1H), 6.97 (s, 2H), 6.41-6.52 (m, 2H), 5.86 (m, 1H), 5.07 (br. s., 3H), 4.17 (d, J=14.00 Hz, 4H), 4.00 (s, 3H), 3.41 (br. s., 3H), 3.12 (br. s., 2H), 2.76 (br. s., 6H), 2.72 (s, 3H). LCMS (ESI) (0-60AB): m/z: 578.3 [M+1].

Embodiment 34

N-(5-((4-(7-Chloro-3,4-dihydro-1H-[1,4]oxazino[4,3-a]indol-10-yl)-5-fluoropyrimidin-2-yl)amino)-2-((2-(dimethylamino)ethyl)(methyl)amino)-4-methoxyphenyl)acrylamide

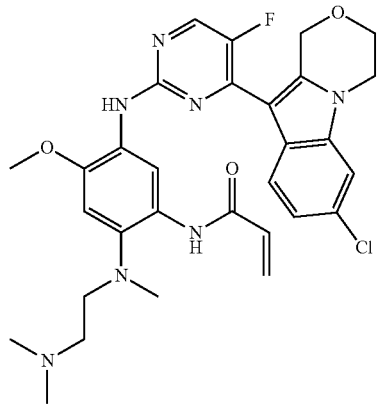 [SMILES: C=CC(=O)Nc1cc(Nc2ncc(F)c(-c3c4n(c5cc(Cl)ccc35)CCOC4)n2)c(OC)cc1N(C)CCN(C)C]

The synthetic process of the Embodiment is the same as the process 10.

Embodiment 34A (6-Chloro-1H-indol-2-yl)methanol

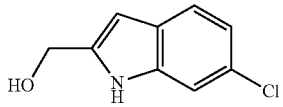 [SMILES: OCc1cc2ccc(Cl)cc2[nH]1]

The Embodiment was prepared according to the method of Embodiment 33C except for replacing 6-fluoro-1-(p-toluenesulfonyl)indole-2-carboxylic acid with 6-chloro-1-tosyl-1H-indole-2-carboxylic acid to deliver the title compound (brown solid, 3.50 g, yield 79.30%). ¹H NMR (400 MHz, CDCl₃): δ 7.50 (d, J=8.0 Hz, 1H), 7.36 (s, 1H), 7.09 (dd, J=4.0, 8.0 Hz, 1H), 6.40 (s, 1H), 4.85 (s, 2H).

Embodiment 34B

7-Chloro-3,4-dihydro-1H-[1,4]oxazino[4,3-a]indole

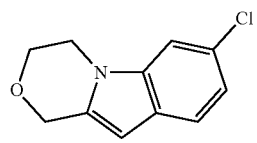 [SMILES: Clc1ccc2cc3n(c2c1)CCOC3]

The Embodiment was prepared according to the method of Embodiment 33D except for replacing 33C with 34A to deliver the title compound (brown solid, 1.30 g, yield 29.17%). ¹H NMR (400 MHz, CDCl₃): δ 7.49 (d, J=8.0 Hz, 1H), 7.30 (s, 1H), 7.11 (dd, J=0.8, 8.0 Hz, 1H), 6.22 (d, J=4.0

Hz, 1H), 4.99 (s, 2H), 4.26-4.14 (m, 2H), 4.10-4.04 (m, 2H). LCMS (ESI) (5-95AB): m/z: 210.0 [M+2].

Embodiment 34C

7-Chloro-10-(2-chloro-5-fluoropyrimidin-4-yl)-3,4-dihydro-1H-[1,4]oxazino[4,3-a]indole

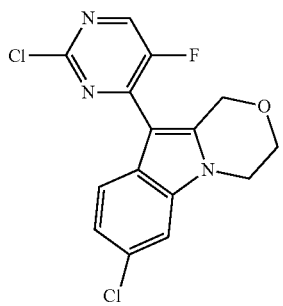 [SMILES: Fc1cnc(Cl)nc1-c1c2n(c3cc(Cl)ccc13)CCOC2]

The Embodiment was prepared according to the method of Embodiment 30A except for replacing 3,4-dihydro-1H-[1,4]oxazino[4,3-a]indole with 34B to deliver the title compound (yellow solid, Mg, yield 26.01%). $^1$H NMR (400 MHz, CDCl$_3$): δ 8.44 (d, J=4.0 Hz, 1H), 7.88 (dd, J=4.0, 8.0 Hz, 1H), 7.39 (s, 1H), 7.31-7.29 (m, 1H), 5.25 (s, 2H), 4.31-4.14 (m, 4H). LCMS (ESI) (5-95AB): m/z: 338.1 [M+1].

Embodiment 34D 4-(7-Chloro-3,4-dihydro-1H-[1,4]oxazino[4,3-a]indol-10-yl)-5-fluoro-N-(4-fluoro-2-methoxy-5-nitrophenyl)pyrimidin-2-amine

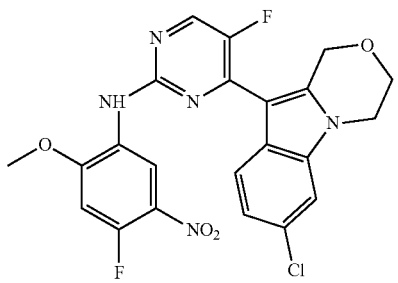

The Embodiment was prepared according to the method of Embodiment 30B except for replacing 30A with 34C to deliver the title compound (yellow solid, 450.00 mg, yield 66.11%). $^1$H NMR (400 MHz, CDCl$_3$): δ 9.25 (d, J=8.0 Hz, 1H), 8.30 (d, J=4.0 Hz, 1H), 7.71 (dd, J=4.0, 8.0 Hz, 1H), 7.57 (s, 1H), 7.30 (d, J=4.0 Hz, 1H), 7.17 (dd, J=4.0, 8.0 Hz, 1H), 6.69 (d, J=12.0 Hz, 1H), 5.16 (s, 2H), 4.23-4.17 (m, 2H), 4.11-4.07 (m, 2H), 3.96 (s, 3H). LCMS (ESI) (5-95AB): m/z: 488.0 [M+1].

Embodiment 34E $N^1$-(4-(7-Chloro-3,4-dihydro-1H-[1,4]oxazino[4,3-a]indol-10-yl)-5-fluoropyrimidin-2-yl)-$N^4$-(2-(dimethylamino)ethyl)-2-methoxy-$N^4$-methyl-5-nitrobenzene-1,4-diamine

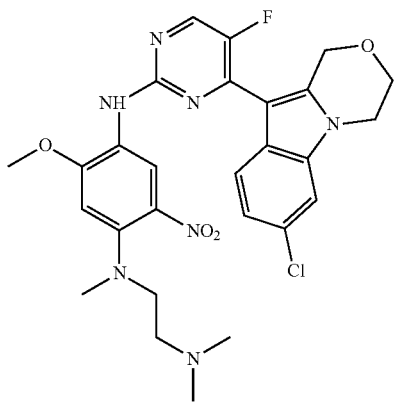 [SMILES: COc1cc(N(C)CCN(C)C)c([N+](=O)[O-])cc1Nc1ncc(F)c(-c2c3n(c4cc(Cl)ccc24)CCOC3)n1]

The Embodiment was prepared according to the method of Embodiment 16A except for replacing Embodiment D and N,N-diethyl-N-methylethane-1,2-diamine with Embodiment 34D and N,N',N'-trimethyl-1,2-ethanediamine respectively to deliver the title compound (red solid, 300.00 mg, yield 85.58%). $^1$H NMR (400 MHz, CDCl$_3$): δ 9.02 (s, 1H), 8.35 (d, J=4.0 Hz, 1H), 7.84-7.75 (m, 1H), 7.53 (s, 1H), 7.38 (d, J=4.0 Hz, 1H), 7.25 (dd, J=4.0, 8.0 Hz, 1H), 6.69 (s, 1H), 5.26 (s, 2H), 4.33-4.24 (m, 2H), 4.20-4.14 (m, 2H), 4.00 (s, 3H), 3.28 (t, J=8.0 Hz, 2H), 2.90 (s, 3H), 2.57 (t, J=8.0 Hz, 2H), 2.28 (s, 6H). LCMS (ESI) (5-95AB): m/z: 570.1 [M+1].

Embodiment 34F $N^4$-(4-(7-Chloro-3,4-dihydro-1H-[1,4]oxazino[4,3-a]indol-10-yl)-5-fluoropyrimidin-2-yl)-$N^1$-(2-(dimethylamino)ethyl)-5-methoxy-$N^1$-methylbenzene-1,2,4-triamine

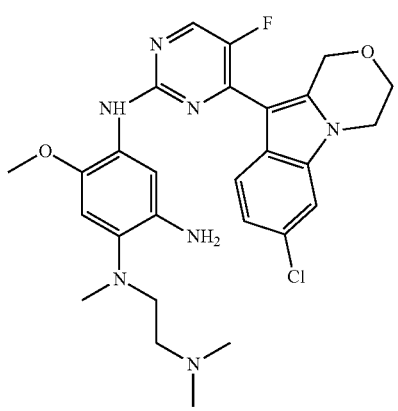

The Embodiment was prepared according to the method of Embodiment 16B except for replacing Embodiment 16A with Embodiment 34E to deliver the title compound (brown solid, 200.00 mg, yield 70.37%). ¹H NMR (400 MHz, CDCl₃): δ 8.22 (d, J=2.8 Hz, 1H), 7.91-7.86 (m, 2H), 7.52 (s, 1H), 7.29 (d, J=4.0 Hz, 1H), 7.16 (dd, J=4.0, 8.0 Hz, 1H), 6.63 (s, 1H), 5.08 (s, 2H), 4.19-4.15 (m, 2H), 4.10-4.06 (m, 2H), 3.77 (s, 3H), 2.88 (t, J=8.0 Hz, 2H), 2.60 (s, 3H), 2.33 (t, J=8.0 Hz, 2H), 2.19 (s, 6H). LCMS (ESI) (5-95AB): m/z: 540.2 [M+1].

Embodiment 34G

N-(5-((4-(7-Chloro-3,4-dihydro-1H-[1,4]oxazino[4,3-a]indol-10-yl)-5-fluoropyrimidin-2-yl)amino)-2-((2-(dimethylamino)ethyl)(methyl)amino)-4-methoxyphenyl)acrylamide

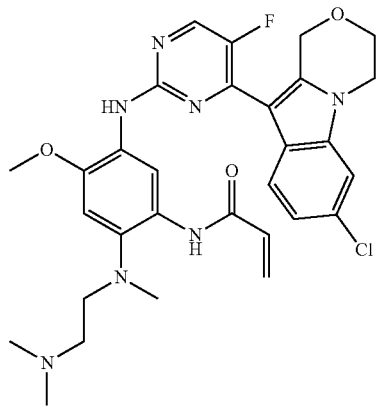 [SMILES: C=CC(=O)Nc1cc(Nc2ncc(F)c(-c3c4n(c5cc(Cl)ccc35)CCOC4)n2)c(OC)cc1N(C)CCN(C)C]

The Embodiment was prepared according to the method of Embodiment 16C except for replacing Embodiment 16B with Embodiment 34F to deliver the title compound (65.50 mg, yield 29.27%). ¹H NMR (400 MHz, CD₃OD): δ 8.98 (s, 1H), 8.36 (d, J=4.0 Hz, 1H), 7.82 (dd, J=4.0, 8.0 Hz, 1H), 7.50 (d, J=0.8 Hz, 1H), 7.16 (dd, J=0.8, 8.0 Hz, 1H), 6.98 (s, 1H), 6.52 (dd, J=12.0, 20.0 Hz, 1H), 6.28 (dd, J=0.8, 20.0 Hz, 1H), 5.77 (dd, J=0.8, 8.0 Hz, 1H), 5.10 (s, 2H), 4.17 (s, 4H), 3.94 (s, 3H), 3.06 (t, J=4.0 Hz, 2H), 2.71 (s, 3H), 2.44 (t, J=4.0 Hz, 2H), 2.30 (s, 6H). LCMS (ESI) (5-95AB): m/z: 594.2 [M+1].

Embodiment 35

N-(2-((2-(Dimethylamino)ethyl)(methyl)amino)-5-((5-fluoro-4-(6-methoxy-3,4-dihydro-1H-[1,4]oxazino[4,3-a]indol-10-yl)pyrimidin-2-yl)amino)-4-methoxyphenyl)acrylamide

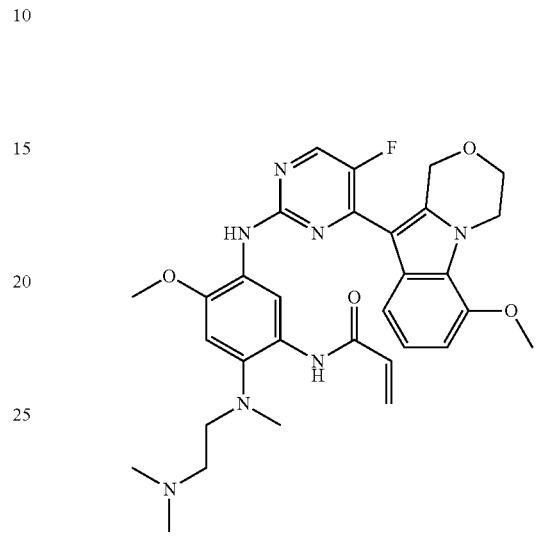

The synthetic process of the Embodiment is the same as the process 10.

Embodiment 35A (7-Methoxy-1H-indol-2-yl)methanol

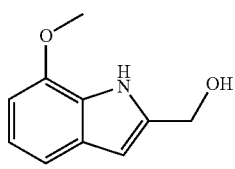

Ethyl-7-methoxy-1H-indole-2-carboxylate (11.00 g, 50.17 mmol) was dissolved in THF (100 mL) at 0° C. and lithium aluminum hydride (2.86 g, 75.26 mmol) was added to the mixture and the reaction mixture was warmed to 25° C. and stirred for 3 hours. LCMS showed the reaction was complete, H₂O (1 mL) and NaOH (1 mL) were added to the reaction mixture, then H₂O (3 mL) was added, filtered and the filtrate was concentrated to deliver the title compound (brown oil, 10.00 g). ¹H NMR (400 MHz, CDCl₃): δ 8.57 (br. s., 1H), 7.20 (d, J=8.0 Hz, 1H), 7.03 (t, J=8.0 Hz, 1H), 6.65 (d, J=8.0 Hz, 1H), 6.40 (d, J=4.0 Hz, 1H), 4.84 (d, J=4.0 Hz, 2H), 3.97 (s, 3H). LCMS (ESI) (5-95AB): m/z: 178.1 [M+1].

Embodiment 35B

6-Methoxy-3,4-dihydro-1H-[1,4]oxazino[4,3-a]indole

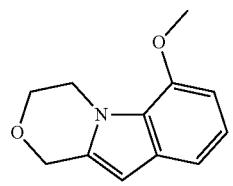

(7-Methoxy-1H-indol-2-yl) methanol (10.00 g, 56.43 mmol) and sodium hydroxide (7.92 g, 141.08 mmol) were dissolved in dichloromethane (300 mL) at 0° C. Under the protection of $N_2$, a solution of phenylvinylsulfone (24.54 g, 67.72 mmol) in dichloromethane (200 mL) was slowly added dropwise to the mixture, and the reaction mixture was warmed to 25° C. and stirred for 3 hours. TLC showed the reaction was complete, $H_2O$ (700 mL) was added to the reaction mixture and extracted with dichloromethane (500 mL×2). The organic layer was washed with saturated brine (1000 mL), dried over anhydrous sodium sulfate (10 g), concentrated and purified by column chromatography (PE:EA=50:1, 20:1) to deliver the title compound (brown solid, 5.80 g, 50.58% yield). $^1$H NMR (400 MHz, CDCl$_3$): δ 7.18 (d, J=8.0 Hz, 1H), 7.02 (t, J=8.0 Hz, 1H), 6.63 (d, J=8.0 Hz, 1H), 6.20 (s, 1H), 4.99 (s, 2H), 4.50-4.57 (m, 2H), 4.10-4.17 (m, 2H), 3.94 (s, 3H).

Embodiment 35C

10-(2-Chloro-5-fluoropyrimidin-4-yl)-6-methoxy-3,4-dihydro-1H-[1,4]oxazino[4,3-a]indole

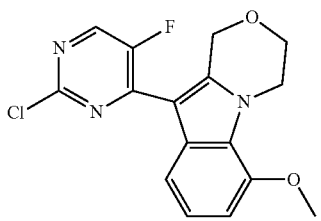 [SMILES: COc1cccc2c(-c3nc(Cl)ncc3F)c3n(c12)CCOC3]

The Embodiment was prepared according to the method of Embodiment 30A except for replacing 3,4-dihydro-1H-[1,4]oxazino[4,3-a]indole with 35B to deliver the title compound (brown solid, 5.80 g, 50.58% yield). $^1$H NMR (400 MHz, CDCl$_3$): δ 8.41 (d, J=4.0 Hz, 1H), 7.48 (dd, J=8.0, 4.00 Hz, 1H) 7.17 (t, J=8.00 Hz, 1H) 6.73 (d, J=8.00 Hz, 1H), 5.22 (s, 2H), 4.65 (t, J=4.00 Hz, 2H), 4.17 (t, J=4.00 Hz, 2H), 3.96 (s, 3H). LCMS (ESI) (5-95AB): m/z: 334.0 [M+1].

Embodiment 35D

5-Fluoro-N-(4-fluoro-2-methoxy-5-nitrophenyl)-4-(6-methoxy-3,4-dihydro-1H-[1,4]oxazino[4,3-a]indol-10-yl)pyrimidin-2-amine

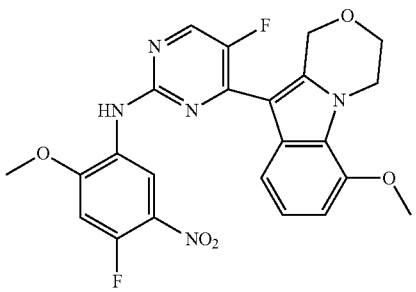

The Embodiment was prepared according to the method of Embodiment 30B except for replacing 30A with 35C to deliver the title compound (yellow solid, 3.2 g). $^1$H NMR (400 MHz, CDCl$_3$): δ 9.37 (d, J=8.00 Hz, 1H), 8.36 (d, J=2.00 Hz, 1H), 7.64 (br. s., 1H), 7.40-7.46 (m, 1H), 7.14 (t, J=8.00 Hz, 1H), 6.67-6.78 (m, 2H), 5.21 (s, 2H), 4.63 (t, J=4.00 Hz, 2H), 4.20 (t, J=4.00 Hz, 2H), 4.03 (s, 3H), 3.96 (s, 3H). LCMS (ESI) (5-95AB): m/z: 484.0 [M+1].

Embodiment 35E

N$^4$-(2-(dimethylamino)ethyl)-N$^1$-(5-fluoro-4-(6-methoxy-3,4-dihydro-1H-[1,4]oxazino[4,3-a]indol-10-yl)pyrimidin-2-yl)-5-methoxy-N$^4$-methyl-5-nitrobenzene-1,4-diamine

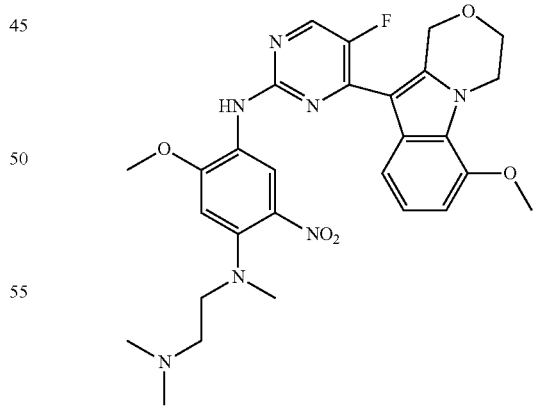

The Embodiment was prepared according to the method of Embodiment 16A except for replacing Embodiment D and N,N-diethyl-N-methylethane-1,2-diamine with Embodiment 35D and N,N',N'-trimethyl-1,2-ethanediamine respectively to deliver the title compound (yellow solid, 3.2 g). LCMS (ESI) (5-95AB): m/z: 566.1 [M+1].

Embodiment 35F

N[1]-(2-(Dimethylamino)ethyl)-N[4]-(5-fluoro-4-(6-methoxy-3,4-dihydro-1H-[1,4]oxazino[4,3-a]indol-10-yl)pyrimidin-2-yl)-5-methoxy-N[1]-methylbenzene-1,2,4-triamine

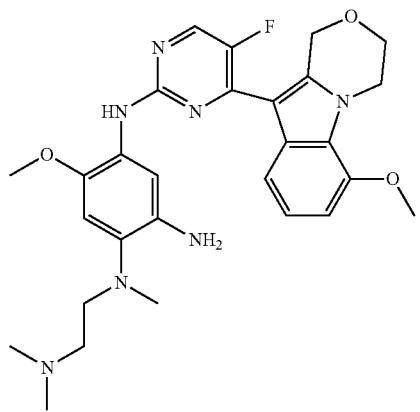

The Embodiment was prepared according to the method of Embodiment 16B except for replacing Embodiment 16A with Embodiment 35E to deliver the title compound (brown oil, 500 mg). $^1$H NMR (400 MHz, CDCl$_3$): δ 8.28 (d, J=4.00 Hz, 1H), 8.03 (s, 1H), 7.58-7.63 (m, 2H), 7.14 (t, J=8.00 Hz, 1H), 6.67-6.72 (m, 2H), 5.13 (s, 2H), 4.62 (t, J=4.00 Hz, 2H), 4.16 (t, J=8.00 Hz, 2H), 3.95 (s, 3H), 3.84 (s, 3H), 2.95 (t, J=8.00 Hz, 2H), 2.67 (s, 3H), 2.39 (t, J=4.00 Hz, 2H), 2.26 (s, 6H). LCMS (ESI) (5-95AB): m/z: 536.1 [M+1].

Embodiment 35G

N-(2-((2-(Dimethylamino)ethyl)(methyl)amino)-5-((5-fluoro-4-(6-methoxy-3,4-dihydro-1H-[1,4]oxazino[4,3-a]indol-10-yl)pyrimidin-2-yl)amino)-4-methoxyphenyl)acrylamide

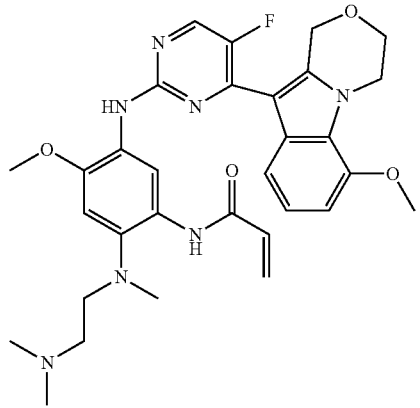

The Embodiment was prepared according to the method of Embodiment 16C except for replacing Embodiment 16B with Embodiment 35F to deliver the title compound (210.00 mg, 330.35 micromolar, 58.98% yield). $^1$H NMR (400 MHz, CD$_3$OD): δ 8.46-8.57 (m, 2H), 8.37 (d, J=3.00 Hz, 1H), 7.40 (dd, J=8.00, 3.45 Hz, 1H) 7.06 (t, J=8.00 Hz, 1H) 6.96 (s, 1H) 6.75 (d, J=8.00b Hz, 1H) 6.39-6.54 (m, 2H) 5.82-5.90 (m, 1H) 5.05 (s, 2H) 4.58 (t, J=5.00 Hz, 2H) 4.13 (t, J=5.00 Hz, 2H) 4.00 (s, 3H) 3.96 (s, 3H) 3.39 (d, J=8.00 Hz, 2H) 3.06-3.18 (m, 2H) 2.70-2.77 (m, 9H). LCMS (ESI) (5-95AB): m/z: 590.3 [M+1].

Embodiment 36

N-(5-((4-(4,4-Dimethyl-3,4-dihydro-H-[1,4]oxazino[4,3-a]indol-10-yl)-5-fluoropyrimidin-2-yl)amino)-2-((2-(dimethylamino)ethyl)(methyl)amino)-4-methoxyphenyl)acrylamide methanesulfonate

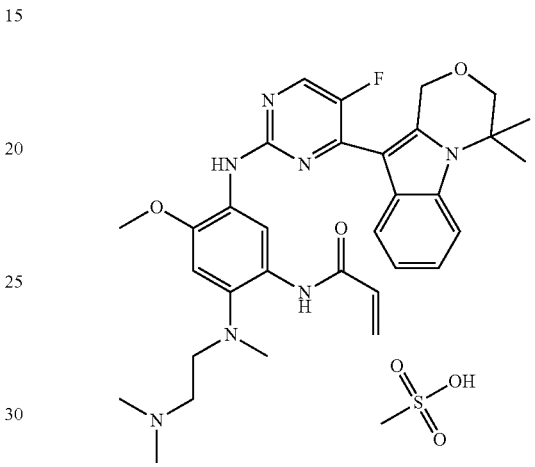

The synthetic process of the Embodiment is the same as the process 10.

Embodiment 36A

Ethyl 1-(2-ethoxy-2-oxoethyl)-1H-indole-2-carboxylate

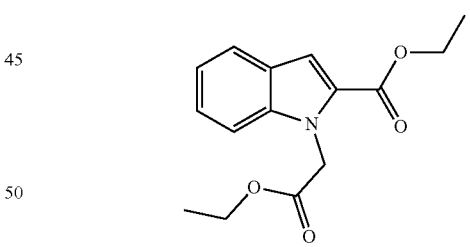

Ethyl indole-2-carboxylate (32.00 g, 169.12 mmol), ethyl bromoacetate (70.61 g, 422.80 mmol) and potassium carbonate (70.12 g, 507.36 mmol) were mixed in acetonitrile (400 mL) and stirred at 80° C. for 20 hours. LCMS showed the the reaction was complete. The reaction mixture was diluted with ethyl acetate (500 mL) and water (500 mL) and separated. The organic phase was concentrated and purified by column chromatography (PE:EA=20:1) to deliver the title compound (46.00 g, 98.80% yield) as a colorless oil. $^1$H NMR (400 MHz, CDCl$_3$): δ 7.72 (d, J=8.1 Hz, 1H), 7.43-7.35 (m, 2H), 7.34-7.29 (m, 1H), 7.20 (t, J=7.5 Hz, 1H), 5.34 (s, 2H), 4.38 (q, J=7.2 Hz, 2H), 4.24 (q, 2H), 1.42 (t, J=7.2 Hz, 3H), 1.28 (t, J=7.1 Hz, 3H). LCMS (ESI) (5-95AB): m/z: 276.2 [M+1].

Embodiment 36B

Ethyl 1-(1-ethoxy-2-methyl-1-oxopropan-2-yl)-1H-indole-2-carboxylate

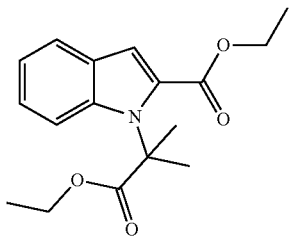 [SMILES: CCOC(=O)c1cc2ccccc2n1C(C)(C)C(=O)OCC]

Potassium bis(trimethylsilyl)amide (1 M, 334.18 mL) was added dropwise to a solution of Embodiment 36A (46.00 g, 167.09 mmol) dissolved in tetrahydrofuran (300 mL) at −70° C. The mixture was stirred at −70° C. for 0.5 hour and then iodomethane (47.43 g, 334.18 mmol) was added dropwise. The mixture was stirred at 5 to 15° C. for 12 hours. TLC showed the reaction was not complete. The mixture was diluted with water (500 mL) and ethyl acetate (500 mL) and separated. The organic phase was concentrated and purified by column chromatography (PE:EA=40:1, 20:1). The resulting product (48 g) was dissolved in tetrahydrofuran (200 mL) and potassium bis(trimethylsilyl)amide (1M, 497.70 mL) was added dropwise at −70° C. The mixture was stirred at −70° C. for 0.5 hour and then iodomethane (70.64 g, 497.70 mmol) was added dropwise. The resulting mixture was stirred at 0° C. for 3 hours. LCMS showed the reaction was complete. The mixture was diluted with water (300 mL) and ethyl acetate (300 mL) and separated. The organic phase was concentrated and purified by column chromatography (PE:EA=30:1) to deliver the title compound (colorless oil, 43.00 g, yield 85.44%). $^1$H NMR (400 MHz, CDCl$_3$): δ 7.67 (dd, J=7.6, 13.6 Hz, 2H), 7.36 (s, 1H), 7.26 (s, 1H), 7.15 (t, J=7.2 Hz, 1H), 4.34 (q, J=7.2 Hz, 2H), 4.16 (q, J=7.2 Hz, 2H), 2.10 (s, 6H), 1.41 (t, J=7.2 Hz, 3H), 1.18 (t, J=7.2 Hz, 3H). LCMS (ESI) (5-95AB): m/z: 304.1 [M+1].

Embodiment 36C 2-(2-(Hydroxymethyl)-1H-indol-1-yl)-2-methylpropan-1-ol

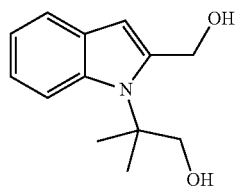 [SMILES: CC(C)(CO)n1c(CO)cc2ccccc21]

Lithium aluminum hydrate (3.75 g, 98.91 mmol) was added in batches to a solution of Embodiment 36B (10.00 g, 32.97 mmol) in tetrahydrofuran (100 mL) at 0° C. The mixture was stirred at 40° C. for 1 hour. TLC showed the reaction was complete. Water (3.75 mL) and 15% aqueous sodium hydroxide solution (3.75 mL) were added dropwise to the mixture at 0° C. and then filtered. The filtrate was concentrated to deliver the title compound (white solid, 7.40 g). $^1$H NMR (400 MHz, CDCl$_3$): δ 7.52 (d, J=7.2 Hz, 2H), 7.13 (t, J=6.8 Hz, 1H), 7.07 (t, J=7.2 Hz, 1H), 6.22 (s, 1H), 4.51 (s, 2H), 3.55 (s, 2H), 3.39 (s, 2H), 1.64 (s, 6H).

Embodiment 36D 4,4-Dimethyl-3,4-dihydro-1H-[1,4]oxazino[4,3-a]indole

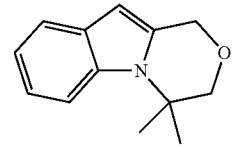

Methanesulfonyl chloride (3.16 g, 27.59 mmol) was added dropwise to a solution of Embodiment 36C (5.50 g, 25.08 mmol), triethylamine (3.81 g, 37.62 mmol) and 4-dimethylaminopyridine (0.16 mL, 2.51 mmol) in DMF (100 mL). The mixture was stirred at 15 to 25° C. for 2 hours. TLC showed the reaction was complete. The mixture was diluted with DMF (200 mL) and sodium hydride (2.01 g, 50.16 mmol) was added. The mixture was stirred at 70° C. for 4 hours. MS of the title compound was monitored by LCMS. Water (2 mL) was added to the mixture and then concentrated to dryness. The concentrated residue was dissolved in dichloromethane (100 mL) and then washed with water (50 mL×2). The organic phase was concentrated and purified by column chromatography (PE:EA=40:1) to deliver the title compound (yellow solid, 1.20 g, yield 23.77%). $^1$H NMR (400 MHz, CDCl$_3$): δ 7.56 (t, J=8.6 Hz, 2H), 7.20-7.05 (m, 2H), 6.20 (s, 1H), 4.97 (s, 2H), 3.80 (s, 2H), 1.68 (s, 6H). LCMS (ESI) (5-95AB): m/z: 202.0 [M+1].

Embodiment 36E 10-(2-Chloro-5-fluoropyrimidin-4-yl)-4,4-dimethyl-3,4-dihydro-1H[1,4]oxazino[4,3-a]indole

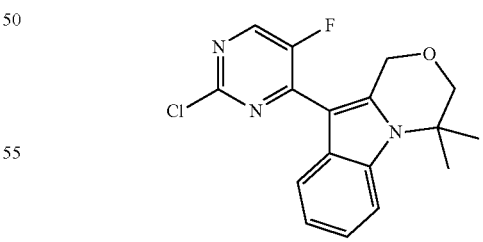

The Embodiment was prepared according to the method of Embodiment 30A by replacing 3,4-dihydro-1H-[1,4]oxazino[4,3-a]indole with 36D to deliver the title compound (yellow solid, 1.30 G, yield 87.66%). $^1$H NMR (400 MHz, CDCl$_3$): δ 8.35 (d, J=2.8 Hz, 1H), 7.87-7.77 (m, 1H), 7.61-7.51 (m, 1H), 7.25-7.13 (m, 2H), 5.10 (s, 2H), 3.78 (s, 2H), 1.67 (s, 6H).

Embodiment 36F 4-(4,4-Dimethyl-3,4-dihydro[1,4]oxazino[4,3-a]indol-10-yl)-5-fluoro-N-(4-fluoro-2-methoxy-5-nitrophenyl)pyrimidin-2-amine

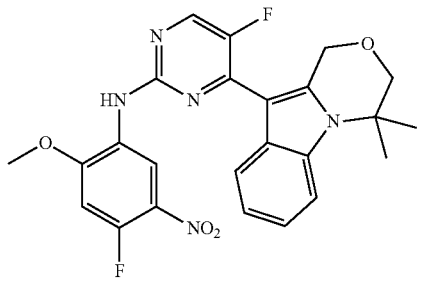

The Embodiment was prepared according to the method of Embodiment 30B by replacing Embodiment 30A with Embodiment 36E to deliver the title compound (dark yellow solid, 1.30 g, 68.88% yield). $^1$H NMR (400 MHz, CDCl$_3$): δ 9.38 (d, J=8.4 Hz, 1H), 8.38 (d, J=2.8 Hz, 1H), 7.89-7.81 (m, 1H), 7.70-7.59 (m, 2H), 7.32-7.19 (m, 1H), 6.76 (d, J=12.0 Hz, 1H), 5.21 (s, 2H), 4.03 (s, 3H), 3.90 (s, 2H), 1.76 (s, 6H). LCMS (ESI) (5-95AB): m/z: 482.0 [M+1].

Embodiment 36G

N$^1$-(4-(4,4-Dimethyl-3,4-dihydro-1H-[1,4]oxazino[4,3-a]indol-10-yl)-5-fluoropyrimidin-2-yl)-N$^4$-(2-(dimethylamino)ethyl)-2-methoxy-1-methyl-5-nitrobenzene-1,4-diamine

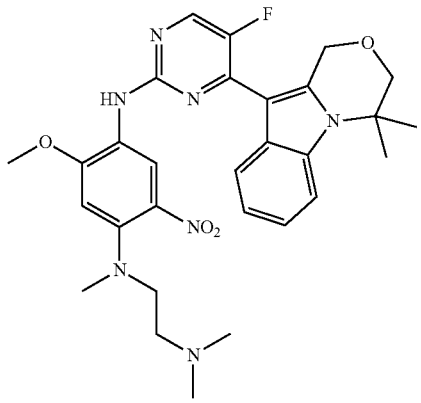

The Embodiment was prepared according to the method of Embodiment 16A except for replacing Embodiment D and N,N-diethyl-N-methylethane-1,2-diamine with Embodiment 36F and N,N',N'-trimethyl-1,2-ethanediamine respectively to deliver the title compound (red solid, 750.00 mg, 80.16% yield). $^1$H NMR (400 MHz, CDCl$_3$): δ 9.07 (s, 1H), 8.34 (d, J=2.5 Hz, 1H), 7.91-7.79 (m, 1H), 7.70-7.60 (m, 1H), 7.56 (s, 1H), 7.25 (dd, J=3.2, 5.6 Hz, 1H), 6.68 (s, 1H), 5.21 (s, 2H), 3.98 (s, 3H), 3.90 (s, 2H), 3.27 (t, J=6.8 Hz, 2H), 2.88 (s, 3H), 2.57 (t, J=6.8 Hz, 2H), 2.27 (s, 6H), 1.75 (s, 6H).

Embodiment 36H

N$^4$-(4-(4,4-Dimethyl-3,4-dihydro-1H-[1,4]oxazino[4,3-a]indol-10-yl)-5-fluoropyrimidin-2-yl)-N$^1$-(2-(dimethylamino)ethyl)-5-methoxy-N$^1$-methylbenzene-1,2,4-triamine

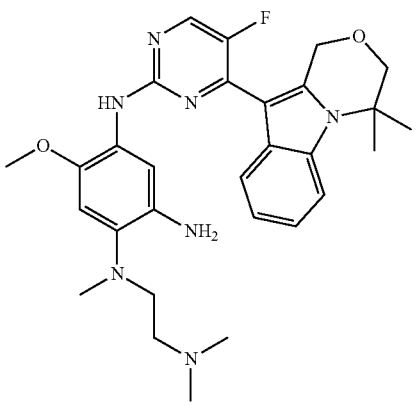

The Embodiment was prepared according to the method of Embodiment 16B except for replacing Embodiment 16A with Embodiment 36G to deliver the title compound (dark yellow solid, 600.00 mg, crude). $^1$H NMR (400 MHz, CDCl$_3$): δ 8.30 (d, J=2.5 Hz, 1H), 8.04 (s, 2H), 7.67-7.58 (m, 2H), 7.25 (dd, J=3.2, 6.4 Hz, 2H), 6.71 (s, 1H), 5.10 (s, 2H), 3.93-3.76 (m, 5H), 2.96 (t, J=6.8 Hz, 2H), 2.67 (s, 3H), 2.40 (t, J=6.8 Hz, 2H), 2.26 (s, 6H), 1.75 (s, 6H).

Embodiment 36I

N$^4$-(4-(4,4-Dimethyl-3,4-dihydro-1H-[1,4]oxazino[4,3-a]indol-10-yl)-5-fluoropyrimidin-2-yl)-N$^1$-(2-(dimethylamino)ethyl)-5-methoxy-N$^1$-methylbenzene-1,2,4-triamine

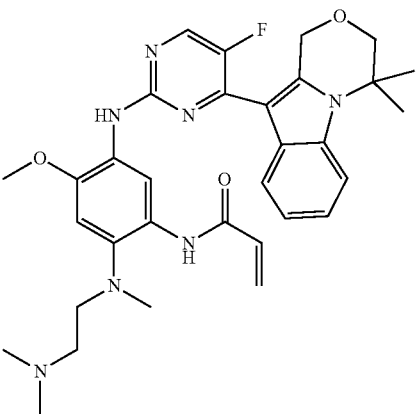

The Embodiment was prepared according to the method of Embodiment 16C by replacing Embodiment 16B with Embodiment 36H to deliver the title compound (dark yellow solid, 330.00 mg, 59.93% yield). $^1$H NMR (400 MHz, CDCl$_3$): δ 9.40 (br. s., 1H), 8.36 (d, J=2.4 Hz, 1H), 7.91-7.77 (m, 1H), 7.65-7.52 (m, 2H), 7.21 (dd, J=2.8, 6.0 Hz, 2H), 6.69 (s, 1H), 6.36 (d, J=16.4 Hz, 1H), 5.68 (d, J=11.2 Hz, 1H), 5.20 (s, 2H), 3.88 (s, 3H), 3.84 (s, 2H), 3.17 (br. s., 2H), 2.76-2.43 (m, 9H), 1.73 (s, 6H). LCMS (ESI) (5-95AB): m/z: 588.2 [M+1].

Embodiment 36J

N-(5-((4-(4,4-Dimethyl-3,4-dihydro-1H-[1,4]ox-azino[4,3-a]indol-10-yl)-5-fluoropyrimidin-2-yl)amino)-2-((2-(dimethylamino)ethyl)(methyl)amino)-4-methoxyphenyl)acrylamide methanesulfonate

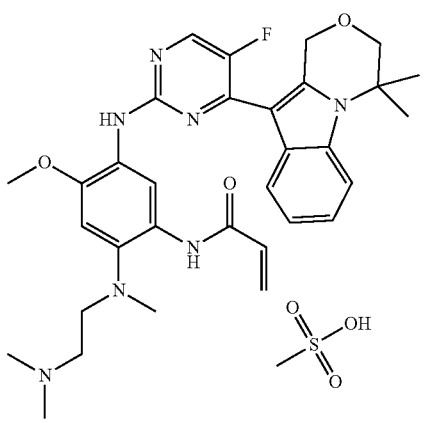

Embodiment 36I (330.00 mg, 561.52 μmol) was added to EA (0.66A) at 70 C and a solution of methanesulfonic acid (53.97 mg, 561.52 μmol) dissolved in EA (0.66 mL) solution was added dropwise to this solution. After the addition, the mixture was stirred at the temperature for 1 hour. There was red precipitation. The mixture was filtered and the filter cake was washed with EA (3 nitrophenyl*2) and dried in vacuo to deliver the title compound (283.00 mg, yield 73.22%). ¹H NMR (400 MHz, CD₃OD): δ 8.39 (d, J=5.2 Hz, 1H), 7.94-7.85 (m, 2H), 7.82 (d, J=8.0 Hz, 1H), 7.38-7.21 (m, 2H), 7.10 (s, 1H), 6.70-6.58 (m, 1H), 6.51-6.38 (m, 1H), 5.87 (d, J=10.8 Hz, 1H), 5.00 (s, 2H), 3.99 (s, 3H), 3.85 (s, 2H), 3.59 (t, J=5.2 Hz, 2H), 3.37 (t, J=5.2 Hz, 2H), 2.93 (s, 6H), 2.83 (s, 3H), 2.73 (s, 4H), 1.74 (s, 6H). LCMS (ESI) (5-95AB): m/z: 588.3 [M+1].

Process 11

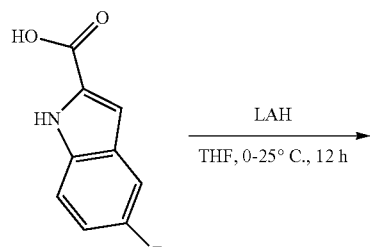

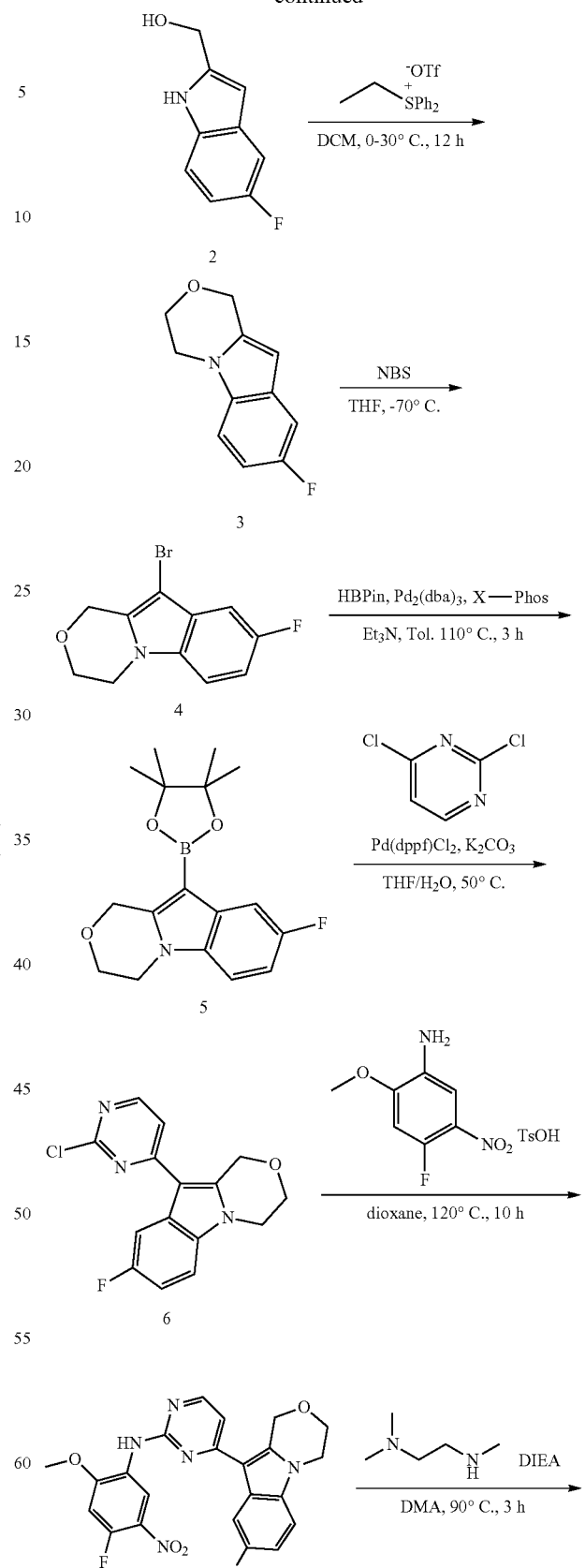

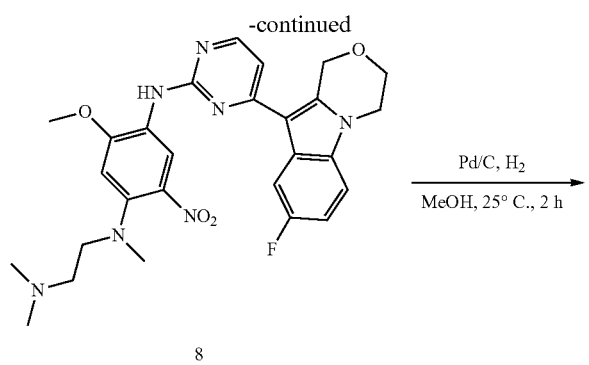

8

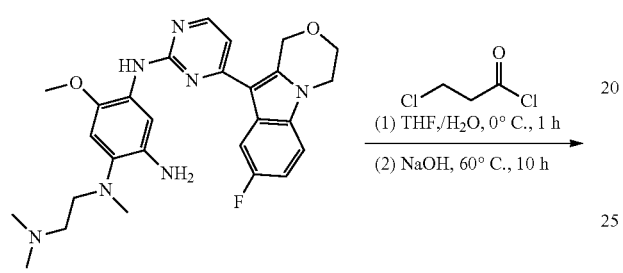

9

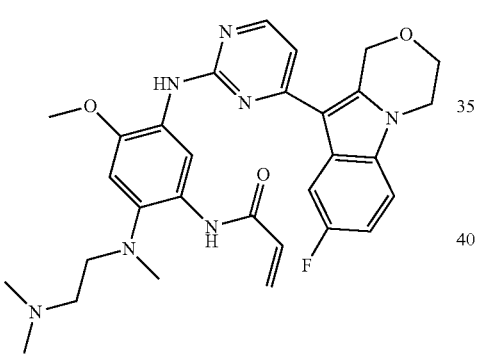

Embodiment 38

Embodiment 37

(5-Fluoro-1H-indol-2-yl)methanol

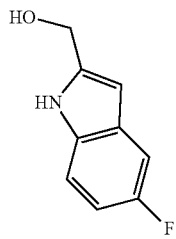

5-Fluoro-1H-indole-2-carboxylic acid (10.00 g, 55.82 mmol) was dissolved in THF (100 mL) at 0° C., LAH (3.18 g, 83.79 mmol) was added to this mixture and stirred at 0 to 25° C. for 4 hours. TLC (PE:EtOAc=1:1) showed the reaction was complete, water (3 mL), 15% NaOH solution (3 mL) and water (9 mL) were added successively to the reaction mixture, and the resulting mixture was filtered and the filtrate was concentrated to deliver the title compound (yellow solid, 9.00 g, yield 85.91%). $^1$H NMR (300 MHz, CDCl$_3$): δ 8.44 (br. S, 1H), 7.20-7.27 (m, 2H), 6.97-6.92 (m, 1H), 6.38 (s, 1H), 4.83 (s, 3H), 2.09 (br. s., 1H).

Embodiment 37B

8-Fluoro-3,4-dihydro-1H-[1,4]oxazino[4,3-a]indole

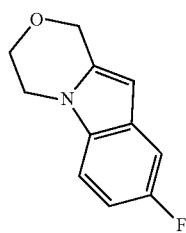 [SMILES: Fc1ccc2c(c1)cc1n2CCOC1]

The Embodiment was prepared according to the method of Embodiment C4 except for replacing 2-hydroxymethyl-indole with (5-fluoro-1H-indol-2-yl)methanol to deliver the title compound (pale yellow solid, 1.30 g, yield 50.54%). $^1$H NMR (400 MHz, CDCl$_3$): δ 7.18-7.27 (m, 2H), 6.95-6.93 (m, 1H), 6.21 (s, 1H), 5.00 (s, 2H), 4.17-4.22 (m, 2H), 4.06-4.11 (m, 2H).

Embodiment 37C

10-Bromo-8-fluoro-3,4-dihydro-1H-[1,4]oxazino[4,3-a]indole

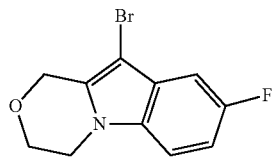 [SMILES: Fc1ccc2c(c1)c(Br)c1n2CCOC1]

Embodiment 37B (5.00 g, 26.15 mmol) was dissolved in THF (100 mL) at −70° C., NBS (5.12 g, 28.77 mmol) was added to the mixture and stirred at −70° C. for 1 hour. TLC (PE:EtOAc=10:1) showed the reaction was complete and the reaction was quenched with saturated NaHCO$_3$ solution (20 mL) and extracted with EtOAc (30 mL*2). The combined organic phases were dried over anhydrous sodium sulfate, the resulting residue was purified by column chromatography (SiO$_2$:PE:EtOAc=200:1 to 25:1) to deliver the title compound (white solid, 5.50 g, yield 77.87%). $^1$H NMR (400 MHz, CDCl$_3$): δ 7.27-7.17 (m, 1H), 7.02-6.99 (m, 1H), 4.93 (s, 2H), 4.22-4.14 (m, 2H), 4.12-4.03 (m, 2H).

Embodiment 37D

8-Fluoro-10-(4,4,5,5-tetramethyl-1,3,2-dioxaborolan-2-yl)-3,4-dihydro-1H-[1,4]oxazino[4,3-a]indole

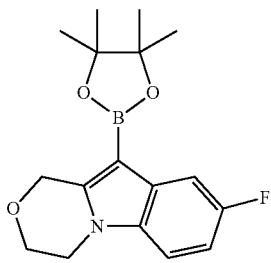 [SMILES: CC1(C)OB(c2c3n(c4ccc(F)cc24)CCOC3)OC1(C)C]

Embodiment 37C (5.50 g, 20.36 mmol) and 4,4,5,5-tetramethyl-1,3,2-dioxaborolane (5.21 g, 40.72 mmol, 5.92 mL) were dissolved in toluene (388.29 micromolar), $Pd_2(dba)_3$ (372.93 mg, 407.20 μmol), $Et_3N$ (6.18 g, 61.08 mmol, 8.47 mL) and X-PHOS (388.29 mg, 814.40 μmol) were added to the mixture, and after replacing with $N_2$, the reaction mixture was warmed to 110° C. and stirred for 3 hours. TLC (PE:DCM=10:1) showed the reaction was complete. The reaction mixture was filtered and concentrated. The residue was purified by column chromatography ($SiO_2$: PE:EtOAc=200:1 to 20:1) to deliver the title compound (pale yellow solid, 6.50 g, yield 90.59%). $^1$H NMR (400 MHz, $CDCl_3$): δ 7.67 (dd, J1=2.4 Hz, J2=10 Hz, 1H), 7.19 (dd, J1=4.4 Hz, J2=8.8 Hz, 1H), 6.97-6.94 (m, 1H), 5.17 (s, 2H), 4.21-4.15 (m, 2H), 4.11-4.05 (m, 2H), 1.36 (s, 12H).

Embodiment 37E 10-(2-Chloropyrimidin-4-yl)-8-fluoro-3,4-dihydro-1H-[1,4]oxazino[4,3-a]indole

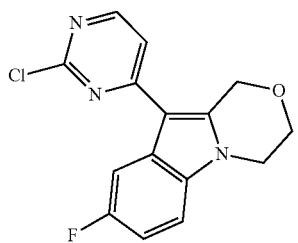 [SMILES: Fc1ccc2c(c1)c(-c1ccnc(Cl)n1)c1n2CCOC1]

Embodiment 37D (1.50 g, 4.73 mmol) and 2,4-dichloropyrimidine (1.41 g, 9.46 mmol) were dissolved in THF (20 mL) and water (3 mL). $Na_2CO_3$ (1.00 mg, 9.46 mmol) and $Pd(dppf)Cl_2.CH_2Cl_2$ (200.00 mg, 244.91 μmol) were added to the mixture and the reaction mixture was warmed to 50° C. and stirred for 5 hours under the protection of nitrogen. TLC (PE:EtOAc=5:1) showed the reaction was complete, water (10 mL) was added to the reaction solution and the THF was removed by concentration. The resulting solid was filtered and beaten with PE:EtOAc (10:1), solid filtered and concentrated to deliver the title compound (white solid, 700.00 g, 38.98%). $^1$H NMR (300 MHz, $CDCl_3$): δ 8.53 (d, J=5.4 Hz, 1H), 7.71 (dd, J1=2.4 Hz, J2=9.9 Hz, 1H), 7.49 (d, J=5.4 Hz, 1H), 7.34-7.31 (m, 1H), 7.10-7.08 (m, 1H), 5.41 (s, 2H), 4.30-4.14 (m, 4H). LCMS (ESI) (5-95AB): m/z: 304.0 [M+1].

Embodiment 37F 4-(8-Fluoro-3,4-dihydro-1H-[1,4]oxazino[4,3-a]indol-10-yl)-N-(4-fluoro-2-methoxy-5-nitrophenyl)-pyrimidin-2-amine

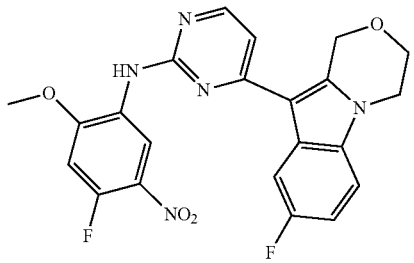 [SMILES: COc1cc(F)c([N+](=O)[O-])cc1Nc1nccc(-c2c3n(c4ccc(F)cc24)CCOC3)n1]

The Embodiment was prepared according to the method of Embodiment D except for replacing Embodiment C with Embodiment 37E to deliver the title compound (gray solid, 700.00 mg, crude). $^1$H NMR (300 MHz, $CDCl_3$): δ 9.40 (d, J=8.1 Hz, 1H), 8.49 (d, J=5.7 Hz, 1H), 7.72 (d, J=9.9 Hz, 1H), 7.57 (s, 1H), 7.15 (d, J=5.4 Hz, 1H), 7.08-7.06 (m, 1H), 6.79 (d, J=12.3 Hz, 1H), 6.65 (d, J=12.0 Hz, 1H), 5.42 (s, 2H), 4.27-4.25 (m, 2H), 4.21-4.19 (m, 2H), 4.06 (s, 3H). LCMS (ESI) (5-95AB): m/z: 454.2 [M+1].

Embodiment 37G $N^4$-(2-(Dimethylamino)ethyl)-$N^1$-(4-(8-fluoro-3,4-dihydro-1H-[1,4]oxazino[4,3-a]indol-10-yl)pyrimidin-2-yl)-2-methoxy-$N^4$-methyl-5-nitrobenzene-1,4-diamine

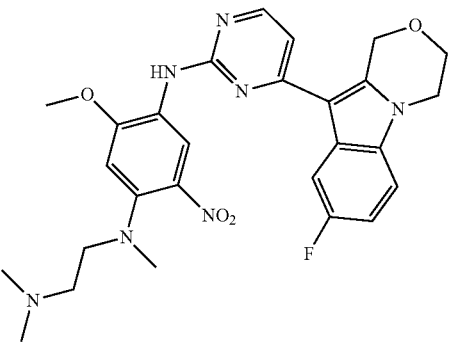 [SMILES: COc1cc(N(C)CCN(C)C)c([N+](=O)[O-])cc1Nc1nccc(-c2c3n(c4ccc(F)cc24)CCOC3)n1]

The Embodiment was prepared according to the method of Embodiment 16A except for replacing Embodiment D and N,N-diethyl-N-methylethane-1,2-diamine with Embodiment 37F and N,N',N'-trimethyl-1,2-ethanediamine respectively to deliver the title compound (brown solid, 140.00 mg, yield 88.89%). $^1$H NMR (400 MHz, $CDCl_3$): δ 8.96 (s, 1H), 8.35 (d, J=5.2 Hz, 1H), 7.62 (dd, J1=2.4 Hz, J2=10.0 Hz, 1H), 7.36 (s, 1H), 7.22 (dd, J1=4.4 Hz, J2=9.0 Hz, 1H), 7.00-6.91 (m, 2H), 6.63 (s, 1H), 6.64-6.60 (m, 1H), 5.33 (s, 2H), 4.21-4.15 (m, 2H), 4.12-4.06 (m, 2H), 3.92 (s, 3H), 3.25-3.18 (m, 2H), 2.82 (s, 3H), 2.54 (t, J=7.2 Hz, 2H), 2.25 (s, 6H). LCMS (ESI) (5-95AB): m/z: 536.4 [M+1].

Embodiment 37H

N[1]-(2-(Dimethylamino)ethyl)-N[4]-(4-(8-fluoro-3,4-dihydro-1H-[1,4]oxazino[4,3-a]indol-10-yl)pyrimidin-2-yl)-5-methoxy-N[1]-methylbenzene-1,2,4-triamine

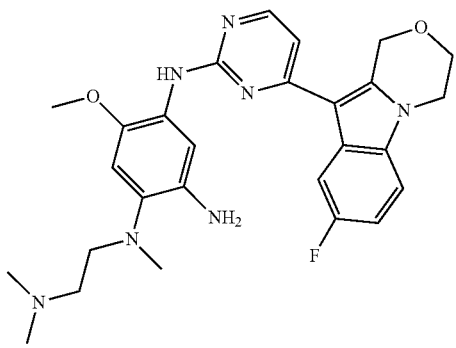

The Embodiment was prepared according to the method of Embodiment 16B except for replacing Embodiment 16A with Embodiment 37G to deliver the title compound (brown solid, 160.00 mg, crude). $^1$H NMR (400 MHz, CDCl$_3$): δ 8.41 (d, J=5.6 Hz, 1H), 7.95 (s, 1H), 7.85-7.82 (m, 1H), 7.80-7.71 (m, 1H), 7.48 (s, 1H), 7.07-7.02 (m, 1H), 6.93 (d, J=5.6 Hz, 1H), 6.73 (s, 1H), 5.38 (s, 2H), 4.27-4.22 (m, 2H), 4.21-4.16 (m, 2H), 3.86 (s, 3H), 3.04-3.00 (m, 2H), 2.70 (s, 3H), 2.49-2.46 (m, 2H), 2.32 (s, 6H). LCMS (ESI) (5-95AB): m/z: 506.1 [M+1].

Embodiment 37I

N-(2-((2-(Dimethylamino)ethyl)(methyl)amino)-5-((4-(8-fluoro-3,4-dihydro-1H-[1,4]oxazino[4,3-a]indol-10-yl)pyrimidin-2-yl)amino)-4-methoxyphenyl)acrylamide

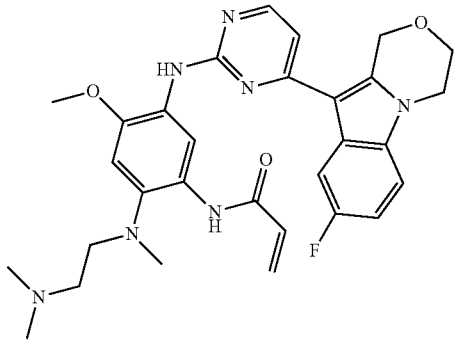 [SMILES: C=CC(=O)Nc1cc(Nc2nccc(-c3c4n(c5ccc(F)cc35)CCOC4)n2)c(OC)cc1N(C)CCN(C)C]

The Embodiment was prepared according to the method of Embodiment 16C except for replacing Embodiment 16B with Embodiment 37H to deliver the title compound (formate, 73.00 mg, yield 37.33%). $^1$H NMR (400 MHz, DMSO-d$_6$): δ 10.13 (s, 1H), 8.60 (s, 1H), 8.33 (d, J=5.2 Hz, 1H), 8.26 (s, 1H), 8.17 (s, 1H), 7.85 (dd, J1=2.0 Hz, J2=10.4 Hz, 1H), 7.51 (dd, J1=4.6 Hz, J2=8.8 Hz, 1H), 7.13-6.97 (m, 3H), 6.44 (dd, J1=10.0 Hz, J2=16.8 Hz, 1H), 6.19 (dd, J1=2.0 Hz, J2=16.8 z, 1H), 5.78-5.67 (m, 1H), 5.07 (s, 2H), 4.18-4.11 (m, 2H), 4.10-4.00 (m, 2H), 3.80 (s, 3H), 2.94 (t, J=5.2 Hz, 2H), 2.70 (s, 3H), 2.44 (t, J=5.6 Hz, 2H), 2.29 (s, 6H). LCMS (ESI) (5-95AB): m/z: 560.1 [M+1].

Embodiment 38

N-(2-((2-(Dimethylamino)ethyl)(methyl)amino)-5-((4-(7-fluoro-3,4-dihydro-1H-[1,4]oxazino[4,3-a]indol-10-yl)pyrimidin-2-yl)amino)-4-methoxyphenyl)acrylamide

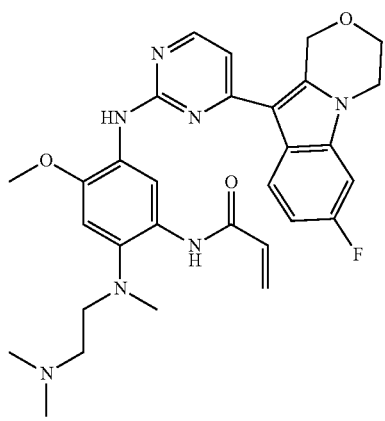 [SMILES: C=CC(=O)Nc1cc(Nc2nccc(-c3c4n(c5cc(F)ccc35)CCOC4)n2)c(OC)cc1N(C)CCN(C)C]

The synthetic process of the Embodiment is the same as the process 11.

Embodiment 38A

Methyl 6-fluoro-1H-indole-2-carboxylate

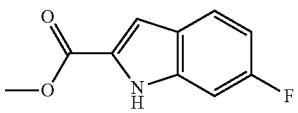

2-Bromo-4-fluoro-benzaldehyde (20.00 g, 98.52 mmol) and methyl-2-aminoacetic acid (18.55 g, 147.78 mmol, hydrochloride) were dissolved in NMP (500 mL), Cs$_2$CO$_3$ (64.20 g, 197.04 mmol) and Cu$_2$O (1.41 g, 9.85 mmol) were added to the mixture and the reaction mixture was warmed to 100° C. and stirred for 16 hours under the protection of nitrogen. TLC (PE:DCM=10:1) showed the reaction finished. The reaction mixture was filtered and concentrated. Water (1000 mL) was added to the residue and extracted with EtOAc (200 mL*2). The combined organic phases were dried over anhydrous sodium sulfate, filtered and concentrated. The resulting residue was purified by column chromatography (SiO$_2$, PE:EtOAc=500:1 to 20:1) to deliver the title compound (yellow solid, 5.00 g, 26.27% yield). $^1$H NMR (400 MHz, CDCl$_3$): δ 9.20 (br. s., 1H), 7.62 (dd, J$_1$=5.2 Hz, J$_2$=8.8 Hz, 1H), 7.21 (d, J=1.2 Hz, 1H), 7.10 (dd, J$_1$=2.0 Hz, J2=9.6 Hz, 1H), 6.94 (dt, J$_1$=2.4 Hz, J$_2$=9.2 Hz, 1H), 3.95 (s, 3H).

Embodiment 38B (6-Fluoro-1H-indol-2-yl)methanol

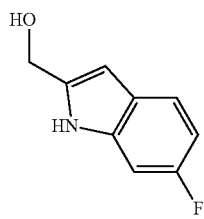 [SMILES: OCc1cc2ccc(F)cc2[nH]1]

The Embodiment was prepared according to the method of Embodiment 37A except for replacing 5-fluoro-1H-indole-2-carboxylic acid with ethyl methyl-6-fluoro-1H-indole-2-carboxylate to deliver the title compound (yellow oil, 4.50 g, 89.49%). $^1$H NMR (400 MHz, CDCl$_3$): δ 8.54 (br. s., 1H), 7.56-7.44 (m, 1H), 7.07-7.00 (m, 1H), 6.91-6.88 (m, 1H), 6.39 (s, 1H), 4.81 (s, 2H).

Embodiment 38C

7-Fluoro-3,4-dihydro-1H-[1,4]oxazino[4,3-a]indole

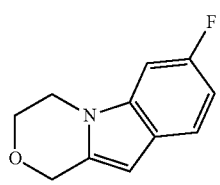 [SMILES: Fc1ccc2cc3n(c2c1)CCOC3]

The Embodiment was prepared according to the method of Embodiment 37B except for replacing (5-fluoro-1H-indol-2-yl)methanol with (6-fluoro-1H-indol-2-yl)methanol to deliver the title compound (brown solid, 1.20 g, 31.10%). $^1$H NMR (400 MHz, CDCl$_3$): δ 7.49 (dd, J1=8.8 Hz, J2=5.2 Hz, 1H), 6.84-7.03 (m, 2H), 6.22 (s, 1H), 4.98 (s, 2H), 4.17-4.22 (m, 2H), 4.02-4.07 (m, 2H).

Embodiment 38D

10-Bromo-7-fluoro-3,4-dihydro-1H-[1,4]oxazino[4,3-a]indole

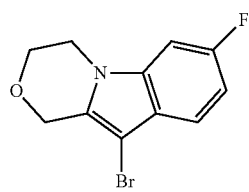 [SMILES: Fc1ccc2c(Br)c3n(c2c1)CCOC3]

The Embodiment was prepared according to the method of Embodiment 37C except for replacing 37B with 38C to deliver the title compound (white solid, 2.20 g, 53.69%). $^1$H NMR (400 MHz, CDCl$_3$): δ 7.42-7.31 (m, 1H), 6.95-6.81 (m, 2H), 4.84-4.73 (m, 2H), 4.11-4.03 (m, 2H), 3.97-3.85 (m, 2H).

Embodiment 38E

7-Fluoro-10-(4,4,5,5-tetramethyl-1,3,2-dioxaborolan-2-yl)-3,4-dihydro-1H-[1,4]oxazino[4,3-a]indole

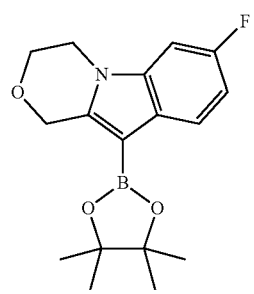 [SMILES: CC1(C)OB(c2c3n(c4cc(F)ccc24)CCOC3)OC1(C)C]

The Embodiment was prepared according to the method of Embodiment 37D except for replacing 37C with 38D to deliver the title compound (pale yellow solid, 2.50 g, 96.72%). $^1$H NMR (300 MHz, CDCl$_3$): δ 7.93-7.83 (m, 1H), 6.99-6.89 (m, 2H), 5.15 (s, 2H), 4.20-4.13 (m, 2H), 4.07-4.00 (m, 2H), 1.34 (s, 12H).

Embodiment 38F 10-(2-Chloropyrimidin-4-yl)-7-fluoro-3,4-dihydro-1H-[1,4]oxazino[4,3-a]indole

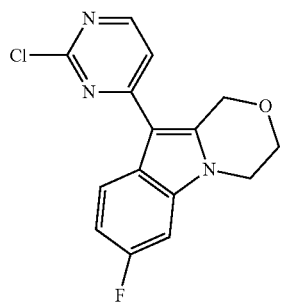 [SMILES: Fc1ccc2c(-c3ccnc(Cl)n3)c3n(c2c1)CCOC3]

The Embodiment was prepared according to the method of Embodiment 37E except for replacing 37D with 38E to deliver the title compound (pale yellow solid, 1.10 g, 47.45%). $^1$H NMR (400 MHz, CDCl$_3$): δ 8.53 (d, J=5.4 Hz, 1H), 7.98 (dd, J=5.2 Hz, J2=9.2 Hz, 1H), 7.53 (d, J=5.2 Hz, 1H), 7.14-7.05 (m, 2H), 5.43-5.35 (m, 2H), 4.26-4.21 (m, 2H), 4.18-4.13 (m, 2H). LCMS (ESI) (5-95AB): m/z: 304.0 [M+1].

Embodiment 38G 4-(7-Fluoro-3,4-dihydro-1H-[1,4]oxazino[4,3-a]
indol-10-yl)-N-(4-fluoro-2-methoxy-5-nitrophenyl)-
pyrimidin-2-amine

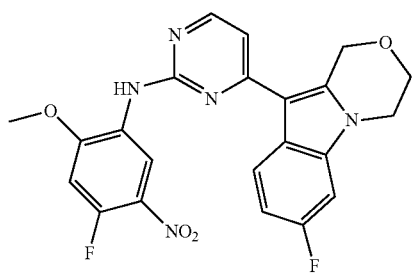 [SMILES: COc1cc(F)c([N+](=O)[O-])cc1Nc1nccc(-c2c3n(c4cc(F)ccc24)CCOC3)n1]

The Embodiment was prepared according to the method of Embodiment D except for replacing Embodiment C with Embodiment 38F to deliver the title compound (brown solid, 2.00 g, crude). $^1$H NMR (400 MHz, CDCl$_3$): δ 9.39 (d, J=8.4 Hz, 1H), 8.48 (d, J=5.2 Hz, 1H), 7.97 (dd, J1=5.2 Hz, J2=8.8 Hz, 1H), 7.57 (s, 1H), 7.19 (d, J=5.2 Hz, 1H), 7.11-7.03 (m, 2H), 6.79 (d, J=12.0 Hz, 1H), 5.40 (s, 2H), 4.30-4.24 (m, 2H), 4.20-4.11 (m, 2H), 4.06 (s, 3H). LCMS (ESI) (5-95AB): m/z: 454.0 [M+1].

Embodiment 38H $N^4$-(2-(Dimethylamino)ethyl)-$N^1$-(4-(7-fluoro-3,4-
dihydro-1H-[1,4]oxazino[4,3-a]indol-10-yl)pyrimi-
din-2-yl)-2-methoxy-$N^4$-methyl-5-nitrobenzene-1,4-
diamine

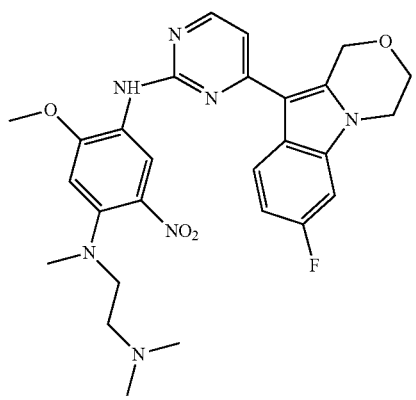 [SMILES: COc1cc(N(C)CCN(C)C)c([N+](=O)[O-])cc1Nc1nccc(-c2c3n(c4cc(F)ccc24)CCOC3)n1]

The Embodiment was prepared according to the method of Embodiment 16A except for replacing Embodiment D and N,N-diethyl-N-methylethane-1,2-diamine with Embodiment 38G and N,N',N'-trimethyl-1,2-ethanediamine respectively to deliver the title compound (brown solid, 1.60 g, 71.70% yield). $^1$H NMR (400 MHz, CDCl$_3$): δ 9.06 (s, 1H), 8.44 (d, J=5.2 Hz, 1H), 8.02-7.92 (m, 1H), 7.66-7.37 (m, 2H), 7.15-7.01 (m, 3H), 6.76 (s, 1H), 5.43 (s, 2H), 4.31-4.23 (m, 2H), 4.19-4.10 (m, 2H), 3.99 (s, 3H), 3.36-3.28 (m, 2H), 2.91 (s, 3H), 2.64-2.61 (m, 2H), 2.32 (s, 6H). LCMS (ESI) (5-95AB): m/z: 536.2 [M+1].

Embodiment 38I $N^1$-(2-(Dimethylamino)ethyl)-$N^4$-(4-(7-fluoro-3,4-
dihydro-1H-[1,4]oxazino[4,3-a]indol-10-yl)pyrimi-
din-2-yl)-5-methoxy-$N^1$-methylbenzene-1,2,4-tri-
amine

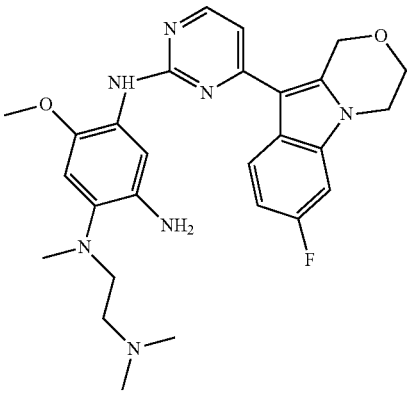 [SMILES: COc1cc(N(C)CCN(C)C)c(N)cc1Nc1nccc(-c2c3n(c4cc(F)ccc24)CCOC3)n1]

The Embodiment was prepared according to the method of Embodiment 16B except for replacing Embodiment 16A with Embodiment 38H to deliver the title compound (brown solid, 1.50 g, yield 89.30%). $^1$H NMR (400 MHz, CDCl$_3$): δ 8.41 (d, J=5.2 Hz, 1H), 8.09 (dd, J1=5.2 Hz, J2=9.6 Hz, 1H), 7.97 (s, 1H), 7.64-7.57 (m, 1H), 7.49 (s, 1H), 7.09-7.06 (m, 1H), 6.97 (d, J=5.2 Hz, 1H), 6.73 (s, 1H), 5.37 (s, 2H), 4.27-4.20 (m, 2H), 4.17-4.10 (m, 2H), 3.86 (s, 3H), 3.04-2.97 (m, 2H), 2.70 (s, 3H), 2.52-2.43 (m, 3H), 2.32 (s, 6H). LCMS (ESI) (5-95AB): m/z: 506.2 [M+1].

Embodiment 38J

N-(2-((2-(Dimethylamino)ethyl)(methyl)amino)-5-
((4-(7-fluoro-3,4-dihydro-1H-[1,4]oxazino[4,3-a]
indol-10-yl)pyrimidin-2-yl)amino)-4-methoxyphe-
nyl)acrylamide

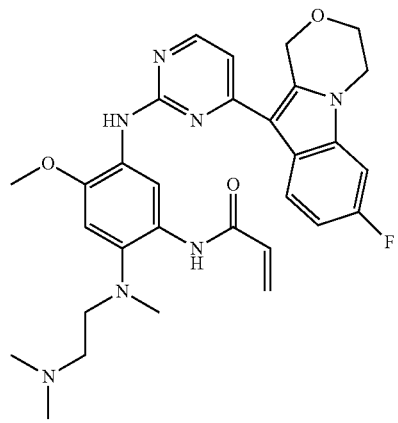 [SMILES: C=CC(=O)Nc1cc(Nc2nccc(-c3c4n(c5cc(F)ccc35)CCOC4)n2)c(OC)cc1N(C)CCN(C)C]

The Embodiment was prepared according to the method of Embodiment 16C except for replacing Embodiment 16B with Embodiment 38I to deliver the title compound (formate, 90.00 mg, yield 39.84%). $^1$H NMR (400 MHz, DMSO-d$_6$): δ 10.14 (s, 1H), 8.61 (s, 1H), 8.34 (d, J=5.2 Hz, 1H), 8.26 (s, 1H), 8.16-8.03 (m, 2H), 7.38 (dd, J1=2.4 Hz, J2=9.6 Hz, 1H), 7.08-6.94 (m, 3H), 6.44 (dd, J1=10.0 Hz, J2=16.8 Hz, 1H), 6.19 (dd, J1=2.0 Hz, J2=16.8 Hz, 1H), 5.76-5.65 (m, 1H), 5.04 (s, 2H), 4.14-4.00 (m, 4H), 3.80 (s, 3H), 2.94 (t, J=5.6 Hz, 2H), 2.70 (s, 3H), 2.42 (t, J=5.6 Hz, 2H), 2.28 (s, 6H). LCMS (ESI) (5-95AB): m/z: 560.3 [M+1].

Embodiment 39

N-(5-((4-(8,9-Dihydro-6H-pyrido[2,3]pyrrolo[4,5-a][1,4]oxazin-5-yl)-5-fluoropyrimidin-2-yl)amino)-2-((2-(dimethylamino)ethyl)(methyl)amino)-4-methoxyphenyl)acrylamide

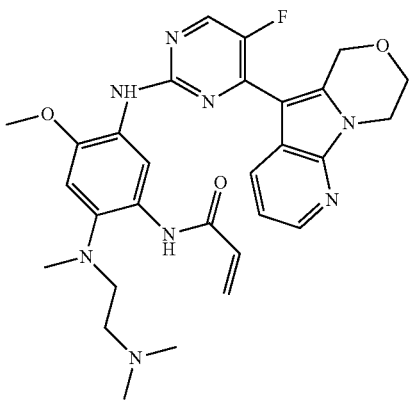 [SMILES: C=CC(=O)Nc1cc(Nc2ncc(F)c(-c3c4n(c5ncccc35)CCOC4)n2)c(OC)cc1N(C)CCN(C)C]

The synthetic process of the Embodiment is the same as the process 11.

Embodiment 39A (1H-Pyrrolo[2,3-b]pyridin-2-yl)methanol

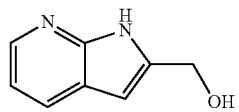 [SMILES: OCc1cc2cccnc2[nH]1]

1-(p-Toluenesulfonyl)pyrrolo[2,3-b]pyridine-2-carboxylic acid (26.00 g, 82.19 mmol) was dissolved in tetrahydrofuran (300 mL) at 0° C., lithium aluminum hydrate (12.48 g, 328.76 mmol) was added and stirred at 20° C. for 32 hours. TLC showed the reaction was complete. Water (13 mL), 15% NaOH (13 mL) and water (39 mL) were added successively to the reaction mixture. The mixture was filtered and the filtrate was concentrated to deliver the crude product. The product was purified by column chromatography (DCM:MeOH=1:0, 10:1) to deliver the title compound (yellow solid, 2.90 g, yield 23.81%). $^1$H NMR (400 MHz, CD$_3$OD): δ 8.14 (dd, J=4.80, 1.20 Hz, 1H), 7.94 (d, J=7.60 Hz, 1H), 7.08 (dd, J=8.00, 4.80 Hz, 1H), 6.42 (s, 1H), 4.77 (s, 3H).

Embodiment 39B 8,9-Dihydro-6H-pyrido[3,4]pyrrolo[3,5-a][1,4]oxazine

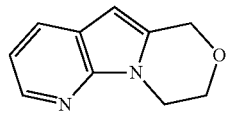 [SMILES: c1cnc2c(c1)cc1n2CCOC1]

(1H-Pyrrolo[2,3-b]pyridin-2-yl)methanol (2.50 g, 16.87 mmol) and possium hydroxide (2.37 g, 42.18 mmol) were dissolved in dichloromethane (900 mL), a solution of phenylvinylsulfone (7.34 g, 20.24 mmol) in DCM (100 mL) was added dropwise to the mixture and the mixture was stirred at 20° C. for 12 hours. TLC showed the reaction was complete, washed with water (100 mL×2) and the organic phase was concentrated to deliver the crude product. The product was purified by column chromatography (DCM:MeOH=1:0, 10:1) to deliver the title compound (white solid, 820.00 mg, yield 27.90%).

Embodiment 39C

5-Bromo-8,9-dihydro-6H-pyrido[2,3]pyrrolo[4,5-a][1,4]oxazine

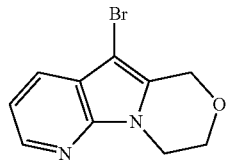 [SMILES: Brc1c2n(c3ncccc13)CCOC2]

The Embodiment was prepared according to the method of Embodiment 37C by replacing Embodiment 37B with Embodiment 39B to deliver the title compound (yellow solid, 180.00 mg, yield 45.99%). LCMS (ESI) (5-95AB): m/z: 253.00 [M+1].

Embodiment 39D 5-(4,4,5,5-Tetramethyl-1,3,2-dioxaborolan-2-yl)-8,9-dihydro-6H-pyrido[3,4]pyrrolo[3,5-a][1,4]oxazine

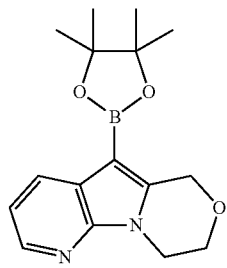 [SMILES: CC1(C)OB(c2c3n(c4ncccc24)CCOC3)OC1(C)C]

The Embodiment was prepared according to the method of Embodiment 37D except for replacing Embodiment 37C with Embodiment 39C. To deliver the title compound (yellow solid, 170.00 mg, yield 73.97%). LCMS (ESI) (5-95AB): m/z: 300.7 [M+1].

Embodiment 39E 5-(2-Chloro-5-fluoropyrimidin-4-yl)-8,9-dihydro-6H-pyrido[2,3]pyrrolo[4,5-a][1,4]oxazine

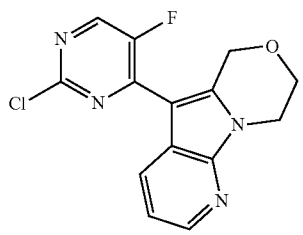 [SMILES: Fc1cnc(Cl)nc1-c1c2n(c3ncccc13)CCOC2]

The Embodiment was prepared according to the method of Embodiment 37E except for replacing Embodiment 37D with Embodiment 39D to deliver the title compound (yellow solid, 90.00 mg, yield 60.29%). $^1$H NMR (400 MHz, CDCl$_3$): δ 8.12-8.58 (m, 4H), 5.35 (br. s., 2H), 4.09-4.59 (m, 4H). LCMS (ESI) (5-95AB): m/z: 305.0 [M+1].

Embodiment 39F 4-(8,9-Dihydro-6H-pyrido[2,3]pyrrolo[4,5-a][1,4]oxazin-5-yl)-5-fluoro-N-(4-fluoro-2-methoxy-5-nitrophenyl)pyrimidin-2-amine

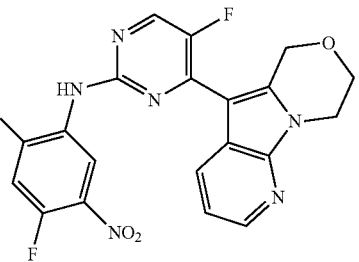

The Embodiment was prepared according to the method of Embodiment 30B except for replacing Embodiment 30A with Embodiment 39E to deliver the title compound (yellow solid, 88.00 mg, yield 65.71%). $^1$H NMR (400 MHz, CDCl$_3$): δ. 9.36 (br. s., 1H), 8.08-8.58 (m, 2H), 7.66 (br. s., 1H), 7.35-7.52 (m, 1H), 6.68-6.88 (m, 1H), 5.34 (br. s., 2H), 4.21-4.55 (m, 4H), 4.08 (br. s., 3H). LCMS (ESI): m/z: 455.0 [M+1].

Embodiment 39G

N$^1$-(4-(8,9-Dihydro-6H-pyrido[2,3]pyrrolo[4,5-α][1,4]oxazin-5-yl)-5-fluoropyrimidin-2-yl)-N$^4$-(2-(dimethylamino)ethyl)-2-methoxy-N$^4$-methyl-5-nitrobenzene-1,4-diamine

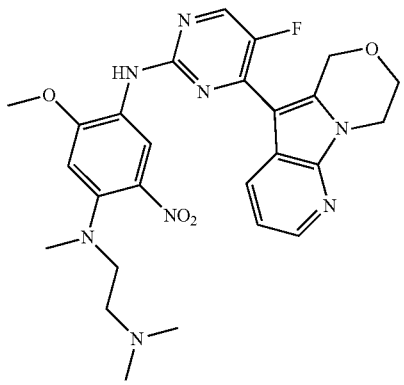 [SMILES: COc1cc(N(C)CCN(C)C)c([N+](=O)[O-])cc1Nc1ncc(F)c(-c2c3n(c4ncccc24)CCOC3)n1]

The Embodiment was prepared according to the method of Embodiment 16A except for replacing Embodiment D and N,N-diethyl-N-methylethane-1,2-diamin with Embodiment 39F and N,N',N'-trimethyl-1,2-ethanediamine to deliver the title compound (yellow solid, 55.00 mg, yield 43.19%). LCMS (ESI) (5-95AB): m/z: 537.2 [M+1].

Embodiment 39H

N$^4$-(4-(8,9-Dihydro-6H-pyrido[2,3]pyrrolo[4,5-α][1,4]oxazin-5-yl)-5-fluoropyrimidin-2-yl)-N$^1$-(2-(dimethylamino)ethyl)-5-methoxy-N$^1$-methylbenzene-1,2,4-triamine

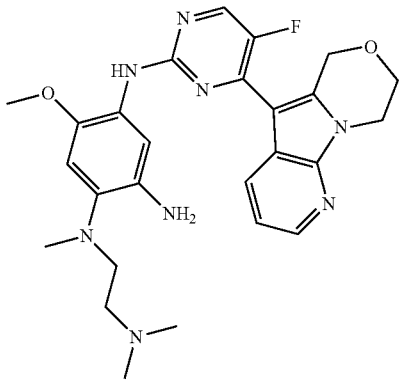 [SMILES: COc1cc(N(C)CCN(C)C)c(N)cc1Nc1ncc(F)c(-c2c3n(c4ncccc24)CCOC3)n1]

The Embodiment was prepared according to the method of Embodiment 16B except for replacing Embodiment 16A with Embodiment 39G to deliver the title compound (yellow solid, 420.00 mg, yield 99.13%). LCMS (ESI) (5-95AB): m/z: 507.2 [M+1].

Embodiment 39I

N-(5-((4-(8,9-Dihydro-6H-pyrido[2,3]pyrrolo[4,5-a][1,4]oxazin-5-yl)-5-fluoropyrimidin-2-yl)amino)-2-((2-(dimethylamino)ethyl)(methyl)amino)-4-methoxyphenyl)acrylamide

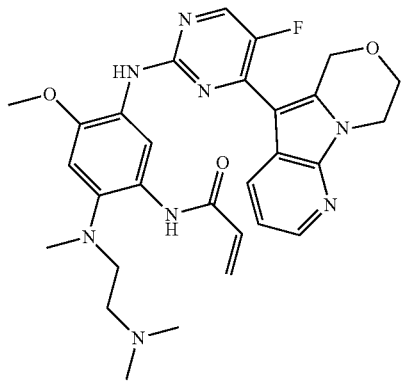 [SMILES: C=CC(=O)Nc1cc(Nc2ncc(F)c(-c3c4n(c5ncccc35)CCOC4)n2)c(OC)cc1N(C)CCN(C)C]

The Embodiment was prepared according to the method of Embodiment 16C except for replacing Embodiment 16B with Embodiment 39H to deliver the title compound (8.60 mg, yield 17.44%). ¹H NMR (400 MHz, CD₃OD): δ 8.54 (br. s., 1H), 8.48 (br. s., 1H), 8.38 (br. s., 1H), 7.81-7.90 (m, 1H), 7.17-7.25 (m, 1H), 6.97 (s, 2H), 6.41-6.52 (m, 2H), 5.86 (m, 1H), 5.07 (br. s., 3H), 4.17 (d, J=14.00 Hz, 4H), 4.00 (s, 3H), 3.41 (br. s., 3H), 3.12 (br. s., 2H), 2.76 (br. s., 6H), 2.72 (s, 3H). LCMS (ESI) (0-60AB): m/z: 578.3 [M+1].

Process 12

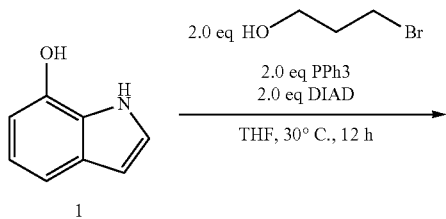

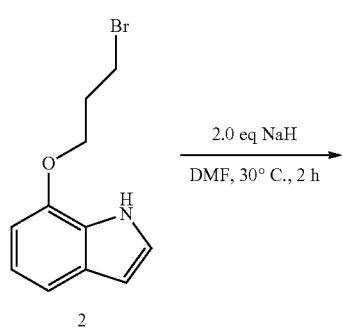

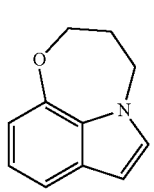

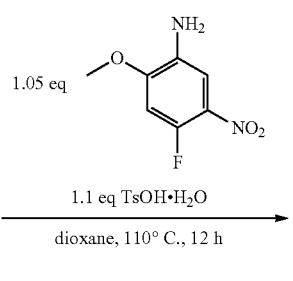

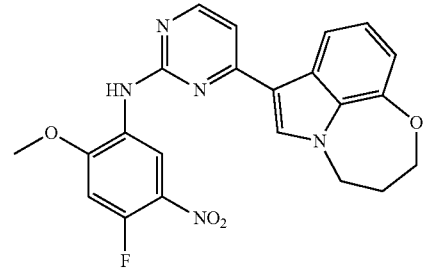

Intermediate F

Embodiment E1

7-(3-Bromopropoxy)-1H-indole

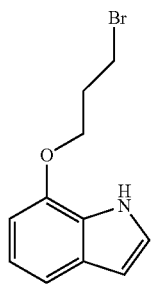 [SMILES: BrCCCOc1cccc2cc[nH]c12]

7-Hydroxyindole (2.60 g, 19.49 mmol) was dissolved in THF (10.00 mL), triphenylphosphine (10.22 g, 38.98 mmol) and 3-bromopropanol (5.42 g, 38.98 mmol) were added and then DIAD (7.88 g, 38.98 mmol) was slowly added dropwise at 10° C. The mixture was stirred at 30° C. for 12 hours and TLC showed the reaction was complete. After concentration, the residue was purified by column chromatography (PE:EA=20:1, 6:1) to deliver the title compound (colorless oil, 3.27 g, yield 66.02%). ¹H NMR (400 MHz, CDCl₃): δ 8.29 (br. s., 1H), 7.18 (d, J=2.13 Hz, 1H), 7.11 (t, J=2.70 Hz, 1H), 6.91-6.98 (m, 1H), 6.59 (d, J=7.65 Hz, 1H), 6.47 (dd, J=3.01, 2.26 Hz, 1H), 4.16-4.28 (m, 2H), 3.52-3.63 (m, 2H), 2.27-2.41 (m, 2H).

Embodiment E2

4-Fluoro-2-methoxy-5-nitroaniline

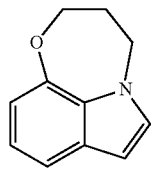 [SMILES: c1cc2c3c(c1)ccn3CCCO2]

Embodiment E1 (2.07 g, 8.15 mmol) was dissolved in DMF (10 mL) at 0° C. and then NaH (0.652 g, 16.30 mmol, 60% purity) was added in batches. The mixture was stirred at 30° C. for 2 hours. TLC showed the reaction was complete, and H$_2$O (10 mL) was added to the reaction mixture, and the mixture was extracted with EA (200 mL). The organic phase was concentrated and purified by column chromatography (PE:EA=30:1, 20:1) to deliver the title compound (white solid, 1.13 g, yield 80.05%). $^1$H NMR (400 MHz, CDCl$_3$): δ 7.27-7.33 (m, 1H), 7.09 (d, J=3.14 Hz, 1H), 7.00-7.06 (m, 1H), 6.81-6.87 (m, 1H), 6.58 (d, J=3.01 Hz, 1H), 4.31-4.38 (m, 2H), 4.18-4.25 (m, 2H), 2.36-2.44 (m, 2H).

Embodiment E 7-(2-Chloropyrimidin-4-yl)-3,4-dihydro-2H-[1,4]oxazepino[2,3,4-hi]indole

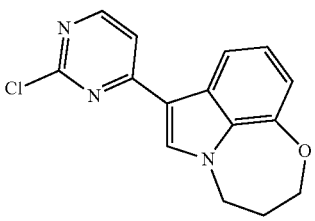 [SMILES: Clc1nccc(-c2cn3c4c(cccc24)OCCC3)n1]

AlCl$_3$ (3.7 g, 27.72 mmol) was dissolved in DME (20 mL) at 10° C. and 2,4-dichloropyrimidine (2.75 g, 18.48 mmol) was added to the mixture and stirred for 0.5 h. Embodiment E2 (1.6 g, 9.24 mmol) was slowly added in batches and the reaction mixture was warmed to 80° C. and stirred for 2 hours. TLC showed the reaction was complete, DCM (500 mL) was added to the reaction mixture. The organic layer was washed with saturated brine (200 mL×2) and concentrated. The crude product was purified by column chromatography (PE:EA=3:1, DCM) to deliver the title compound (yellow solid, 1.3 g, yield 49.24%). $^1$H NMR (400 MHz, CDCl$_3$): δ 8.45-8.52 (m, 1H), 7.90-8.01 (m, 2H), 7.52 (d, J=5.40 Hz, 1H), 7.17-7.27 (m, 1H), 6.94 (d, J=7.78 Hz, 1H), 4.26-4.46 (m, 4H), 2.35-2.50 (m, 2H).

Embodiment F 4-(3,4-Dihydro-2H-[1,4]oxazepino[2,3,4-hi]indol-7-yl)-N-(4-fluoro-2-methoxy-5-nitro phenyl)pyrimidin-2-amine

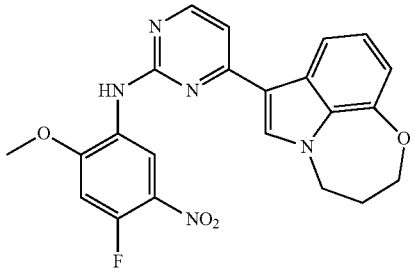 [SMILES: COc1cc(F)c([N+](=O)[O-])cc1Nc1nccc(-c2cn3c4c(cccc24)OCCC3)n1]

Embodiment E (2.4 g, 8.40 mmol) and 4-fluoro-2-methoxy-5-nitro-phenylamine (1.64 g, 8.82 mmol), p-toluenesulfonic acid (1.76 g, 1.1 mmol) was added to 1,4-dioxane (90 mL), the reaction mixture was warmed to 110° C. and stirred for 12 hours. LCMS showed the reaction was complete, ammonia (50 mL) was added to the reaction mixture to adjust the pH of the solution to 8. The mixture was cooled to 20° C. and filtered. The solid was washed with methanol (50 mL) and dried to deliver the title compound (yellow solid, 3.00 g, 82.02% yield). $^1$H NMR (400 MHz, CDCl$_3$): δ 9.10 (d, J=8.41 Hz, 1H), 8.28-8.48 (m, 3H), 8.07 (d, J=7.78 Hz, 1H), 7.26-7.42 (m, 2H), 7.01 (t, J=7.84 Hz, 1H), 6.78 (d, J=7.53 Hz, 1H), 4.34 (d, J=4.64 Hz, 4H), 4.02 (s, 3H), 2.34 (br. s., 2H).

Embodiment 40

N-(5-((4-(3,4-Dihydro-2H-[1,4]oxazepino[2,3,4-hi]indol-7-yl)pyrimidin-2-yl)amino)-2-((2-(dimethylamino)ethyl)(methyl)amino)-4-methoxyphenyl)acrylamide

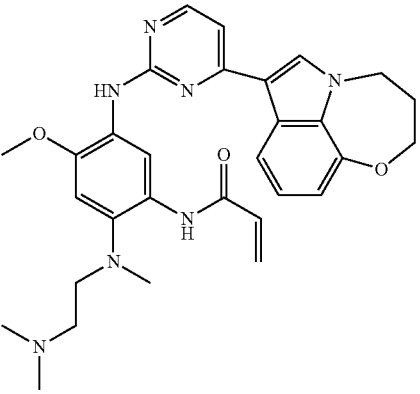 [SMILES: C=CC(=O)Nc1cc(Nc2nccc(-c3cn4c5c(cccc35)OCCC4)n2)c(OC)cc1N(C)CCN(C)C]

Embodiment 40A

N¹-(4-(3,4-Dihydro-2H-[1,4]oxazepino[2,3,4-hi]
indol-7-yl)pyrimidin-2-yl)-N⁴-(2-(dimethylamino)
ethyl)-2-methoxy-N⁴-methyl-5-nitrobenzene-1,4-
diamine

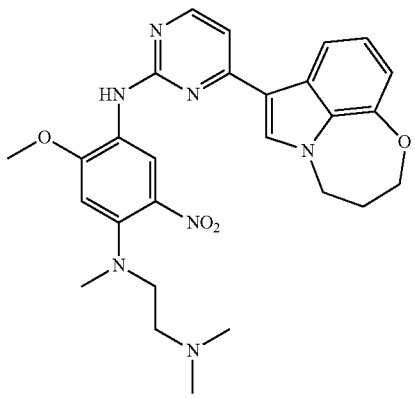 [SMILES: COc1cc(N(C)CCN(C)C)c([N+](=O)[O-])cc1Nc1nccc(-c2cn3c4c(cccc24)OCCC3)n1]

The Embodiment was prepared according to the method of Embodiment 16A except for replacing Embodiment D and N,N-diethyl-N-methylethane-1,2-diamine with Embodiment F and N,N',N'-trimethyl-1,2-ethanediamine respectively to deliver the title compound (yellow solid, 1.00 g, 82.15% yield). ¹H NMR (400 MHz, CDCl₃): δ 9.62 (s, 1H), 8.42 (d, J=5.27 Hz, 1H), 8.32 (s, 1H), 7.80 (d, J=7.91 Hz, 1H), 7.52-7.61 (m, 1H), 7.14-7.25 (m, 2H), 6.91 (d, J=7.65 Hz, 1H), 6.70 (s, 1H), 4.35-4.51 (m, 4H), 4.01 (s, 3H), 3.33 (t, J=7.09 Hz, 2H), 2.93 (s, 3H), 2.63 (t, J=7.09 Hz, 2H), 2.45 (dt, J=10.29, 5.40 Hz, 2H), 2.32 (s, 6H).

Embodiment 40B

N⁴-(4-(3,4-Dihydro-2H-[1,4]oxazepino[2,3,4-hi]
indol-7-yl)pyrimidin-2-yl)-N-(2-(dimethylamino)
ethyl)-5-methoxy-N¹-methylbenzene-1,2,4-triamine

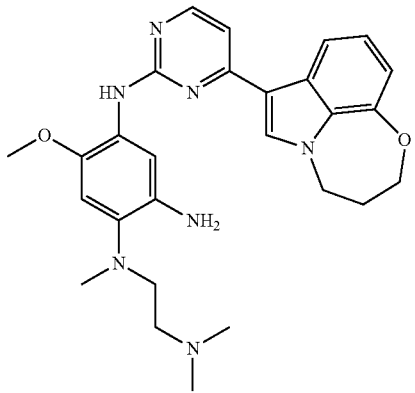 [SMILES: COc1cc(N(C)CCN(C)C)c(N)cc1Nc1nccc(-c2cn3c4c(cccc24)OCCC3)n1]

The Embodiment was prepared according to the method of Embodiment 16B except for replacing Embodiment 16A with Embodiment 40A to deliver the title compound (yellow solid, 0.8 g, yield 85.01%). ¹H NMR (400 MHz, CDCl₃): δ 8.27 (d, J=5.27 Hz, 1H), 8.08 (t, J=3.95 Hz, 2H), 7.70 (s, 1H), 7.53 (s, 1H), 7.10 (t, J=7.91 Hz, 1H), 6.94 (d, J=5.27 Hz, 1H), 6.83 (d, J=7.65 Hz, 1H), 6.61-6.66 (m, 1H), 4.20-4.34 (m, 4H), 3.75-3.80 (m, 3H), 2.94 (t, J=6.78 Hz, 2H), 2.62 (s, 3H), 2.42 (t, J=6.59 Hz, 2H), 2.30-2.38 (m, 2H), 2.26 (s, 6H).

Embodiment 40C

N-(5-((4-(3,4-Dihydro-2H-[1,4]oxazepino[2,3,4-hi]
indol-7-yl)pyrimidin-2-yl)amino)-2-((2-(dimethyl-
amino)ethyl)(methyl)amino)-4-methoxyphenyl)acry-
lamide

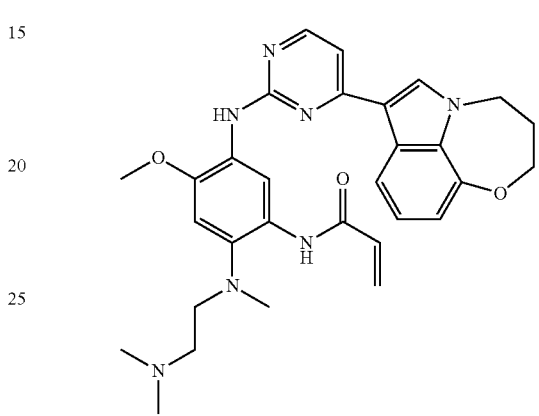

The Embodiment was prepared according to the method of Embodiment 16C except for replacing Embodiment 16B with Embodiment 40B to deliver the title compound (120.00 mg, 71.15% yield). ¹H NMR (400 MHz, CDCl₃): δ 10.21 (br. s., 1H), 9.84 (s, 1H), 9.07 (br. s., 1H), 8.40 (d, J=2.0 Hz, 1H), 7.81-7.68 (m, 2H), 7.22 (d, J=4.0 Hz, 1H), 7.14 (t, J=8.0 Hz, 1H), 6.87 (d, J=8.0 Hz, 1H), 6.81 (s, 1H), 6.48-6.31 (m, 2H), 5.78-5.64 (m, 1H), 4.64-4.52 (m, 2H), 4.45-4.36 (m, 2H), 3.90 (s, 3H), 2.90 (t, J=4.0 Hz, 2H), 2.72 (s, 3H), 2.48-2.36 (m, 2H), 2.33-2.21 (m, 8H). LCMS (ESI) (5-95AB): m/z: 542.2 [M+1].

Embodiment 41

N-(5-((4-(3,3-Dimethyl-3,4-dihydro-2H-[1,4]oxaze-
pino[2,3,4-hi]indol-7-yl)pyrimidin-2-yl)amino)-2-
((2-(dimethylamino)ethyl)(methyl)amino)-4-
methoxyphenyl)acrylamide

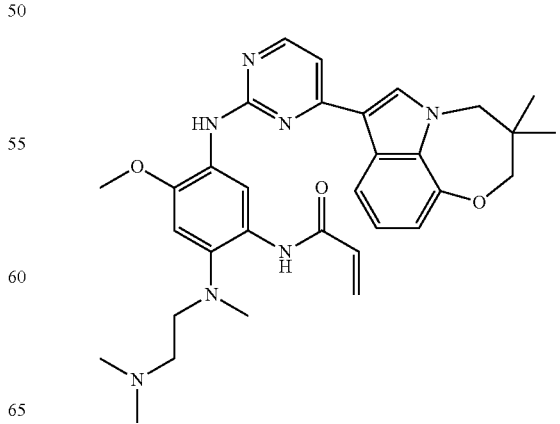

Embodiment 41A 7-(3-Chloro-2,2-dimethylpropoxy)-1H-indole

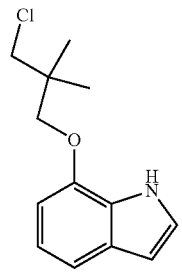 [SMILES: CC(C)(CCl)COc1cccc2cc[nH]c12]

7-Hydroxyindole (5.00 g, 37.55 mmol), 3-chloro-2,2-dimethyl-propan-1-ol (6.91 g, 56.33 mmol), triphenyl (1.57 g, 6.00 mmol) were dissolved in THF (150 mL), and after replacing with nitrogen, DIAD (15.19 g, 75.10 mmol) was added dropwise to the mixture. The mixture was stirred at 70° C. for 12 hours. TLC showed the reaction was complete, the reaction solution was concentrated to dryness. The crude product was purified by column chromatography (PE:EA=50:1, 20:1) to deliver the title compound (white solid, 3.5 g, yield 39.21%). $^1$H NMR (400 MHz, CDCl$_3$): δ 7.29 (s, 1H), 7.21 (t, J=4.0 Hz, 1H), 7.03 (t, J=8.0 Hz, 1H), 6.68 (d, J=8.0 Hz, 1H), 6.58-6.53 (m, 1H), 3.96 (s, 2H), 3.65 (s, 2H), 1.20 (s, 6H). LCMS (ESI) (5-95AB): m/z: 238.1 [M+1].

Embodiment 41B 3,3-Dimethyl-3,4-dihydro-2H-[1,4]oxazepino[2,3,4-hi]indole

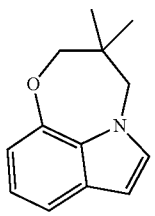

Embodiment 41A (3.50 g, 14.72 mmol) was dissolved in DMF (50 mL) at 0° C. and NaH (1.18 g, 29.44 mmol) was added to the mixture and stirred at 70° C. for 2 hours. TLC showed the reaction was complete, water (50 mL) was added to the mixture, extracted with EA (50 mL×2), the organic layer was dried over anhydrous sodium sulfate, concentrated and purified by column chromatography (PE:EA=20:1, 10:1) to deliver the title compound (white solid, 2.80 g, yield 94.51%). $^1$H NMR (400 MHz, CDCl$_3$): δ 7.28 (d, J=1.0 Hz, 1H), 7.29-7.26 (m, 1H), 7.03-6.97 (m, 2H), 6.79 (dd, J=0.8, 7.7 Hz, 1H), 6.52 (d, J=3.1 Hz, 1H), 4.05-3.98 (m, 2H), 3.87 (s, 2H), 1.17 (s, 6H). LCMS (ESI) (5-95AB): m/z: 202.2 [M+1].

Embodiment 41C 7-(2-Chloropyrimidin-4-yl)-3,3-dimethyl-3,4-dihydro-2H-[1,4]oxazepino[2,3,4-hi]indole

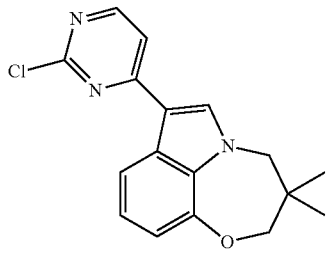 [SMILES: CC1(C)COc2cccc3c(-c4ccnc(Cl)n4)cn(c23)C1]

The Embodiment was prepared according to the method of Embodiment E except for replacing Embodiment E2 with Embodiment 41B to deliver the title compound (yellow solid, 2.30 g, yield 64.13%). $^1$H NMR (400 MHz, CDCl$_3$): δ 8.47 (d, J=4.0 Hz, 1H), 7.92 (d, J=8.0 Hz, 1H), 7.87 (s, 1H), 7.49 (d, J=4.0 Hz, 1H), 7.19 (t, J=9.0 Hz, 1H), 6.90 (d, J=8.0 Hz, 1H), 4.05 (s, 2H), 4.00 (s, 2H), 1.17 (s, 6H). LCMS (ESI) (5-95AB): m/z: 314.0 [M+1].

Embodiment 41D 4-(3,3-Dimethyl-3,4-dihydro-2H-[1,4]oxazepino[2,3,4-hi]indol-7-yl)-N-(4-fluoro-2-methoxy-5-nitrophenyl)pyrimidin-2-amine

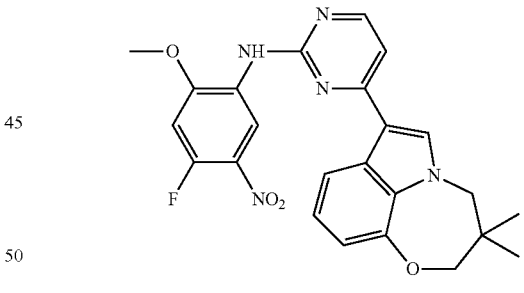

The Embodiment was prepared according to the method of Embodiment F except for replacing Embodiment E with Embodiment 41C to deliver the title compound (yellow solid, 3.00 g, yield 88.31%). $^1$H NMR (400 MHz, CDCl$_3$): δ 9.85 (d, J=8.0 Hz, 1H), 8.45 (d, J=4.0 Hz, 1H), 8.20 (s, 1H), 7.78 (d, J=8.0 Hz, 1H), 7.64 (s, 1H), 7.26 (br. s., 1H), 7.18 (t, J=8.0 Hz, 1H), 6.89 (d, J=8.0 Hz, 1H), 6.77 (d, J=12.0 Hz, 1H), 4.11 (s, 2H), 4.08 (s, 2H), 4.05 (s, 3H), 3.71 (s, 2H), 1.21 (s, 6H). LCMS (ESI) (5-95AB): m/z: 464.0 [M+1].

Embodiment 41E

N¹-(4-(3,3-Dimethyl-3,4-dihydro-2H-[1,4]oxazepino[2,3,4-hi]indol-7-yl)pyrimidin-2-yl)-N⁴-(2-(dimethylamino)ethyl)-2-methoxy-1-methyl-5-nitrobenzene-1,4-diamine

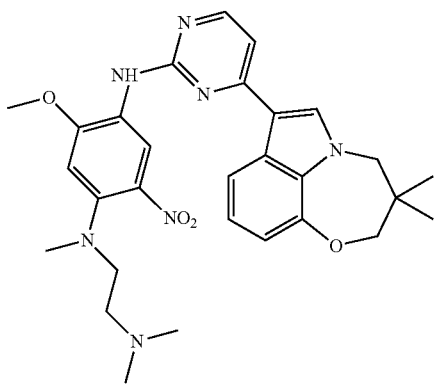

The Embodiment was prepared according to the method of Embodiment 16A except for replacing Embodiment D and N,N-diethyl-N-methylethane-1,2-diamine with Embodiment 41D and N,N',N'-trimethyl-1,2-ethanediamine respectively to deliver the title compound (yellow solid, 1.70 g, 96.16% yield). ¹H NMR (400 MHz, CDCl₃): δ 9.55 (s, 1H), 8.41 (d, J=4.0 Hz, 1H), 8.20 (s, 1H), 7.78 (d, J=8.0 Hz, 1H), 7.60-7.50 (m, 1H), 7.23-7.13 (m, 2H), 6.87 (d, J=8.0 Hz, 1H), 6.69 (s, 1H), 4.11 (s, 2H), 4.07 (s, 2H), 4.00 (s, 3H), 3.36-3.26 (m, 2H), 2.92 (s, 3H), 2.61 (t, J=8.0 Hz, 2H), 2.35-2.24 (m, 6H), 1.21 (s, 6H). LCMS (ESI) (5-95AB): m/z: 546.2 [M+1].

Embodiment 41F

N⁴-(4-(3,3-Dimethyl-3,4-dihydro-2H-[1,4]oxazepino[2,3,4-hi]indol-7-yl)pyrimidin-2-yl)-N¹-(2-(dimethylamino)ethyl)-5-methoxy-N¹-methylbenzene-1,2,4-triamine

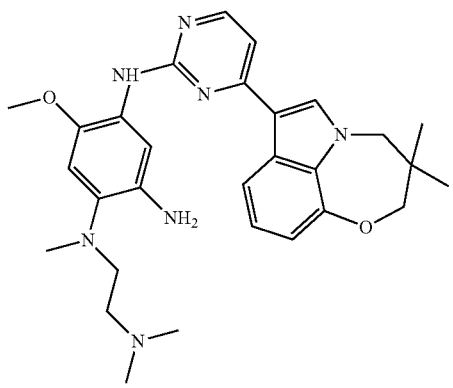

The Embodiment was prepared according to the method of Embodiment 16B except for replacing Embodiment 16A with Embodiment 41E to deliver the title compound (yellow solid, 1.50 g, yield 93.24%). ¹H NMR (400 MHz, CDCl₃): δ 8.35 (d, J=4.0 Hz, 1H), 8.18-8.08 (m, 2H), 7.76-7.69 (m, 1H), 7.60 (s, 1H), 7.17 (t, J=8.0 Hz, 1H), 7.02 (d, J=4.0 Hz, 1H), 6.88 (d, J=8.0 Hz, 1H), 6.72 (s, 1H), 4.06 (s, 2H), 4.00 (s, 2H), 3.86 (s, 3H), 2.99 (t, J=6.0 Hz, 2H), 2.69 (s, 3H), 2.49-2.39 (m, 2H), 2.28 (s, 6H), 1.19 (s, 6H). LCMS (ESI) (5-95AB): m/z: 516.2 [M+1].

Embodiment 41G

N-(5-((4-(3,3-Dimethyl-3,4-dihydro-2H-[1,4]oxazepino[2,3,4-hi]indol-7-yl)pyrimidin-2-yl)amino)-2-((2-(dimethylamino)ethyl)(methyl)amino)-4-methoxyphenyl)acrylamide The Embodiment was prepared according to the method of Embodiment 16C except for replacing Embodiment 16B with Embodiment 41F to deliver the title compound (brown solid, 1.30 g, yield 95.57%). ¹H NMR (400 MHz, CDCl₃): δ 10.24 (s, 1H), 9.85 (s, 1H), 9.08 (s, 1H), 8.40 (d, J=4.0 Hz, 1H), 7.74 (s, 1H), 7.68 (d, J=8.0 Hz, 1H), 7.21 (d, J=4.0 Hz, 1H), 7.13 (t, J=8.0 Hz, 1H), 6.87-6.79 (m, 2H), 6.50-6.32 (m, 2H), 5.72 (dd, J=2.0, 8.0 Hz, 1H), 4.26 (s, 2H), 4.07 (s, 2H), 3.89 (s, 3H), 2.92-2.85 (m, 2H), 2.71 (s, 3H), 2.29 (br. s., 2H), 2.27 (s, 6H), 1.18 (s, 6H). LCMS (ESI) (5-95AB): m/z: 570.2 [M+1].

Embodiment 41H

N-(5-((4-(3,3-Dimethyl-3,4-dihydro-2H-[1,4]oxazepino[2,3,4-hi]indol-7-yl)pyrimidin-2-yl)amino)-2-((2-(dimethylamino)ethyl)(methyl)amino)-4-methoxyphenyl)acrylamide methanesulfonate

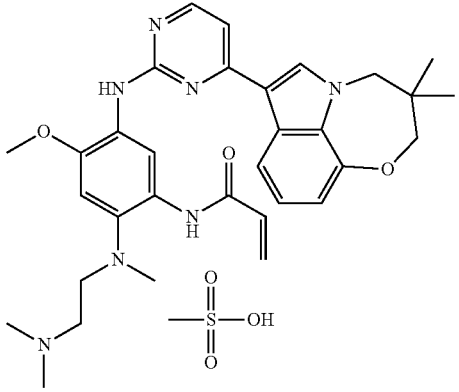

The Embodiment was prepared according to the method of Embodiment 36J except for replacing Embodiment 36I with Embodiment 41G to deliver the title compound (1.36 g, yield 89.43%). $^1$H NMR (400 MHz, CD$_3$OD): δ 8.68 (s, 1H), 8.29 (d, J=4.0 Hz, 1H), 8.10 (s, 1H), 7.99 (d, J=8.0 Hz, 1H), 7.21 (d, J=4.0 Hz, 1H), 7.03 (t, J=8.0 Hz, 1H), 6.97 (s, 1H), 6.74 (d, J=8.0 Hz, 1H), 6.60-6.42 (m, 2H), 5.93-5.82 (m, 1H), 4.06 (s, 2H), 4.03 (s, 2H), 4.02 (s, 3H), 3.48 (t, J=6.0 Hz, 2H), 3.30-3.24 (m, 2H), 2.88 (s, 6H), 2.72 (s, 3H), 2.70 (s, 3H), 1.15 (s, 6H). LCMS (ESI) (0-60AB): m/z: 570.2 [M+1].

Embodiment 42

N-(5-((4-(3H-Spiro[[1,4]oxazino[2,3,4-hi]indole-2,1'-cyclopropan]-6-yl)pyrimidin-2-yl)amino)-2-((2-(dimethylamino)ethyl)(methyl)amino)-4-methoxyphenyl)acrylamide

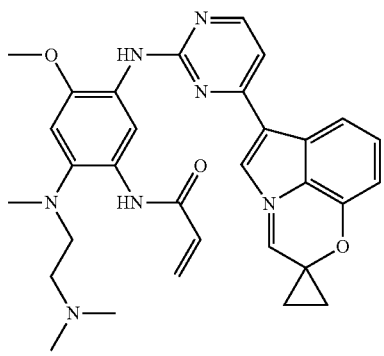

Embodiment 42A 1-(2-Nitrophenoxy)cyclopropanecarboxylic acid

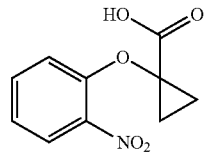 [SMILES: O=C(O)C1(Oc2ccccc2[N+](=O)[O-])CC1]

1-Fluoro-2-nitrobenzene (10.37 g, 73.47 mmol) and 1-hydroxycyclopropanecarboxylic acid (5.00 g, 48.98 mmol) were dissolved in DMF (100 mL) at 0° C., NaH (4.90 g, 122.45 mmol) was added in batches and the mixture was stirred at 80° C. for 12 hours. TLC showed the reaction was substantially complete. Water (20 mL) was added thereto, extracted with EA (100 mL×2), the pH of the aqueous phase was adjusted to 3 with 6N HCl, and the aqueous phase was extracted with EA (100 mL×3). The organic layers were combined and dried over anhydrous sodium sulfate and concentrated to dryness to deliver the title compound (yellow solid, 6.00 g, yield 54.89%). $^1$H NMR (400 MHz, CDCl$_3$): δ 7.84 (dd, J=2.0, 8.0 Hz, 1H), 7.56-7.48 (m, 1H), 7.20 (d, J=8.0 Hz, 1H), 7.10 (t, J=8.0 Hz, 1H), 1.80-1.73 (m, 2H), 1.55-1.49 (m, 2H).

Embodiment 42B

Spiro[benzo[b][1,4]oxazine-2,1'-cyclopropan]-3(4H)-one

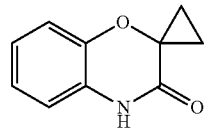 [SMILES: O=C1Nc2ccccc2OC12CC2]

Embodiment 42A (11.00 g, 49.29 mmol), NH$_4$Cl (10.55 g, 197.15 mmol) and iron powder (11.01 g, 197.15 mmol) were dissolved in ethanol (15 mL) and water (2 mL). The reaction solution was replaced with nitrogen and heated to 90° C. and stirred for 12 hours. TLC showed the reaction was complete. The reaction solution was cooled and filtered, and the filter cake was washed with ethanol and the filtrate was concentrated to dryness to deliver the title compound (yellow solid, 7.5 g, 98.89% yield). $^1$H NMR (400 MHz, CDCl$_3$): δ 9.43 (br. s., 1H), 7.12-6.65 (m, 1H), 1.62-1.02 (m, 4H). LCMS (ESI) (5-95AB): m/z: 176.0 [M+1].

Embodiment 42C 3,4-Dihydrospiro[benzo[b][1,4]oxazine-2,1'-cyclopropane]

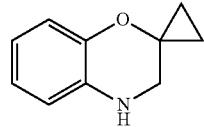 [SMILES: c1ccc2c(c1)NCC1(CC1)O2]

Embodiment 42B (8.50 g, 48.52 mmol) was dissolved in THF (100 mL), LiAlH$_4$ (4.60 g, 121.30 mmol) was added at 70° C. and stirred for 2 hours. LCMS monitored the reaction was complete. Water (4.6 mL), 15% NaOH (4.6 mL) and water (13.8 mL) were added successively to the mixture, and the mixture was stirred for 30 minutes. The mixture was filtered and the filtrate was concentrated to dryness to deliver the title compound (yellow oil, yield 98.89%). $^1$H NMR (400 MHz, CDCl$_3$): δ 6.85-6.77 (m, 1H), 6.77-6.72 (m, 1H), 6.71-6.65 (m, 2H), 3.86 (br. s., 1H), 3.33 (d, J=2.0 Hz, 2H), 1.11-1.03 (m, 2H), 0.74-0.67 (m, 2H). LCMS (ESI) (5-95AB): m/z: 162.1 [M+1].

Embodiment 42D 4-(2,2-Diethoxyethyl)-3,4-dihydrospiro[benzo[b][1,4]oxazine-2,1'-cyclopropane]

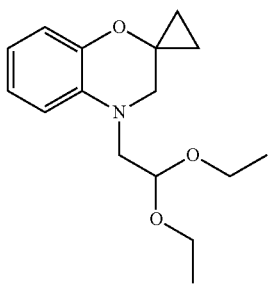 [SMILES: CCOC(CN1CC2(CC2)Oc2ccccc21)OCC]

Embodiment 42C (7.50 g, 46.53 mmol), K$_2$CO$_3$ (9.65 g, 69.8 mmol), KI (772.33 mg, 4.65 mmol) and 2-bromo-1,1-diethoxyethane (18.34 g, 93.06 mmol) were dissolved in DMF (50 mL). After replacing with nitrogen, the mixture was heated to 130° C. and stirred for 12 hours. TLC showed a small amount of raw material remaining. Water (150 mL) was added to the mixture and extracted with DCM (100 mL×2). The organic layer was dried over anhydrous sodium sulfate and concentrated. The crude product was purified by column chromatography (PE:EA=1000:1, 100:1) to deliver the title compound (yellow oil, 8.0 g, yield 61.99%). $^1$H NMR (400 MHz, CDCl$_3$): δ 6.90-6.82 (m, 1H), 6.72 (d, J=8.0 Hz, 2H), 6.63-6.56 (m, 1H), 4.79-4.66 (m, 1H), 3.80-3.69 (m, 2H), 3.64-3.53 (m, 2H), 3.46-3.38 (m, 4H), 1.28-1.17 (m, 6H), 1.05-0.97 (m, 2H), 0.73-0.61 (m, 2H).

Embodiment 42E

3H-Spiro[[1,4]oxazino[2,3,4-hi]indole-2,1'-cyclopropane]

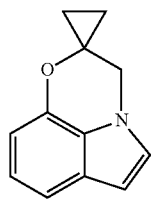 [SMILES: c1cc2c3c(c1)ccn3CC1(CC1)O2]

AlCl$_3$ (10.1 g, 75.72 mmol) was added to DCM (50 mL) at 0° C., and a solution of Embodiment 42D (7.00 g, 25.24 mmol) was dissolved in DCM (130 mL) was added drop-wise to the mixture. The mixture was stirred at 0° C. for 10 minutes, TLC showed a small amount of raw material remaining. The mixture was slowly poured into ice water (300 mL) and quenched with DCM (300 mL×2). The organic layer was dried over anhydrous sodium sulfate and concentrated by column chromatography (PE:EA=1000:1, 100:1) to deliver the title compound (yellow oil, 3.2 g, yield 68.45%). $^1$H NMR (400 MHz, CDCl$_3$): δ 7.26-7.23 (m, 1H), 7.08 (d, J=2.0 Hz, 1H), 6.99 (t, J=8.0 Hz, 1H), 6.62 (d, J=8.0 Hz, 1H), 6.51 (d, J=2.0 Hz, 1H), 4.19 (s, 2H), 1.27-1.19 (m, 2H), 0.88-0.81 (m, 2H).

Embodiment 42F 6-(2-Chloropyrimidin-4-yl)-3H-spiro[[1,4]oxazino[2,3,4-hi]indole-2,1'-cyclopropane]

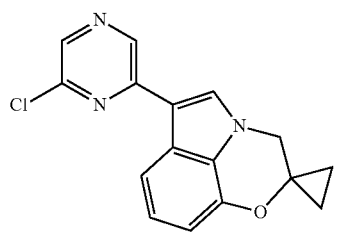 [SMILES: Clc1cncc(-c2cn3c4c(cccc24)OC2(CC2)C3)n1]

The Embodiment was prepared according to the method of Embodiment E except for replacing Embodiment E2 with Embodiment 42E to deliver the title compound (yellow solid, 1.30 g, 67.38% yield). $^1$H NMR (400 MHz, CDCl$_3$): δ 8.49 (d, J=4.0 Hz, 1H), 8.02 (s, 1H), 7.72 (d, J=8.0 Hz, 1H), 7.54 (d, J=4.0 Hz, 1H), 7.19 (t, J=8.0 Hz, 1H), 6.76-6.71 (m, 1H), 4.27 (s, 2H), 1.28-1.23 (m, 2H), 0.91-0.85 (m, 2H) LCMS (ESI) (5-95AB): m/z: 298.0 [M+1].

Embodiment 42G

N-(4-Fluoro-2-methoxy-5-nitrophenyl)-4-(3H-spiro[[1,4]oxazino[2,3,4-hi]indole-2,1'-cyclopropan]-6-yl)pyrimidin-2-amine

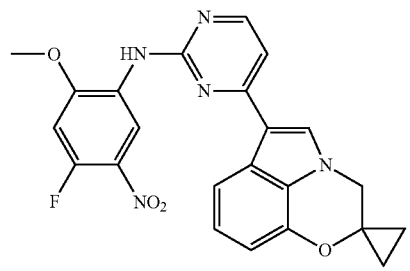 [SMILES: COc1cc(F)c([N+](=O)[O-])cc1Nc1nccc(-c2cn3c4c(cccc24)OC2(CC2)C3)n1]

The Embodiment was prepared according to the method of Embodiment F except for replacing Embodiment E with Embodiment 42F to deliver the title compound (yellow solid, 1.80 g, yield 92.06%). $^1$H NMR (400 MHz, CDCl$_3$): δ 9.90 (d, J=8.0 Hz, 1H), 8.48-8.42 (m, 1H), 8.33 (s, 1H), 7.71-7.58 (m, 2H), 7.28 (s, 1H), 7.17 (t, J=8.0 Hz, 1H), 6.82-6.67 (m, 2H), 4.40-4.26 (m, 2H), 4.08-3.99 (m, 3H), 1.31-1.17 (m, 2H), 1.02-0.82 (m, 2H). LCMS (ESI) (5-95AB): m/z: 448.1 [M+1].

Embodiment 42H

N[1]-(4-(3H-Spiro[[1,4]oxazino[2,3,4-hi]indole-2,1'-cyclopropan]-6-yl)pyrimidin-2-yl)-N[4]-(2-(dimethylamino)ethyl)-2-methoxy-N[4]-methyl-5-nitrobenzene-1,4-diamine

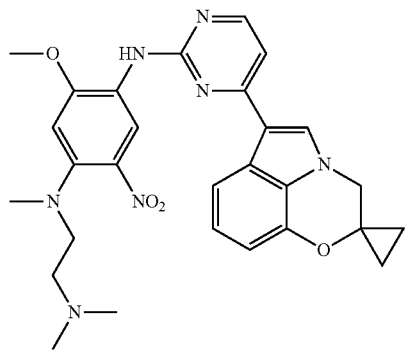 [SMILES: COc1cc(N(C)CCN(C)C)c([N+](=O)[O-])cc1Nc1nccc(-c2cn3c4c(cccc24)OC2(CC2)C3)n1]

The Embodiment was prepared according to the method of Embodiment 16A except for replacing Embodiment D and N,N-diethyl-N-methylethane-1,2-diamine with Embodiment 42G and N,N',N'-trimethyl-1,2-ethanediamine respectively to deliver the title compound (yellow solid, 1.80 g, yield 84.55%). $^1$H NMR (400 MHz, CDCl$_3$): δ 9.63 (s, 1H), 8.42 (d, J=4.0 Hz, 1H), 8.35 (s, 1H), 7.63 (d, J=8.0 Hz, 1H), 7.58-7.53 (m, 1H), 7.22 (d, J=4.0 Hz, 1H), 7.15 (t, J=8.0 Hz, 1H), 6.73-6.67 (m, 2H), 4.42-4.31 (m, 2H), 4.00 (s, 3H), 3.36-3.26 (m, 2H), 2.91 (s, 3H), 2.61 (t, J=8.0 Hz, 2H), 2.33-2.26 (m, 6H), 1.25-1.19 (m, 2H), 0.92-0.84 (m, 2H). LCMS (ESI) (5-95AB): m/z: 530.2 [M+1].

Embodiment 42I

N[4]-(4-(3H-Spiro[[1,4]oxazino[2,3,4-hi]indole-2,1'-cyclopropan]-6-yl)pyrimidin-2-yl)-N[1]-(2-(dimethylamino)ethyl)-5-methoxy-N[1]-methylbenzene-1,2,4-triamine

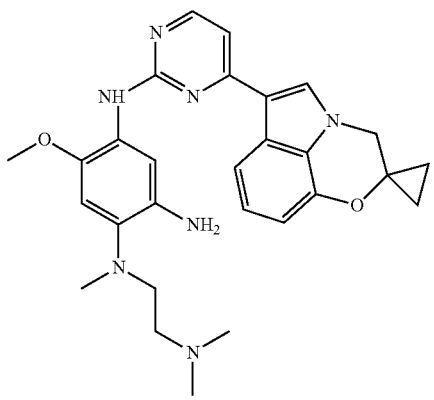 [SMILES: COc1cc(N(C)CCN(C)C)c(N)cc1Nc1nccc(-c2cn3c4c(cccc24)OC2(CC2)C3)n1]

The Embodiment was repeated according to the method of Embodiment 16B except for replacing Embodiment 16A with Embodiment 42H to deliver the title compound (yellow solid, 1.60 g, yield 94.12%). $^1$H NMR (400 MHz, CDCl$_3$): δ 8.41-8.32 (m, 1H), 8.18-8.13 (m, 1H), 7.91-7.82 (m, 2H), 7.60 (s, 1H), 7.18-7.12 (m, 1H), 7.06 (d, J=4.0 Hz, 1H), 6.76-6.67 (m, 2H), 4.27 (s, 2H), 3.86-3.84 (m, 3H), 3.00-2.93 (m, 2H), 2.69 (s, 3H), 2.42 (t, J=8.0 Hz, 2H), 2.29-2.25 (m, 6H), 1.26-1.21 (m, 2H), 0.92-0.83 (m, 2H). LCMS (ESI) (5-95AB): m/z: 500.2 [M+1].

Embodiment 42J

N-(5-((4-(3H-Spiro[[1,4]oxazino[2,3,4-hi]indole-2,1'-cyclopropan]-6-yl)pyrimidin-2-yl)amino)-2-((2-(dimethylamino)ethyl)(methyl)amino)-4-methoxyphenyl)acrylamide

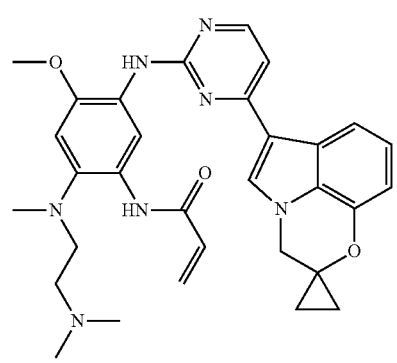 [SMILES: C=CC(=O)Nc1cc(Nc2nccc(-c3cn4c5c(cccc35)OC3(CC3)C4)n2)c(OC)cc1N(C)CCN(C)C]

The Embodiment was prepared according to the method of Embodiment 16C except for replacing Embodiment 16B with Embodiment 42I to deliver the title compound (1.25 g, yield 85.09%). $^1$H NMR (400 MHz, CDCl$_3$): δ 10.23 (br. s., 1H), 9.85 (s, 1H), 9.21 (br. s., 1H), 8.40 (d, J=4.0 Hz, 1H), 7.75 (s, 1H), 7.58 (d, J=8.0 Hz, 1H), 7.20 (d, J=4.0 Hz, 1H), 7.12 (t, J=8.0 Hz, 1H), 6.81 (s, 1H), 6.67 (d, J=8.0 Hz, 1H), 6.35 (d, J=4.0 Hz, 2H), 5.68 (t, J=6.0 Hz, 1H), 4.39 (s, 2H), 3.90 (s, 3H), 2.98-2.85 (m, 2H), 2.71 (s, 3H), 2.30-2.22 (m, 8H), 1.25-1.19 (m, 2H), 0.87 (s, 2H). LCMS (ESI) (5-95AB): m/z: 554.2 [M+1].

Embodiment 43

N-(5-((4-(3H-Spiro[[1,4]oxazino[2,3,4-hi]indole-2,1'-cyclopropan]-6-yl)pyrimidin-2-yl)amino)-2-((2-(dimethylamino)-2-methylpropyl)(methyl)amino)-4-methoxyphenyl)acrylamide

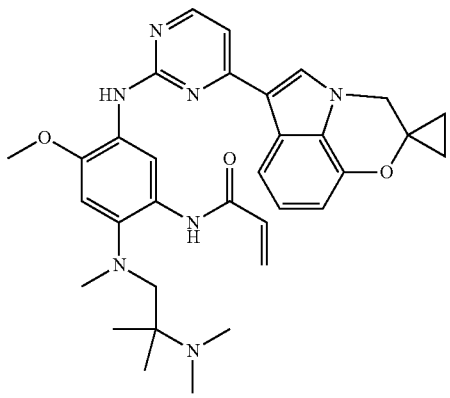 [SMILES: C=CC(=O)Nc1cc(Nc2nccc(-c3cn4c5c(cccc35)OC3(CC3)C4)n2)c(OC)cc1N(C)CC(C)(C)N(C)C]

Embodiment 43A

N$^1$-(4-(3H-Spiro[[1,4]oxazino[2,3,4-hi]indole-2,1'-cyclopropan]-6-yl)pyrimidin-2-yl)-N$^4$-(2-(dimethylamino)-2-methylpropyl)-2-methoxy-N$^4$-methyl-5-nitrobenzene-1,4-diamine

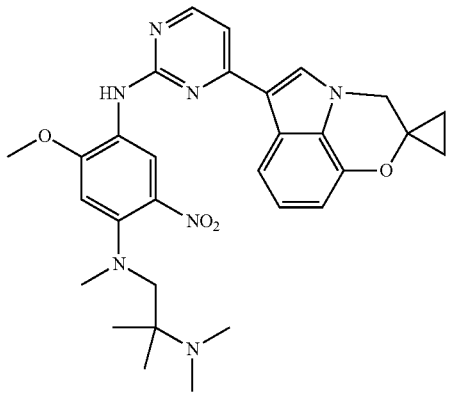 [SMILES: COc1cc(N(C)CC(C)(C)N(C)C)c([N+](=O)[O-])cc1Nc1nccc(-c2cn3c4c(cccc24)OC2(CC2)C3)n1]

The Embodiment was prepared according to the method of Embodiment 16A except for replacing Embodiment D and N,N-diethyl-N-methylethane-1,2-diamine with Embodiment 42G and N$^1$,N$^2$,N$^2$,2-tetramethylpropane-1,2-diamine respectively to deliver the title compound (yellow solid, 500 mg, yield 39.01%). $^1$H NMR (400 MHz, CDCl$_3$): δ 9.61 (s, 1H), 8.43 (d, J=4.0 Hz, 1H), 8.27 (s, 1H), 7.74-7.58 (m, 2H), 7.31 (s, 1H), 7.23 (d, J=4.0 Hz, 1H), 7.16 (t, J=8.0 Hz, 1H), 6.71 (d, J=8.0 Hz, 1H), 4.34 (s, 2H), 4.22-4.11 (m, 3H), 3.86 (br. s., 2H), 3.03 (s, 3H), 2.73 (s, 6H), 1.43 (s, 6H), 1.28-1.22 (m, 2H), 0.91-0.86 (m, 2H). LCMS (ESI) (5-95AB): m/z: 558.2 [M+1].

Embodiment 43B

N$^4$-(4-(3H-Spiro[[1,4]oxazino[2,3,4-hi]indole-2,1'-cyclopropan]-6-yl)pyrimidin-2-yl)-N$^1$-(2-(dimethylamino)-2-methylpropyl)-5-methoxy-N$^1$-methylbenzene-1,2,4-triamine

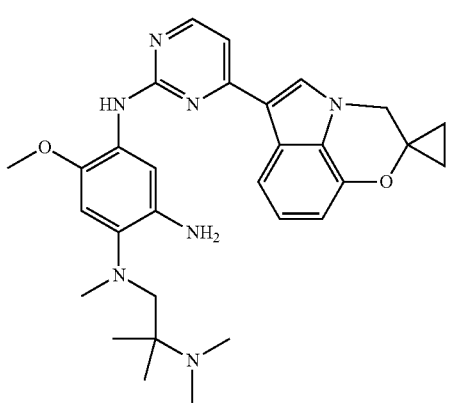 [SMILES: COc1cc(N(C)CC(C)(C)N(C)C)c(N)cc1Nc1nccc(-c2cn3c4c(cccc24)OC2(CC2)C3)n1]

The Embodiment was prepared according to the method of Embodiment 16B except for replacing Embodiment 16A with Embodiment 43A to deliver the title compound (yellow solid, 300.00 mg, yield 63.41%). $^1$H NMR (400 MHz, CD$_3$OD): δ 8.31 (d, J=4.0 Hz, 1H), 8.22 (s, 1H), 8.11 (s, 1H), 7.85 (d, J=8.0 Hz, 1H), 7.23 (d, J=4.0 Hz, 1H), 7.09 (t, J=8.0 Hz, 1H), 7.04 (s, 1H), 6.65-6.62 (m, 1H), 4.37 (s, 2H), 3.92 (s, 3H), 3.29 (s, 2H), 2.83 (s, 3H), 2.74 (s, 6H), 1.24 (s, 6H), 1.16-1.12 (m, 2H), 0.95-0.92 (m, 2H). LCMS (ESI) (5-95AB): m/z: 528.3 [M+1].

Embodiment 43C

N-(5-((4-(3H-Spiro[[1,4]oxazino[2,3,4-hi]indole-2,1'-cyclopropan]-6-yl)pyrimidin-2-yl)amino)-2-((2-(dimethylamino)-2-methylpropyl)(methyl)amino)-4-methoxyphenyl)acrylamide

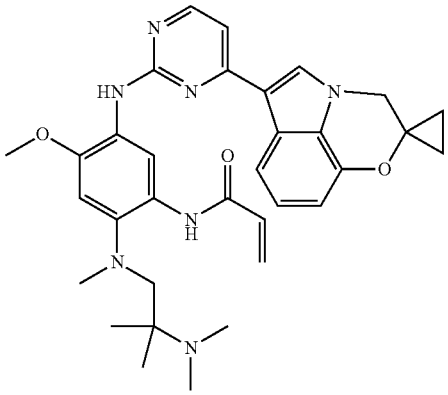 [SMILES: C=CC(=O)Nc1cc(Nc2nccc(-c3cn4c5c(cccc35)OC3(CC3)C4)n2)c(OC)cc1N(C)CC(C)(C)N(C)C]

The Embodiment was prepared according to the method of Embodiment 16C except for replacing Embodiment 16B with Embodiment 43B to deliver the title compound (230.00 mg, yield 69.54%). $^1$H NMR (400 MHz, CD$_3$OD): δ 8.56 (br. s., 1H), 8.29 (d, J=4.0 Hz, 1H), 8.09 (br. s., 1H), 7.82 (d, J=8.0 Hz, 1H), 7.22 (d, J=4.0 Hz, 1H), 7.14 (s, 1H), 7.02 (t, J=8.0 Hz, 1H), 6.60-6.49 (m, 3H), 5.90 (dd, J=4.0, 7.9 Hz, 1H), 4.34 (s, 2H), 4.03 (s, 3H), 3.69-3.41 (m, 2H), 2.80 (s, 3H), 2.75 (s, 6H), 1.34 (s, 6H), 1.16-1.11 (m, 2H), 0.95-0.90 (m, 2H). LCMS (ESI) (5-95AB): m/z: 582.4 [M+1].

Biochemical Experiments

Experimental Materials

Enzyme: EGFR wild type, EGFR T790M/L858R, EGFR T790M and INSR were purchased from Life technology (Madison, Wis.), EGFR d746-750/T790M was purchased from Carna Biosciences (Japan).

HTRF Kit was purchased from Cis-Bio International which contained the Eu-labeled TK1 antibody, XL665 and biotin-labeled TK1 polypeptide substrates.

Detecting instrument: Envision (PerkinElmer).
Experimental Method

The test compound was diluted 3-fold to obtain 10 doses of which the final concentration was from 300 nM to 0.015 nM.

Wild-Type EGFR Enzyme Reaction Mixture System:

0.05 nM Wild-type EGFR, 1 μM biotin-TK1 peptide, 25 μM ATP enzyme buffer, a total of which was 10 μL. The reaction plate was white Proxiplate 384-Plus plate (PerkinElmer) and the mixture was reacted at 23° C. for 60 minutes.

EGFR T790M/L858R Enzyme Reaction Mixture System:
0.04 nM EGFR T790M/L858R, 1 µM biotin-TK1 peptide, 20 µM ATP enzyme buffer, a total of which was 10 µL. The reaction plate was white Proxiplate 384-Plus plate (PerkinElmer) and the mixture was reacted at 23° C. for 60 minutes.

EGFR d746-750/T790M Enzyme Reaction Mixture System:
0.025 nM EGFR d746-750/T790M, 1 µM biotin-TK1 peptide, 40 µM ATP enzyme buffer, a total of which was 10 µL. The reaction plate was white Proxiplate 384-Plus plate (PerkinElmer) and the mixture was reacted at 23° C. for 60 minutes.

EGFR T790M Enzyme Reaction Mixture System:
0.03 nM EGFR T790M, 1 µM biotin-TK1 peptide, 10 µM ATP enzyme buffer, a total of which was 10 µL. The reaction plate was white Proxiplate 384-Plus plate (PerkinElmer) and the mixture was reacted at 23° C. for 60 minutes.

INSR Enzyme Reaction Mixture System:
0.5 nM INSR, 1 µM biotin-TK1 peptide, 35 µM ATP enzyme buffer, a total of which was 10 µL. The reaction plate was white Proxiplate 384-Plus plate (PerkinElmer) and the mixture was reacted at 23° C. for 60 minutes.

Reaction Detection: 10 µL of detection reagent containing Antibody 2 nM and XL665 62.5 nM was added, and the reagent was incubated at 23° C. for 60 minutes. The plates were read by Envision.

Data Analysis

The reading is converted to the suppression rate (%) by the following formula (Min−Ratio)/(Max−Min)*100%. $IC_{50}$ Data was measured by four-parameter curve fitting (Model 205 in XLFIT5, iDBS).

Cell Experiments

Experimental Materials

RPMI1640, fetal bovine serum, penicillin/streptomycin solution were purchased from Life Technology (Madison, Wis.). Cell Titer-Glo luminescent cell viability reagents were purchased from Promega (Madison, Wis.). A431 cell line and NCI-H1975 cell line were purchased from European Collection of Cell Cultures (ECACC). Plate Reader Instrument: Envision (PerkinElmer).

Experimental Method

384-Well plates, 300 of A431 cells and NCI-H1975 cells were inoculated per well, a volume of which was 45 µL. And the plates were incubated overnight in a $CO_2$ incubator at 37° C. The test compound was diluted 3-fold to obtain 10 dose concentrations, the final concentrations of which were from 10 M to 0.508 nM, two wells. The middle plates were filled with 49 µL of medium per well. 1 µL of compound in the gradient dilution compound plates was transferred to the middle plates and mixed well. And then 5 µL liquid in the middle plates was taken to the cell plates. The cells were incubated in a $CO_2$ incubator for 6 days. After 6 days, 25 µL of detection reagents was added. And then the mixture was incubated at room temperature for 10 minutes and the plates were read by Envision.

Data Analysis

The reading is converted to the suppression rate by the following formula (%) (Max−Sample)/(Max−Min)*100%. IC50 Data was measured by Four-parameter curve fitting (Model 205 in XLFIT5, iDBS).

The inhibitory $IC_{50}$ date of the wild-type EGFR enzyme of the present invention, EGFR L858R/T790M enzyme, EGFR d746-750/T790M enzyme, NCI-H1975 cells EGFR L858R/T790M, and A431 cells EGFR WT were shown in Table 1.

TABLE 1

| Embodiment | EGFR WT $IC_{50}$ (nM) | EGFR L858R/T79M $IC_{50}$ (nM) | EGFR d746-750/T790M $IC_{50}$ (nM) | EGFR L858R/T790M NCI-H1975 cell $IC_{50}$ (nM) | EGFR WT A431 cell $IC_{50}$ (nM) | A431:NCI-H1975 (ratio) |
|---|---|---|---|---|---|---|
| 1 | 1.49 | 0.32 | 0.39 | 10.38 | 714.46 | 71.4 |
| 2 | 4.31 | 0.55 | 0.67 | 4745 | >10000 | >2.1 |
| 3 | 1.58 | 0.21 | 0.19 | 67.15 | 854.19 | 12.7 |
| 4 | 59.99 | 3.25 | 2.70 | 434 | 4622.85 | 10.6 |
| 5 | 7.28 | 0.93 | 0.97 | 19 | 2673 | 140.6 |
| 6 | 20.29 | 3.07 | 3.29 | 4329 | >10000 | >2.1 |
| 7 | 32.97 | 2.19 | 2.59 | 496 | 3724 | 7.5 |
| 8 | 5.22 | 0.91 | 0.64 | 474 | 5458 | 11.5 |
| 9 | 6.28 | 0.75 | 0.51 | 111 | 1440 | 13.0 |
| 10 | 27.48 | 2.19 | 1.89 | 283 | 2260 | 8.0 |
| 11 | 0.53 | 0.23 | 0.20 | 6.1 | 270 | 44.3 |
| 12 | 0.43 | 0.33 | 0.31 | 4.8 | 369 | 76.9 |
| 13 | 0.65 | 0.24 | 0.18 | 5.4 | 545 | 101.0 |
| 14 | 0.60 | 0.27 | 0.33 | 13 | 134 | 10.3 |
| 15 | 1.03 | 0.36 | 0.37 | 15 | 230 | 15.3 |
| 16 | 4.0 | 0.29 | 0.33 | 17 | 1064 | 63 |
| 17 | 0.89 | 0.21 | 0.18 | 4.1 | 777 | 189.5 |
| 18 | 1.9 | 0.20 | 0.18 | 7 | 518 | 74 |
| 19 | 2.7 | 0.30 | 0.26 | 29 | 965 | 33 |
| 20 | 0.66 | 0.20 | 0.17 | 4.0 | 164 | 41.0 |
| 21 | / | / | / | 50 | 1437 | 29 |
| 22 | / | / | / | 50.4 | 1327 | 26 |
| 23 | / | / | / | 63 | 1570 | 25 |
| 24 | 36.4 | 1.9 | 1.3 | 172 | 2658 | 15 |
| 25 | 0.81 | 0.20 | 0.13 | 4.0 | 248 | 62 |
| 26 | / | / | / | 102 | 2210 | 22 |
| 27 | 1.7 | 0.21 | 0.19 | 5.0 | 485 | 97 |
| 28 | 1.5 | 0.20 | 0.20 | 11 | 517 | 47 |
| 29 | 5.1 | 0.38 | 0.38 | 25 | 1180 | 47 |

TABLE 1-continued

| Embodiment | EGFR WT IC$_{50}$ (nM) | EGFR L858R/T79M IC$_{50}$ (nM) | EGFR d746-750/T790M IC$_{50}$ (nM) | EGFR L858R/T790M NCI-H1975 cell IC$_{50}$ (nM) | EGFR WT A431 cell IC$_{50}$ (nM) | A431:NCI-H1975 (ratio) |
|---|---|---|---|---|---|---|
| 30 | 0.80 | 0.14 | 0.16 | 15 | 823 | 55 |
| 31 | 2.0 | 0.2 | 0.3 | 96 | 1290 | 13.4 |
| 32 | 0.3 | 0.1 | 0.2 | 3 | 597 | 199 |
| 33 | 2.6 | 0.5 | 0.4 | 90 | 693 | 7.7 |
| 34 | 2.0 | 0.8 | 0.6 | 68 | 2104 | 31 |
| 35 | 1.5 | 1.2 | 0.6 | 107 | 971 | 9.1 |
| 36 | 2.7 | 1.3 | 1.3 | 175 | 438 | 2.5 |
| 37 | 0.35 | 0.1 | 0.1 | 12.5 | 303 | 24 |
| 38 | 0.6 | 0.09 | 0.1 | 7 | 317 | 45 |
| 39 | 5.3 | 0.5 | 0.6 | 288 | 1574 | 5.5 |
| 40 | 0.8 | 0.3 | 0.4 | 23 | 279 | 12 |
| 41 | 4.9 | 1.5 | 2.6 | 201 | 1715 | 8.5 |
| 42 | 0.8 | 0.2 | 0.2 | 177 | 846 | 4.8 |
| 43 | / | / | / | 264 | 548 | 2.1 |

The inhibitory IC$_{50}$ data for INSR enzyme of the compounds of the present invention were shown in Table 2.

TABLE 2

| Embodiment | INSR_IC50 (nM) |
|---|---|
| 1 | 404 |
| 3 | 886 |
| 17 | 341 |
| 18 | 633 |
| 25 | 333 |
| 27 | 570 |
| 30 | 393 |
| 37 | 440 |
| 38 | 310 |

Pharmacodynamics Study In Vivo

The following pharmacodynamics data in vivo showed that the compound of the present invention exhibited strong antitumor activity and reduced tumor volume in the NCD-H1975 non-small cell lung cancer patient-derived xenograft (CDX) model (BALB/c nude mice). For example, after 21 days of administration, the tumor volume of the representative compounds 30, 33, 34, 40, 42 and 43 decreased from the beginning of about 149 mm$^3$ to 3-39 mm$^3$.

The pharmacological experiments in vivo were performed on BALB/c nude mice that subcutaneously implanted NCI-H1975 lung cancer patient-derived xenograft (CDX).

BALB/c nude mice, female, 6-8 weeks, weighted about 18-22 grams, the mice were kept in a special pathogen-free environment, and in a single ventilation cage (5 mice per cage). The bedding and water of all the cages were disinfected before use. All animals were free to obtain standard certified commercial laboratory diets. A total of 100 mice were purchased from Beijing Vital for research. The tumor tissue (20-30 mm$^3$) was implanted subcutaneously in the right ventricle of each mouse for tumor growth. The experiment was started when the average tumor volume reached about 150-200 mm$^3$. The test compound was orally administered daily (compound 30 was administered at 10 mg/kg, compound 33, 34, 40, 42 and 43 were administered at 20 mg/kg and compound AZD9291 was administered continuously for 21 days at 5 mg/kg, the data were shown in Table 3). The tumor volume was measured twice a week with a two-dimensional caliper and the volume was measured in cubic millimeters and calculated by the following formula: V=V=0.5 a×b2, where a and b were the major and minor diameters of the tumor, respectively. The antitumor efficacy was determined by dividing the average tumor size of the animals treated with the compound increased by the average tumor size of the untreated animals increased.

TABLE 3

| Compounds of the embodiments | Tumor Volume (mm$^3$) | | | | | | |
|---|---|---|---|---|---|---|---|
| | 0 day | 4 days | 7 days | 11 days | 14 days | 18 days | 21 days |
| Vehicle | 149 | 281 | 434 | 750 | 1476 | 1785 | 2141 |
| AZD 9291 | 149 | 86 | 64 | 52 | 66 | 25 | 15 |
| 30 | 149 | 115 | 90 | 48 | 34 | 22 | 17 |
| 33 | 148 | 91 | 68 | 43 | 27 | 9 | 3 |
| 34 | 149 | 102 | 80 | 70 | 59 | 35 | 31 |
| 40 | 148 | 108 | 85 | 91 | 91 | 84 | 39 |
| 42 | 149 | 85 | 69 | 57 | 47 | 20 | 13 |
| 43 | 148 | 92 | 65 | 61 | 45 | 23 | 17 |

Selectivity Study In Vivo

The following selective experimental data in vivo showed that the compound of the present invention exhibited good selectivity in vivo in A431 human skin squamous cell carcinoma-derived xenograft (CDX) model (BALB/c nude mice). In this model, the less inhibitory effect on the tumor, the better the selectivity in vivo. For example, after 21 days of administration (20 mg/kg), the tumor volume of the representative compounds 17, 30, 37 and 38 (Experiment 1, the results were shown in Table 4) increased from about 175 mm$^3$ to 1201-1434 mm$^3$, while Afatinib (7.5 mg/kg) only increased to 479 mm$^3$. After 21 days of administration (20 mg/kg), the tumor volume of representative compounds 33, 34 and 40 (experimental results, see Table 5) increased from at the beginning of about 144 mm$^3$ to 1135-1708 mm$^3$, and AZD9291 (5 mg/Kg) only increased to 321 mm$^3$.

The selective experiments in vivo were performed on BALB/c nude mice that subcutaneously implanted human skin squamous cell A431 xenograft (CDX).

BALB/c nude mice, female, 6-8 weeks, weighted about 18-20 grams, the mice were kept in a special pathogen-free environment and in a single ventilation cage (5 mice per cage). The bedding and water of all the cages were disinfected before use. All animals were free to obtain standard certified commercial laboratory diets. All mice were purchased from mice of Shanghai BK Laboratory Animal Co., LTD for research. The tumor tissue (20-30 mm$^3$) was implanted subcutaneously in the right ventricle of each mouse for tumor growth. The experiment was started when the average tumor volume reached about 150-200 mm³. The test compound was orally administered (compounds 17, 30, 37 and 38 were administered once daily at 20 mg/kg, the compound AZD9291 was administered once daily at 5 mg/kg, the compound CO-1686 was administered twice daily at 50 mg/kg, the compound Erlotinib was administered once daily at 75 mg/kg and the compound Afatinib was administered once daily at 7.5 mg/kg, 21 days of continuous administration. The data were shown in Table 4; compounds 33, 34, 40, 42 and 43 were administered once daily at 20 mg/kg and compound AZD9291 was administered once daily at 5 mg/kg, 21 days of continuous administration. The data were shown in Table 5). The tumor volume was measured twice a week with a two-dimensional caliper and the volume was measured in cubic millimeters and calculated by the following formula: V=V=0.5 a×b2, where a and b were the major and minor diameters of the tumor, respectively. The antitumor efficacy was determined by dividing the average tumor size of the animals treated with the compound increased by the average tumor size of the untreated animals increased.

TABLE 4

| Compounds of the embodiments | Tumor Volume (mm³) | | | | | | |
|---|---|---|---|---|---|---|---|
| | 0 day | 3 days | 7 days | 10 days | 14 days | 17 days | 21 days |
| Vehicle | 177 | 299 | 644 | 815 | 1067 | 1235 | 1673 |
| AZD 9291 | 175 | 280 | 421 | 459 | 545 | 575 | 780 |
| CO-1686 | 175 | 324 | 557 | 678 | 830 | 1094 | 1307 |
| Erlotinib | 175 | 214 | 351 | 374 | 467 | 511 | 721 |
| Afatinib | 175 | 216 | 269 | 296 | 390 | 369 | 479 |
| 17 | 177 | 228 | 406 | 512 | 610 | 844 | 1201 |
| 30 | 174 | 276 | 537 | 718 | 963 | 1184 | 1375 |
| 37 | 175 | 266 | 586 | 763 | 812 | 1130 | 1345 |
| 38 | 176 | 270 | 573 | 826 | 955 | 1126 | 1434 |

TABLE 5

| Compounds of the embodiments | Tumor Volume (mm³) | | | | | | |
|---|---|---|---|---|---|---|---|
| | 0 day | 4 days | 7 days | 11 days | 14 days | 18 days | 21 days |
| Vehicle | 146 | 264 | 469 | 630 | 958 | 1333 | 1689 |
| AZD 9291 | 146 | 153 | 154 | 219 | 277 | 330 | 321 |
| 33 | 144 | 202 | 317 | 428 | 618 | 930 | 1221 |
| 34 | 146 | 237 | 435 | 646 | 987 | 1357 | 1708 |
| 40 | 144 | 212 | 316 | 445 | 672 | 895 | 1135 |
| 42 | 144 | 226 | 314 | 424 | 534 | 661 | 737 |
| 43 | 144 | 238 | 355 | 516 | 687 | 820 | 963 |

The clinical data of EGFR TKIs showed that non-selective inhibition of wild-type EGFR has side effects, including rash and diarrhea; inhibition of insulin receptor (INSR) can lead to hyperglycemia and hyperinsulinemia. Tables 1 to 5 showed that many compounds not only had excellent activity and selectivity in vitro for L858R/EGFR T790M and EGFR790M, but also had good efficacy and selectivity in vivo, and the selectivity is manifested by the low inhibitory activity against wild-type EGFR (A431) and insulin receptor (INSR). These selective data in vitro, in vivo showed that the compounds will have better safety.

What is claimed is:
1. A compound of formula (I) or a pharmaceutically acceptable salt thereof,

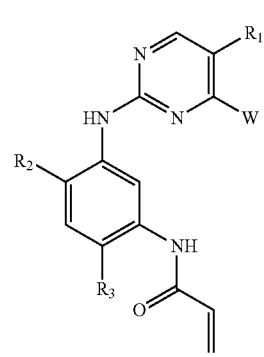

(I)

wherein,
w is

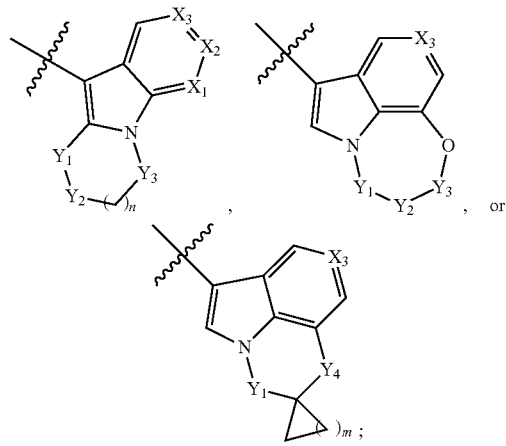

, or $n=0$, 1, or 2;
$m=1$, 2, or 3;
each of $Y_1$, $Y_3$, and $Y_4$ is independently selected from the group consisting of —O—, —S—, —C(R)$_2$—, —N(R)—, —S(=O)$_2$—, —S(=O)—, —C(=O)—, and —C(=S)—;
$Y_2$ is —O—, —S—, —N(R)—, —S(=O)$_2$—, —S(=O)—, or —C(=S)—;
$X_1$ is $CR_{X1}$, or N;
$X_2$ is $CR_{X2}$, or N;
$X_3$ is $CR_{X3}$, or N;
each of $R_{X1}$, $R_{X2}$, $R_{X3}$ is independently selected from H, F, Cl, Br, I, CN, OH, SH, or NH$_2$, or each of $R_{X1}$, $R_{X2}$, $R_{X3}$ is independently selected from the group consisting of $C_{1-6}$ alkyl and $C_{1-6}$ heteroalkyl, and the aforesaid group is optionally substituted by 1, 2, 3, or 4 R(s),
$R_1$ is H, F, Cl, Me, CN, or CF$_3$;
$R_2$ is $R_{02}$, $OR_{02}$, or $SR_{02}$;
$R_{02}$ is independently selected from the group consisting of $C_{1-4}$ alkyl, $C_{1-4}$ heteroalkyl, and $C_{3-5}$ cycloalkyl-(CH$_2$)$_{0-3}$—, and the aforesaid group is optionally substituted by 1, 2, 3, or 4 R(s);
$R_3$ is selected from the group consisting of $C_{1-6}$ alkyl, $C_{1-6}$ heteroalkyl, $C_{2-4}$ alkynyl, 3 to 7 membered cycloalkyl, 3 to 7 membered cycloalkyl-L-, 3 to 7 membered heterocycloalkyl, 3 to 7 membered heterocycloalkyl-L-, each of which is optionally substituted by 1, 2, 3, or 4 R(s);

L is selected from —O—, —S—, —C(=O)—, —S(=O)$_2$—, or —S(=O)—, or L is selected from the group consisting of NH, C$_{1-4}$ alkyl, and C$_{1-4}$ heteroalkyl, and the aforesaid group is optionally substituted by 1, 2, 3, or 4 R(s);

the "hetero" represents a heteroatom or a hetero-atomic group, which is selected from —C(=O)NH—, —NH—, —O—, —S—, N, =O, =S, —C(=O)O—, —C(=O)—, —C(=S)—, —S(=O)—, or —S(=O)$_2$—;

the number of the heteroatom or the hetero-atomic group is independently selected from 0, 1, 2, or 3;

R is selected from H, F, Cl, Br, I, OH, or CN, or R is selected from the group consisting of NH$_2$, C$_{1-4}$ alkyl, C$_{1-4}$ heteroalkyl, 3 to 7 membered cycloalkyl, and 3 to 7 membered heterocycloalkyl, and the aforesaid group is optionally substituted by 1, 2, 3, or 4 R'(s); and R' is selected from F, Cl, Br, I, CN, OH, NH$_2$, CF$_3$, NHCH$_3$, CH$_2$OCH$_3$, or N(CH$_3$)$_2$.

2. A compound of formula (I) or a pharmaceutically acceptable salt thereof,

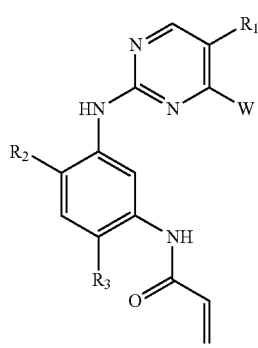

(I)

wherein,
w is selected from

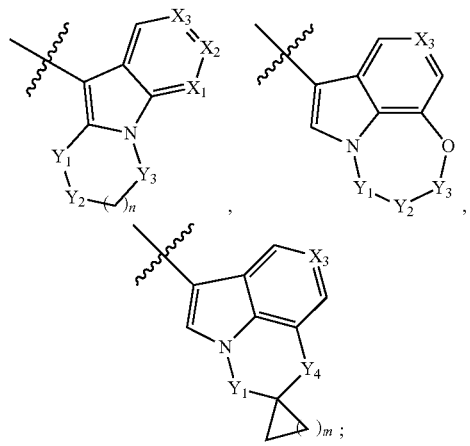

n=0;
m=1, 2, or 3;
each of Y$_1$, Y$_3$, and Y$_4$ is independently selected from the group consisting of —O—, —S—, —C(R)$_2$—, —N(R)—, —S(=O)$_2$—, —S(=O)—, —C(=O)—, and —C(=S)—;

Y$_2$ is —C(R)$_2$—;
X$_1$ is CR$_{X1}$, or N;
X$_2$ is CR$_{X2}$, or N;
X$_3$ is CR$_{X3}$, or N;
each of R$_{X1}$, R$_{X2}$, R$_{X3}$ is independently selected from H, F, Cl, Br, I, CN, OH, SH, or NH$_2$, or each of R$_{X1}$, R$_{X2}$, R$_{X3}$ is independently selected from the group consisting of C$_{1-6}$ alkyl and a C$_{1-6}$ heteroalkyl, and the aforesaid group is optionally substituted by one, two, three, or four R(s), R$_1$ is H, F, Cl, Me, CN, or CF$_3$;
R$_2$ is R$_{O2}$, OR$_{O2}$, or SR$_{O2}$;
R$_{O2}$ is independently selected from the group consisting of C$_{1-4}$ alkyl, C$_{1-4}$ heteroalkyl, and C$_{3-5}$ cycloalkyl-(CH$_2$)$_{0-3}$—, and the aforesaid group is optionally substituted by one, two, three, or four R(s);

R$_3$ is selected from the group consisting of C$_{1-6}$ alkyl, C$_{1-6}$ heteroalkyl, C$_{2-4}$ alkynyl, 3 to 7 membered cycloalkyl, 3 to 7 membered cycloalkyl-L-, 3 to 7 membered heterocycloalkyl, and 3 to 7 membered heterocycloalkyl-L-, and the aforesaid group is optionally substituted by one, two, three, or four R(s);

L is —O—, —S—, —C(=O)—, —S(=O)$_2$—, or —S(=O)—, or L is selected from the group consisting of NH, C$_{1-4}$ alkyl, and C$_{1-4}$ heteroalkyl, and the aforesaid group is optionally substituted by one, two, three, or four R(s);

the "hetero" represents a heteroatom or a hetero-atomic group, which is selected from —C(=O)NH—, —NH—, —O—, —S—, N, =O, =S, —C(=O)O—, —C(=O)—, —C(=S)—, —S(=O)—, or —S(=O)$_2$—;

the number of the heteroatom or the hetero-atomic group is independently selected from 0, 1, 2, or 3;

R is H, F, Cl, Br, I, OH, or CN, or R is selected from the group consisting of NH$_2$, C$_{1-4}$ alkyl, C$_{1-4}$ heteroalkyl, 3 to 7 membered cycloalkyl, and 3 to 7 membered heterocycloalkyl, and the aforesaid group is optionally substituted by one, two, three, or four R'(s); and R' is F, Cl, Br, I, CN, OH, NH$_2$, CF$_3$, NHCH$_3$, CH$_2$OOCH$_3$, or N(CH$_3$)$_2$.

3. The compound or the pharmaceutically acceptable salt thereof according to claim 1, wherein R is H, F, Cl, Br, I, OH, NH$_2$, CN, Me, Et, CF$_3$, N(CH$_3$)$_2$, N(CD$_3$)$_2$, NHCH$_3$,

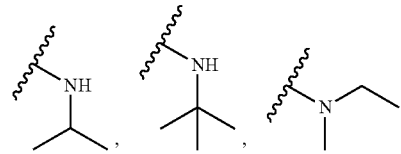

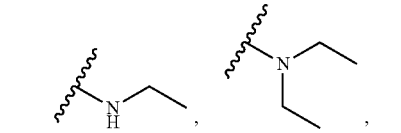

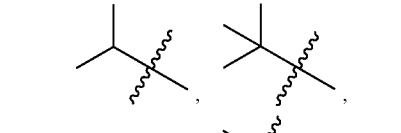

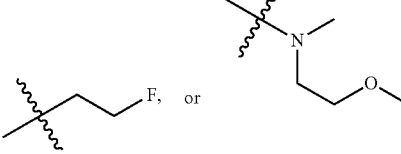

4. The compound or the pharmaceutically acceptable salt thereof according to claim 1, wherein $Y_1$, $Y_3$ and $Y_4$ are independently selected from —O—, —S—, —CH$_2$—, —CF$_2$—, —CHF—, —C(Me)$_2$-, —CH(Me)-, —CH(OH)—, —C(=O)—, —S(=O)$_2$—, or —S(=O)—; and $Y_2$ is —O—, —S—, —S(=O)$_2$—, or —S(=O)—.

5. The compound or the pharmaceutically acceptable salt thereof according to claim 1, wherein $Y_1$, $Y_3$ and $Y_4$ are independently selected from —O—, —S—, —CH$_2$—, —CF$_2$—, —CHF—, —C(Me)$_2$-, —CH(Me)-, —CH(OH)—, —C(=O)—, —S(=O)$_2$-, or —S(=O)—, and $Y_2$ is —CH$_2$—, —CF$_2$—, —CHF—, —C(Me)$_2$-, —CH(Me)-, or —CH(OH)—.

6. The compound or the pharmaceutically acceptable salt thereof according to claim 1, wherein the moiety

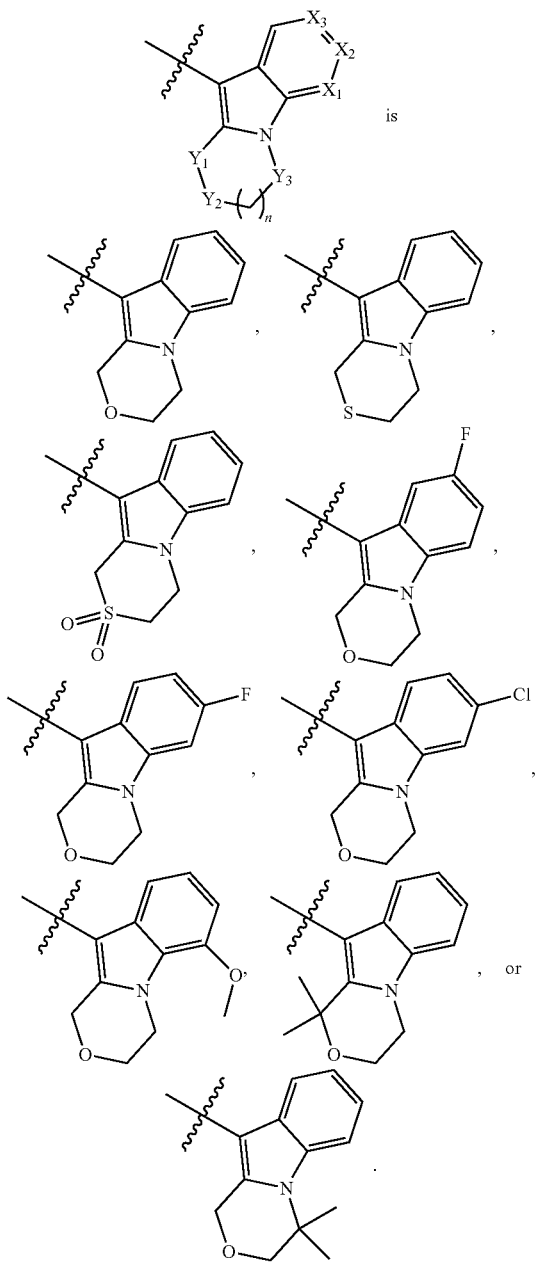

7. The compound or the pharmaceutically acceptable salt thereof according to claim 2, wherein the moiety

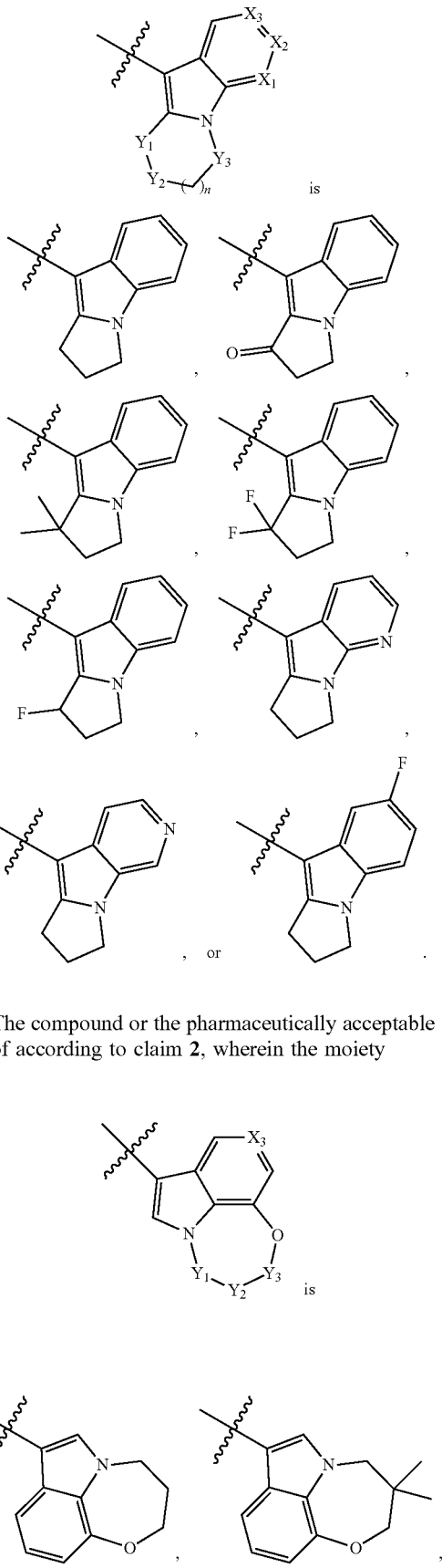

8. The compound or the pharmaceutically acceptable salt thereof according to claim 2, wherein the moiety

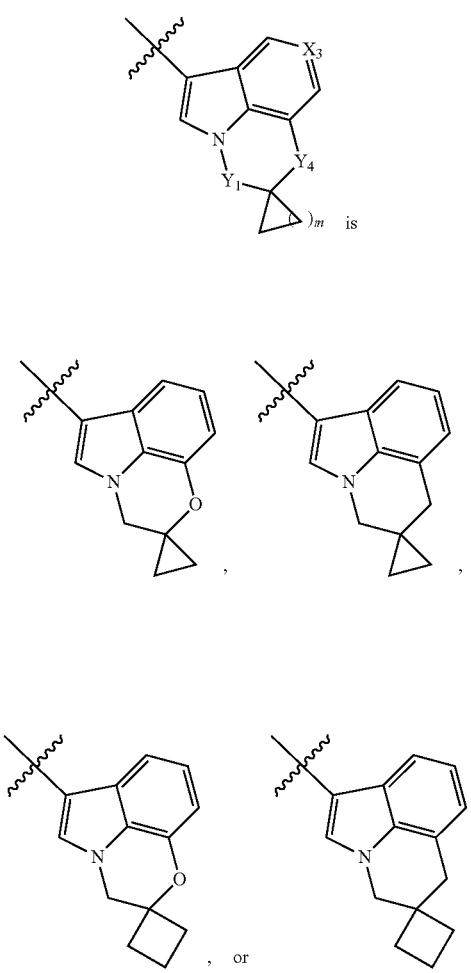

9. The compound or the pharmaceutically acceptable salt thereof according to claim 1, wherein the moiety

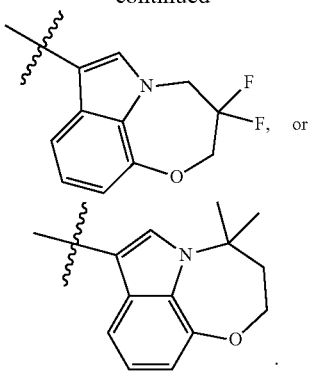 is

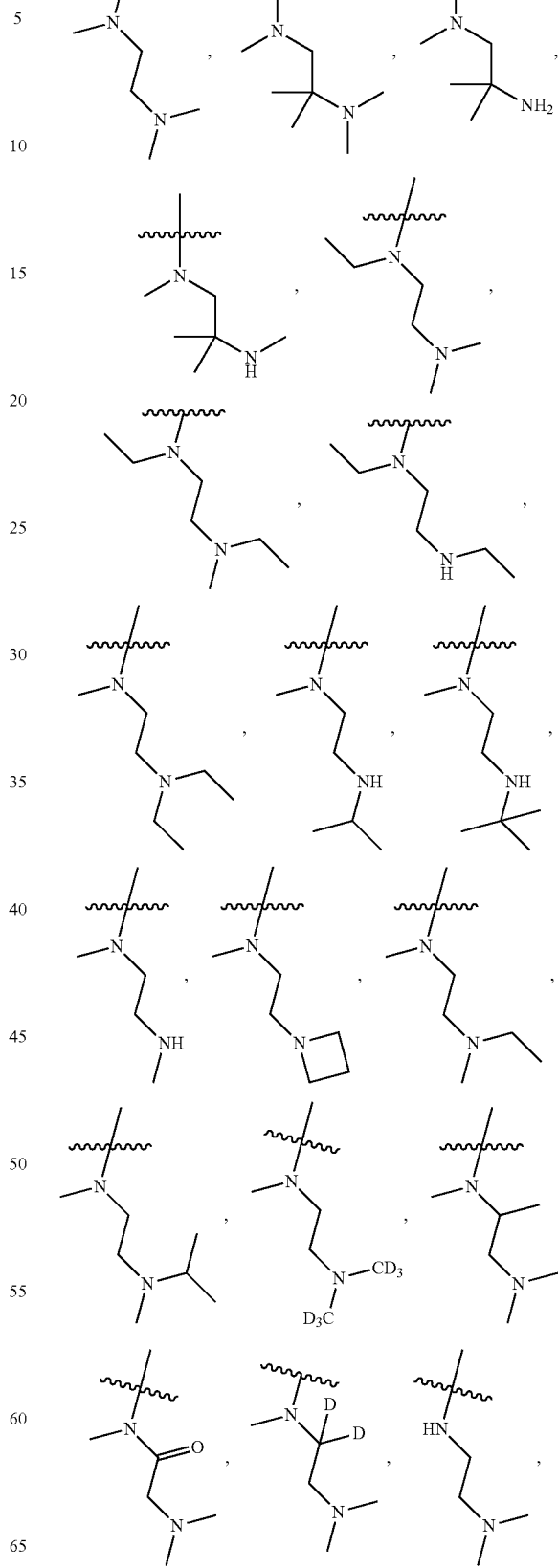

10. The compound or the pharmaceutically acceptable salt thereof according to claim 1, wherein L is —O—, —S—, —C(=O)—, —S(=O)$_2$—, or —S(=O)—, or L is selected from the group consisting of NH, C$_{1-3}$ alkyl, —O—C$_{1-3}$ alkyl, —S—C$_{1-3}$ alkyl, and —NH—C$_{1-3}$ alkyl, and the aforesaid group is optionally substituted by one, two, or three R(s).

11. The compound or the pharmaceutically acceptable salt thereof according to claim 1, wherein R$_3$ is 211
-continued
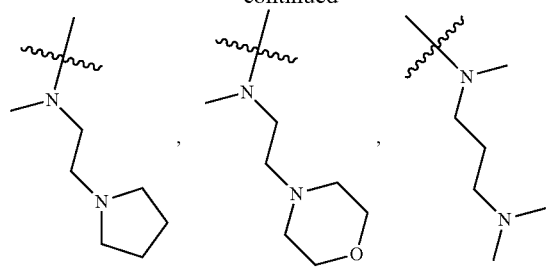
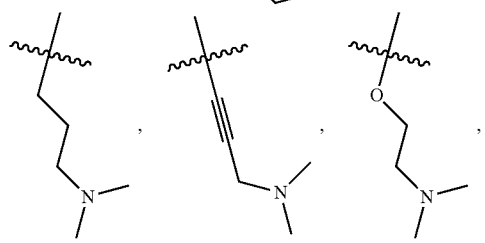
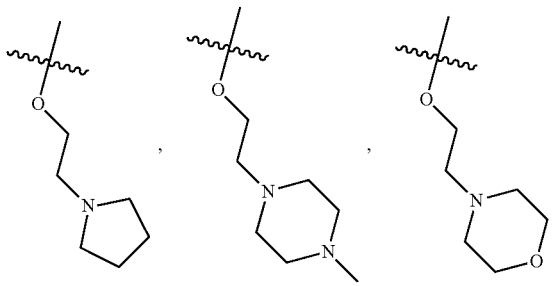
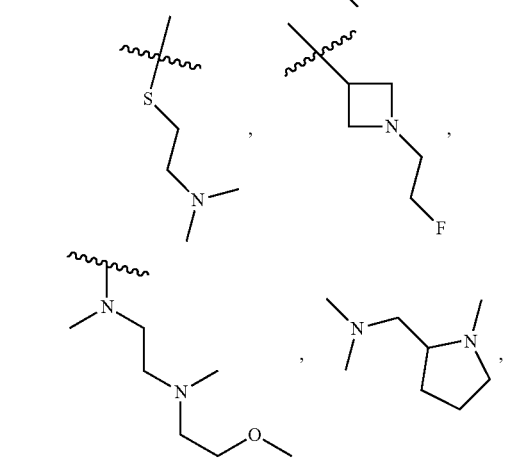
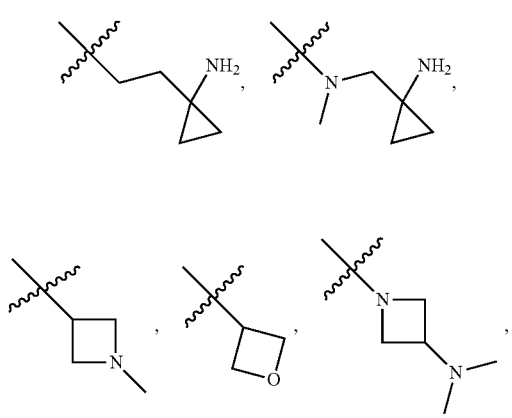
212
-continued
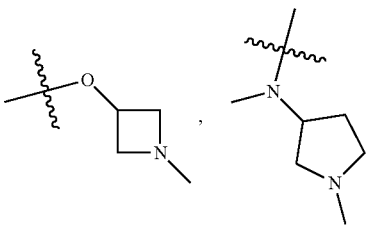
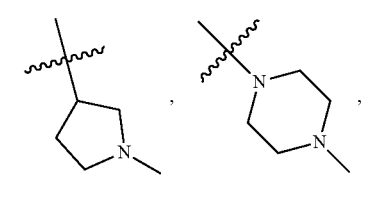
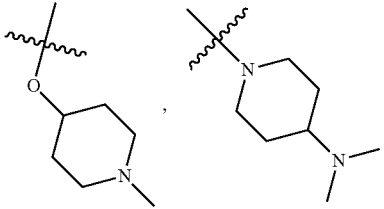
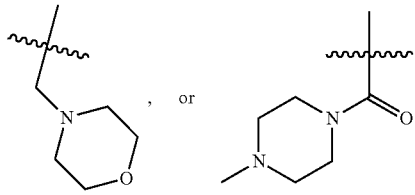
12. The compound or the pharmaceutically acceptable salt thereof according to claim 1, wherein $R_{o2}$ is Me, $CHF_2$, $CH_2CH_3$, or $CH(CH_3)_2$.
13. A compound having the following formula:
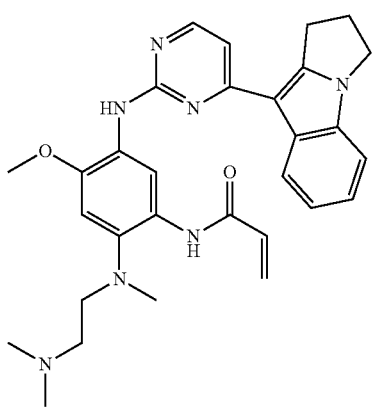

213
-continued
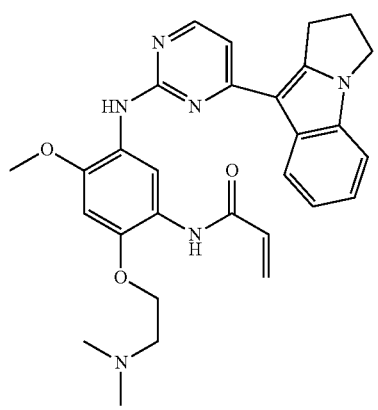
214
-continued
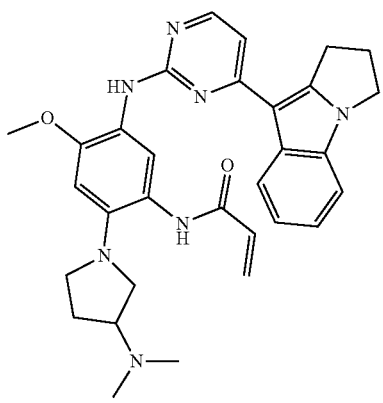
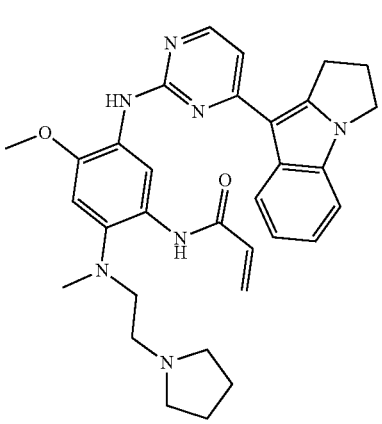
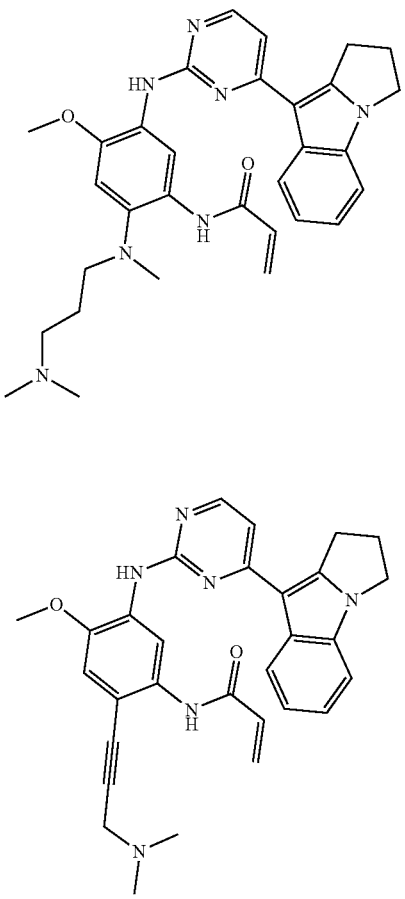
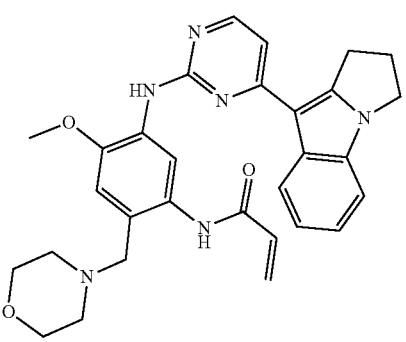

215
-continued
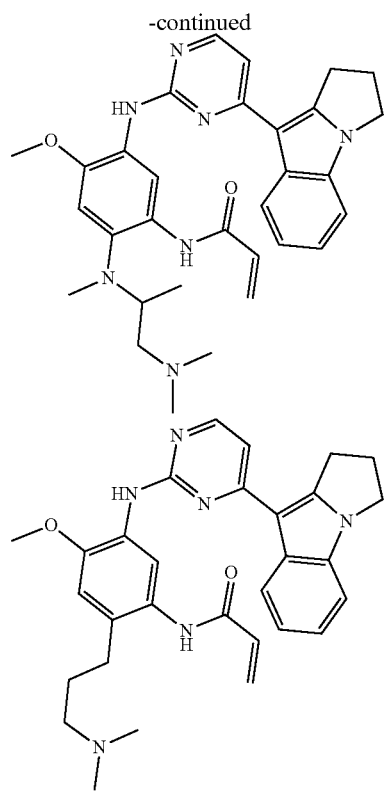
216
-continued
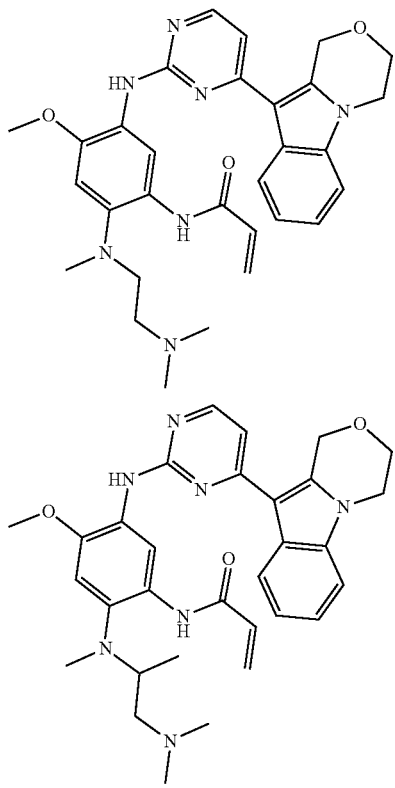

217                                    218
-continued                             -continued
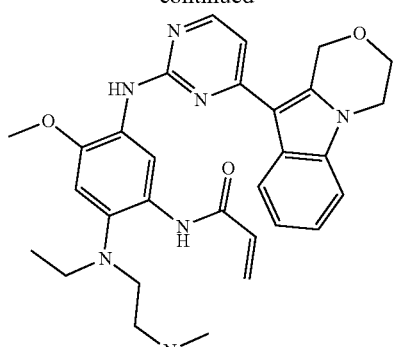
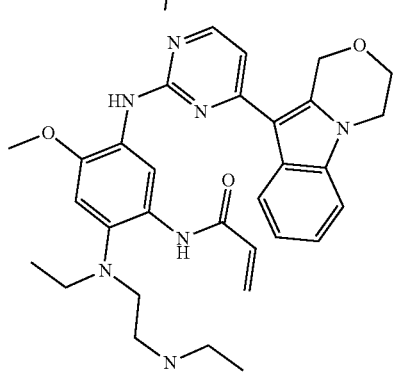
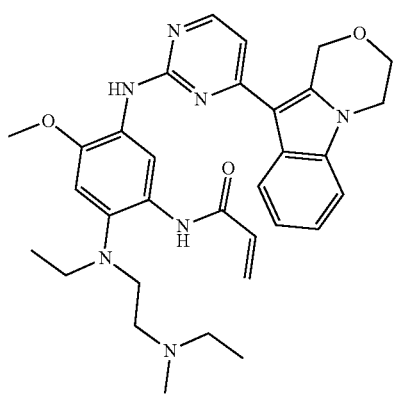
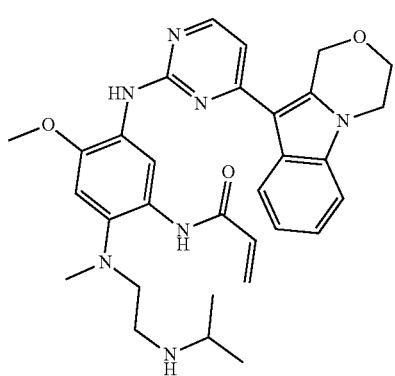

219
-continued
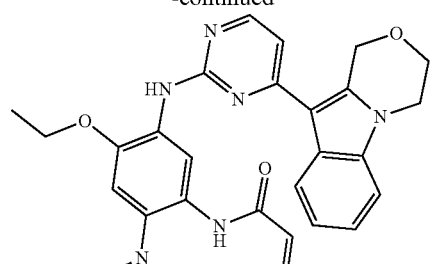
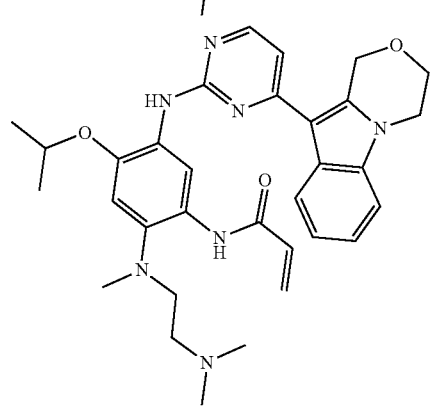
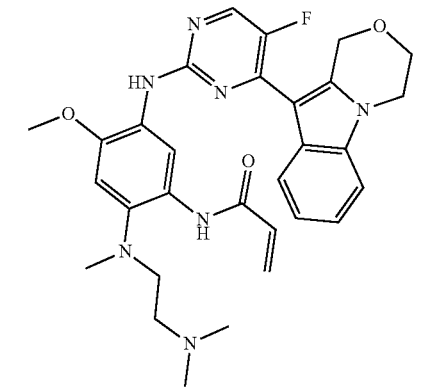
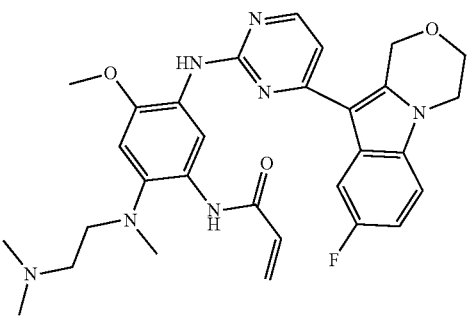
220
-continued
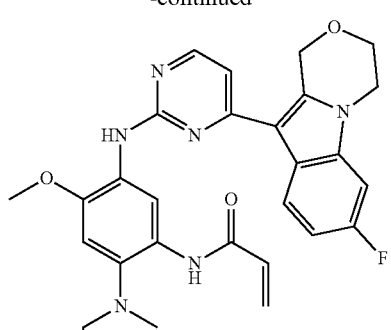
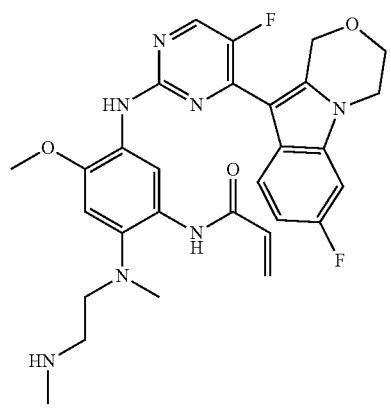
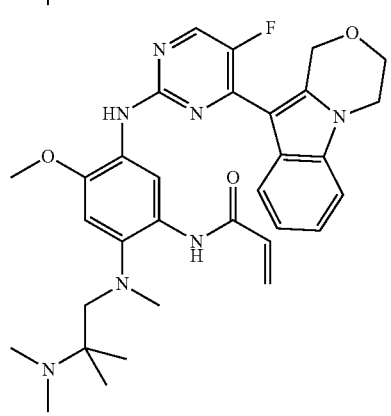
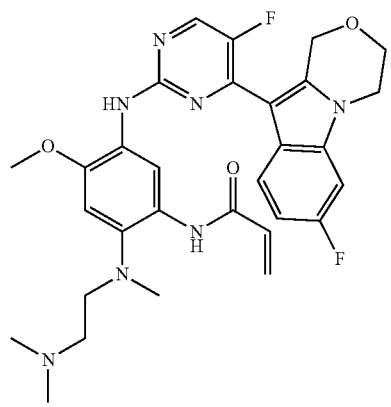

221
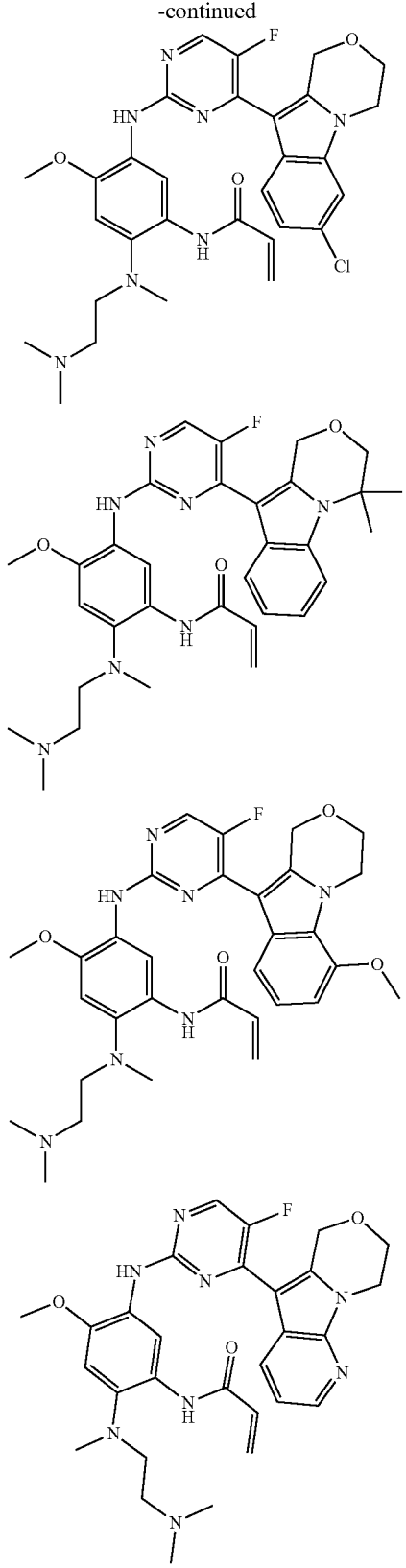
222
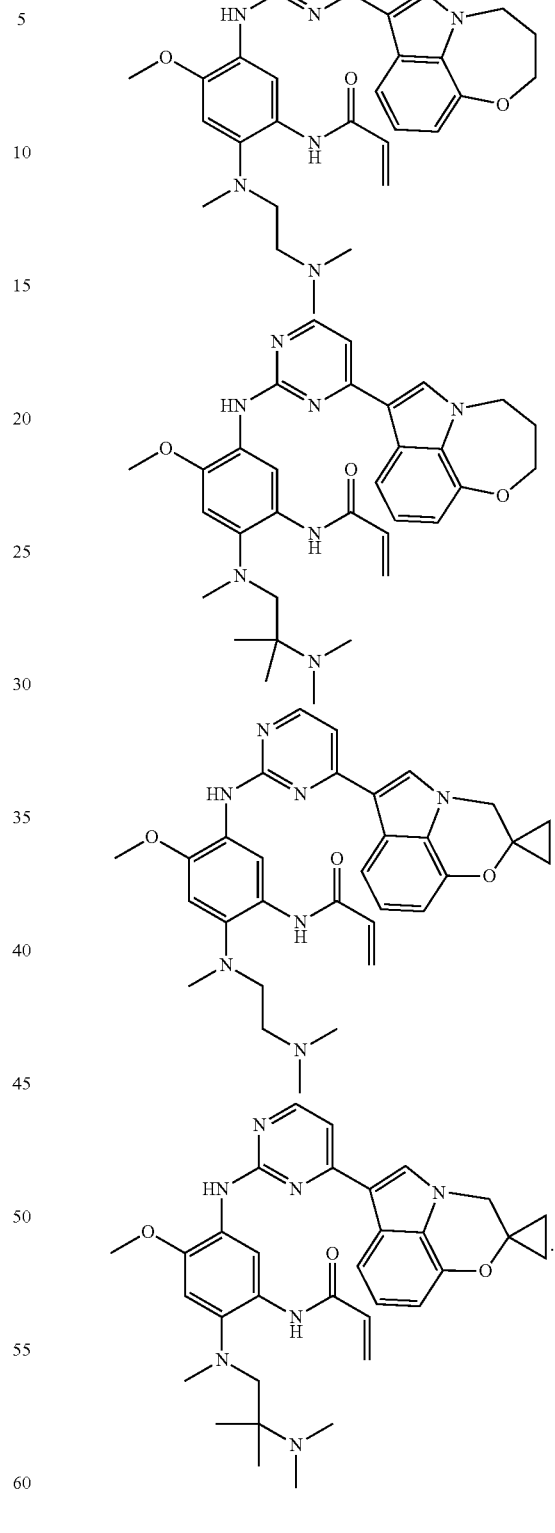
* * * * *